(12) United States Patent
Bry et al.

(10) Patent No.: US 11,666,611 B2
(45) Date of Patent: *Jun. 6, 2023

(54) DEFINED THERAPEUTIC MICROBIOTA AND METHODS OF USE THEREOF

(71) Applicant: THE BRIGHAM AND WOMEN'S HOSPITAL, INC., Boston, MA (US)

(72) Inventors: Lynn Bry, Jamaica Plain, MA (US); Georg Gerber, Newton, MA (US); Jessica Allegretti, Boston, MA (US); Richard Lavin, Brighton, MA (US); Nicholas DiBenedetto, Meford, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/771,979

(22) PCT Filed: Dec. 11, 2018

(86) PCT No.: PCT/US2018/065023
§ 371 (c)(1),
(2) Date: Jun. 11, 2020

(87) PCT Pub. No.: WO2019/118510
PCT Pub. Date: Jun. 20, 2019

(65) Prior Publication Data
US 2021/0069264 A1 Mar. 11, 2021

Related U.S. Application Data

(60) Provisional application No. 62/665,754, filed on May 2, 2018, provisional application No. 62/597,116, filed on Dec. 11, 2017.

(51) Int. Cl.
*A61K 35/742* (2015.01)
*A61P 31/04* (2006.01)
(Continued)

(52) U.S. Cl.
CPC .......... *A61K 35/742* (2013.01); *A61K 9/0031* (2013.01); *A61K 9/0053* (2013.01);
(Continued)

(58) Field of Classification Search
CPC ........ A61K 39/00; A61K 39/02; A61K 39/08; A61K 49/00
(Continued)

(56) References Cited

U.S. PATENT DOCUMENTS 10,265,349 B2 * 4/2019 Chatila ................. A61K 35/744
10,391,131 B2 * 8/2019 Chatila ................. A61K 35/744
(Continued)

FOREIGN PATENT DOCUMENTS

WO 2014110493 A1 7/2014
WO 2016059350 A1 4/2016
(Continued)

OTHER PUBLICATIONS

Collins et al., (Microbiol Spectr. Sep. 2017; 5(5): pp. 1-25). (Year: 2017).*

*Primary Examiner* — Jana A Hines
(74) *Attorney, Agent, or Firm* — Nixon Peabody LLP; David S. Resnick; Mark J. FitzGerald

(57) ABSTRACT

Described herein are methods and compositions for the use of treating and/or preventing *Clostridium difficile* infections, including recurrent *C. difficile* infections, in a subject. Aspects of the technology relate to administering to a subject in need thereof a composition comprising a defined therapeutic microbiota comprising, e.g. Clostridial species. Also described herein are biomarker profiles, including a
(Continued)

biomarker profile comprising two groups of Clostridial species, that is predictive of the likelihood of recurrent *C. difficile* infection and/or susceptibility to initial *C. difficile* infection.

8 Claims, 39 Drawing Sheets

Specification includes a Sequence Listing.

(51) Int. Cl.
| | | |
|---|---|---|
| *A61K 9/00* | (2006.01) | |
| *A61K 35/741* | (2015.01) | |
| *A61K 45/06* | (2006.01) | |
| *A61K 47/18* | (2017.01) | |
| *A61K 47/34* | (2017.01) | |
| *A61K 47/42* | (2017.01) | |
| *C12Q 1/06* | (2006.01) | |
| *C12Q 1/26* | (2006.01) | |
| *C12Q 1/37* | (2006.01) | |

(52) U.S. Cl.
CPC ............ *A61K 35/741* (2013.01); *A61K 45/06* (2013.01); *A61K 47/183* (2013.01); *A61K 47/34* (2013.01); *A61K 47/42* (2013.01); *A61P 31/04* (2018.01); *C12Q 1/06* (2013.01); *C12Q 1/26* (2013.01); *C12Q 1/37* (2013.01); *G01N 2800/50* (2013.01); *G01N 2800/52* (2013.01)

(58) Field of Classification Search
USPC .................. 424/9.1, 9.2, 234.1, 236.1, 239.1
See application file for complete search history.

(56) References Cited

U.S. PATENT DOCUMENTS 10,898,527 B2 * 1/2021 Chatila ................ A61K 35/745
2017/0087196 A1   5/2017 Pamer et al.

FOREIGN PATENT DOCUMENTS

WO          2017079450 A1    5/2017
WO     WO-2017079450 A1 *  5/2017 ............. A61K 35/74

* cited by examiner

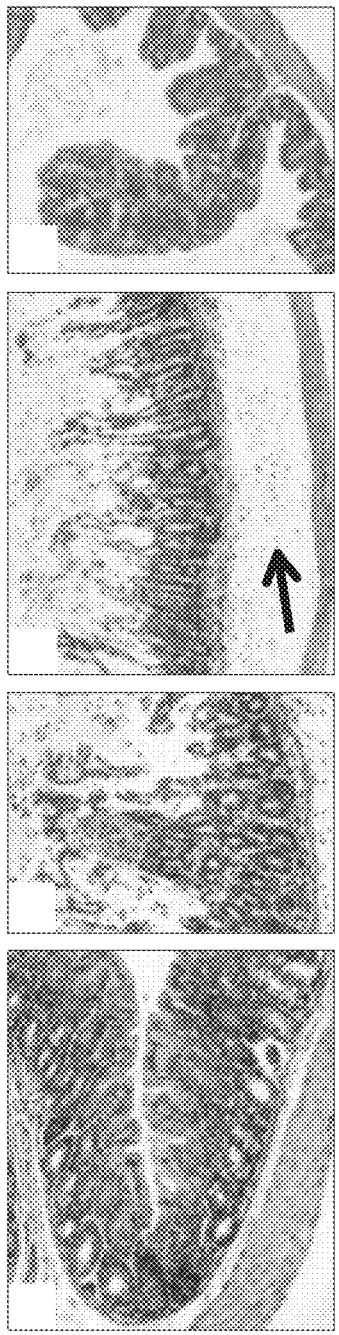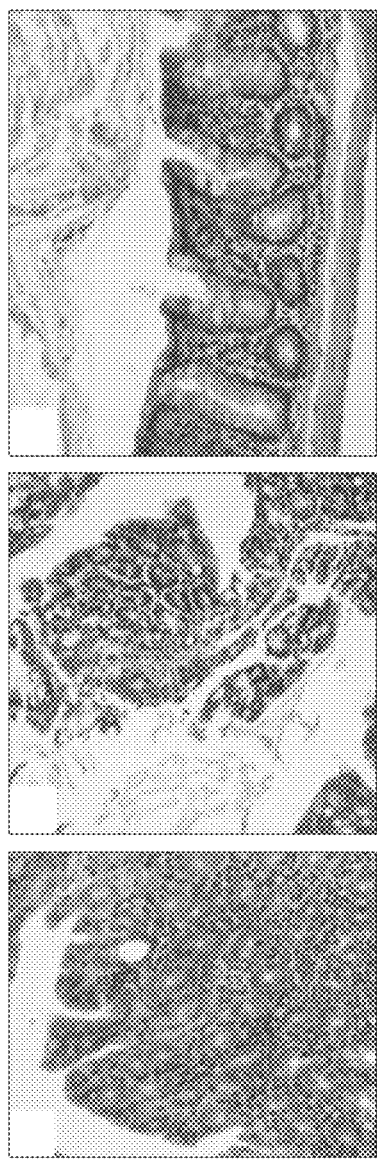

| Feature | *C. difficile* | *C. bifermentans* | *C. sardiniense* | *C. scindens* |
|---|---|---|---|---|
| GF CDI protection | N/A | 100% | 0% | 80% |
| GLM growth | Good | Poor (need Se?) | Good | Good |
| Gelatin hydrolysis | Weakly + | Positive | Positive | Negative |
| Chopped Meat | Negative | Digestion (<48hr) | Negative | Negative |
| Casein/milk | Negative | Digestion | Curd only | Negative |
| 7a dehydratase | No | No | Yes | Yes |
| Choloylglycine hydrolase | No | Yes | No | No |
| D-proline reductase | Yes | Yes | No | Yes |
| Glycine reductase | Yes | Yes | No | Yes |
| codY | Yes | Yes | Yes | Yes |
| ccpA | Yes | Yes | Yes | Yes |
| prdR | Yes | No/Unk | N/A | Unknown |

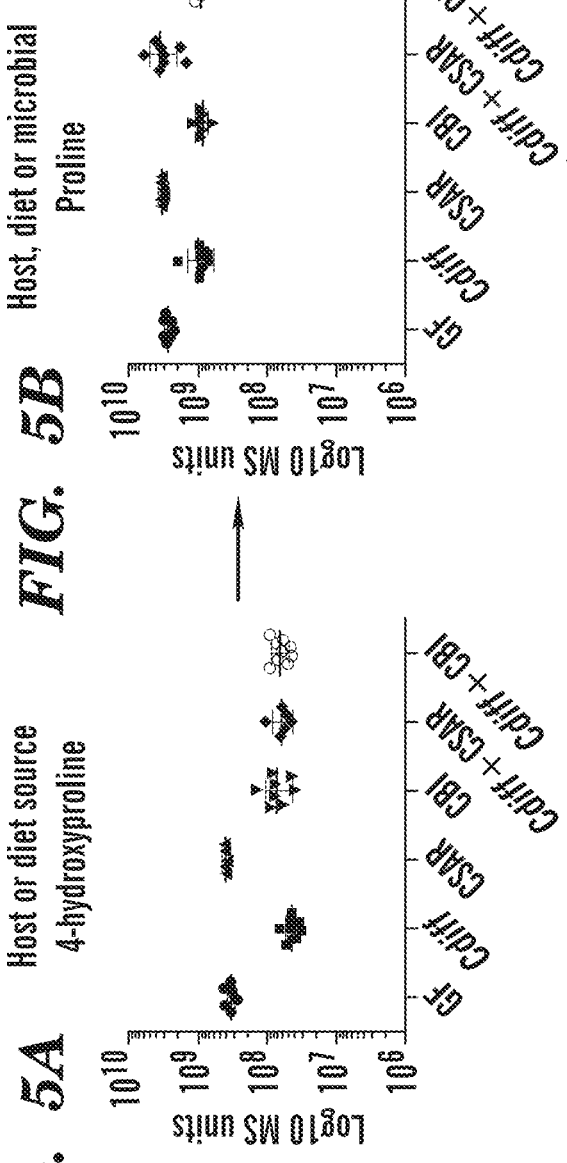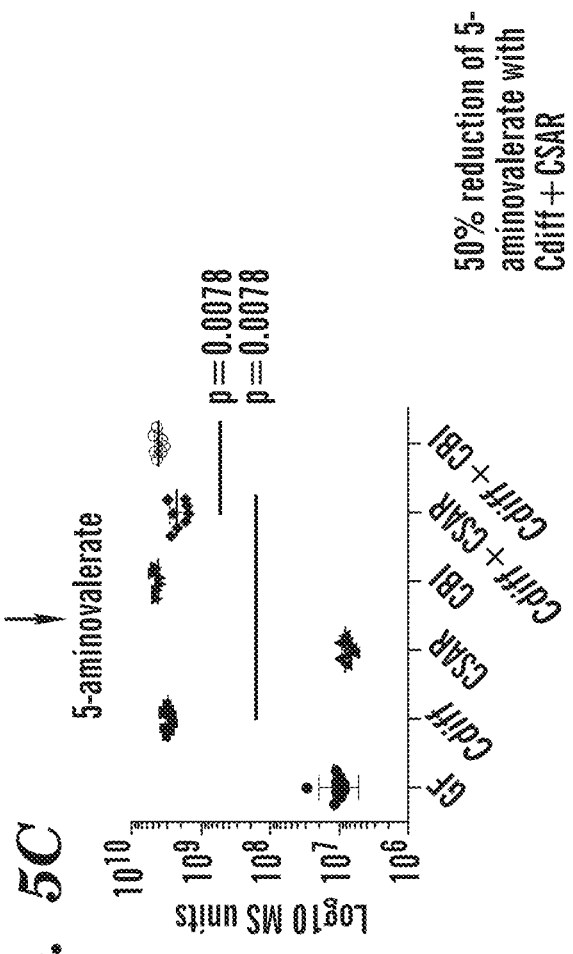

FIG. 6A

| Condition | pH | Acetate | Propionate | Butyrate | Isobutyrate | Isovalerate | Isocaproate | Valerate | Caproate |
|---|---|---|---|---|---|---|---|---|---|
| PY+glucose | 5.5 | 7.52 | 4.73 | 6.78 | 2.26 | 1.64 | 2.5 | 1.70 | 0.22 |
| PY+mannitol | 5.0 | 3.39 | ND | 3.56 | 1.34 | 1.24 | 3.04 | 0.25 | ND |
| PY+sorbitol | 6.0 | 3.81 | 4.19 | 9.52 | 2.16 | 1.54 | 2.38 | 1.97 | 0.24 |

FIG. 6B

| Species | Media | Acetate | Propionate | Butyrate | Isobutyrate | Isovalerate | Isocaproate |
|---|---|---|---|---|---|---|---|
| C. bifermentans | PYG | 26.55 | 1.871 | 0.258 | 1.45 | 1.98 | 4.51 |
| C. bifermentans | PY | 26.15 | 10.24 | 0.14 | 4.95 | 4.65 | 4.9 |
| C. scindens | PYG | 20.22 | ND | ND | ND | ND | ND |
| C. scindens | PY | 2.65 | ND | ND | ND | ND | ND |
| C. sardiniense | PYG | 11.56 | ND | 15.69 | ND | ND | ND |
| C. sardiniense | PY | 7.66 | ND | 39 | ND | ND | ND |

| Gene | Log2 fold change CD:CBI+CD | p value | q value |
|---|---|---|---|
| tcdR | -5.605 | 6.92E-10 | 2.33E-07 |
| tcdA | -3.515 | 4.03E-09 | 9.67E-07 |
| tcdB | -3.362 | 9.60E-10 | 2.93E-07 |
| eutH | 3.356 | 6.15E-05 | 3.18E-03 |
| eutK | 3.092 | 1.97E-04 | 7.97E-03 |
| eutL | 3.205 | 4.56E-04 | 1.49E-02 |
| eutN | 3.628 | 5.90E-05 | 3.1E-03 |

FIG. 7

DEFINED THERAPEUTIC MICROBIOTA AND METHODS OF USE THEREOF

CROSS-REFERENCE TO RELATED APPLICATION

This application is a 35 U.S.C. § 371 National Phase Entry of International Application No. PCT/US2018/065023 filed Dec. 11, 2018, which designates the U.S., and which claims benefit under 35 U.S.C. § 119(e) of the U.S. Provisional Application Nos 62/597,116 filed Dec. 11, 2017 and 62/665,754 filed May 2, 2018, the contents of each of which are incorporated herein by reference in their entirety.

GOVERNMENT SUPPORT

This invention was made with Government support under Grant Nos. P30DK034854 and T32HL007627 awarded by the National Institutes of Health and under Grant No. HR0011-15-C-0094 awarded by the U.S. Department of Defense. The Government has certain rights in the invention.

TECHNICAL FIELD

The technology described herein relates to the treatment or prevention of host pathology involving bacterial toxin production.

SEQUENCE LISTING

The instant application contains a Sequence Listing which has been submitted electronically in ASCII format and is hereby incorporated by reference in its entirety. Said ASCII copy, created on Dec. 28, 2018, is named 043214-090870WOPT_SL.txt and is 116,476 bytes in size.

BACKGROUND

The healthy human gastrointestinal tract is generally host to 300 to 1,000 or more different species of microorganisms. These commensal organisms serve a wide range of functions increasingly recognized as mutualistic and directly connected to the health of the host, including assisting digestion, metabolism, immune function, and colonization resistance against pathogens, among others (Guarner, F. "Enteric flora in health and disease." Digestion 73 Suppl 1:5-12 (2006)).

*Clostridium difficile* (*C. difficile*) infection is the most common cause of nosocomial diarrhea, most often arising in individuals treated with antibiotics, accounting for 10-20% of antibiotic-associated diarrhea and most cases of colitis associated with antibiotic use. *C. difficile* can be present in the healthy gut microbiota, but the pathogen's biomass and toxin production is kept in check by the indigenous gut flora. Further, when stressed, *C. difficile* can generate spores that can tolerate extreme conditions many active bacteria cannot, and *C. difficile* spores are also resistant to antibiotics and many cleaners. Thus, as the normal intestinal flora is disturbed by antibiotic use, the *C. difficile* spores can remain, leading to their germination and proliferation a large population of *C. difficile*; perturbation of the healthy microbiota caused by antibiotic use is believed to provide an advantage to *C. difficile*, allowing it to proliferate and elaborate toxins. The mortality for *C. difficile* infection is estimated at 1-2.5%, contributing to 15,000-30,000 deaths annually in the U.S. (Ananthakrishnan, A. N. "*Clostridium difficile* infection: epidemiology, risk factors and management," Nat Rev Gastroenterol Hapatol, 8:17-26 (2011).

While the importance of other microbial species in suppressing *C. difficile* populations is generally acknowledged, and some species, including Lactobacilli, Enterococci, and some Bifidobacteria and *Bacteroides* species, have shown varying degrees of inhibitory activity against *C. difficile* (Borriello, S. P., and Barclay, F. E. 1986. Ibid.; Naaber, P. et al. "Inhibition of *Clostridium difficile* strains by intestinal *Lactobacillus* species." J Med Microbiol 53:551-4 (2004); Rolfe, R. D. et al. "Bacterial interference between *Clostridium difficile* and normal fecal flora." J. Infect. Dis. 143:470-475 (1981); Lee, Y. J. et al. "Identification and screening for antimicrobial activity against *Clostridium difficile* of *Bifidobacterium* and *Lactobacillus* species isolated from healthy infant faeces." Int J Antimicrob Agents 21:340-6 (2003)), it is not clear which species are essential for suppressing *C. difficile* in the healthy gut.

SUMMARY

The technology described herein is related to the discovery of commensal bacteria that can suppress toxin production by Gram-positive toxigenic bacteria such as *C. difficile* and thereby treat or prevent the development of toxin-mediated pathology. Indeed, it was found that as few as a single species of bacterium can provide complete protection from otherwise fatal *C. difficile* infection in murine models described herein. Suppression of toxin production provides an alternative route to treatment of *C. difficile*-mediated pathology, in that it can be sufficient for treatment to just suppress production of the pathology-generating toxin without necessarily killing the microbe.

Described herein are defined therapeutic microbiota that treat and/or prevent *C. difficile* infection, as the term is used herein, including recurrent *C. difficile* infection. Highly effective therapeutic microbiota include species that are highly proteolytic and that promote Stickland fermentation by *C. difficile*. In one embodiment, the single, highly proteolytic, Stickland fermenting species *Clostridium bifermentans* can provide complete protection against fatal *C. difficile* infection. In another embodiment, a defined consortium of just two species, *C. bifermentans* and *C. scindens*, another proteolytic, Stickland fermenting Clostridial species, provides highly effective protection against pathology caused by *C. difficile* and its toxin production. It is anticipated that other proteolytic, Stickland fermenting species can also provide benefits, including, as non-limiting example, other proteolytic, Stickland fermenting Clostridia.

The examination of the mechanisms through which the identified bacterial species affect *C. difficile* toxin production provide insight into the ability to suppress the expression of toxins by other toxigenic species of Gram positive, spore-forming anaerobes, as well as insights into the properties of other species likely to perform the same toxin-suppression.

Also described herein is the identification of a biomarker profile, comprising two groups of Clostridial species, that is predictive of the likelihood of recurrent *C. difficile* infection and/or susceptibility to initial *C. difficile* infection. When the relative abundance of these groups in a microbiota sample are low relative to healthy gut microbiota, it is considerably more likely that *C. difficile* infection will arise and/or be recurrent.

Also described herein are diagnostic methods that exploit markers such as proteolytic activity or protease expression, markers of Stickland fermentation (at the protein, nucleic acid, and/or metabolite levels), including: i) methods for the determination of the efficacy of bacteriotherapy for infection with a toxigenic, Gram positive, spore-forming bacterium such as *C. difficile*; ii) methods for predicting the likelihood of recurrent infection with a toxigenic, Gram positive, spore-forming bacterium such as *C. difficile*; and iii) methods of determining the likelihood of infection with a toxigenic, Gram positive, spore-forming bacterium such as *C. difficile*.

In one aspect, described herein is a pharmaceutical composition comprising an oral formulation comprising *C. scindens* and *C. bifermentans* bacteria.

In another aspect, described herein is a composition comprising *C. scindens* and *C. bifermentans* bacteria, wherein one or both of the *C. scindens* and *C. bifermentans* bacteria is in dried, viable form.

In another aspect, described herein is a pharmaceutical composition comprising a formulation comprising *C. scindens* and *C. bifermentans* bacteria, wherein the composition does not comprise *Bacteroides* species or *Escherichia* species.

In one embodiment of these aspects and all such aspects described herein, one or both of the *C. scindens* and *C. bifermentans* bacteria are in spore form.

In another embodiment of these aspects and all such aspects described herein, one or both of the *C. scindens* and *C. bifermentans* bacteria are not in spore form.

In another embodiment of these aspects and all such aspects described herein, the *C. scindens* and *C. bifermentans* bacteria are present as a mixture of metabolically active and spore forms.

In another embodiment of these aspects and all such aspects described herein, the composition comprises a capsule or microcapsule, or a composition formulated for enteric delivery.

In another embodiment of these aspects and all such aspects described herein, wherein one or both of the *C. scindens* and *C. bifermentans* bacteria are in dried viable form.

In another embodiment of these aspects and all such aspects described herein, the composition does not comprise *C. sardiniensis* bacteria.

In another embodiment of these aspects and all such aspects described herein, the composition does not comprise any other *Clostridium* species.

In another embodiment of these aspects and all such aspects described herein, the composition does not contain *Bacteroides* species or *Escherichia coli*.

In another embodiment of these aspects and all such aspects described herein, the formulation comprises no other bacteria.

In another aspect, described herein is a pharmaceutical composition comprising an oral formulation comprising a first bacterial population that has 16S rDNA with a sequence at least 97% identical to a 16S rDNA sequence present in a reference *C. scindens* bacterium, and a second bacterial population that has 16S rDNA with a sequence at least 97% identical to a 16S rDNA sequence present in a reference *C. bifermentans* bacterium.

In another aspect described, herein is a composition comprising a first bacterial population that has 16S rDNA with a sequence at least 97% identical to a 16S rDNA sequence present in a reference *C. scindens* bacterium, and a second bacterial population that has 16S rDNA with a sequence at least 97% identical to a 16S rDNA sequence present in a reference *C. bifermentans* bacterium, wherein one or both of the *C. scindens* and *C. bifermentans* bacteria is in dried, viable form.

In another aspect, described herein is a pharmaceutical composition comprising a formulation comprising a first bacterial population that has 16S rDNA with a sequence at least 97% identical to a 16S rDNA sequence present in a reference *C. scindens* bacterium, and a second bacterial population that has 16S rDNA with a sequence at least 97% identical to a 16S rDNA sequence present in a reference *C. bifermentans* bacterium wherein the composition does not comprise *Bacteroides* species or *Escherichia* species.

In one embodiment of these aspects and all such aspects described herein, one or both of the *C. scindens* and *C. bifermentans* bacteria are in spore form.

In another embodiment of these aspects and all such aspects described herein, one or both of the *C. scindens* and *C. bifermentans* bacteria are not in spore form.

In another embodiment of these aspects and all such aspects described herein, the *C. scindens* and *C. bifermentans* bacteria are present as a mixture of metabolically active and spore forms.

In another embodiment of these aspects and all such aspects described herein, the composition comprises a capsule or microcapsule, or a composition formulated for enteric delivery.

In another embodiment of these aspects and all such aspects described herein, one or both of the *C. scindens* and *C. bifermentans* bacteria are in dried viable form.

In another embodiment of these aspects and all such aspects described herein, the composition does not comprise *C. sardiniensis* bacteria.

In another embodiment of these aspects and all such aspects described herein, the composition does not comprise *Bacteroides* species or *Escherichia coli*.

In another embodiment of these aspects and all such aspects described herein, the composition does not comprise any other *Clostridium* species.

In another embodiment of these aspects and all such aspects described herein, the composition in which the formulation comprises no other bacteria.

In another embodiment of these aspects and all such aspects described herein, further comprises a prebiotic.

In another embodiment of these aspects and all such aspects described herein, the composition further comprises a microbe that supports *C. scindens* and/or *C. bifermentans*.

In another embodiment of these aspects and all such aspects described herein, the microbe that supports *C. scindens* is *Ruminococcus obeum*.

In another embodiment of these aspects and all such aspects described herein, the composition is for use in the treatment of *C. difficile* infection.

In one embodiment of this aspect and all such aspects described herein, the use comprises suppressing the expression of *C. difficile* toxin.

In another embodiment of this aspect and all such aspects described herein, the use comprises promoting a shift towards use of the proline reductase pathway of Stickland fermentation in *C. difficile*.

In another embodiment of this aspect and all such aspects described herein, the use comprises inducing CodY activity or expression in *C. difficile*.

In another embodiment of this aspect and all such aspects described herein, the use comprises promoting ethanolamine utilization by *C. difficile*.

In another aspect described herein is a method comprising administering a composition of any embodiment of the aspects above to a subject in need thereof.

In one embodiment of this aspect and all such aspects described herein is a method, the subject has or has been diagnosed with *C. difficile* infection.

In another embodiment of this aspect and all such aspects described herein, the *C. difficile* infection is recurrent.

In another embodiment of this aspect and all such aspects described herein, the subject is at risk of *C. difficile* infection or recurrent *C. difficile* infection.

In another embodiment of this aspect and all such aspects described herein, the administration is oral.

In another embodiment of this aspect and all aspects described herein the method comprises administering a composition directly to the colon of a subject in need thereof.

In another embodiment of this aspect and all such aspects described herein, administration is via colonoscopy or enema.

In another embodiment of this aspect and all such aspects described herein, the method the subject is receiving or has recently received antibiotic treatment.

In another aspect, described herein is a method of treating an infection, the method comprising administering an antibiotic and a composition of the aspects described herein.

In another aspect, as described herein is a method of treating an infection compromising administering an antibiotic and a composition as described herein, wherein the composition is administered before or concurrently with the antibiotic.

In another aspect, described herein is a method of treating an infection compromising administering an antibiotic and a composition as described herein, wherein the composition is administered after a course of an antibiotic.

In another aspect, described herein is a method of predicting recurrence of *C. difficile* infection in a subject, the method comprising:
  (a) determining the relative abundance of all operational taxonomic units (OTUs) in a sample of the subject's stool that are >90% identical to a reference sequence of *C. scindens;*
  (b) determining the relative abundance of all operational taxonomic units (OTUs) in a sample of the subject's stool that are >90% identical to a reference sequence of *C. hylemonae*; and
  (c) summing the relative abundances determined in steps (a) and (b), wherein a sum of relative abundances less than or equal to 1% indicates an increased risk of *C. difficile* recurrence relative to a subject in which the sum of relative abundances is greater than 1%.

In another embodiment of this aspect, the reference sequences for *C. scindens* and *C. hylemonae* are 16S rDNA sequences.

In another embodiment of this aspect, the determining steps are performed on samples taken before, during or after the subject has been treated with antibiotics for *C. difficile* infection.

In another embodiment of this aspect, the determining steps are performed on samples taken after the subject has been treated with antibiotics for *C. difficile* infection.

In another embodiment of this aspect, and all such aspects described herein, the method further comprises the step, when the sum of relative abundances is at or below 1%, of administering a composition as described herein above.

In another aspect, described herein is a method of suppressing expression of a bacterial toxin in a subject, the method comprising administering a defined bacterial microbiota comprising at least one bacterial organism that encodes and secretes a protease and/or performs Stickland fermentation.

In another aspect, described herein is a method of treating or preventing a pathology caused by expression of a bacterial toxin, the method comprising administering a defined bacterial microbiota comprising at least one bacterial organism that encodes and secretes a protease and/or performs Stickland fermentation.

In another aspect, described herein is a method of promoting CodY expression or activity in a *C. difficile* bacterium in a subject, the method comprising administering a defined bacterial microbiota comprising a bacterial organism that encodes and secretes a protease and/or performs Stickland fermentation.

In another aspect, described herein is a method of promoting ethanolamine utilization by a *C. difficile* bacterium in a subject, the method comprising administering a defined bacterial microbiota comprising a bacterial organism that encodes and secretes a protease and/or performs Stickland fermentation.

In one embodiment of these aspects and all such aspects described herein, at least one bacterial organism encodes and secretes at least one protease selected from the group consisting of: a protease of PATRIC ID fig|186802.30.peg.279; a protease of PATRIC ID fig|186802.30.peg.290; a protease of PATRIC ID fig|186802.30.peg.313; a protease of PATRIC ID fig|186802.30.peg.414; a protease of PATRIC ID fig|186802.30.peg.543; a protease of PATRIC ID fig|186802.30.peg.2205; a protease of PATRIC ID fig|186802.30.peg.2313; a protease of PATRIC ID fig|186802.30.peg.2680; a protease of PATRIC ID fig|186802.30.peg.2745; a protease of PATRIC ID fig|186802.30.peg.2746; a protease of PATRIC ID fig|186802.30.peg.830; a protease of PATRIC ID fig|186802.30.peg.921; a protease of PATRIC ID fig|186802.30.peg.936; a protease of PATRIC ID fig|186802.30.peg.3000; a protease of PATRIC ID fig|186802.30.peg.3018; a protease of PATRIC ID fig|186802.30.peg.3019; and a protease of PATRIC ID fig|186802.30.peg.3065.

In another embodiment of these aspects and all such aspects described herein, at least one protease performs the proteolysis reaction of enzymes of Enzyme Commission number (E.C. number) EC 3.4.21.-; EC 3.4.21.53; or EC 3.4.21.92.

In another embodiment of these aspects and all such aspects described herein, at least one bacterial organism encodes and expresses one or more of D-proline reductase, Glycine reductase, Thioredoxin, or Choloylglycine hydrolase.

In another embodiment of these aspects and all such aspects described herein, the at least one bacterial organism falls within Clostridial cluster I, XI, or XIVa, and does not express a pathology-causing bacterial toxin.

In another embodiment of these aspects and all such aspects described herein, the bacterial organism in Clostridial cluster I is selected from *C. sporogenes*, and *C. histolyticum*.

In another embodiment of these aspects and all such aspects described herein, the bacterial organism in Clostridial cluster XI is selected from *C. bifermentans, C. hiranonis*, and *P. anaerobius*.

In another embodiment of these aspects and all such aspects described herein, the bacterial organism in Clostridial cluster XIVa is selected from *C. scindens, C. clostriiforme*, and *C. nexile*.

In another embodiment of these aspects and all such aspects described herein, the at least one bacterial organism inhibits sorbitol/mannitol fermentation by *C. difficile*.

In another embodiment of these aspects and all such aspects described herein, the at least one bacterial organism promotes Stickland fermentation through the acceptor amino acid proline, or activation of proline reductase.

In another embodiment of these aspects and all such aspects described herein, the at least one bacterial organism promotes 5-aminovalerate production.

In another embodiment of these aspects and all such aspects described herein, the bacterial toxin is a *C. difficile* toxin.

In another embodiment of these aspects and all such aspects described herein, the bacterial organism is *C. bifermentans* and/or *C. scindens*.

In another embodiment of these aspects and all such aspects described herein, suppressing expression of a bacterial toxin comprises inhibition of butyrate, codY, ccpA, tcdR, and/or tcdA production.

In another aspect, described herein is a method of suppressing expression of a bacterial toxin in the gut of a subject, the method comprising administering at least one amino acid that is metabolized by Stickland fermentation.

In another aspect, described herein is a method of treating or preventing a pathology caused by expression of a bacterial toxin, the method comprising administering at least one amino acid that is metabolized by Stickland fermentation.

In one embodiment of this aspect and all such aspects described herein, the at least one amino acid is a Stickland donor or Stickland acceptor.

In another embodiment of this aspect and all such aspects described herein, the Stickland donor is selected from the group consisting of: alanine, leucine, valine, isoleucine, tryptophan, tyrosine and phenylalanine.

In another embodiment of this aspect and all such aspects described herein, the Stickland acceptor is selected from the group consisting of: glycine and proline.

In another embodiment of this aspect and all such aspects described herein, the amino acid is a branched-chain amino acid, a branched-keto amino acid, or an aromatic amino acid.

In another embodiment of this aspect and all such aspects described herein, the at least one amino acid promotes 5-aminovalerate production.

In another embodiment of this aspect and all such aspects described herein, the bacterial toxin is a *C. difficile* toxin.

In another embodiment of this aspect and all such aspects described herein, suppression of the expression of a bacterial toxin comprises inhibition of butyrate, codY, ccpA, tcdR, and/or tcdA activity or production.

In another aspect, described herein is a method of determining the therapeutic efficacy of a bacterial organism for treatment of a pathology involving expression of a toxin, produced by a Gram-positive spore-forming bacterium, the method comprising measuring in a biological sample obtained from an individual administered the bacterial organism one or more of:
  a) the amount and/or activity of a secreted proteolytic enzyme;
  b) the amount and/or activity of bacterial proline reductase;
  c) the amount or concentration of one or more branched short-chain fatty acids;
  d) the amount or concentration of one or more branched keto acids; and
  e) the amount or concentration of Stickland donor and/or Stickland acceptor amino acids and/or 5-aminovalerate;

In one embodiment of this aspect and all such aspects described herein, the bacterial toxin is produced by a Gram-positive, spore-forming bacterium.

In another embodiment of this aspects and all such aspects described herein, the bacterial toxin is a *C. difficile* toxin.

In another embodiment of this aspect and all such aspects described herein, the pathology comprises expression of a toxin by *C. difficile*.

In another embodiment of this aspect and all such aspects described herein, Stickland donor amino acids are selected from leucine, isoleucine, valine, alanine, phenylalanine, tryptophan, tyrosine and Stickland acceptor amino acids are selected from glycine, proline, and hydroxyproline.

In another embodiment of this aspect and all such aspects described herein, the sample is a stool sample or a sample from within the colon of the individual.

In another aspect, described herein is a method to predict the risk of developing a disease involving a toxin produced by a Gram positive, spore-forming bacterium, the method comprising measuring in a biological sample obtained from an individual one or more of the following:
  a) the amount and/or activity of a secreted proteolytic enzyme;
  b) the amount and/or activity of bacterial proline reductase;
  b) the amount or concentration of one or more branched short-chain fatty acids;
  c) the amount or concentration of one or more branched keto acids; and
  e) the amount or concentration of Stickland donor and/or Stickland acceptor amino acids; and comparing the amount, concentration or activity measured in one or more of (a)-(e) to a reference, wherein an amount, concentration or activity in one or more of (a)-(e) below the reference indicates increased risk of developing a disease involving a toxin produced by a Gram positive, spore-forming bacterium.

In one embodiment of this aspect and all such aspects described herein, the disease involves expression of a toxin by *C. difficile*.

In another embodiment of this aspect and all such aspects described herein, the reference comprises a biological sample from a healthy individual.

In another embodiment of this aspect and all such aspects described herein, the biological sample is a stool sample or a sample from within the colon of the individual.

In another embodiment of this aspect and all such aspects described herein, two or more of (a)-(e) are measured.

In another embodiment of this aspect and all such aspects described, three or more of (a)-(e) are measured.

In one embodiment of this aspect and all such aspects described herein, four or more, of (a)-(e) are measured.

In another aspect, described herein is a method of identifying a candidate bacterial organism that is likely to suppress the expression of a toxin by a Gram-positive, spore-forming bacterial pathogen, the method comprising:
  a) identifying from a database of bacterial genetic information a candidate bacterial organism having in its genome:
    i) one or more genes encoding a secreted protease enzyme; and/or
    ii) a gene encoding a proline reductase enzyme; and b) assaying a sample comprising the candidate bacterial organism for the expression of a secreted protease enzyme and/or the proline reductase enzyme;

wherein the detection of expression of the secreted protease enzyme and/or the expression of the proline reductase enzyme indicates that the candidate bacterial organism is likely to suppress expression of a toxin by a Gram-positive, spore-forming bacterial pathogen.

In one embodiment of this aspect and all such aspects described herein, the candidate bacterial organism is not an opportunistic gut pathogen in humans.

In one embodiment of this aspect and all such aspects described herein, the proline reductase enzyme is an enzyme of E.C. 1.21.4.1.

In another aspect, described herein is a method to predict the risk of developing a spore-forming, toxin-producing Gram-positive bacterial pathogen in the gut or other location, or its recurrence, comprising measuring in a biological sample
(a) amounts or unit activity of proteolytic activity;
(b) concentrations of branched short chain fatty acids;
(c) concentrations of branched keto acids; and/or
(d) concentrations of Stickland donor and Stickland acceptor amino acids, wherein an increase in the amount or activity of at least one of (a)-(d) relative to a biological sample obtained prior to administration identifies a risk of developing a spore-forming, toxin-producing Gram-positive bacterial pathogen in the gut or other location.

In one embodiment of this aspect and all such aspects described herein, the method further comprising, prior to measuring, administering the bacterial organism or amino acid to the subject.

In another embodiment of this aspect and all such aspects described herein, the biological sample is obtained from a subject.

In another embodiment of this aspect and all such aspects described herein, the biological sample is a stool sample.

In another embodiment of this aspect and all such aspects described herein, the biological sample is obtained from the gut.

In another embodiment of this aspect and all such aspects described herein, the gram-positive bacterial pathogen is *C. difficile* infection.

In another embodiment of a composition comprising a defined bacterial microbiota as described herein, the composition further comprises an amount of one or more free Stickland donor and/or Stickland acceptor amino acids effective to promote Stickland fermentation by a species in the composition or by *C. difficile* after the composition is administered to a subject.

In another embodiment of a composition comprising a defined bacterial microbiota as described herein, the composition further comprises an amount of a polypeptide substrate effective for proteolysis by proteolytic activity of a bacterial species in the composition to generate amino acids fermentable by Stickland fermentation.

In one embodiment, the polypeptide substrate comprises casein, collagen and/or gelatin. In another embodiment, the polypeptide substrate comprises a synthetic polymer or copolymer polypeptide hydrolysable by a proteolytic activity of a species in the composition to generate Stickland fermentable amino acids.

In one embodiment, the synthetic polymer comprises a poly[N] polymer, where N is a Stickland donor amino acid selected from leucine, isoleucine, valine, alanine, phenylalanine, tryptophan, and tyrosine or a Stickland acceptor amino acids selected from glycine and proline.

In another embodiment, the synthetic copolymer comprises a poly[N,X] copolymer, where N and X are Stickland donor amino acids selected from leucine, isoleucine, valine, alanine, phenylalanine, tryptophan, and tyrosine or Stickland acceptor amino acids selected from glycine and proline.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in microbiology, molecular biology and medicine can be found, for example, in *The Merck Manual of Diagnosis and Therapy*, 19th Edition, published by Merck Sharp & Dohme Corp., 2011 (ISBN 978-O-911910-19-3); Robert S. Porter et al. (eds.), Black, Jacquelyn G. *Microbiology: Principles and Explorations*, 9$^{th}$ *Edition*: Wiley; 9$^{th}$ Edition, 2014, Moore, Veranus A. *Principles of Microbiology: A Treatise on Bacteria, Fungi and Protozoa*: Forgotten Books, 2012, *The Encyclopedia of Molecular Cell Biology and Molecular Medicine*, published by Blackwell Science Ltd., 1999-2012 (ISBN 9783527600908); and Robert A. Meyers (ed.), *Molecular Biology and Biotechnology: a Comprehensive Desk Reference*, published by VCH Publishers, Inc., 1995 (ISBN 1-56081-569-8); Lewin's Genes XI, published by Jones & Bartlett Publishers, 2014 (ISBN-1449659055); Michael Richard Green and Joseph Sambrook, *Molecular Cloning: A Laboratory Manual*, 4$^{th}$ ed., Cold Spring Harbor Laboratory Press, Cold Spring Harbor, N.Y., USA (2012) (ISBN 1936113414); Davis et al., *Basic Methods in Molecular Biology*, Elsevier Science Publishing, Inc., New York, USA (2012) (ISBN 044460149X); *Laboratory Methods in Enzymology: DNA*, Jon Lorsch (ed.) Elsevier, 2013 (ISBN 0124199542); *Current Protocols in Molecular Biology* (*CPMB*), Frederick M. Ausubel (ed.), John Wiley and Sons, 2014 (ISBN 047150338X, 9780471503385), *Current Protocols in Protein Science* (*CPPS*), John E. Coligan (ed.), John Wiley and Sons, Inc., 2005; and *Current Protocols in Immunology* (*CPI*) (John E. Coligan, ADA M Kruisbeek, David H Margulies, Ethan M Shevach, Warren Strober (eds.) John Wiley and Sons, Inc., 2003 (ISBN 0471142735, 9780471142737), the contents of which are all incorporated by reference herein in their entireties.

It should be understood, as discussed elsewhere herein and as known in the art, that healthy individuals can have detectable levels of *C. difficile* bacteria in their gut, but that the pathogen biomass and toxin production are kept in balance by components of the healthy gut microbiota and do not cause disease until that balance is disturbed, often, but not necessarily exclusively, by antibiotic treatment for a different infection. Thus, as used herein, the term "*C. difficile* infection" or "CDI" refers not to the mere presence of *C. difficile* bacteria, but to expression of *C. difficile* toxin by such bacteria at a level that causes symptoms, and/or to an overgrowth of *C. difficile* bacteria relative to levels in healthy individuals, with accompanying gastrointestinal pathology, including diarrhea, among other signs and symptoms. *C. difficile* overgrowth includes or results in the elaboration of *C. difficile* toxins (which include *C. difficile* toxins A and B, and cytolethal distending toxins A and B), which are detectable in stool samples of those with *C. difficile* infection using, for example, commercially available immunoassays (e.g., lateral flow "dipstick" assays). *C. difficile* overgrowth also increases (as that term is used herein) the relative biomass of *C. difficile* in the stool as compared to healthy stool.

"Recurrent" *C. difficile* infection refers to *C. difficile* infection that occurs after an initial treatment for *C. difficile* infection, generally antibiotic therapy. Recurrence can occur, for example, days, weeks or months after an initial infection has been treated, including up to 8 months or more after the initial infection.

As used herein, "bacteriotherapy" refers to the administration of live bacteria for the treatment or prevention of a disease or disorder, including, but not limited to *C. difficile* infection. As the term is used herein, the bacteria administered are viable and metabolically active, or become metabolically active after administration. Thus, bacteriotherapy can include administration of metabolically active bacteria and/or the administration of dried (e.g., lyophilized) viable bacteria or bacterial spores or a mixture or combination of these. It is preferred that bacteriotherapy as described herein result in the proliferation of the administered bacteria, and preferably establishment of a persistent presence of a population of such bacteria in the gut. A "persistent" presence is one that is detectable at least one week or more after administration, including, for example, at least two weeks, at least three weeks, at least four weeks, at least five weeks, at least six weeks, at least seven weeks, at least eight weeks or more, including essentially indefinite establishment of the administered species or strain in the gut of the subject. To the extent that administration does not result in a persistent presence, re-administration, including re-administration at regular intervals is specifically contemplated.

As used herein, the term "oral formulation" refers to a pharmaceutical formulation formulated to be suitable for oral administration. Oral formulations include, for example, elixirs and suspensions including an active agent or agents that render the agent or agents suitable, or more suitable than the agent alone, for oral administration, and can include, for example, cryoprotectants, reducing agents to protect against oxygen exposure, sweeteners or other agents to enhance palatability. Oral formulations also include, for example, formulations in capsules or microcapsules, which can be standard or designed to dissolve substantially only after passage through the acidic environment of the stomach—i.e., enteric encapsulation. Oral formulations can also include, for example, an antacid, which can modify the pH of the stomach and thereby promote survival of a bacteriotherapy composition. Oral formulations also include, for example, an active agent or agents in admixture with or as a component of a foodstuff.

As used herein, the term "viable" encompasses metabolically active, proliferative as well as dried forms of bacteria that can be reconstituted to provide metabolically active, proliferative bacteria, and spores that can germinate to provide metabolically active, proliferative bacteria. It is contemplated that non-viable, killed cells or an extract or preparation derived therefrom may have benefit for inhibiting *C. difficile* infection. It is also contemplated that while not proliferative, bacterial cells that have been rendered non-proliferative, e.g., by irradiation, yet retain metabolic activity, can also provide a benefit for inhibiting *C. difficile* infection. In such instances, regular administration of preparations of killed or proliferatively inactivated bacteria as described herein would be specifically contemplated.

As used herein, the term "dried, viable form" refers to a preparation of bacteria that have been dried, e.g., lyophilized, yet retain the capacity, upon re-hydration, to become metabolically and proliferatively active. Methods for the preparation of dried, viable bacteria are known to those of skill in the art. Indeed, *C. scindens, C. bifermentans* and *C. hylemonae* species available from American Type Culture Collection (ATCC) are shipped in dried, viable form.

As used herein, the term "does not comprise species X," "does not contain species X," means, at a minimum, that a composition does not comprise viable species X. In one embodiment, the composition does not contain species X at all—i.e., even dead or inactivated bacteria of species X are excluded. Similarly, the term "comprises no other bacteria," means, at a minimum, that the subject composition does not comprise any viable bacteria other than those specified. In one embodiment, "comprises no other bacteria" means the formulation does not comprise any other bacteria at all, whether dead or alive.

As used herein, a "prebiotic" refers to an ingredient that allows or promotes specific changes, both in the composition and/or activity in the gastrointestinal microbiota that may (or may not) confer benefits upon the host. A prebiotic is not directly digestible by humans, but that is readily digestible by and promotes the growth or establishment of one or more probiotic and/or commensal microbes. Non-limiting examples of prebiotics include but are not limited to inulin, fructooligosaccharides, galactooligosaccharides, hemicelluloses (e.g., arabinoxylan, xylan, xyloglucan, and glucomannan), chitin, lactulose, mannan oligosaccharides, oligofructose-enriched inulin, gums (e.g., guar gum, gum arabic and carrageenan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides. In one embodiment, a prebiotic comprises a sugar or carbohydrate e.g., a starch or other carbohydrate polymer, or protein formulation that can be digested by *C. bifermentans* and *C. scindens*, but not readily by other commensals, and therefore promotes selective expansion of these species.

As used herein, the term "defined bacterial microbiota" refers to one or a combination of known bacteria in a composition to be administered for bacteriotherapy. In a defined bacterial microbiota, the component bacteria are all known and prepared from pure culture; a defined bacterial microbiota excludes stool or fecal material. In one embodiment, the relative proportions of members of a defined microbial microbiota are defined and deliberately set.

As used herein, the term "probiotic" refers to microorganisms that form at least a part of the transient or endogenous flora or microbial consortium and thereby exhibit a beneficial prophylactic and/or therapeutic effect on the host organism. Probiotics are generally known to be clinically safe (i.e., non-pathogenic) by those skilled in the art.

As used herein, a microbe that "supports" another produces one or more metabolites that promotes the growth or maintenance of another microbe. Alternatively, or in addition, a microbe that "supports" another microbe provides or contributes to an environment, e.g., a pH, redox status, nutritional status, or other environmental component that promotes growth of the other, or, for example, inhibits the growth of a third species or class of microbes that inhibits the desired species.

As used herein, the term "at risk" as applied to risk of *C. difficile* infection refers to an individual in a high risk category for *C. difficile* infection. These include, for example, those who are receiving or have recently completed a course of antibiotic therapy for a different infection (or for a first infection with *C. difficile*), those of advanced age, those who are hospitalized or under nursing home care, those who have had prior *C. difficile* infection, those taking medication for gastric acid suppression (e.g., with proton pump inhibitors or histamine-2 receptor antagonists), those undergoing gastrointestinal procedures, those undergoing chemotherapy, those with inflammatory bowel disease, and those who are immunosuppressed. Additional risk factors include low relative abundance of the biomarker or indicator species *C. scindens* and/or *C. hylemonae*, as described herein below.

As used herein, the term "recently received," in reference to antibiotic treatment refers to having received the last dose of a course of antibiotics to treat *C. difficile* or another infection. In this context, one has "recently received" antibiotic treatment if the last dose of a course was given two days, three days, four days, five days, six days, one week, eight days, nine days, ten days, eleven days, twelve days, thirteen days, two weeks, fifteen days, sixteen days, seventeen days, eighteen days, nineteen days, twenty days, three weeks, twenty-two days, twenty-three days, twenty-four days, twenty-five days, twenty-six days, twenty-seven days or four weeks previously.

As used herein, the term "operational taxonomic unit (OTU, plural OTUs)" refers to a terminal leaf in a phylogenetic tree and is defined by a specific genetic sequence and all sequences that share a specified degree of sequence identity to this sequence. The specific genetic sequence may be the 16S rRNA sequence or a portion of the 16S rRNA sequence, or it may be a functionally conserved housekeeping gene found broadly across the eubacterial kingdom. OTUs generally share at least 97%, 98%, or 99% sequence identity in the reference sequence, although lower numbers can be applied—it follows that the lower the % identity to the reference sequence, the more species will be encompassed, and the more variation between members of the OTU grouping.

As used herein, the term "clade" refers to the set of OTUs or members of a phylogenetic tree downstream of a statistically valid node in a phylogenetic tree. The clade comprises a set of terminal leaves in the phylogenetic tree that is a distinct monophyletic evolutionary unit.

In microbiology, "16S sequencing" or "16S rRNA" or "16S-rRNA" or "16S" refers to sequence derived by characterizing the nucleotides that comprise the 16S ribosomal RNA gene(s). The bacterial 16S rDNA is approximately 1500 nucleotides in length and is used in reconstructing the evolutionary relationships and sequence similarity of one bacterial isolate to a second isolate using phylogenetic approaches. 16S sequences are used for phylogenetic reconstruction as they are in general highly conserved, but contain specific hypervariable regions that harbor sufficient nucleotide diversity to differentiate genera and species of most bacteria, as well as fungi.

The "V1-V9 regions" of the 16S rRNA refers to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. Brosius et al., Complete nucleotide sequence of a 16S ribosomal RNA gene from *Escherichia coli*, PNAS 75(10):4801-4805 (1978). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. In another embodiment, the full length of a 16S rRNA is used to characterize an OTU. A person of ordinary skill in the art can identify the specific hypervariable regions of a candidate 16S rRNA by comparing the candidate sequence in question to the reference sequence and identifying the hypervariable regions based on similarity to the reference hypervariable regions.

As used herein, a "protease" is an enzyme which degrades proteins or peptides into smaller components or amino acids. A "proteolytic" species of bacteria or a "proteolytic" anaerobe is an anaerobic bacterial species that expresses and secretes a protease enzyme that generates amino acids fermentable by Stickland fermentation. A "highly" proteolytic species expresses and secretes proteolytic activity at least as great or greater than that of *C. scindens* as measured by methods known in the art or described herein. In one embodiment, a "highly" proteolytic species expresses and secretes a proteolytic activity at least as great or greater than that of *C. bifermentans*.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. Where applicable, a decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate mammal such as a non-human primate, rodent, domestic animal or game animal. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, or canine species, e.g., dog, fox or wolf. Mammals other than humans can be advantageously used as subjects that represent models of human disease e.g., *C. difficile* infection. A subject can be male or female. The terms "individual," "patient" and "subject" are used interchangeably herein.

A subject can be one who has been previously diagnosed with or identified as suffering from or having a condition in need of treatment (e.g. *C. difficile* infection) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors. Risk factors for *C. difficile* infection include, but are not limited to, receiving antibiotic therapy for a different infection (or for a first infection with *C. difficile*), advanced age, hospitalization or nursing home care, prior *C. difficile* infection, gastric acid suppression (e.g., with proton pump inhibitors or histamine-2 receptor antagonists), gastrointestinal procedures, chemotherapy, inflammatory bowel disease, and immunosuppression. In addition, in those infected with *C. difficile*, low levels of vitamin D have been shown to be an independent predictor of poor outcome and are associated with higher recurrence. Additional risk factors include low relative abundance of the biomarker or indicator species *C. scindens* and/or *C. hylemonae* as described herein below.

A "subject in need" of treatment for a particular condition can be a subject having that condition, diagnosed as having that condition, or at risk of developing that condition.

As used herein, the term "suppressing expression of a bacterial toxin" refers to conditions or treatment(s) that inhibit or reduce, as the terms are defined herein, the expression of a toxin by a bacterium in a subject. In one embodiment, the inhibition or reduction is sufficient to reduce one or more symptoms or one or more markers of bacterial infection in a subject. In one embodiment, the inhibition or reduction is to a level that does not cause symptoms or detectable pathology in the subject. In another embodiment, the suppression acts upon toxin production without necessarily reducing biomass or viability of the bacterium.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. *C. difficile* infection, including recurrent *C. difficile* infection. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. Treatment can include suppression of bacterial toxin production, e.g., to a degree such that pathology or symptoms caused by the toxin are reduced.

As used herein, the term "pharmaceutical composition" refers to an active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be an artificial or engineered carrier, e.g., a carrier in which the active ingredient would not be found to occur in nature. Where the active agent includes one or more bacterial species, whether in active metabolic, dried viable or spore form, the carrier will be compatible with the bacteria and will not interfere with viability or activity of the bacteria.

As used herein, the term "administering," refers to the placement of a therapeutic or pharmaceutical composition as disclosed herein into a subject by a method or route which results in at least partial delivery of the agent at a desired site. Pharmaceutical compositions comprising agents as disclosed herein can be administered by any appropriate route which results in an effective treatment in the subject. Common routes of administration for bacteriotherapies include oral administration, often, but not necessarily in the form of one or more capsules, and direct administration to the lower GI tract, e.g., via enema or colonoscope.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the technology.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other terms are defined within the description of the various aspects and embodiments of the technology of the following.

BRIEF DESCRIPTION OF THE DRAWINGS

FIGS. 1A-1J presents experimental data of *C. difficile* gnotobiotic mouse survival studies. FIG. 1A shows a schematic of the Gnotobiotic mouse colonization model of *C. difficile* infection. Adult Swiss-Webster mice were pre-colonized with a commensal species (*C. bifermentans, C. scindens* or *C. sardiniense* for 7 days, prior to oral challenge with 1000 *C. difficile* spores (ATCC 43255 strain). The survival curve shows the survival post-challenge with *C. difficile*. At least 8 mice across 2 experiments were assessed per timepoint. Biological samples for metabolomics and microbial gene expression analysis were taken at the following time points: GF controls (first arrow), after 7 days of commensal colonization (second arrow), at 20 hours of *C. difficile* infection (third arrow), alone or with the given pre-colonized commensal. At least 8 mice across 2 experiments were assessed per timepoint. FIG. 1B: Swiss-Webster germfree mice were associated with a commensal: *C. bifermentans, C. sardiniense* or *C. scindens* for 7 days, prior to challenge with 1000 spores of *C. difficile* strain ATCC43255. Control germfree mice received *C. difficile* alone. The survival curve shows the survival post-challenge with *C. difficile*. FIG. 1C: Body condition scores (BCS) of the mice were monitored daily to assess activity, feeding, grooming and tissue turgor for additional clinical symptoms of infection. Swiss-Webster germfree mice associated with a commensal: *C. bifermentans, C. sardiniense, C. scindens*, prior to challenge with 1000 spores of *C. difficile* strain ATCC43255. Control germfree mice received *C. difficile* alone. FIGS. 1D-1J show representative images of H&E stained sections of the colon of the mice. FIG. 1D shows a representative image of a healthy colon from a conventional mouse, 200× magnification showing intact epithelial crypts, mucosal and muscular layers. FIG. 1E shows a representative image of a colon of a Gnotobiotic mouse 24 hours after *C. difficile* infection showing denudation of the surface epithelium and massive neutrophil influx (200× magnification). FIG. 1F shows a representative image of colon of a Gnotobiotic mouse pre-colonized with *C. sardiniense*, 24 hr after *C. difficile* challenge showing massive tissue edema (arrow), epithelial denudation and neutrophil influx, consistent with a toxic megacolon picture (100× magnification). FIG. 1G shows a representative image of colon of a Gnotobiotic mouse pre-colonized with *C. bifermentans*, 24 hr after *C. difficile* challenge with some epithelial ballooning but no overt epithelial disruptions or tissue edema (200×). FIG. 1H shows a representative image of colon of a Gnotobiotic mouse with *C. scindens* 28 days after *C. difficile* challenge showing intact epithelium and residual inflammatory mucosal infiltrate consisting of neutrophils and lymphocytes (200×). FIG. 1I shows a representative image of colon of a Gnotobiotic mouse precolonized with *C. scindens* and 28 days after *C. difficile* challenge, showing a focal area of epithelial damage with surrounding intact epithelium and submucosal (200×). FIG. 1J shows a representative image of colon of a Gnotobiotic mouse precolonized with *C. bifermentans* at 28 days post-challenge with intact epithelium and submucosa. Resolving inflammatory infiltrates from infection, which are largely lymphocytic, can be seen. However, ongoing areas of focus epithelial damage were not noted.

FIG. 2A shows the results of an ELISA of cecal contents from germfree Swiss-Webster mice that were collected at 24 and 48 hours after oral challenge with 1000 spores of the *C. difficile* ATCC-43255 strain. ToxinB was detected by ELISA and concentration in cecal contents calculated against a standard curve of purified toxinB. 4-8 mice were assayed per condition. Toxin levels in *C. sardiniense* pre-colonized mice were assessed from those that had survived to 24 or 48 hours. FIGS. 2B-2C present experimental data that show *C. bifermentans* suppresses toxin production without altering *C. difficile* biomass. FIG. 2B shows a bar graph showing *C. difficile* biomass in shed stool samples in the indicated days post-challenge. FIG. 2C shows the levels of *C. difficile* toxin production with indicated conditions. *C. bifermentans* precolonization prevents a spike in *C. difficile* toxin production.

FIG. 3A shows a schematic of the therapeutic intervention: adult conventional mice were treated with intraperitoneal clindamycin 24 hours before receiving 1×10^4 spores of *C. difficile* strain ATCC 43255. Approximately 20 hours after dosing, as mice first developed signs of symptomatic infection, animals received 5×10^7 CFU of *C. bifermentans* or *C. sardiniense*, or control vehicle alone, by gavage and were monitored for 2 additional weeks. FIG. 3B shows the survival curves of clindamycin-treated conventional mice infected with *C. difficile* and gavaged 20 hours later, upon onset of symptomatic infection, with vehicle alone, 5×10^7 CFU of *C. bifermentans* or 5×10^7 CFU of *C. sardiniense*. At least 8 mice across 2 experimental replicates were studied for each condition.

FIGS. 4A-4B present experimental data showing that *Clostridium bifermentans* is a highly proteolytic Stickland fermenting species. FIG. 4A shows representative images of chopped meat anaerobic culturing broth inoculated and incubated with either *C. bifermentans, C. hiranonis, C. sardiniense, C. scindens, C. ramosum,* or *C. difficile* and assessed for their proteolytic activity using a biochemical protease assay protease in a biological sample. FIG. 4B lists features of the strains with *C. difficile, C. bifermentans, C. sardiniense* and *C. scindens*.

FIGS. 5A-5I present experimental data showing that *Clostridium bifermentans* promotes Stickland fermentation by the Gram-positive toxigenic bacterium *C. difficile*. The cecal contents of germfree Swiss-Webster mice were collected 20 hours after infection with *C. difficile* and untargeted metabolomic analysis of cecal samples was performed. FIGS. 5A-5D show the MassSpectometry profiles of Stickland acceptor amino acids in cecal contents of germfree Swiss-Webster mice at 20 hours of infection with *C. difficile*. Y axis is Log10 MassSpec units of detected compounds. X axis indicates experimental condition: GF-germfree controls (no bacteria); Cdiff-challenge with 1000 *C. difficile* spores of strain ATCC43255; CSAR-7 days mono-association with *C. sardiniense*; CBI-7 days mono-association with *C. bifermentans*; Cdiff+CSAR-mice mono-associated with *C. sardiniense* for 7 days followed by *C.* difficile challenge; Cdiff+CBI-mice mono-associated with *C. bifermentans* for 7 days followed by *C. difficile* challenge. Each group has 8 mice across two experimental replicates. FIG. 5E shows the Mass Spectrometry profiles of cecal branched-chain amino acids and degradation products in gnotobiotic colonized mice. MassSpectrometry profiles of Stickland donor, branched chain amino acids in cecal contents of germfree Swiss-Webster mice at 20 hours of infection with *C. difficile*. Y axis is Log10 MassSpec units of detected compounds. X axis indicates experimental condition: GF-germfree controls (no bacteria); Cdiff-challenge with 1000 *C. difficile* spores of strain ATCC43255; CSAR-7 days mono-association with *C. sardiniense*; CBI-7 days mono-association with *C. bifermentans*; Cdiff+CSAR-mice mono-associated with *C. sardiniense* for 7 days followed by *C. difficile* challenge; Cdiff+CBI-mice mono-associated with *C. bifermentans* for 7 days followed by *C. difficile* challenge. Each group has 8 mice across two experimental replicates. Leucine, isoleucine and valine; levels elevated in Cdiff+CSAR mice, consistent with toxic megacolon picture. Cdiff and CSAR+*C. difficile* infected mice, which have a more severe clinical and histologic picture have 10× elevated keto-acid derivatives of the BCAA over Cdiff+CBI colonized mice, providing potential biomarkers for a more severe infection. Hydroxy-acid intermediates showing elevation with CSAR alone and CSAR+Cdiff. Isolavaerate, branched-short chain fatty acid product of Stickland fermentations, present in cecal contents of mice colonized with *C. difficile* and/or *C. bifermentans*, indicating in vivo Stickland fermenting of leucine as a donor amino acids. Other branched SCFA, sobutyrate, isocaproate and Valerate were not assayable by this method and are not shown. FIG. 5F shows that *C. difficile* and *C. bifermentans* use aromatic amino acids in vivo in Stickland reactions. Cecal aromatic amino acids and metabolites in specifically-associated GF mice. Y-axis shows log 10 MS Units. X-axis indicates the colonized state of the mice. 8 adult Swiss-Webster mice at baseline (GF), +7 days commensal colonization with *C. sardiniense* (CSAR) or *C. bifermentans* (CBI), 20 hours of infection with *C. difficile* or 20 hours of infection after 7 days of commensal colonization (Cdiff CSAR, Cdiff+CBI). phenylalanine in cecal contents. Elevated amounts with Cdiff+CSAR relating to toxic megacolon picture. Stickland phenylalanine metabolites that are only present or elevated in mice associated with a Stickland fermenter. *C. difficile* is the dominant producer of phenylacetate, phenyllactate and phenylpyruvate. *C. bifermentans* is the dominant producer of phenylpropionate. Levels of *C. diff* dominant metabolites are reduced in the presence of *C. bifermentans*. Tryptophan levels and indoleacetate Stickland metabolite; other Stickland metabolites not present or detectable in the Metabolon panel. Both *C. diff* and CBI use tryptophan in Stickland reactions per elevated production of indoleacetate. tyrosine and Stickland tyrosine metabolites. Both species produce 4-hydroxphenylacetate. Cdiff specifically produces para-cresol (host sulfated derivative shown, native molecule not detected in Metabolon panel). CBI specifically produces 3(4-hydroyphenyl-propionate). FIG. 5G shows the commensal and *C. difficile* carbohydrate utilization in vivo. Cecal sugars and metabolites in specifically-associated GF mice. Y-axis shows log 10 MS Units. X-axis indicates the colonized state of the mice. 8 adult Swiss-Webster mice at baseline (GF), +7 days commensal colonization with *C. sardiniense* (CSAR) or *C. bifermentans* (CBI), 20 hours of infection with *C. difficile* (*C. difficile*) or 20 hours of infection after 7 days of commensal colonization (Cdiff CSAR, Cdiff+CBI). Baseline levels of sugars and metabolites shown in germfree mice. When metabolized microbially, amounts decrease from baseline. Levels of glucose in germfree mice versus those colonized with single species show some glucose use by commensals or *C. difficile* but levels increase when two species are co-colonized. Commensal and *C. difficile* metabolize fructose in cecal contents with inhibition of metabolism when co-colonized. *C. difficile* alone metabolizes mannitol/sorbitol with some inhibition of metabolism when co-colonized with *C. saridniense*. Elevated pyruvate produced in infections with *C. difficile* or *C. difficile*+CSAR. Lactate levels increase with *C. difficile* infection by itself or with commensals. Succinate levels increase with *C. difficile* by itself or with CSAR but do not change significantly with CBI as compared to CBI-alone. FIG. 5H-5I shows a representative Mass Spectrometry plot for *C. sardiniense* (CSAR) (FIG. 5H) and for *C. bifermentans* (CBI) (FIG. 5I).

FIGS. 6A-6B presents the experimental results of *C. difficile* Short Chain Fatty Acids (SCFA) profile produced in vitro. FIG. 6A shows the concentrations of *C. difficile* Short Chain Fatty Acids (SCFA) produced in vitro (mM). Cultures were grown in 10 mL of pre-reduced peptone-yeast (PY) broth at starting pH=7 with 1% glucose, 1% mannitol or 1% sorbitol for 72 hours at 37° C. under anaerobic conditions. 100 uL of broth supernatant was extracted and run on an Agilent GC/LC flame ionization detector (FID) instrument with internal standard to quantitate production of short chain fatty acids acetate, propionate and butyrate and the branched short chain fatty acids isobutyrate, isovalerate, isocaproate, valerate or capropate. ND=Not detected below the threshold of detection. FIG. 6B shows the experimental results of the commensal Short Chain Fatty Acids (SCFA) profiles produced in vitro (mM). Millimolar concentrations of SCFA in liquid culture supernatants. Cultures were grown in 10 mL of pre-reduced peptone-yeast (PY) broth or PY+1% glucose (PYG), for 24 hours at 37° C. under anaerobic conditions. 100 uL of broth supernatant was extracted and run on an Agilent GCLC flame ionization detector (FID) instrument with internal standard to quantitate production of short chain fatty acids acetate, propionate and butyrate and the branched short chain fatty acids isobutyrate, isovalerate and isocaproate. ND=Not detected below the threshold of detection; caproate and valerate were not detected in the commensals (data not shown).

FIG. 7 presents the experimental results showing the gene expression of the *C. difficile* toxin PaLoc and eut (ethanolamine) operon. Comparison of PaLoc and eut gene expression by bacterial RNAseq of cecal contents from *C. difficile*-infected gnotobiotic Swiss-Webster mice at 20 hours post-inoculation, compared with *C. bifermentans* colonized mice for 7 days prior to challenge with *C. difficile* for 20 hours. At least 4 mice/group evaluated. *C. bifermentans* colonized mice show a >48× decrease in *C. difficile* tcdR gene expression with concomitant >10× decreases in toxinA (tcdA) and toxinB (tcdB) gene expression. In contrast, *C. difficile* structural proteins for the ethanolamine carboxysome (eutH, eutK, eutL, eutN) are up-regulated >10× when *C. difficile* is inoculated into a *C. bifermentans*-colonized mouse.

DETAILED DESCRIPTION

Figure 1A:
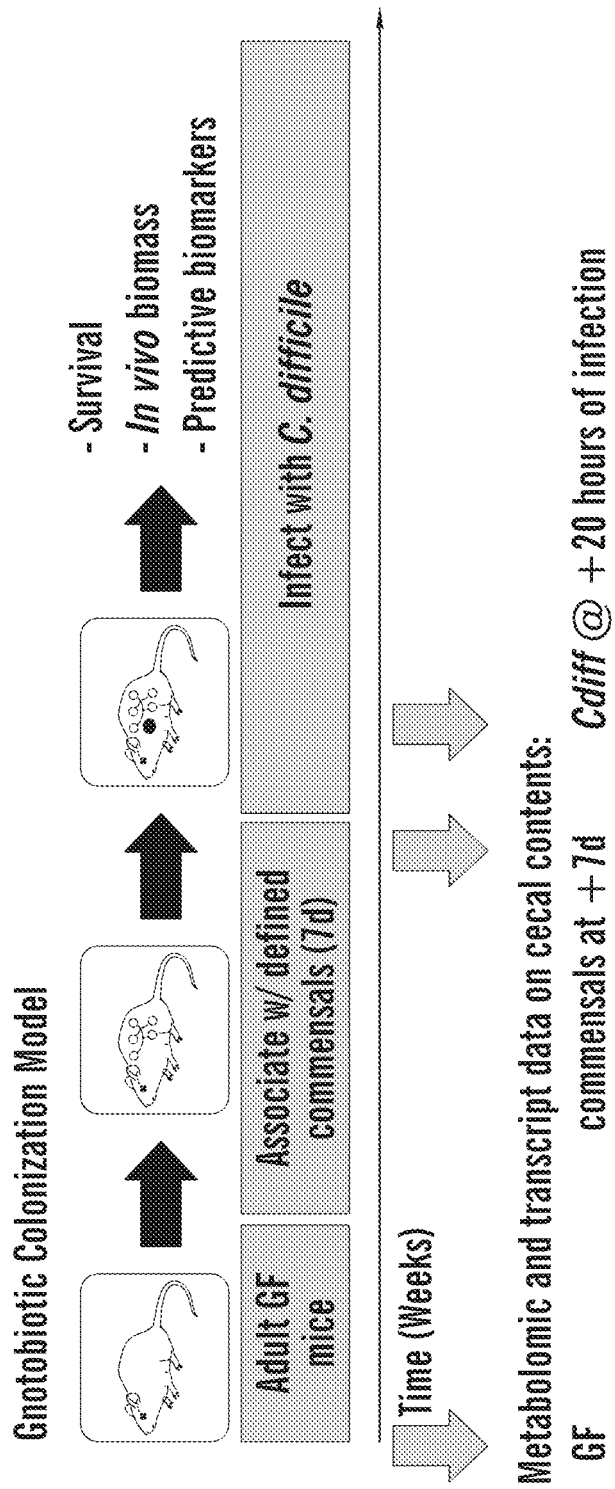

By its very name, *C. difficile* is notorious for being difficult to treat. Not only is the *C. difficile* organism resistant to multiple antibiotics commonly used to treat bacterial infections in clinical settings (e.g., aminoglycosides, lincomycin, tetracyclines, erythromycin, clindamycin, penicillins, cephalosporins, and fluoroquinolones), but the use of such antibiotics to treat other infections is one of the greatest risk factors for developing *C. difficile* pathology. Add to that the ability of *C. difficile* to sporulate and essentially wait until even an antibiotic that kills its metabolically active form is gone, and it truly deserves its name and reputation.

Toxigenic strains of *C. difficile* cause pseudomembranous colitis, a severe infectious disease of the colon. Infection often arises with disruptions to the gut microbiota, commonly after use of antibiotics that ablate protective commensals. *C. difficile* elaborates toxins when starved for carbon, nitrogen or energy (=high levels of NAD+). The toxins rapidly destroy the gut epithelial barrier enabling release of host-derived proteins and carbohydrate sources into the gut lumen which the pathogen then metabolizes. When co-existing with "beneficial" commensal species, *C. difficile* remains energetically stable and does not elaborate significant toxin. For patients failing multiple rounds of antibiotic treatment, who develop recurrent *C. difficile* infections, fecal microbiota transplant (FMT) is highly efficacious through its restoration of healthy gut microbial communities. However, the mechanisms of action of FMT, and specific microbes needed to halt toxin production and reduce pathogen biomass remain ill-defined. While microbial conversion of primary host bile acids to secondary acids have been hypothesized to play a key role, mechanisms of action have highlighted effects upon germination of *C. difficile* spores (primary bile acids stimulate; secondary bile acids inhibit) and less so on metabolic factors that modulate toxin production or overall pathogen biomass.

The technology described herein is related to the discovery of commensal bacteria that can suppress toxin production by Gram-positive toxigenic bacteria such as *C. difficile* and thereby treat or prevent the development of toxin-mediated pathology. Indeed, it was found that as few as a single species of bacteria can provide complete protection from otherwise fatal *C. difficile* infection in murine models described herein. Suppression of toxin production provides an alternative route to treatment of *C. difficile*-mediated pathology, in that it can be sufficient for treatment to just suppress production of the pathology-generating toxin without necessarily killing the microbe.

It is discovered that commensal bacteria that suppress toxin production by Gram-positive toxigenic bacteria such as *C. difficile* strongly express and secrete protease enzyme activity that generates free amino acids that can be fermented by *C. difficile* via Stickland fermentation, which metabolizes free amino acids to generate energy. Without wishing to be bound by theory, the picture that emerges is that in order to avoid toxin production by Gram-positive toxigenic bacteria such as *C. difficile*, the gut environment needs to provide energy and nutrients sufficient to keep such bacteria from becoming stressed and responding by toxin production. Thus, commensal bacteria that secrete proteolytic enzymes can provide therapeutic benefits in suppressing toxin production by Stickland-fermenting Gram-positive toxigenic bacteria such as *C. difficile*. It is noted that among the protective commensal species found to have protective effects were bacteria that are themselves capable of Stickland fermentation, including, for example, *C. bifermentans* and *C. scindens*.

Examination of the effects of protective commensals as described herein provides insights into the mechanisms of protection and further targets for manipulation of toxin production and biomarkers useful for evaluation of, for example, the likelihood of *C. difficile* recurrence, or the efficacy of treatment.

The following provides additional details regarding *C. difficile* and the discoveries of highly protective/therapeutic commensal species, and considerations to facilitate the performance of the methods and compositions for the prevention, treatment, prognosis and diagnosis that exploit these discoveries.

*Clostridium difficile*

*Clostridium* is a genus of Gram-positive bacteria including around 100 species, which includes several significant human pathogens, including the causative agent of botulism and an important cause of diarrhea, *Clostridium difficile*. Pathogenic *Clostridium* strains include but are not limited to *C. botulinum* that can produce botulinum toxin in food or wounds and can cause botulism. *Clostridium difficile* can flourish when other members of the gut microbiota are killed during antibiotic therapy, leading to superinfection and potentially fatal pseudomembranous colitis (a severe necrotizing disease of the large intestine). *Clostridium perfringens* causes a wide range of symptoms, from food poisoning to cellulitis, fasciitis, and gas gangrene. *Clostridium* tetanii causes tetanus. *Clostridium sordellii* can cause a fatal infection in rare cases after medical abortions.

*C. difficile* is a Gram-positive, anaerobic, spore-forming and toxin-producing *bacillus*, belonging to cluster XI of the *Clostridium* genus and commonly occurs in the hospital environment, and in the intestines of humans and domesticated animals. *C. difficile* can cause a spectrum of clinical conditions in humans, collectively known as *C. difficile* infections (CDI), which range from mild and possibly recurrent diarrhea to life-threatening complications such as pseudomembranous colitis (PMC), toxic megacolon and colonic perforation. As discussed elsewhere herein, *C. difficile* can occur in the gut of healthy individuals, but be maintained at a level that does not cause illness and/or have the expression of *C. difficile* toxin suppressed to a degree that the organism does not cause illness.

The clinical spectrum of *C. difficile* ranges from asymptomatic colonization, mild and self-limiting disease to a severe, life-threatening pseudomembranous colitis, toxic megacolon, sepsis and death. CDI is defined when there is the presence of symptomatic diarrhea defined by three or more unformed stools per 24 h and at least one of the following criteria: a positive laboratory assay for *C. difficile* toxin A and/or B or toxin-producing *C. difficile* organism in a stool sample or pseudomembranous colitis or colonic histopathology characteristic of CDI revealed by endoscopy. Toxin is detected, e.g., by immunoassay for the A and or B toxin proteins, and/or by RT-PCR for the toxin-encoding nucleic acids. CDI can be associated with an increased abundance of toxin-producing *C. difficile* strains, leading to high toxin concentrations within the colon resulting in inflammation and damage of the colonocytes.

The various strains of *C. difficile* may be classified by a number of methods. One of the most commonly used is polymerase chain reaction (PCR) ribotyping in which PCR is used to amplify the 16S-23S rRNA gene intergenic spacer region of *C. difficile*. Reaction products from this provide characteristic band patterns identifying the bacterial ribotype of isolates. Toxinotyping is another typing method in which the restriction patterns derived from DNA coding for the *C. difficile* toxins are used to identify strain toxinotype. The differences in restriction patterns observed between toxin genes of different strains are also indicative of sequence variation within the *C. difficile* toxin family. Toxin B shows sequence variation in some regions. For example, there's an approximate 13% sequence difference with the C-terminal 60 kDa region of toxinotype 0 Toxin B compared to the same region in toxinotype III.

*C. difficile* uses a variety of carbon and nitrogen sources for energy and metabolism. Within the gut environment, these sources can originate from the diet, from other commensals, or from the host, particularly when elaborating toxin to disrupt mucosal barriers. Known carbon sources include sugars such as glucose, fructose, mannose, mannitol or sorbitol, the latter two of which are poorly absorbed in the gut and reach the colon. Sources of carbon and nitrogen include amino groups and ethanolamine, a breakdown product of host phosphatidyl ethanolamine from eukaryotic cell membranes, other commensals, or the diet. As noted elsewhere herein, when preferred energy sources or nutrients for *C. difficile* run low or become limiting, *C. difficile* toxin production is induced.

*C. difficile* Toxins

As noted above, *C. difficile* encodes two toxin proteins, referred to as TcdA and TcdB, or simply herein as *C. difficile* toxin A and toxin B. TcdA and TcdB are broadly classified as AB toxins, wherein a B subunit is involved in the delivery of an enzymatic A subunit into the cytosol of a target cell. The enzymatic A subunit of TcdA is an N-terminal glucosyltransferase domain (GTD) that inactivates members of the Rho family of small GTPases by glucosylation. The B subunit is composed of three regions: a combined repetitive oligopeptides (CROPS) domain, a delivery/pore-forming domain and an autoprocessing domain (APD).

TcdA is encoded by the tcdA gene. Sequences for TcdA are known for a number of species, e.g., for *C. difficile* 630 (the TcdA NCBI Gene ID is 4914076) and polypeptide sequence (e.g., YP_001087137.1 (SEQ ID NO: 1). The sequence for the TcdA polypeptide is as follows (SEQ ID NO: 1):

```
                                                          (SEQ ID No: 1)
   1    msliskeeli klaysirpre neyktiltnl deynklttnn nenkylqlkk lnesidvfmn 61    kyktssrnra lsnlkkdilk eviliknsnt spveknlhfv wiggevsdia leyikqwadi 121    naeyniklwy dseaflvntl kkaivesstt ealqlleeei qnpqfdnmkf ykkrmefiyd 181    rqkrfinyyk sqinkptvpt iddiikshlv seynrdetvl esyrtnslrk insnhgidir 241    anslfteqel lniysqelln rgnlaaasdi vrllalknfg gvyldvdmlp gihsdlfkti 301    srpssigldr wemikleaim kykkyinnyt senfdkldqq lkdnfkliie sksekseifs 361    klenlnvsdl eikiafalgs vinqaliskq gsyltnlvie qvknryqfln qhlnpaiesd 421    nnftdttkif hdslfnsata ensmfltkia pylqvgfmpe arstislsgp gayasayydf 481    inlqentiek tlkasdlief kfpennlsql teqeinslws fdqasakyqf ekyvrdytgg 541    slsedngvdf nkntaldkny llnnkipsnn veeagsknyv hyiiqlqgdd isyeatcnlf 601    sknpknsiii qrnmnesaks yflsddgesi lelnkyripe rlknkekvkv tfighgkdef 661    ntsefarlsv dslsneissf ldtikldisp knvevnllgc nmfsydfnve etypgkllls 721    imdkitstlp dvnknsitig anqyevrins egrkellahs gkwinkeeai msdlsskeyi 781    ffdsidnklk aksknipgla sisediktll ldasvspdtk filnnlklni essigdyiyy 841    eklepvknii hnsiddlide fnllenvsde lyelkklnnl dekylisfed isknnstysv 901    rfinksnges vyvetekeif skysehitke istiknsiit dvngnlldni qldhtsqvnt 961    lnaaffiqsl idyssnkdvl ndlstsvkvq lyaqlfstgl ntiydsiqlv nlisnavndt 1021    invlptiteg ipivstildg inlgaaikel ldehdpllkk eleakvgvla inmslsiaat 1081    vasivgigae vtifllpiag isagipslvn nelilhdkat svvnyfnhls eskkygplkt 1141    eddkilvpid dlviseidfn nnsiklgtcn ilameggsgh tvtgnidhff sspsisship 1201    slsiysaigi etenldfskk immlpnapsr vfwwetgavp glrslendgt rlldsirdly 1261    pgkfywrfya ffdyaittlk pvyedtniki kldkdtrnfi mptittneir nklsysfdga 1321    ggtyslllss ypistninls kddlwifnid nevreisien gtikkgklik dvlskidink 1381    nkliignqti dfsgdidnkd ryifltceld dkisliiein lvaksyslll sgdknylisn 1441    lsniiekint lgldskniay nytdesnnky fgaisktsqk siihykkdsk nilefyndst 1501    lefnskdfia edinvfmkdd intitgkyyv dnntdksidf sislvsknqv kvnglylnes 1561    vyssyldfvk nsdghhntsn fmnlfldnis fwklfgfeni nfvidkyftl vgktnlgyve 1621    ficdnnknid iyfgewktss skstifsgng rnvvvepiyn pdtgedists ldfsyeplyg 1681    idryinkvli apdlytslin intnyysney ypeiivlnpn tfhkkvninl dsssfeykws
```

-continued

```
1741  tegsdfilvr yleesnkkil qkirikgils ntqsfnkmsi dfkdikklsl gyimsnfksf
1801  nseneldrdh lgfkiidnkt yyydedsklv kglininnsl fyfdpiefnl vtgwqtingk
1861  kyyfdintga alisykiing khfyfnndgv mqlgvfkgpd gfeyfapant qnnniegqai
1921  vyqskfltln gkkyyfdnds kavtgwriin nekyyfnpnn aiaavglqvi dnnkyyfnpd
1981  taiiskgwqt vngsryyfdt dtaiafngyk tidgkhfyfd sdcvvkigvf stsngfeyfa
2041  pantynnnie gqaivyqskf ltlngkkyyf dnnskavtgw qtidskkyyf ntntaeaatg
2101  wqtidgkkyy fntntaeaat gwqtidgkky yfntntaias tgytiingkh fyfntdgimq
2161  igvfkgpngf eyfapantda nniegqaily gnefltlngk kyyfgsdska vtgwriinnk
2221  kyyfnpnnai aaihlctinn dkyyfsydgi lqngyitier nnfyfdanne skmvtgvfkg
2281  pngfeyfapa nthnnniegq aivyqnkflt lngkkyyfdn dskavtgwqt idgkkyyfnl
2341  ntaeaatgwq tidgkkyyfn lntaeaatgw qtidgkkyyf ntntfiastg ytsingkhfy
2401  fntdgimqig vfkgpngfey fapanthnnn iegqailyqn kfltlngkky yfgsdskavt
2461  glrtidgkky yfntntavav tgwqtingkk yyfntntsia stgytiisgk hfyfntdgim
2521  qigvfkgpdg feyfapantd anniegqair yqnrflylhd niyyfgnnsk aatgwvtidg
2581  nryyfepnta mgangyktid nknfyfrngl pqigvfkgsn gfeyfapant danniegqai
2641  ryqnrflhll gkiyyfgnns kavtgwqtin gkvyyfmpdt amaaagglfe idgviyffgv
2701  dgvkapgiyg
```

The tcdA gene sequence for *C. difficile* 630 is as follows (SEQ ID NO:2):

(SEQ ID NO: 2)
```
   1  atgtctttaa tatctaaaga agagttaata aaactcgcat atagcattag accaagagaa
  61  aatgagtata aaactatact aactaattta gacgaatata ataagttaac tacaaacaat
 121  aatgaaaata aatatttaca attaaaaaaa ctaaatgaat caattgatgt ttttatgaat
 181  aaatataaaa cttcaagcag aaatagagca ctctctaatc taaaaaaaga tatattaaaa
 241  gaagtaattc ttattaaaaa ttccaataca agccctgtag aaaaaaattt acattttgta
 301  tggataggtg agaagtcag tgatattgct cttgaataca taaaacaatg ggctgatatt
 361  aatgcagaat ataatattaa actgtggtat gatagtgaag cattcttagt aaatacacta
 421  aaaaaggcta tagttgaatc ttctaccact gaagcattac agctactaga ggaagagatt
 481  caaaatcctc aatttgataa tatgaaatt tacaaaaaaa ggatggaatt tatatatgat
 541  agacaaaaaa ggtttataaa ttattataaa tctcaaatca ataaacctac agtacctaca
 601  atagatgata ttataaagtc tcatctagta tctgaatata atagagatga aactgtatta
 661  gaatcatata gaacaaattc tttgagaaaa ataaatagta atcatgggat agatatcagg
 721  gctaatagtt tgtttacaga acaagagtta ttaaatattt atagtcagga gttgttaaat
 781  cgtggaaatt tagctgcagc atctgacata gtaagattat tagccctaaa aaattttggc
 841  ggagtatatt tagatgttga tatgcttcca ggtattcact ctgatttatt taaaacaata
 901  tctagaccta gctctattgg actagaccgt gggaaatga taaaattaga ggctattatg
 961  aagtataaaa aatatataaa taattataca tcagaaaact ttgataaact tgatcaacaa
1021  ttaaaagata attttaaact cattatagaa agtaaaagtg aaaaatctga gatattttct
1081  aaattagaaa atttaaatgt atctgatctt gaaattaaaa tagctttcgc tttaggcagt
1141  gttataaatc aagccttgat atcaaaacaa ggttcatatc ttactaacct agtaatagaa
```

-continued

```
1201   caagtaaaaa atagatatca attttaaaac caacaccta acccagccat agagtctgat
1261   ataacttca cagatactac taaaatttt catgattcat tatttaattc agctaccgca
1321   gaaaactcta tgtttttaac aaaaatagca ccatacttac aagtaggttt tatgccagaa
1381   gctcgctcca caataagttt aagtggtcca ggagcttatg cgtcagctta ctatgattc
1441   ataaatttac aagaaaatac tatagaaaaa actttaaaag catcagattt aatagaattt
1501   aaattcccag aaaataatct atctcaattg acagaacaag aaataaatag tctatggagc
1561   tttgatcaag caagtgcaaa atatcaattt gagaaatatg taagagatta tactggtgga
1621   tctctttctg aagacaatgg ggtagacttt aataaaaata ctgccctcga caaaaactat
1681   ttattaaata ataaaattcc atcaaacaat gtagaagaag ctggaagtaa aaattatgtt
1741   cattatatca tacagttaca aggagatgat ataagttatg aagcaacatg caatttattt
1801   tctaaaaatc ctaaaaatag tattattata caacgaaata tgaatgaaag tgcaaaaagc
1861   tacttttaa gtgatgatgg agaatctatt ttagaattaa ataaatatag gatacctgaa
1921   agattaaaaa ataaggaaaa agtaaaagta acctttattg gacatggtaa agatgaattc
1981   aacacaagcg aatttgctag attaagtgta gattcacttt ccaatgagat aagttcattt
2041   ttagatacca taaaattaga tatatcacct aaaaatgtag aagtaaactt acttggatgt
2101   aatatgttta gttatgattt taatgttgaa gaacttatc ctgggaagtt gctattaagt
2161   attatggaca aaattacttc cactttacct gatgtaaata aaaattctat tactatagga
2221   gcaaatcaat atgaagtaag aattaatagt gagggaagaa aagaacttct ggctcactca
2281   ggtaaatgga taaataaaga agaagctatt atgagcgatt tatctagtaa agaatacatt
2341   tttttgatt ctatagataa taagctaaaa gcaaagtcca agaatattcc aggattagca
2401   tcaatatcag aagatataaa aacattatta cttgatgcaa gtgttagtcc tgatacaaaa
2461   tttattttaa ataatcttaa gcttaatatt gaatcttcta ttggtgatta catttattat
2521   gaaaaattag agcctgttaa aaatataatt cacaattcta tagatgattt aatagatgag
2581   ttcaatctac ttgaaaatgt atctgatgaa ttatatgaat taaaaaaatt aaataatcta
2641   gatgagaagt atttaatatc ttttgaagat atctcaaaaa ataattcaac ttactctgta
2701   agatttatta acaaaagtaa tggtgagtca gtttatgtag aaacagaaaa agaaatttt
2761   tcaaaatata gcgaacatat tacaaaagaa ataagtacta taagaatag tataattaca
2821   gatgttaatg gtaatttatt ggataatata cagttagatc atacttctca agttaataca
2881   ttaaacgcag cattctttat tcaatcatta atagattata gtagcaataa agatgtactg
2941   aatgatttaa gtacctcagt taaggttcaa ctttatgctc aactatttag tacaggttta
3001   aatactatat atgactctat ccaattagta aatttaatat caaatgcagt aaatgatact
3061   ataaatgtac tacctacaat aacagagggg atacctattg tatctactat attagacgga
3121   ataaacttag gtgcagcaat taaggaatta ctagacgaac atgacccatt actaaaaaaa
3181   gaattagaag ctaaggtggg tgtttagca ataaatatgt cattatctat agctgcaact
3241   gtagcttcaa ttgttggaat aggtgctgaa gttactattt tcttattacc tatagctggt
3301   atatctgcag gaataccttc attagttaat aatgaattaa tattgcatga taaggcaact
3361   tcagtggtaa actattttaa tcattgtct gaatctaaaa aatatggccc tcttaaaaca
3421   gaagatgata aaatttttagt tcctattgat gatttagtaa tatcagaaat agattttaat
3481   aataattcga taaaactagg aacatgtaat atattagcaa tggaggggg atcaggacac
3541   acagtgactg gtaatataga tcactttttc tcatctccat ctataagttc tcatattcct
```

```
                      -continued
3601   tcattatcaa tttattctgc aataggtata gaaacagaaa atctagattt ttcaaaaaaa
3661   ataatgatgt tacctaatgc tccttcaaga gtgttttggt gggaaactgg agcagttcca
3721   ggtttaagat cattggaaaa tgacggaact agattacttg attcaataag agatttatac
3781   ccaggtaaat tttactggag attctatgct tttttcgatt atgcaataac tacattaaaa
3841   ccagtttatg aagacactaa tattaaaatt aaactagata aagatactag aaacttcata
3901   atgccaacta taactactaa cgaaattaga aacaaattat cttattcatt tgatggagca
3961   ggaggaactt actctttatt attatcttca tatccaatat caacgaatat aaatttatct
4021   aaagatgatt tatggatatt taatattgat aatgaagtaa gagaaatatc tatagaaaat
4081   ggtactatta aaaaggaaa gttaataaaa gatgttttaa gtaaaattga tataaataaa
4141   aataaactta ttataggcaa tcaaacaata gattttcag gcgatataga taataaagat
4201   agatatatat tcttgacttg tgagttagat gataaaatta gtttaataat agaaataaat
4261   cttgttgcaa aatcttatag tttgttattg tctggggata aaaattattt gatatccaat
4321   ttatctaata ttattgagaa aatcaatact ttaggcctag atagtaaaaa tatagcgtac
4381   aattacactg atgaatctaa taataaatat tttggagcta tatctaaaac aagtcaaaaa
4441   agcataatac attataaaaa agacagtaaa aatatattag aattttataa tgacagtaca
4501   ttagaattta acagtaaaga ttttattgct gaagatataa atgtatttat gaaagatgat
4561   attaatacta taacaggaaa atactatgtt gataataata ctgataaaag tatagatttc
4621   tctatttctt tagttagtaa aaatcaagta aaagtaaatg gattatattt aaatgaatcc
4681   gtatactcat cttaccttga ttttgtgaaa aattcagatg gacaccataa tacttctaat
4741   tttatgaatt tatttttgga caatataagt ttctggaaat tgtttgggtt tgaaaatata
4801   aattttgtaa tcgataaata ctttacccct gttggtaaaa ctaatcttgg atatgtagaa
4861   tttatttgtg acaataataa aaatatagat atatattttg gtgaatggaa aacatcgtca
4921   tctaaaagca ctatatttag cggaaatggt agaaatgttg tagtagagcc tatatataat
4981   cctgatacgg gtgaagatat atctacttca ctagattttt cctatgaacc tctctatgga
5041   atagatagat atatcaataa agtattgata gcacctgatt tatatacaag tttaataaat
5101   attaatacca attattattc aaatgagtac taccctgaga ttatagttct taacccaaat
5161   acattccaca aaaaagtaaa tataaattta gatagttctt cttttgagta taaatggtct
5221   acagaaggaa gtgactttat tttagttaga tacttagaag aaagtaataa aaaaatatta
5281   caaaaaataa gaatcaaagg tatcttatct aatactcaat catttaataa aatgagtata
5341   gattttaaag atattaaaaa actatcatta ggatatataa tgagtaattt taaatcattt
5401   aattctgaaa atgaattaga tagagatcat ttaggattta aaataataga taataaaact
5461   tattactatg atgaagatag taaattagtt aaaggattaa tcaatataaa taattcatta
5521   ttctattttg atcctataga atttaactta gtaactggat ggcaaactat caatggtaaa
5581   aaatattatt ttgatataaa tactggagca gctttaatta gttataaaat tattaatggt
5641   aaacactttt attttaataa tgatggtgtg atgcagttgg gagtatttaa aggacctgat
5701   ggatttgaat attttgcacc tgccaatact caaaataata acatagaagg tcaggctata
5761   gtttatcaaa gtaaattctt aactttgaat ggcaaaaaat attatttga taatgactca
5821   aaagcagtca ctggatggag aattattaac aatgagaaat attactttaa tcctaataat
5881   gctattgctg cagtcggatt gcaagtaatt gacaataata gtattattt caatcctgac
5941   actgctatca tctcaaaagg ttggcagact gttaatggta gtagatacta ctttgatact
6001   gataccgcta ttgccttaa tggttataaa actattgatg gtaaacactt ttattttgat
```

-continued

```
6061  agtgattgtg tagtgaaaat aggtgtgttt agtacctcta atggatttga atattttgca 6121  cctgctaata cttataataa taacatagaa ggtcaggcta tagtttatca aagtaaattc 6181  ttaactttga atggtaaaaa atattacttt gataataact caaaagcagt taccggatgg 6241  caaactattg atagtaaaaa atattacttt aatactaaca ctgctgaagc agctactgga 6301  tggcaaacta ttgatggtaa aaatattac tttaatacta acactgctga agcagctact 6361  ggatggcaaa ctattgatgg taaaaatat tactttaata ctaacactgc tatagcttca 6421  actggttata caattattaa tggtaaacat ttttatttta atactgatgg tattatgcag 6481  ataggagtgt ttaaaggacc taatggattt gaatattttg cacctgctaa tacggatgct 6541  aacaacatag aaggtcaagc tatactttac caaaatgaat tcttaacttt gaatggtaaa 6601  aaatattact ttggtagtga ctcaaaagca gttactggat ggagaattat taacaataag 6661  aaatattact ttaatcctaa taatgctatt gctgcaattc atctatgcac tataaataat 6721  gacaagtatt actttagtta tgatggaatt cttcaaaatg gatatattac tattgaaaga 6781  aataaatttct attttgatgc taataatgaa tctaaaatgg taacaggagt atttaaagga 6841  cctaatggat ttgagtattt tgcacctgct aatactcaca ataataacat agaaggtcag 6901  gctatagttt accagaacaa attcttaact ttgaatggca aaaaatatta ttttgataat 6961  gactcaaaag cagttactgg atggcaaacc attgatggta aaaaatatta ctttaatctt 7021  aacactgctg aagcagctac tggatggcaa actattgatg gtaaaaaata ttactttaat 7081  cttaacactg ctgaagcagc tactggatgg caaactattg atggtaaaaa atattacttt 7141  aatactaaca cttttcatagc ctcaactggt tatacaagta ttaatggtaa acatttttat 7201  tttaatactg atggtattat gcagataggg gtgtttaaag gacctaatgg atttgaatac 7261  tttgcacctg ctaatactca ataataac atagaaggtc aagctatact ttaccaaaat 7321  aaattcttaa ctttgaatgg taaaaaatat tactttggta gtgactcaaa agcagttacc 7381  ggattgcgaa ctattgatgg taaaaaatat tactttaata ctaacactgc tgttgcagtt 7441  actggatggc aaactattaa tggtaaaaaa tactacttta atactaacac ttctatagct 7501  tcaactggtt atacaattat tagtggtaaa catttttatt ttaatactga tggtattatg 7561  cagataggag tgtttaaagg acctgatgga tttgaatact ttgcacctgc taatacagat 7621  gctaacaata tagaaggtca agctatacgt tatcaaaata gattcctata tttacatgac 7681  aatatatatt atttttggtaa taattcaaaa gcagctactg gttgggtaac tattgatggt 7741  aatagatatt acttcgagcc taatacagct atgggtgcga atggttataa aactattgat 7801  aataaaaatt tttactttag aaatggttta cctcagatag gagtgtttaa agggtctaat 7861  ggatttgaat actttgcacc tgctaatacg gatgctaaca atatagaagg tcaagctata 7921  cgttatcaaa atagattcct acatttactt ggaaaaatat attactttgg taataattca 7981  aaaagcagtta ctggatggca aactattaat ggtaaagtat attacttat gcctgatact 8041  gctatggctg cagctggtgg acttttcgag attgatggtg ttatatattt ctttggtgtt 8101  gatggagtaa aagcccctgg gatatatggc taa
```

TcdB is encoded by the tcdB gene. Sequences for TcdB are known for a number of species, e.g., for *C. difficile* 630 (the TcdB NCBI Gene ID is 4914074) and polypeptide sequence (e.g., YP_001087135.1 (SEQ ID NO: 3). The sequence for the TcdB gene product is as follows (SEQ ID NO: 3):

```
                                                              (SEQ ID No: 3)
   1  mslvnrkqle kmanvrfrtq edeyvailda leeyhnmsen tvvekylklk dinsltdiyi
  61  dtykksgrnk alkkfkeylv tevlelknnn ltpveknlhf vwiggqindt ainyinqwkd
 121  vnsdynvnvf ydsnaflint lkktvvesai ndtlesfren lndprfdynk ffrkrmeiiy
 181  dkqknfinyy kaqreenpel iiddivktyl sneyskeide lntyieesln kitqnsgndv
 241  rnfeefknge sfnlyeqelv erwnlaaasd ilrisalkei ggmyldvdml pgiqpdlfes
 301  iekpssvtvd fwemtkleai mkykeyipey tsehfdmlde evqssfesvl asksdkseif
 361  sslgdmeasp levkiafnsk giinqglisv kdsycsnliv kqienrykil nnslnpaise
 421  dndfntttnt fidsimaean adngrfmmel gkylrvgffp dvkttinlsg peayaaayqd
 481  llmfkegsmn ihlieadlrn feisktnisq steqemaslw sfddarakaq feeykrnyfe
 541  gslgeddnld fsqnivvdke yllekissla rssergyihy ivqlqgdkis yeaacnlfak
 601  tpydsvlfqk niedseiayy ynpgdgeiqe idkykipsii sdrpkikltf ighgkdefnt
 661  difagfdvds lsteieaaid lakedispks ieinllgcnm fsysinveet ypgklllkvk
 721  dkiselmpsi sqdsiivsan qyevrinseg rrelldhsge winkeesiik disskeyisf
 781  npkenkitvk sknlpelstl lqeirnnsns sdieleekvm lteceinvis nidtqiveer
 841  ieeaknltsd sinyikdefk liesisdalc dlkqqneled shfisfedis etdegfsirf
 901  inketgesif vetektifse yanhiteeis kikgtifdtv ngklvkkvnl dtthevntln
 961  aaffiqslie ynsskeslsn lsvamkvqvy aqlfstglnt itdaakvvel vstaldetid
1021  llptlseglp iiatiidgvs lgaaikelse tsdpllrqei eakigimavn lttattaiit
1081  sslgiasgfs illvplagis agipslvnne lvlrdkatkv vdyfkhvslv etegvftlld
1141  dkimmpqddl viseidfnnn sivlgkceiw rmeggsghtv tddidhffsa psityrephl
1201  siydvlevqk eeldlskdlm vlpnapnrvf awetgwtpgl rslendgtkl ldrirdnyeg
1261  efywryfafi adalittlkp ryedtnirin ldsntrsfiv piitteyire klsysfygsg
1321  gtyalslsqy nmginielse sdvwiidvdn vvrdvtiesd kikkgdllieg ilstlsieen
1381  kiilnshein fsgevngsng fvsltfsile ginaiievdl lsksykllis gelkilmlns
1441  nhiqqkidyi gfnselqkni pysfvdsegk engfingstk eglfvselpd vvliskvymd
1501  dskpsfgyys nnlkdvkvit kdnvniltgy ylkddikisl sltlqdekti klnsvhldes
1561  gvaeilkfmn rkgntntsds lmsflesmni ksifvnflqs nikfildanf iisgttsigq
1621  feficdendn iqpyfikfnt letnytlyvg nrqnmivepn ydlddsgdis stvinfsqky
1681  lygidscvnk vvispniytd einitpvyet nntypevivl danyinekin vnindlsiry
1741  vwsndgndfi lmstseenkv sqvkirfvnv fkdktlankl sfnfsdkqdv pvseiilsft
1801  psyyedglig ydlglvslyn ekfyinnfgm mvsgliyind slyyfkppvn nlitgfvtvg
1861  ddkyyfnpin ggaasigeti iddknyyfnq sgvlqtgvfs tedgfkyfap antldenleg
1921  eaidftgkli ideniyyfdd nyrgavewke ldgemhyfsp etgkafkgln qigdykyyfn
1981  sdgvmqkgfv sindnkhyfd dsgvmkvgyt eidgkhfyfa engemqigvf ntedgfkyfa
2041  hhnedlgnee geeisysgil nfnnkiyyfd dsftavvgwk dledgskyyf dedtaeayig
2101  lslindgqyy fnddgimqvg fvtindkvfy fsdsgiiesg vqniddnyfy iddngivqig
2161  vfdtsdgyky fapantvndn iygqaveysg lvrvgedvyy fgetytietg wiydmenesd
2221  kyyfnpetkk ackginlidd ikyyfdekgi mrtglisfen nnyyfnenge mqfgyinied
```

-continued

```
2281  kmfyfgedgv mqigvfntpd gfkyfahqnt ldenfegesi nytgwldlde kryyftdeyi 2341  aatgsviidg eeyyfdpdta qlvise
```

The tcdB gene sequence for *C. difficile* 630 is as follows (SEQ ID NO: 4):

```
                                                                (SEQ ID NO: 4)
   1  atgagtttag ttaatagaaa acagttagaa aaaatggcaa atgtaagatt tcgtactcaa 61  gaagatgaat atgttgcaat attggatgct ttagaagaat atcataatat gtcagagaat 121  actgtagtcg aaaaatattt aaaattaaaa gatataaata gtttaacaga tatttatata 181  gatacatata aaaaatctgg tagaaataaa gccttaaaaa aatttaagga atatctagtt 241  acagaagtat tagagctaaa gaataataat ttaactccag ttgagaaaaa tttacatttt 301  gtttggattg gaggtcaaat aaatgacact gctattaatt atataaatca atggaaagat 361  gtaaatagtg attataatgt taatgttttt tatgatagta atgcatttt gataaacaca 421  ttgaaaaaaa ctgtagtaga atcagcaata aatgatacac ttgaatcatt tagagaaaac 481  ttaaatgacc ctagatttga ctataataaa ttcttcagaa acgtatgga ataatttat 541  gataaacaga aaaatttcat aaactactat aaagctcaaa gagaagaaaa tcctgaactt 601  ataattgatg atattgtaaa gacatatctt tcaaatgagt attcaaagga gatagatgaa 661  cttaatacct atattgaaga atccttaaat aaaattacac agaatagtgg aaatgatgtt 721  agaaactttg aagaatttaa aaatggagag tcattcaact tatatgaaca agagttggta 781  gaaaggtgga atttagctgc tgcttctgac atattaagaa tatctgcatt aaaagaaatt 841  ggtggtatgt atttagatgt tgatatgtta ccaggaatac aaccagactt atttgagtct 901  atagagaaac ctagttcagt aacagtggat ttttgggaaa tgacaaagtt agaagctata 961  atgaaataca agaatatat accagaatat acctcagaac attttgacat gttagacgaa 1021  gaagttcaaa gtagttttga atctgttcta gcttctaagt cagataaatc agaaatattc 1081  tcatcacttg gtgatatgga ggcatcacca ctagaagtta aaattgcatt taatagtaag 1141  ggtattataa atcaagggct aatttctgtg aaagactcat attgtagcaa tttaatagta 1201  aaacaaatcg agaatagata taaatattg aataatagtt taaatccagc tattagcgag 1261  gataatgatt ttaatactac aacgaatacc tttattgata gtataatggc tgaagctaat 1321  gcagataatg gtagatttat gatggaacta ggaaagtatt taagagttgg tttcttccca 1381  gatgttaaaa ctactattaa cttaagtggc cctgaagcat gcggcagc ttatcaagat 1441  ttattaatgt ttaaagaagg cagtatgaat atccatttga tagaagctga tttaagaaac 1501  tttgaaatct ctaaaactaa tatttctcaa tcaactgaac aagaaatggc tagcttatgg 1561  tcatttgacg atgcaagagc taaagctcaa tttgaagaat ataaaggaa ttattttgaa 1621  ggttctcttg gtgaagatga taatcttgat tttctcaaa atatagtagt tgacaaggag 1681  tatcttttag aaaaaatatc ttcattagca agaagttcag agagaggata tacactat 1741  attgttcagt tacaaggaga taaaattagt tatgaagcag catgtaactt atttgcaaag 1801  actccttatg atagtgtact gtttcagaaa aatatagaag attcagaaat tgcatattat 1861  tataatcctg gagatggtga aatacaagaa atagacaagt ataaaattcc aagtataatt 1921  tctgatagac ctaagattaa attaacattt attggtcatg gtaaagatga atttaatact 1981  gatatatttg caggttttga tgtagattca ttatccacag aaatagaagc agcaatagat 2041  ttagctaaag aggatatttc tcctaagtca atagaaataa atttattagg atgtaatatg
```

-continued

```
2101  tttagctact ctatcaacgt agaggagact tatcctggaa aattattact taaagttaaa
2161  gataaaatat cagaattaat gccatctata agtcaagact ctattatagt aagtgcaaat
2221  caatatgaag ttagaataaa tagtgaagga agaagagaat tattggatca ttctggtgaa
2281  tggataaata aagaagaaag tattataaag gatatttcat caaaagaata tatatcattt
2341  aatcctaaag aaaataaaat tacagtaaaa tctaaaaatt tacctgagct atctacatta
2401  ttacaagaaa ttagaaataa ttctaattca agtgatattg aactagaaga aaaagtaatg
2461  ttaacagaat gtgagataaa tgttatttca aatatagata cgcaaattgt tgaggaaagg
2521  attgaagaag ctaagaattt aacttctgac tctattaatt atataaaaga tgaatttaaa
2581  ctaatagaat ctatttctga tgcactatgt gacttaaaac aacagaatga attagaagat
2641  tctcatttta tatcttttga ggacatatca gagactgatg agggatttag tataagattt
2701  attaataaag aaactggaga atctatattt gtagaaactg aaaaaacaat attctctgaa
2761  tatgctaatc atataactga agagatttct aagataaaag gtactatatt tgatactgta
2821  aatggtaagt tagtaaaaaa agtaaattta gatactacac acgaagtaaa tactttaaat
2881  gctgcatttt ttatacaatc attaatagaa tataaatagtt ctaaagaatc tcttagtaat
2941  ttaagtgtag caatgaaagt ccaagtttac gctcaattat ttagtactgg tttaaatact
3001  attacagatg cagccaaagt tgttgaatta gtatcaactg cattagatga aactatagac
3061  ttacttccta cattatctga aggattacct ataattgcaa ctattataga tggtgtaagt
3121  ttaggtgcag caatcaaaga gctaagtgaa acgagtgacc cattattaag acaagaaata
3181  gaagctaaga taggtataat ggcagtaaat ttaacaacag ctacaactgc aatcattact
3241  tcatcttttgg ggatagctag tggatttagt atacttttag ttcctttagc aggaatttca
3301  gcaggtatac caagcttagt aaacaatgaa cttgtacttc gagataaggc aacaaaggtt
3361  gtagattatt taaacatgt tcattagtt gaaactgaag gagtatttac tttattagat
3421  gataaaataa tgatgccaca agatgattta gtgatatcag aaatagattt taataataat
3481  tcaatagttt taggtaaatg tgaaatctgg agaatggaag gtggttcagg tcatactgta
3541  actgatgata tagatcactt cttttcagca ccatcaataa catatagaga gccacactta
3601  tctatatatg acgtattgga agtacaaaaa gaagaacttg atttgtcaaa agatttaatg
3661  gtattaccta atgctccaaa tagagtattt gcttgggaaa caggatggac accaggttta
3721  agaagcttag aaaatgatgg cacaaaactg ttagaccgta taagagataa ctatgaaggt
3781  gagttttatt ggagatattt tgcttttata gctgatgctt taataacaac attaaaacca
3841  agatatgaag atactaatat aagaataaat ttagatagta atactagaag ttttatagtt
3901  ccaataataa ctacagaata tataagagaa aaattatcat attctttcta tggttcagga
3961  ggaacttatg cattgtctct ttctcaatat aatatgggta taaaatataga attaagtgaa
4021  agtgatgttt ggattataga tgttgataat gttgtgagag atgtaactat agaatctgat
4081  aaaattaaaa aaggtgattt aatagaaggt attttatcta cactaagtat tgaagagaat
4141  aaaattatct taaatagcca tgagattaat ttttctggtg aggtaaatgg aagtaatgga
4201  tttgtttctt taacattttc aattttagaa ggaatataaatg caattataga agttgattta
4261  ttatctaaat catataaatt acttatttct ggcgaattaa aaatattgat gttaaattca
4321  aatcatattc aacagaaaat agattatata ggattcaata gcgaattaca gaaaaatata
4381  ccatatagct ttgtagatag tgaaggaaaa gagaatggtt ttattaatgg ttcaacaaaa
4441  gaaggtttat ttgtatctga attacctgat gtagttctta taagtaaggt ttatatggat
```

```
4501  gatagtaagc cttcatttgg atattatagt aataatttga aagatgtcaa agttataact
4561  aaagataatg ttaatatatt aacaggttat tatcttaagg atgatataaa aatctctctt
4621  tctttgactc tacaagatga aaaaactata aagttaaata gtgtgcattt agatgaaagt
4681  ggagtagctg agattttgaa gttcatgaat agaaaaggta atacaaatac ttcagattct
4741  ttaatgagct ttttagaaag tatgaatata aaaagtattt tcgttaattt cttacaatct
4801  aatattaagt ttatattaga tgctaatttt ataataagtg gtactacttc tattggccaa
4861  tttgagttta tttgtgatga aaatgataat atacaaccat atttcattaa gtttaataca
4921  ctagaaacta attatacttt atatgtagga aatagacaaa atatgatagt ggaaccaaat
4981  tatgatttag atgattctgg agatatatct tcaactgtta tcaatttctc tcaaaagtat
5041  ctttatggaa tagacagttg tgttaataaa gttgtaattt caccaaatat ttatacagat
5101  gaaataaata taacgcctgt atatgaaaca aataatactt atccagaagt tattgtatta
5161  gatgcaaatt atataaatga aaaataaat gttaatatca atgatctatc tatacgatat
5221  gtatggagta atgatggtaa tgattttatt cttatgtcaa ctagtgaaga aaataaggtg
5281  tcacaagtta aaataagatt cgttaatgtt tttaaagata agactttggc aaataagcta
5341  tcttttaact ttagtgataa acaagatgta cctgtaagtg aaataatctt atcatttaca
5401  ccttcatatt atgaggatgg attgattggc tatgatttgg gtctagtttc tttatataat
5461  gagaaatttt atattaataa ctttggaatg atggtatctg gattaatata tattaatgat
5521  tcattatatt attttaaacc accagtaaat aatttgataa ctggatttgt gactgtaggc
5581  gatgataaat actactttaa tccaattaat ggtggagctg cttcaattgg agagacaata
5641  attgatgaca aaaattatta tttcaaccaa agtggagtgt tacaaacagg tgtatttagt
5701  acagaagatg gatttaaata ttttgcccca gctaatacac ttgatgaaaa cctagaagga
5761  gaagcaattg attttactgg aaaattaatt attgacgaaa atatttatta ttttgatgat
5821  aattatagag gagctgtaga atggaaagaa ttagatggtg aaatgcacta ttttagccca
5881  gaaacaggta agcttttaa aggtctaaat caaataggtg attataaata ctatttcaat
5941  tctgatggag ttatgcaaaa aggatttgtt agtataaatg ataataaaca ctattttgat
6001  gattctggtg ttatgaaagt aggttacact gaaatagatg gcaagcattt ctactttgct
6061  gaaaacggag aaatgcaaat aggagtattt aatacagaag atggatttaa atattttgct
6121  catcataatg aagatttagg aaatgaagaa ggtgaagaaa tctcatattc tggtatatta
6181  aatttcaata ataaaattta ctattttgat gattcattta cagctgtagt tggatggaaa
6241  gatttagagg atggttcaaa gtattatttt gatgaagata cagcagaagc atatataggt
6301  ttgtcattaa taaatgatgg tcaatattat tttaatgatg atggaattat gcaagttgga
6361  tttgtcacta taaatgataa agtcttctac ttctctgact ctggaattat agaatctgga
6421  gtacaaaaca tagatgacaa ttatttctat atagatgata atggtatagt tcaaattggt
6481  gtatttgata cttcagatgg atataaatat tttgcacctg ctaaactgt aaatgataat
6541  atttacggac aagcagttga atatagtggt ttagttagag ttggtgaaga tgtatattat
6601  tttggagaaa catatacaat tgagactgga tggatatatg atatggaaaa tgaaagtgat
6661  aaatattatt tcaatccaga aactaaaaaa gcatgcaaag gtattaattt aattgatgat
6721  ataaaatatt attttgatga gaagggcata atgagaacgg tccttatatc atttgaaaat
6781  aataattatt acttaatga gaatggtgaa atgcaatttg gttatataaa tatagaagat
6841  aagatgttct attttggtga agatggtgtc atgcagattg gagtatttaa tacaccagat
6901  ggatttaaat actttgcaca tcaaaatact ttggatgaga attttgaggg agaatcaata
```

```
6961  aactatactg gttggttaga tttagatgaa aagagatatt attttacaga tgaatatatt 7021  gcagcaactg gttcagttat tattgatggt gaggagtatt attttgatcc tgatacagct 7081  caattagtga ttagtgaata g
```

Outbreaks of CDI have been reported with Toxin A-negative/Toxin B-positive strains, which indicates that Toxin B is also capable of playing a key role in the disease pathology. TcdA and TcdB are 308 and 270 kDa proteins, respectively. The toxins belong to the family of large clostridial toxins (LCTs), which are a group of homologous, high molecular weight proteins that further include the lethal and hemorrhagic toxins from *C. sordellii* (TcsL and TcsH, respectively), α-toxin from *C. novyi* (Tcnα) and a cytotoxin from *C. perfringens* (TpeL). The homologous proteins intoxicate host cells through a multistep mechanism that involves (i) receptor binding and endocytosis, (ii) pore formation and translocation of the GTD across the endosomal membrane, (iii) autoprocessing and release of GTD into the cytosol, and (iv) glucosylation of host Rho GTPase. Both Toxins A and B also contain a second enzyme activity in the form of a cysteine protease which appears to play a role in the release of the effector domain into the cytosol after translocation. The *C. difficile* binary toxin modifies cell actin by a mechanism which involves the transfer of an ADP-ribose moiety from NAD onto its target protein. Given the similarities in toxin structure and the genetic similarities of Clostridial species, it is likely that the expression of toxins of other spore-forming toxigenic *Clostridium* species are regulated in a similar manner to that of *C. difficile*, i.e., in a manner sensitive to environmental conditions that can be influenced by commensal bacteria as described herein.

Additional bacterial toxins, including additional Clostridial toxins, are described in Table 1.

TABLE 1

Bacterial toxins and their mechanism of action.

| Toxin | Organism/Result of Gram stain | Mechanism | Clinical Features |
|---|---|---|---|
| Toxin A/toxin B | *Clostridium difficile* (gram-positive) | Inhibits cytoskeletal action in epithelial cells | Diarrhea, vomiting |
| Anthrax toxins (edema toxin [EF], lethal toxin [LF]) | *Bacillus anthracis* (gram-positive) | Adenylyl cyclase (EF), metalloprotease (LF) | Edema and skin necrosis; shock |
| Adenylate cyclase toxin | *Bordetella pertussis* (gram-negative) | Adenylyl cyclase | Tracheobronchitis |
| Botulinum toxins (C2/C3 toxin) | *Clostridium botulinum* (gram-positive) | Blocks release of acetylcholine, ADP-ribosyltransferase | Muscle paralysis, botulism |
| Lecithinase (α-toxin; perfringolysin O) | *Clostridium perfringens* (gram-positive) | Phospholipase | Gangrene; destraction of phagocytes |
| Tetanus toxin | *Clostridium tetani* (gram-positive) | Blocks release of inhibitory neurotransmitters | Spasms and rigidity of the voluntary muscles; characteristic symptom of "lockjaw" |
| Diphtheria toxin | *Corynebacterium diphtheria* (gram-positive) | ADP-ribosylates EF-2, inhibiting protein synthesis | Respiratory infection; complicating myocarditis with accompanying neurologic toxicity |
| CNF-1, CNF-2 | *Escherichia coli* (gram-negative) | Affects ρ-GTP-binding regulators | Diarrhea |
| Heat-stable toxin | *Escherichia coli* (gram-negative) | Secondary message regulation | Diarrhea |
| Hemolysin | *Escherichia coli* (gram-negative) | Heptameric pore-forming complex (hemolysin) | Urinary tract infections |
| Shiga-like toxin | *Escherichia coli* (gram-negative) | Stops host protein synthesis | Hemolytic-uremic syndrome, dysentery |
| Exotoxin A | *Pseudomonas aeruginosa* (gram-negative) | ADP-ribosylates elongation factor-2 (EF-2), inhibiting protein synthesis | Respiratory distress; possible role as virulence factor in lung infections of cystic fibrosis patients |
| Shiga toxin | *Shigella dysenteriae* (gram-negative) | Stops host protein synthesis | Dysentery |
| α-Toxin | *Staphylococcus aureus* (gram-positive) | Heptameric pore-forming complex (hemolysin) | Abscess formation |
| Toxic shock syndrome toxin 1 (TSST-1) | *Staphylococcus aureus* (gram-positive) | Superantigen activates T-cell populations, cross-linking $V_\beta$TCR and class II MHC | Cytokine cascade elicits shock; capillary leak syndrome and hypotension |
| Pneumolysin | *Streptococcus pneumonia* (gram-positive) | Pore-forming complex (hemolysin) | Pneumonia |
| Pyrogenic exotoxin | *Streptococcus pyogenes* (gram-positive) | Superantigen activates T-cell populations, cross-linking $V_\beta$TCR and class II MHC | Cytokine cascade elicits shock; capillary leak syndrome and hypotension |
| Streptolysin O | *Streptococcus pyogenes* (gram-positive) | Pore-forming complex (hemolysin) | "Strep" throat, scarlet fever |

TABLE 1-continued

Bacterial toxins and their mechanism of action.

| Toxin | Organism/Result of Gram stain | Mechanism | Clinical Features |
| --- | --- | --- | --- |
| Cholera toxin | *Vibrio cholera* (gram-negative) | Disrupts adenylyl cyclase | Watery diarrhea, loss of electrolytes and fluids |

Abbreviations used: ADP, adenosine diphosphate;
EF, elongation factor;
LF, lethal factor;
GTP, guanosine triphosphate;
TCR, T-cell receptor;
MHC, major histocompatability complex Regulation of *C. difficile* Toxin Gene Expression

*C. difficile*'s pathogenicity locus, PaLoc, contains the toxin operon with genes tcdA, tcdB and tcdE that respectively encode the A and B portions of the toxin and a putative holin involved in toxin export. In addition to the toxins TcdA and TcdB, the PaLoc in pathogenic strains encodes TcdR, a member of the extracytoplasmic function family of alternative sigma factors that plays a critical role in activating the expression of tcdA and tcdB; transcription of the tcdA and tcdB genes requires TcdR to enable RNA polymerase to have specificity to bind the toxin gene promoters. Within *C. difficile*, multiple nutritional regulators influence PaLoc gene expression at the level of tcdR and the tcdAEB operon genes. In particular, *C. difficile* primarily elaborates toxin under starvation conditions to extract nutrients from the host and to also enable shedding of spores. Exogenously added glucose, amino acids—proline and leucine in particular, as well as cysteine, inhibit toxin production through codY, ccpA, rex and/or prdR activation. Exogenously added butyrate induces toxin production, while butanol does not. The symptoms of CDI correlate with the expression of TcdR. The genes encoding TcdA (tcdA) and TcdB (tcdB) are located within a 19.6-kb chromosomal region that makes up the PaLoc. The activity of TcdR is modulated by TcdC, an anti-sigma factor that destabilizes the TcdR-core RNA polymerase complex. TcdC seems to be most active in rapidly growing cells.

Stickland Fermentation

Stickland reactions couple metabolism of pairs of amino acids in which one amino acid, acting as an electron donor, is oxidatively deaminated or decarboxylated and a second amino acid, acting as an electron acceptor, is reduced or reductively deaminated (Stickland, L. H., Biochem. J. 28: 1746-1759 (1934). The most efficient electron donors are leucine, isoleucine, and alanine, and the most efficient acceptors are glycine, proline. Hydroxyproline is also an efficient Stickland acceptor.

*C. difficile*, like other cluster XI species of clostridia, uses Stickland fermentations to extract energy from amino acids. Donor amino acids include the electron-rich branched chain amino acids leucine, isoleucine and valine (BCAA), aromatic amino acids phenylalanine, tyrosine and tryptophan, and acceptor amino acids glycine and proline. Cellular proline and glycine reductases transfer electrons from Stickland donor amino acids to recipients proline and glycine. The reaction consumes one NADH to one NAD+ in the reductive pathway, with release of ammonia and the branched short-chain fatty acids isocaproate, isobutyrate and isovalerate, and regenerates 2 NAD+ to NADH in the oxidative pathway. to regenerate NAD+ to NADH.

The reduction of the Stickland acceptors glycine and proline is performed by two selenium-dependent reductases, glycine reductase (GR) and D-Proline reductase (PR), respectively. GR catalyzes the reductive deamination of glycine to acetyl phosphate and ammonium, and PR reductively cleaves D-proline to 5-aminovalerate. The glycine reductase and proline reductase operons, respectively, mediate these reactions. Each reductase is comprised of multiple polypeptides and is dependent upon selenocysteine residues for activity. FIG. 5A-5I show metabolites from the input donor or acceptor amino acids. In one embodiment described is that the Stickland donor amino acids proline and glycine have a powerful inhibitory effect on *C. difficile* toxin production.

Genes encoding the *C. difficile* GR and PR subunits are clustered in two distinct genetic loci (grd and prd, respectively) on the chromosome of *C. difficile* strain 630. The grd locus contains eight genes. Two of the genes, grdA and grdB, likely encode the selenocysteine-containing subunits of GR. The seven genes of the prd operon include prdF, that encodes a d-proline racemase, and prdB, that encodes the selenium-containing subunit of PR.

In one embodiment, prdR activates the proline reductase operon and represses the glycine reductase operon. prdR suppresses the expression of *C. difficile* toxins by inhibiting butyrate, coDY, ccpA, tcdR, and/or tcdA production. The Stickland fermentation pathway using proline as the Stickland acceptor generates NADH and the metabolite 5-aminovalerate from proline. The acetate-generating pathway generates NADH and the metabolite acetate from glycine. *C. difficile* consumes large amounts of NADH in the carbohydrate metabolism pathway from acetate. Therefore, acetate-generating pathways are more prone to inducing a stress response pathway, leading to the generation of butyrate, codY, ccpA, tcdR, and/or tcdA toxins.

In one embodiment, the method of treating or preventing a pathology caused by expression of a bacterial toxin compromises administering at least one bacterial organism that encodes and expresses one or more of D-Proline reductase (PR), Glycine reductase (GR), thioredoxin, or choloylglycine.

As noted above, the *C. difficile* pathogen can also utilize sugars, sugar alcohols, and ethanolamine for energy production (carbohydrate metabolism and other energy production approaches used by *C. difficile* are discussed further below). Toxin production in *C. difficile* responds to environmental conditions, including the availability of specific nutrients, temperature changes, and alteration of the redox potential. The presence of a rapidly metabolizable carbon source or certain amino acids inhibits toxin gene expression. When cells are grown in rich medium, the toxin genes are transcribed only when the cells reach stationary phase. While not wishing to be bound by theory, this is fully consistent with the discovery that protective commensal species are highly proteolytic and induce genes in *C. difficile* that, for example, promote the use of ethanolamine in the gut environment as an energy source.

Nutritional regulators within *C. difficile*, including codY, ccpA, and rex sense aspects of amino acid, sugar, Stickland reactions and NAD+/NADH pools respectively. Each of these regulons also exerts effects on PaLoc gene expression through direct and indirect mechanisms.

Upon binding of BCAA and GTP, codY strongly represses tcdR transcription, with subsequent reduction of tcdAEB gene expression. ccpA, active under carbon starvation conditions, binds the tcdAEB operon promoter, enhancing toxin expression if the tcdR sigma factor has been expressed. Thus, starvation where carbohydrates and Stickland amino acids are limiting induces expression of toxin. Under conditions of nutrient sufficiency, codY, ccpA and rex act coordinately through direct and indirect mechanisms to repress the expression of PaLoc genes. Notably, exogenous in vitro addition of Stickland amino acids or carbohydrate energy sources represses *C. difficile* toxin expression through the above mechanisms, while exogenous addition of butyrate, a key end product of anaerobic carbohydrate fermentation, can alone induce toxin expression. Together, these gene regulatory systems promote *C. difficile* toxin expression under conditions of starvation and energy limitation by sensing preferred sources for intracellular energy production.

NAD+/NADH

Figure 9:
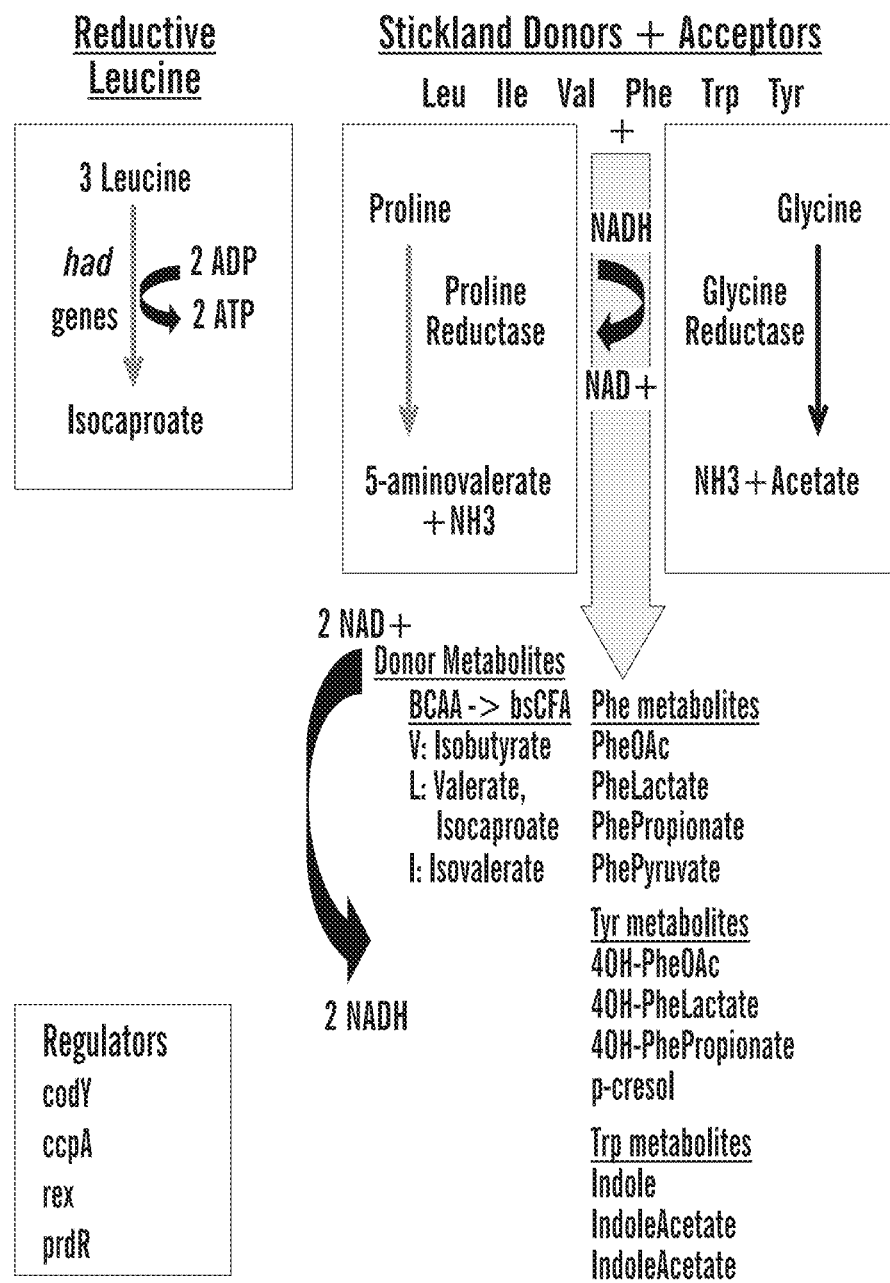
FIG. 9 shows a schematic of the metabolic pathways utilized by *C. difficile*.
Figure 9:
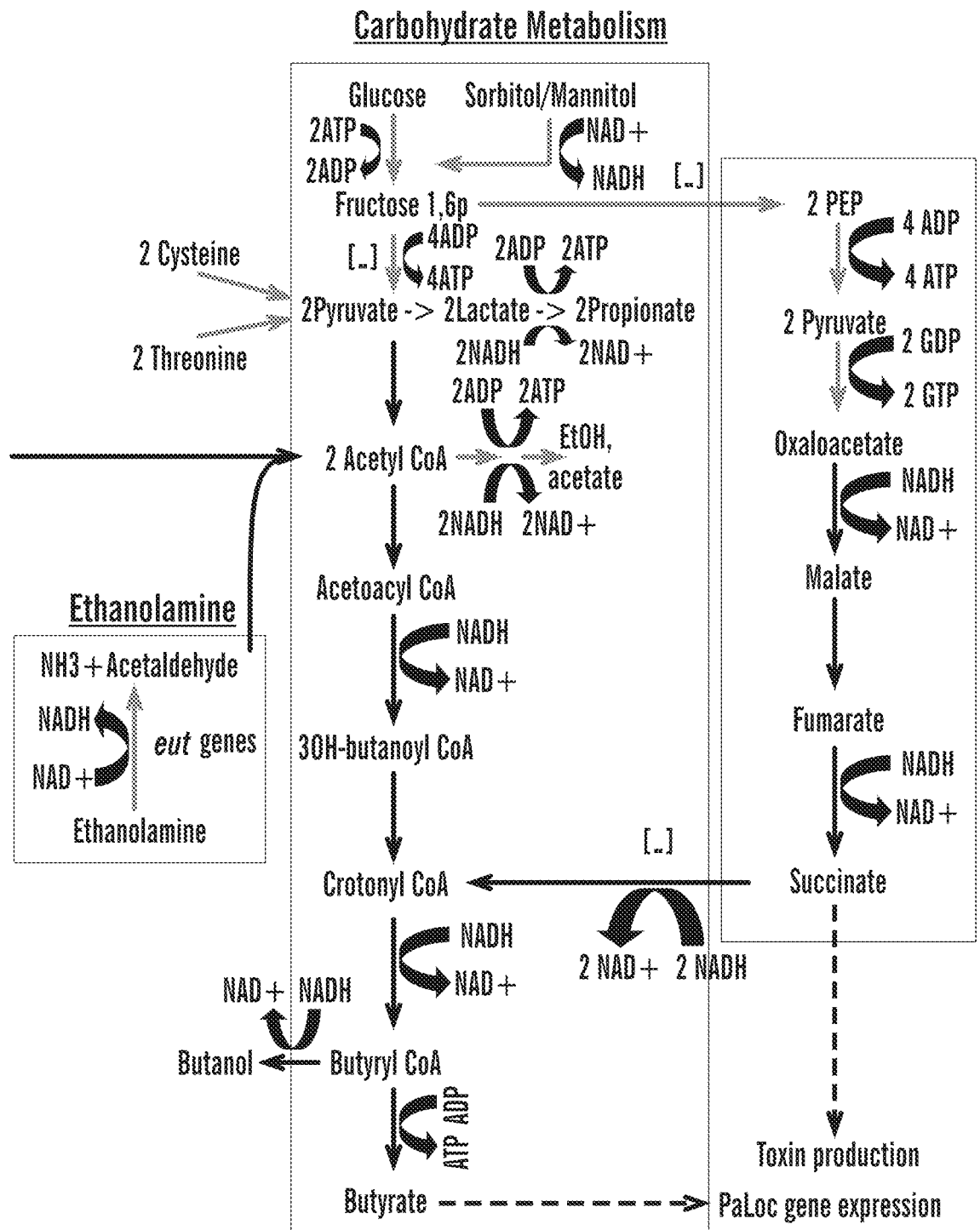

The balance of NAD+ to NADH influences the expression of *C. difficile* toxin. The Stickland reaction involves the coupled oxidation and reduction of pairs of amino acids to generate ATP and NAD+. The oxidative pathway generates ATP and NADH, while the reductive pathway regenerates NAD+ from NADH. Proline reductase (PR) and glycine reductase (GR) expression are specifically induced in the presence of proline and glycine, respectively, and carry out the respective reduction of these amino acids. Moreover, the addition of proline to the growth medium decreases the expression of GR-encoding genes, suggesting a preferential utilization of proline for NAD+ regeneration. PrdR, which is a regulator that responds to proline, mediates both the proline-dependent activation of PR and the proline-dependent repression of toxin genes and the GR operon. When proline is limiting in the medium or if PrdR or PR is inactive, the alternative reductive pathways are induced. In fact, both PrdR and a functional PR are indirectly required for the proline-dependent regulation of the alternative reductive pathways in response to the intracellular concentration of NADH and NAD+. This process involves the global redox-sensing regulator Rex. In a number of Gram-positive bacteria, Rex acts as a repressor of genes that are important for growth using fermentation. Rex directly senses changes in redox status and is only active as a DNA-binding protein when the intracellular NADH/NAD+ ratio is low. The protein Rex is stimulated by NAD+ but inhibited by NADH. Although Rex, like PrdR, controls the proline-responsive expression of these alternative reductive pathways, Rex also mediates the proline-dependent repression of toxin gene expression, probably through the regulation of butyrate production. As a result, when proline is not limiting the NADH/NAD+ ratio is low and Rex is active as a repressor of the alternative NAD+ regeneration pathways. In contrast, if proline becomes limiting, the NADH/NAD+ ratio increases and NADH prevents Rex-dependent repression of the alternative pathways. The regeneration of NAD+ using these alternative reductive pathways leads to an accumulation of butyrate, a compound that stimulates toxin synthesis as shown in FIG. 9.

In one embodiment, the method of treating or preventing a pathology caused by expression of a bacterial toxin compromises administering at least one bacterial organism that promotes Stickland fermentation by *C. difficile*. In another embodiment, the bacterial organism itself performs Stickland fermentation—bacteria that have evolved to perform Stickland fermentation tend to express, among other things, extracellular proteolytic activities that can feed amino acids into the Stickland fermentation pathway for *C. difficile*.

The following discusses the *C. difficile* toxin regulatory factors involved in sensing environmental conditions.

TcdR

TcdR or "alternative RNA polymerase sigma factor TcdR" is encoded by the tcdR gene. Sequences for TcdR are known for a number of species, e.g., for *C. difficile* 630 (the TcdR NCBI Gene ID is 4914073) and polypeptide sequence (e.g., YP_001087134.1 (SEQ ID NO: 5). The sequence for the TcdR gene product is as follows (SEQ ID NO: 5):

```
                                                      (SEQ ID No: 5)
  1  mqksfyeliv larnnsvddl qeilfmfkpl vkklsrvlhy eegetdliif fieliknikl 61  ssfseksdai ivkyihksll nktfelsrry skmkfnfvef denilnmknn yqsksvfeed 121  icffeyilke lsgiqrkvif ykylkgysdr eisvklkisr qavnkaknra fkkikkdyen 181  yfnl
```

The tcdR gene sequence for *C. difficile* 630 is as follows (SEQ ID NO: 6):

```
                                                      (SEQ ID NO: 6)
  1  atgcaaaagt cttttatga  attaattgtt ttagcaagaa ataactcagt agatgatttg 61  caagaaattt tatttatgtt taagccatta gtaaaaaaac ttagtagagt tttacattat 121  gaagagggag aaacagattt aataatattt tttattgaat aataaaaaa  tattaaatta 181  agtagctttt cagaaaaaag cgatgctatt atagtcaaat atattcataa atcattactg 241  aataagactt ttgagttgtc tagaagatat tctaaaatga agtttaattt tgtagaattt 301  gatgaaaata tcttaaatat gaaaaataat tatcaaagta agtctgtttt tgaggaagat
```

```
361 atttgttttt tcgaatatat tttgaaagaa ttatctggta ttcaaagaaa agttattttt 421 tataaatatt taaaaggata ttctgataga gaaatatcag tgaaattaaa aatatctaga 481 caagctgtta ataaggctaa aaatagagca tttaaaaaaa taaaaaaaga ctatgaaaat 541 tattttaact tgtaa
```

TcdR polypeptide expression can be detected or measured via immunoassay, e.g., via an ELISA using antibodies raised against TcdR. TcdR expression can also be detected or measured by RT-PCR using primers specific for the tcdR mRNA.

CodY

CodY or "transcriptional repressor CodY" refers to a protein encoded by the codY gene. CodY is a sensor of carbon and nitrogen, and binds GTP and leucine to become active. When active, it represses transcription through a number of genes. C. difficile actively undergoing Stickland fermentations (abundant leucine and energy) represses toxin production in part through CodY's effects on tcdR and tcd operon gene expression. Transcription of the tcdR gene is repressed during the rapid exponential growth phase by CodY. CodY is active in cells with an excess of branched-chain amino acids (isoleucine, leucine, and valine) and GTP. When the cells reach stationary phase, the intracellular concentrations of these ligands decrease and CodY is less able to bind as a repressor, leading to derepression of tcdR transcription.

Sequences for CodY are known for a number of species, e.g., for C. difficile 630 (the codY NCBI Gene ID 4915868) and polypeptide sequence (e.g., YP_001087769.1 (SEQ ID NO: 7). The sequence for the codY gene product is as follows (SEQ ID NO: 7):

```
                                                        (SEQ ID No: 7)
  1 masevlqktr kinktlqtsg gssvsfdlla galgdvlssn vyvvsakgkv lglhlndvqd 61 ssviedeytk qkkfsdeytq nvlkidetle nlngekilei fpeehgrlqk yttvvpilgs 121 gqrlgtlvls rysnsfnddd lviaeysatv vgleilraig eeleeemrkk avvqmaigtl 181 syseleaveh ifaeldgkeg llvaskiadr vgitrsvivn alrkfesagv iesrslgmkg 241 thirilndkl tdelkklknn q
```

The coDY gene sequence for C. difficile 630 is as follows (SEQ ID NO: 8):

```
                                                        (SEQ ID NO: 8)
  1 atggcaagtg aagtgttaca aaaaacaagg aaaataaata aaacattaca aacaagtggt 61 ggaagcagtg tctcttttga tttactggcc ggagcattgg gcgacgtttt aagttctaat 121 gtttatgtag taagtgcaaa aggtaaagta ctaggtcttc atttaaatga tgttcaagac 181 agttcagtta tagaagatga gtatactaag caaaagaaat ttcagatga atatactcaa 241 aatgtgttaa aaattgatga aacattagaa aatttaaatg gtgagaagat attagaaatc 301 tttcctgaag aacatggaag attacaaaaa tatactacag tagttccaat attaggaagc 361 ggtcaaagat taggaacatt ggtactttca agatattcaa attcattcaa tgatgatgat 421 ttagtaatag ctgaatacag tgcaactgtt gttggtcttg aaatattaag agcaataggt 481 gaagaattag aagaagaaat gagaaagaaa gctgtagttc aaatggcaat aggcactctg 541 tcctactccg agcttgaagc agttgaacat attttttgctg aattggatgg aaaagaaggt 601 ctacttgtag caagtaagat agctgataga gttggtataa ctaggtctgt aatagtaaat 661 gcacttagaa aatttgagag tgcaggtgtg atagaatcaa gatcattagg tatgaaaggt 721 actcatataa gaatacttaa tgacaaactt acagatgaat taaaaaaatt aaaaaacaat 781 caataa
```

CodY polypeptide expression can be detected or measured via immunoassay, e.g., via an ELISA using antibodies raised against CodY. CodY expression can also be detected or measured by RT-PCR using primers specific for the codY mRNA.

CcpA

Catabolite control protein A, CcpA, senses carbon state within the cell and is a global regulator of carbon metabolism in Gram-positive bacteria. In *B. subtilis*, fructose derivatives of glucose bind and activate CcpA. Regulation of *C. difficile* toxin production by carbon source is mediated at least in part by CcpA, which is a direct repressor of the tcdA and tcdB genes.

CcpA protein is encoded by the ccpA gene. Sequences for CcpA are known for a number of species, e.g., for *C. difficile* 630 (the CcpA NCBI Gene ID 4915199) and polypeptide sequence (e.g., YP_001087548.1 (SEQ ID NO: 9). The sequence for the CcpA gene product is as follows (SEQ ID NO: 9):

```
                                                       (SEQ ID No: 9)
  1  mkgnitikdv akqagvsist vsrvindskp vtdevkqkvl eviketgyip nplarslvtk 61  ksqligvivp evsdsfvnev lngieevakm ydydillant ysdkeqelks inllrakqve 121  givmiswive qehinyiqnc gipatyiskt arnydiytvs tsneeatfdm tehlikkghe 181  kiafimtskd dtvlemerla gyekalsnnn ieldksliky ggtdyesgyn smkellddgi 241  iphaafvtgd eaaigainai cdagykvped isvagfndvk iarmyrpklt tvyqplydmg 301  avairmvikl inkelienkk ielpyrivdr esvterkk
```

The CcpA gene sequence for *C. difficile* 630 is as follows (SEQ ID NO:10):

```
                                                       (SEQ ID NO: 10)
  1  atgaaaggca atataacgat aaaagatgtt gctaaacaag caggagtgtc aatatctact 61  gtatctagag ttataaatga ttcaaaacct gtaactgatg aagtcaaaca aaaagtttta 121  gaggttataa aagagactgg atatatacca aatccacttg ctagaagctt agtaacaaag 181  aagagtcaat taatagggt aatagttcca gaagtttcag attcttttgt taatgaggtg 241  ttaaatggga tagaagaggt tgctaaaatg tatgactatg atattctttt agcgaataca 301  tactctgata aggaacaaga acttaagagt ataaatctat tgagagcaaa acaagtggaa 361  ggtatagtta tgatttcatg gatagttgaa caagaacata tcaactatat acaaaattgt 421  ggaataccag cgacatatat aagtaaaact gctagaaatt atgatatata tacagtaagt 481  actagcaacg aagaagctac ttttgatatg acagagcatc ttataaagaa aggtcatgaa 541  aagatagctt ttataatgac gagtaaagat gatactgttt tagaaatgga aagacttgct 601  ggttatgaga aagcactttc aaataacaat atagaattag acaagagttt gattaagtat 661  ggtggaactg attatgagag tggatacaat agtatgaaag aactattaga tgatggaata 721  atacctcatg cggcttttgt aacaggtgat gaggctgcca taggtgctat aaatgctata 781  tgtgatgctg gatataaggt tccagaagac atatctgttg caggatttaa tgatgttaag 841  atagctagaa tgtatagacc taaacttact acagtatatc aacctctata cgatatggga 901  gcagtagcaa taagaatggt tataaaatta ataataagg aattaattga aaataagaaa 961  atagaattac cttatagaat tgttgataga gaaagtgtta cagaaagaaa aaaataa
```

CcpA polypeptide expression can be detected or measured via immunoassay, e.g., via an ELISA using antibodies raised against CcpA. CcpA expression can also be detected or measured by RT-PCR using primers specific for the ccpA mRNA.

Rex

Rex or "redox-sensing transcriptional repressor" senses energy state of the cell, particularly the concentration of NADH/NAD+. When activated by low energy (high concentrations of NAD+), Rex is known to indirectly lead to toxin expression, though the mechanisms of action are not well described. High NAD+ and butyrate levels, the latter possibly reflective of NADH consumption, are believed to promote C. difficile toxin production through this pathway.

Sequences for Rex and the gene sequence encoding it are known for a number of species, e.g., for C. difficile 630 (the rex NCBI Gene ID 4914836) and polypeptide sequence (e.g., YP_001086640.1 (SEQ ID NO:11). The sequence for the Rex gene product is as follows (SEQ ID NO: 11):

```
                                                    (SEQ ID NO: 11)
  1  mlgnknisma virrlpkyhr ylgdlldrdi qrisskelsd iigftasqir qdlnnfggfg 61  qqgygynvea lhteigkilg ldrpynavlv gagnlgqaia nyagfrkagf eikalfdanp 121  rmiglkiref evldsdtled fiknnnidia vlcipkngaq evinrvvkag ikgvwnfapl 181  dlevpkgviv envniteslf tlsylmkegk
```

The rex gene sequence for C. difficile 630 is as follows (SEQ ID NO:12):

```
                                                    (SEQ ID NO: 12)
  1    atgttgggaa ataaaaatat atcaatggca gttataagaa ggctcccaaa atatcataga 61    tatcttggag acttattaga tagggatata caaagaatat cttctaaaga attgagtgat 121    ataatagggt ttaccgcttc tcaaataaga caagatttaa acaactttgg tggatttgga 181    caacaaggat atggttataa tgtagaagct cttcatactg agataggtaa aattcttggg 241    ttggatcgac catacaacgc agttcttgta ggagcaggta acttaggaca agctatagcc 301    aattatgcag gatttagaaa agctggattc gagataaaag ctttatttga tgcaaatcct 361    agaatgatag gtttaaagat aagagagttt gaagtattag attcagatac tttagaagac 421    tttataaaaa acaataatat agatattgct gtattatgta tacctaaaaa tggagcacaa 481    gaagttatta atagagttgt aaaagctgga atcaaaggtg tatggaattt tgcaccttta 541    gatttagaag ttccgaaagg tgttatagtt gaaaatgtaa acttaacaga aagtttattt 601    accttatcgt atttaatgaa agaaggaaag tag
```

Rex polypeptide expression can be detected or measured via immunoassay, e.g., via an ELISA using antibodies raised against Rex. Rex expression can also be detected or measured by RT-PCR using primers specific for the rex mRNA.

Energy status of C. difficile is important for determining whether the pathogen expresses toxin. The following considers various pathways in addition to Stickland fermentation that C. difficile uses to extract energy needed for metabolism from its environment.

C. difficile Carbohydrate Utilization

Figure 5D:
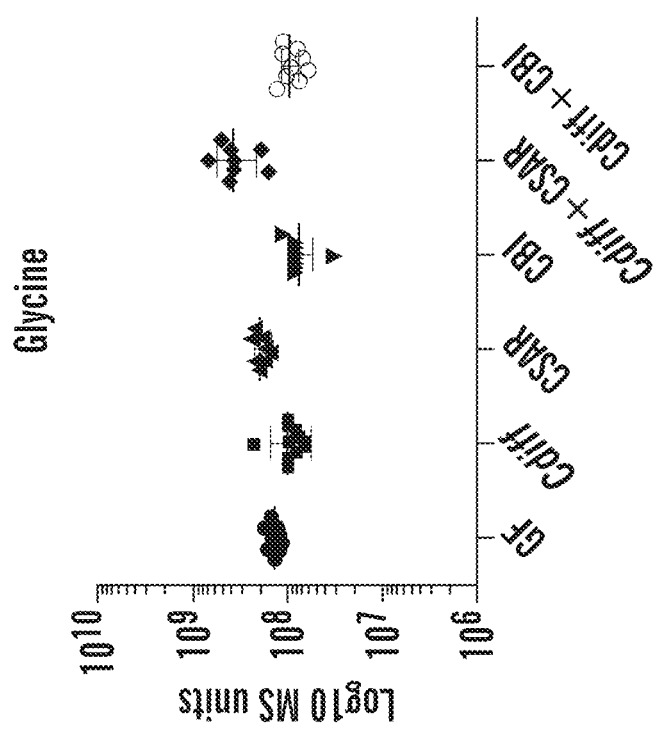
Figure 5E:
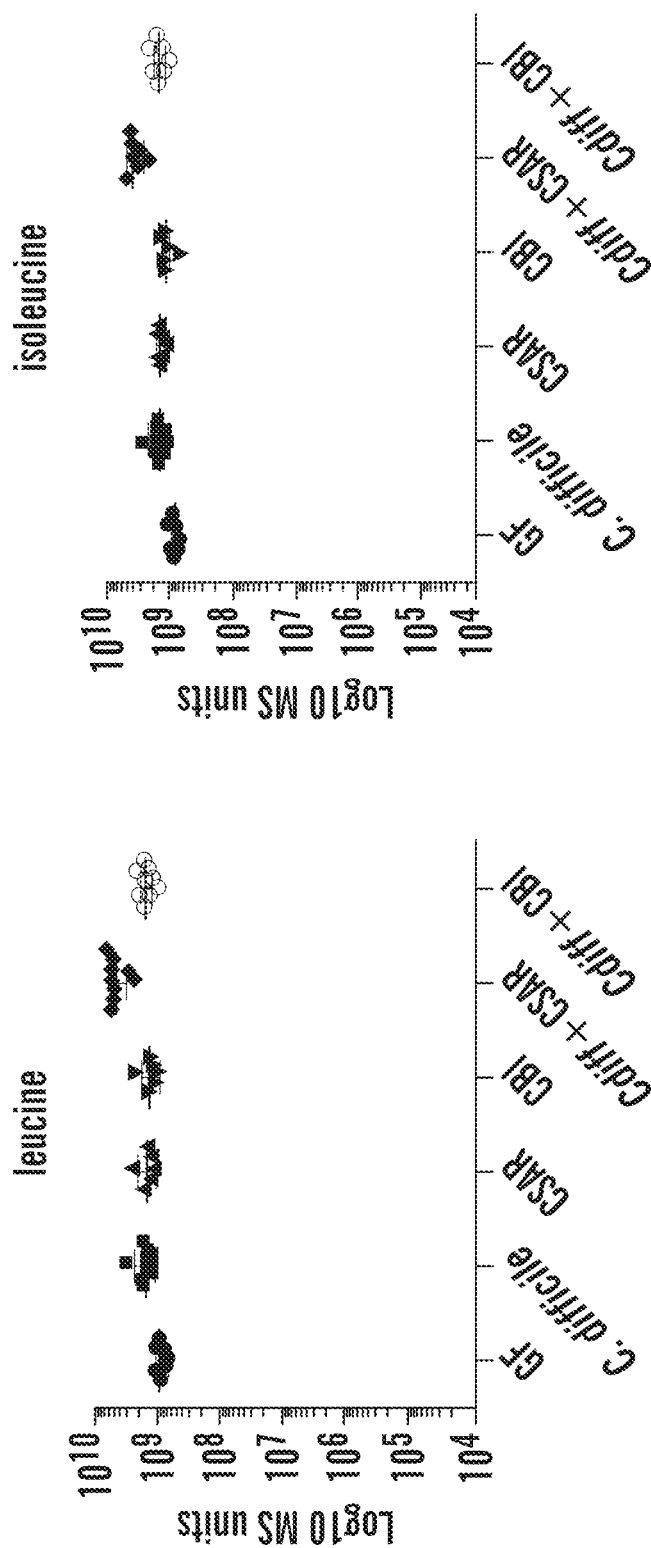
Figure 5E:
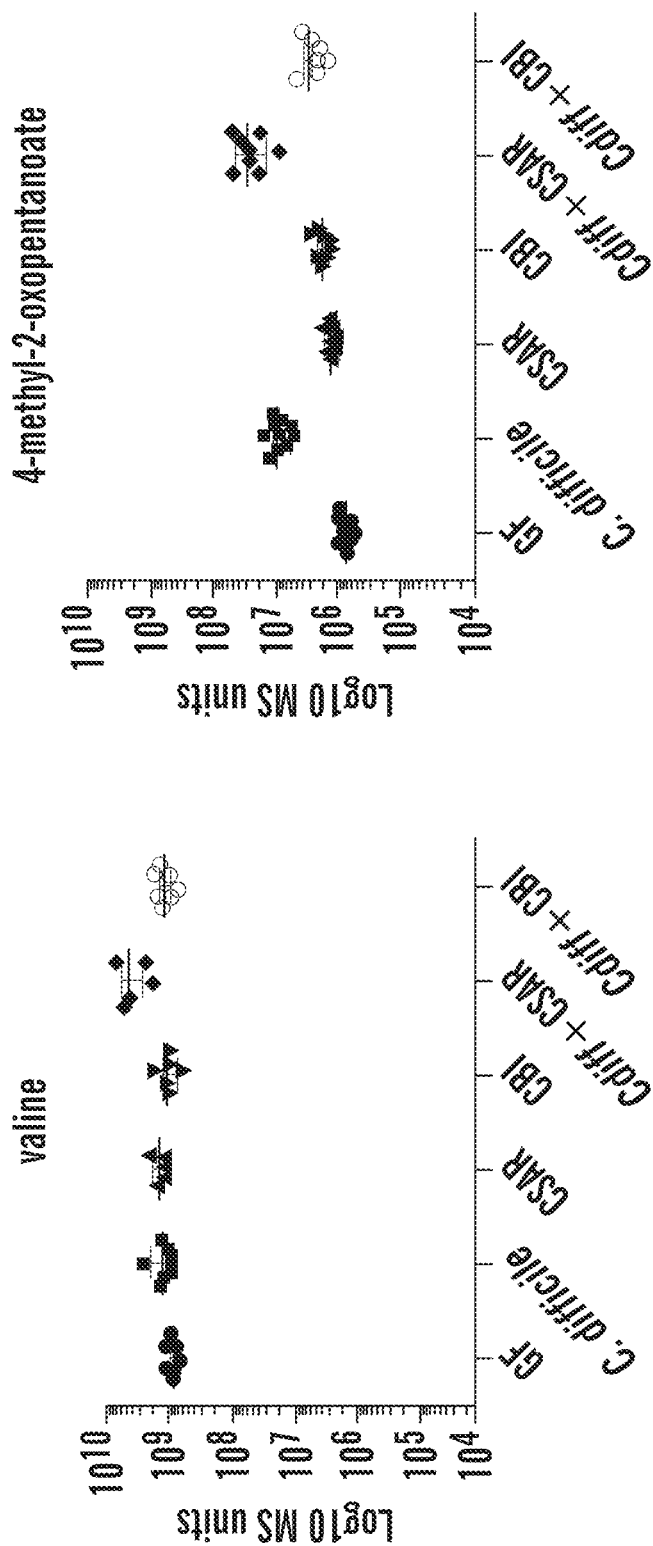
Figure 5E:
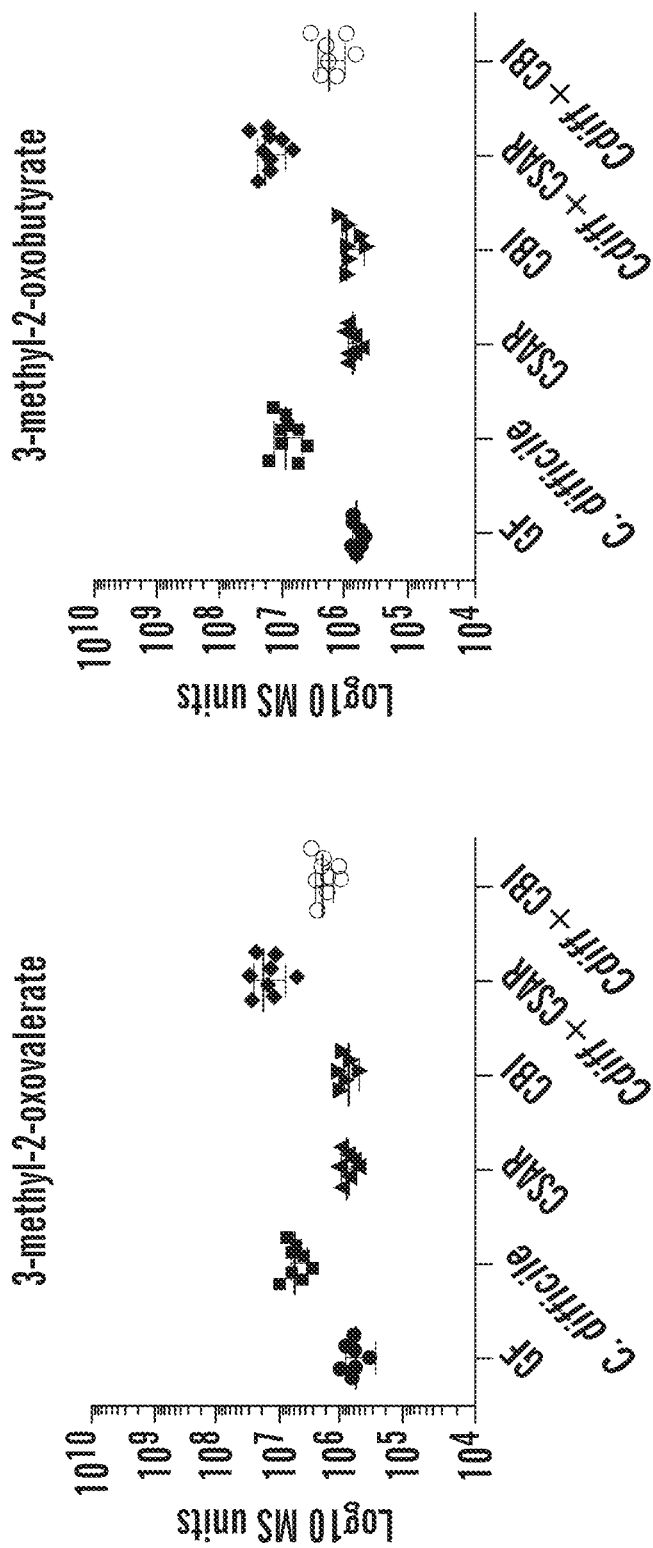
Figure 5E:
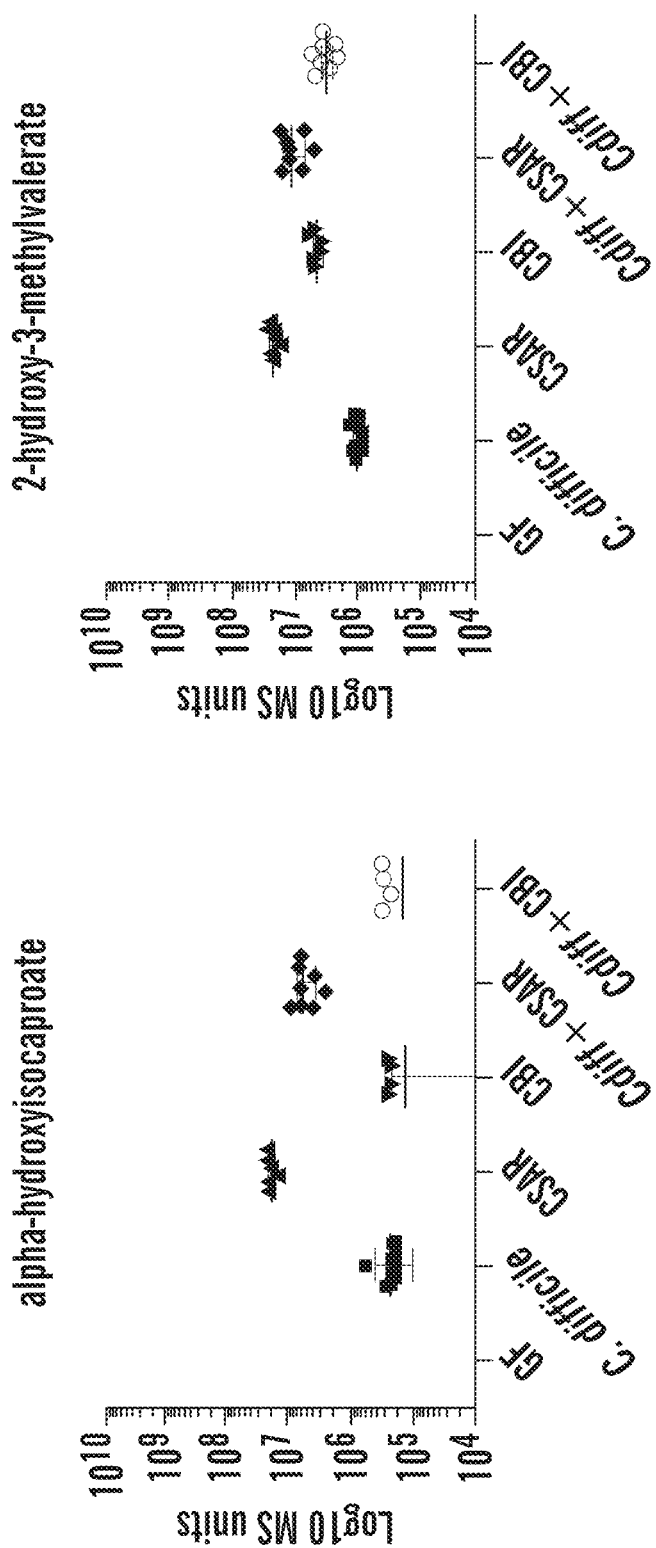
Figure 5E:
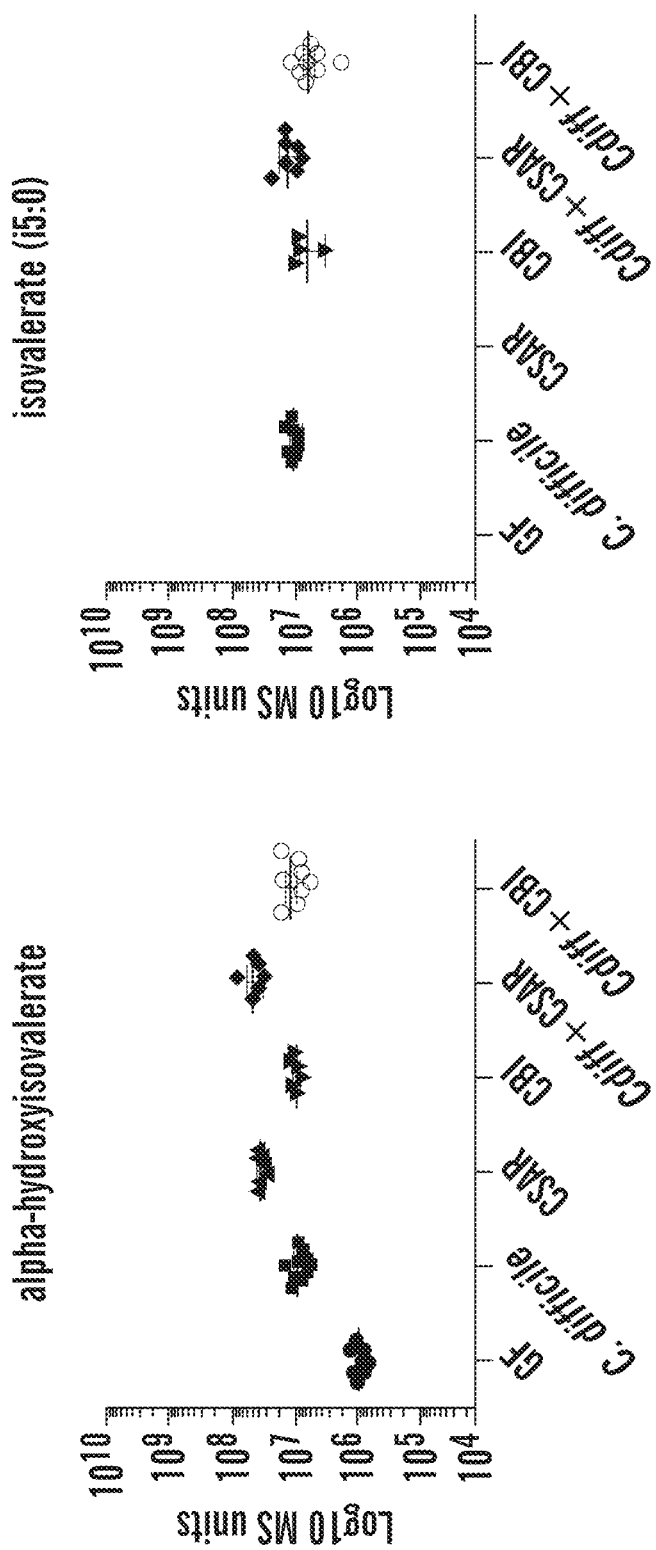
Figure 5F:
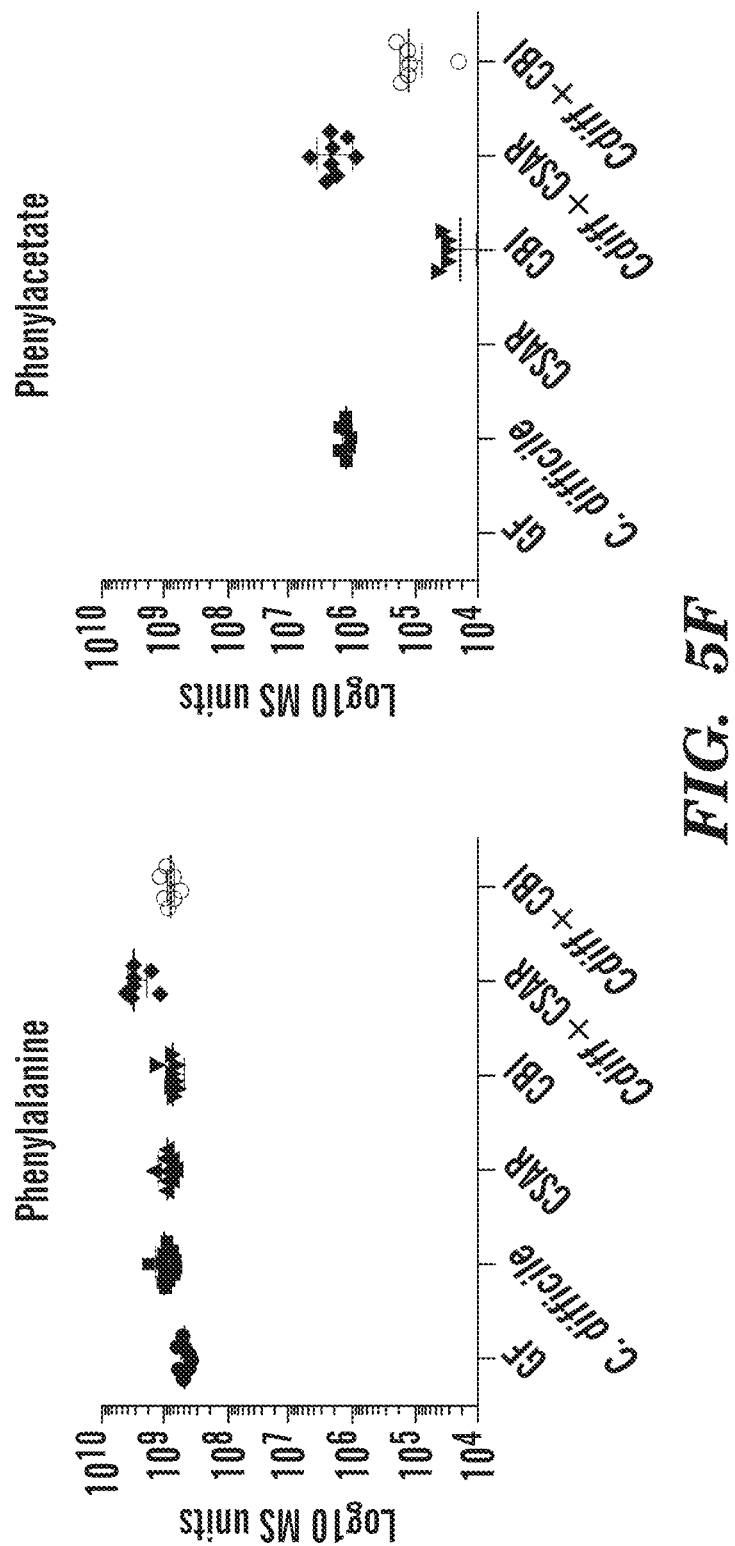
Figure 5F:
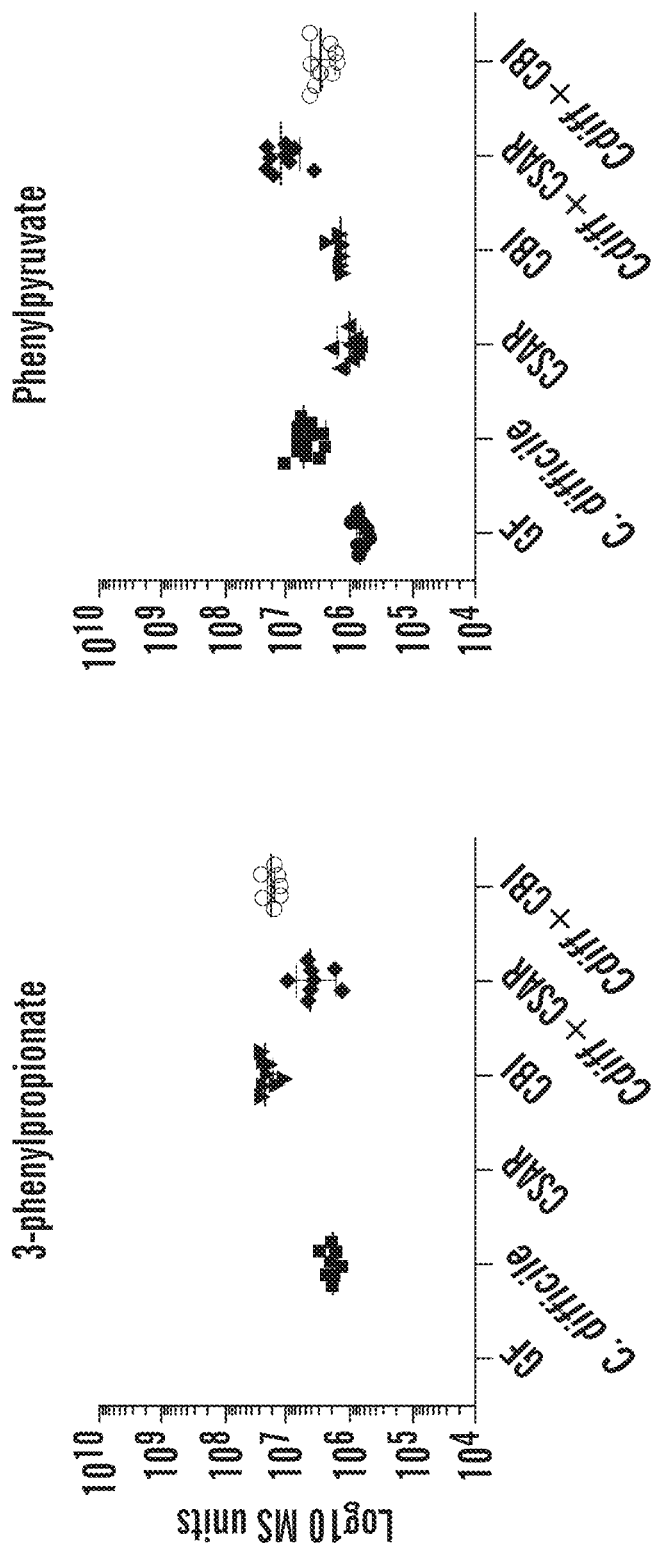
Figure 5F:
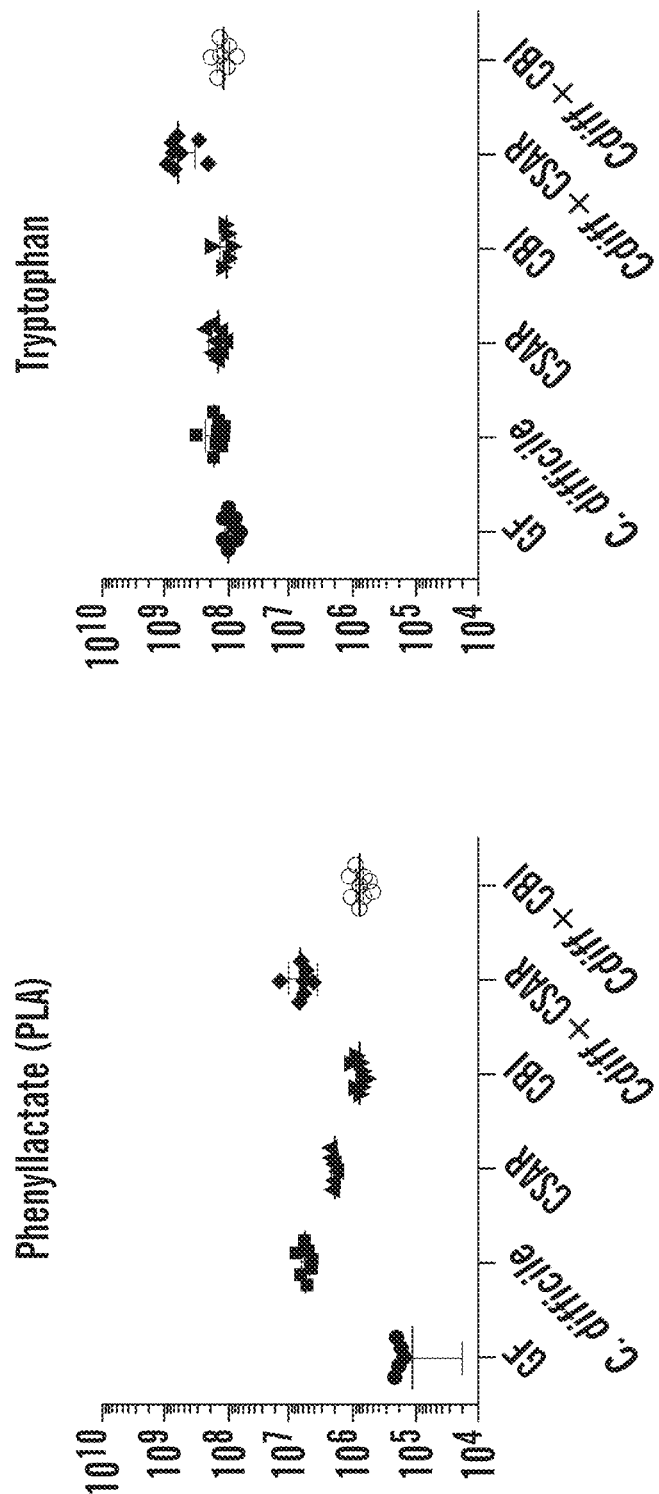
Figure 5F:
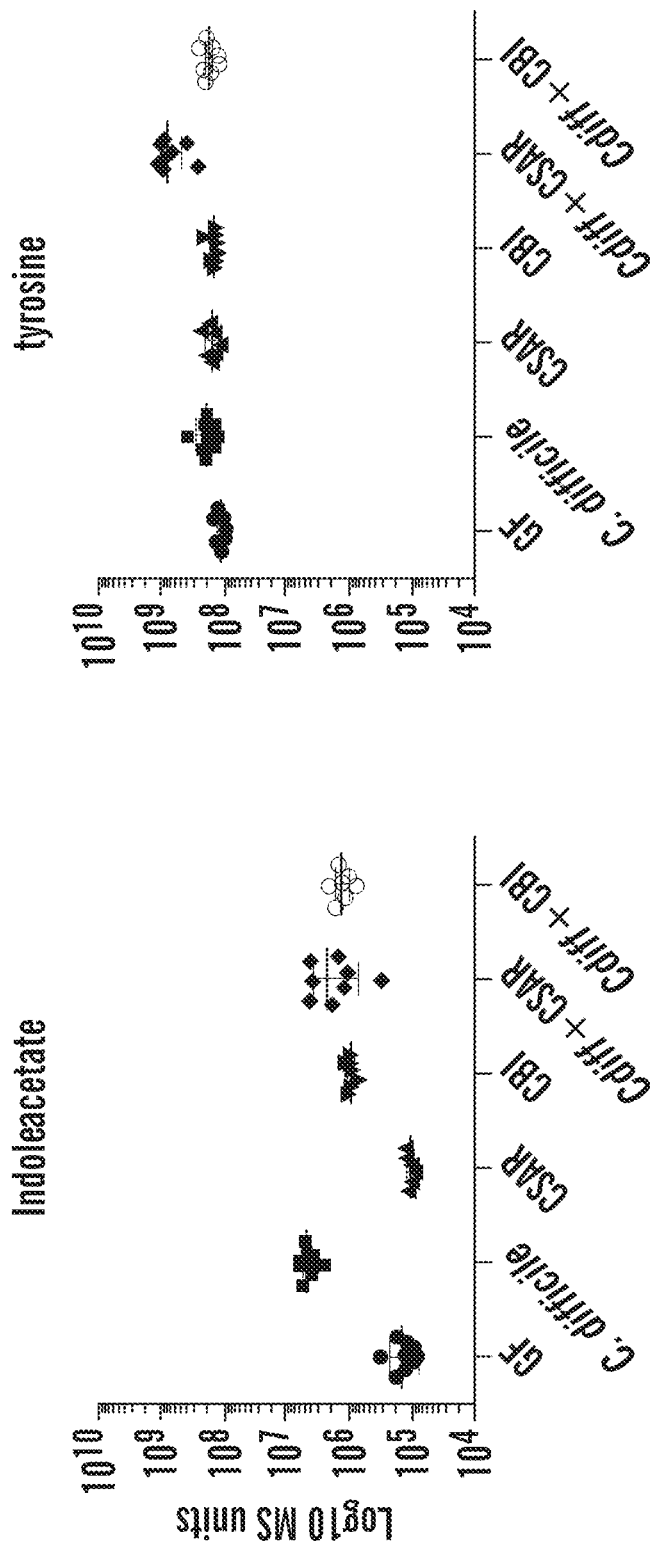
Figure 5F:
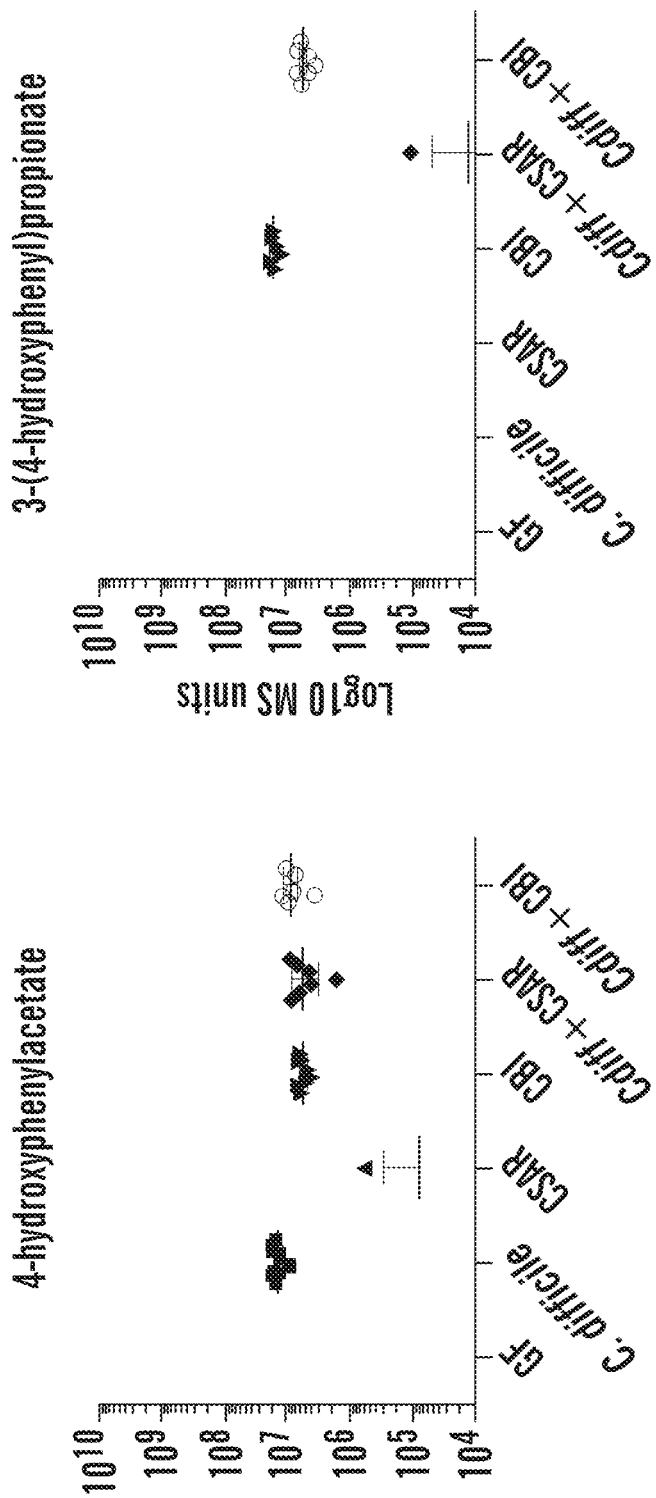
Figure 5F:
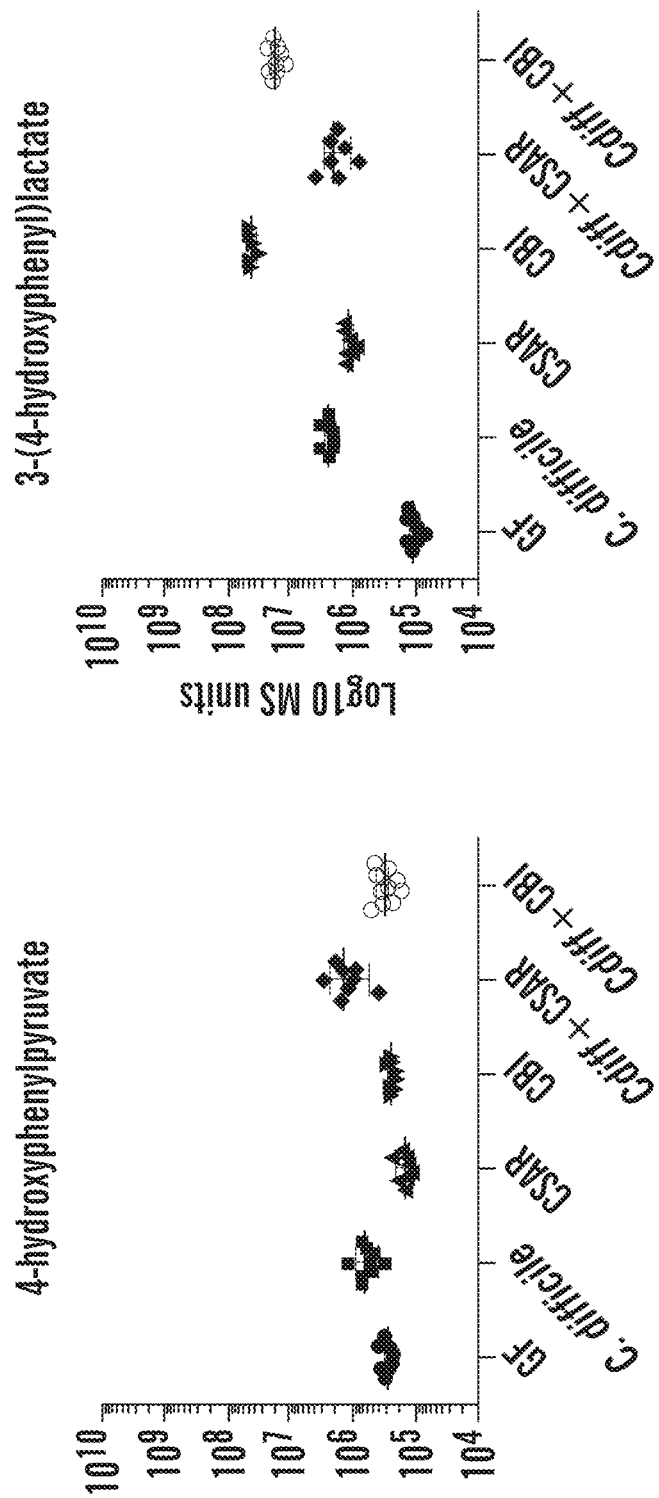
Figure 5F:
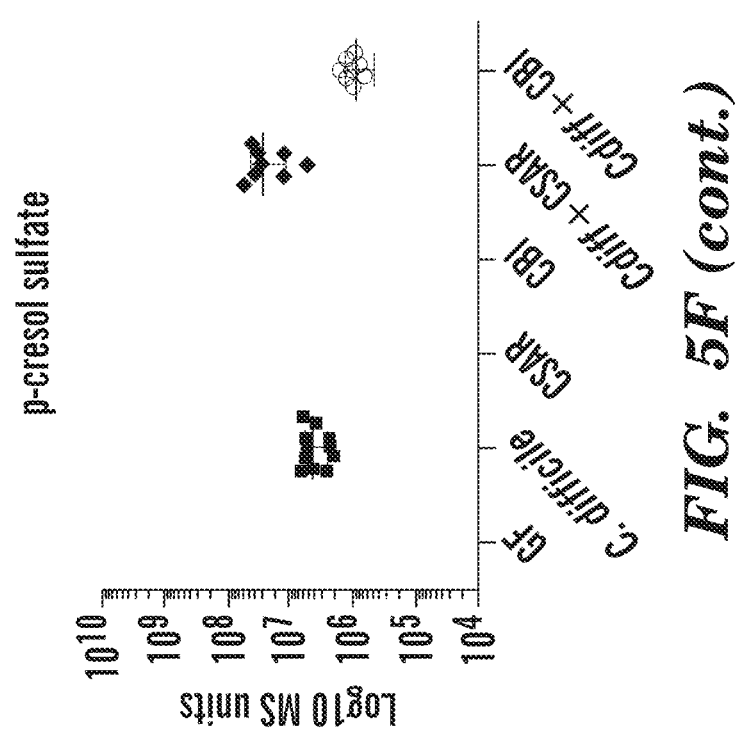
Figure 5G:
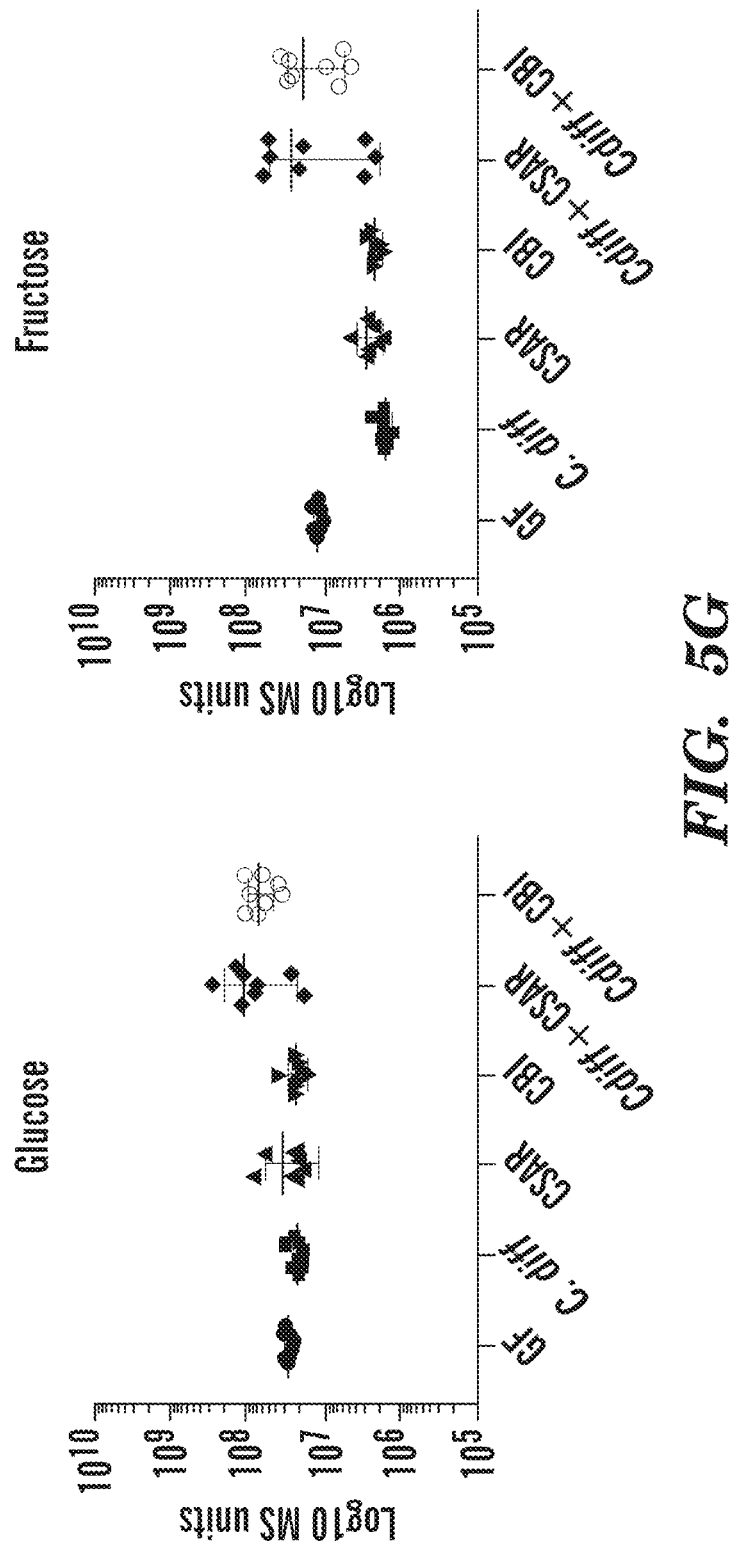
Figure 5G:
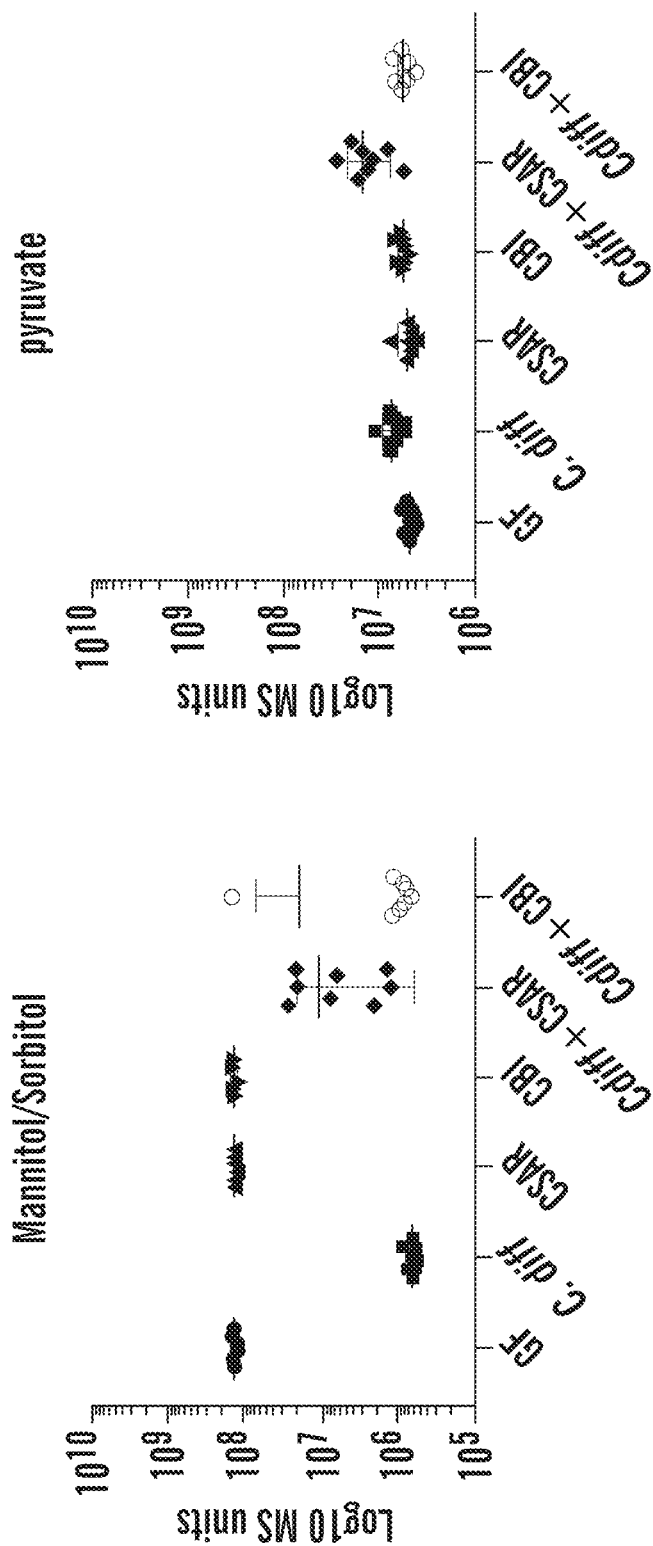
Figure 5G:
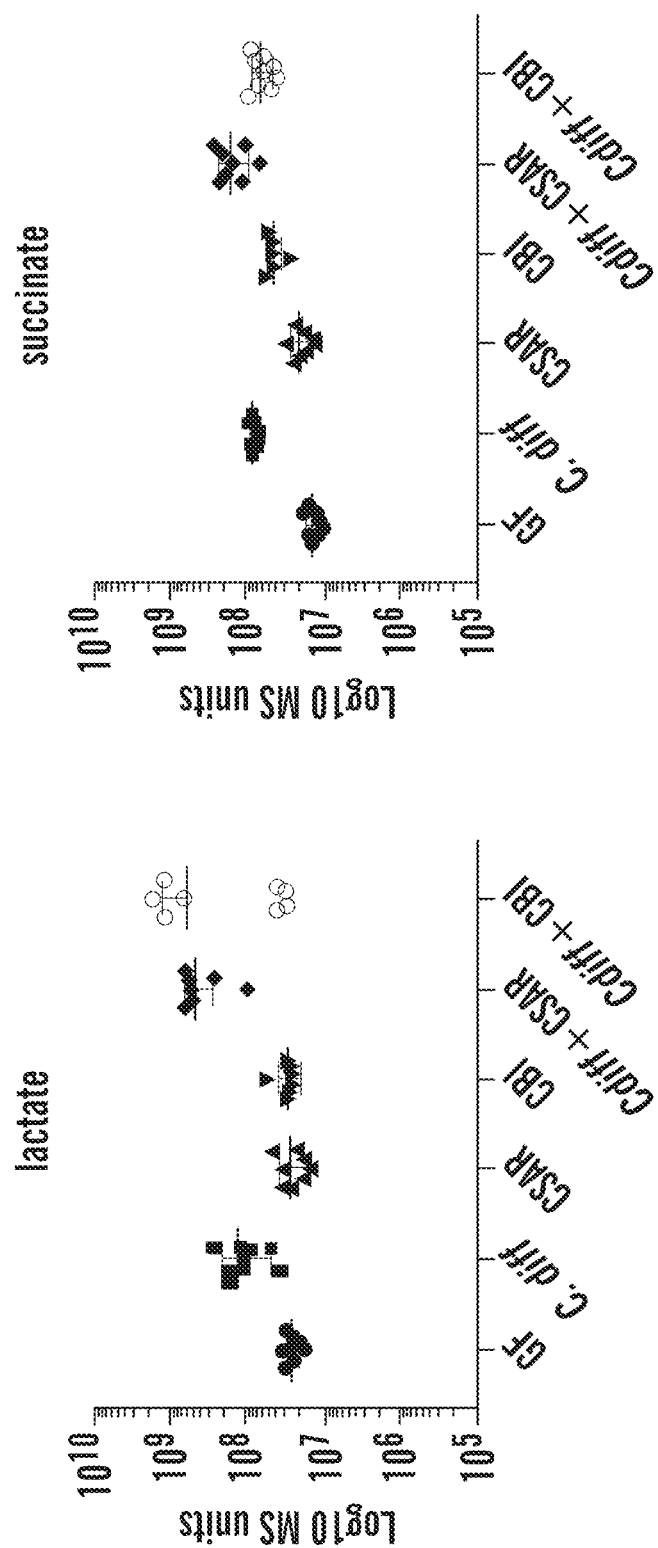
Figure 5H:
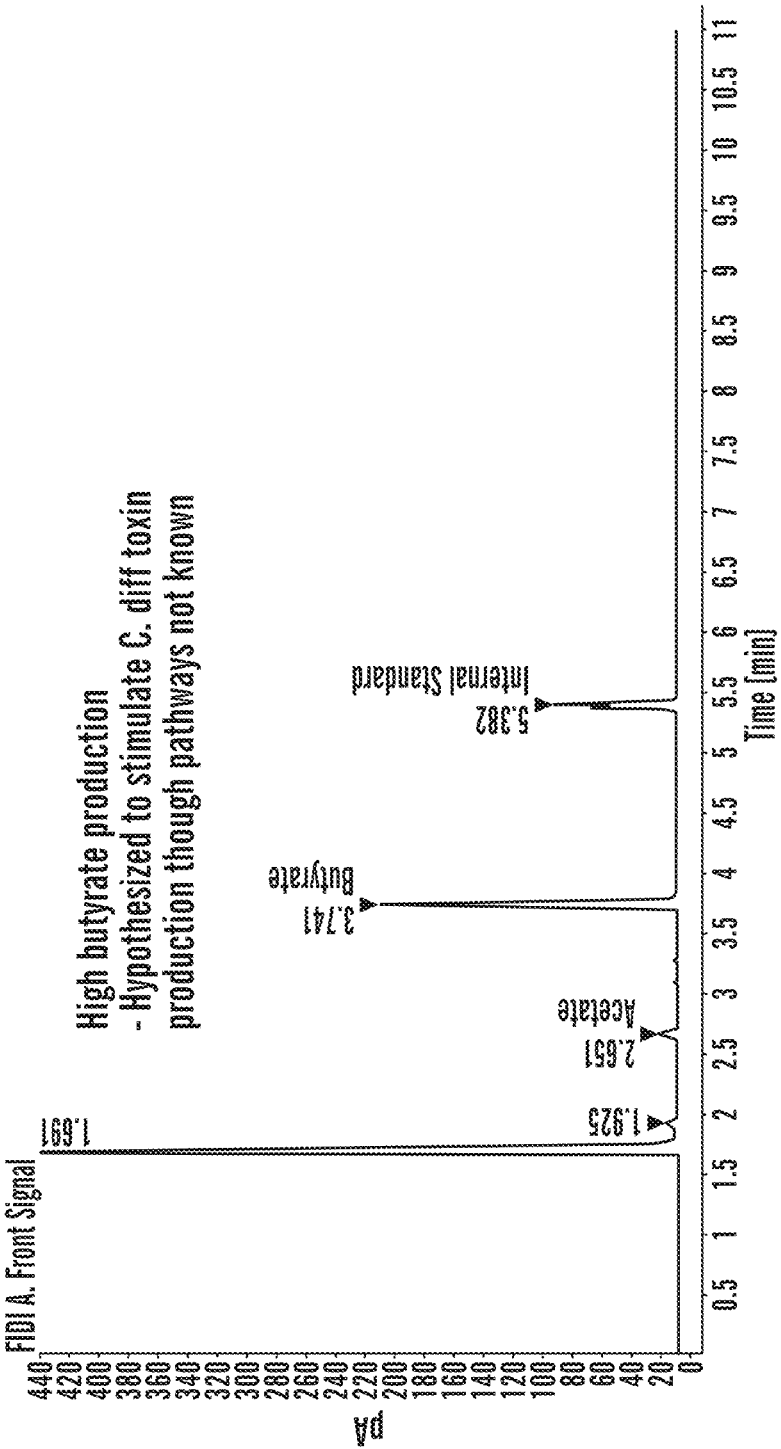
Figure 5I:
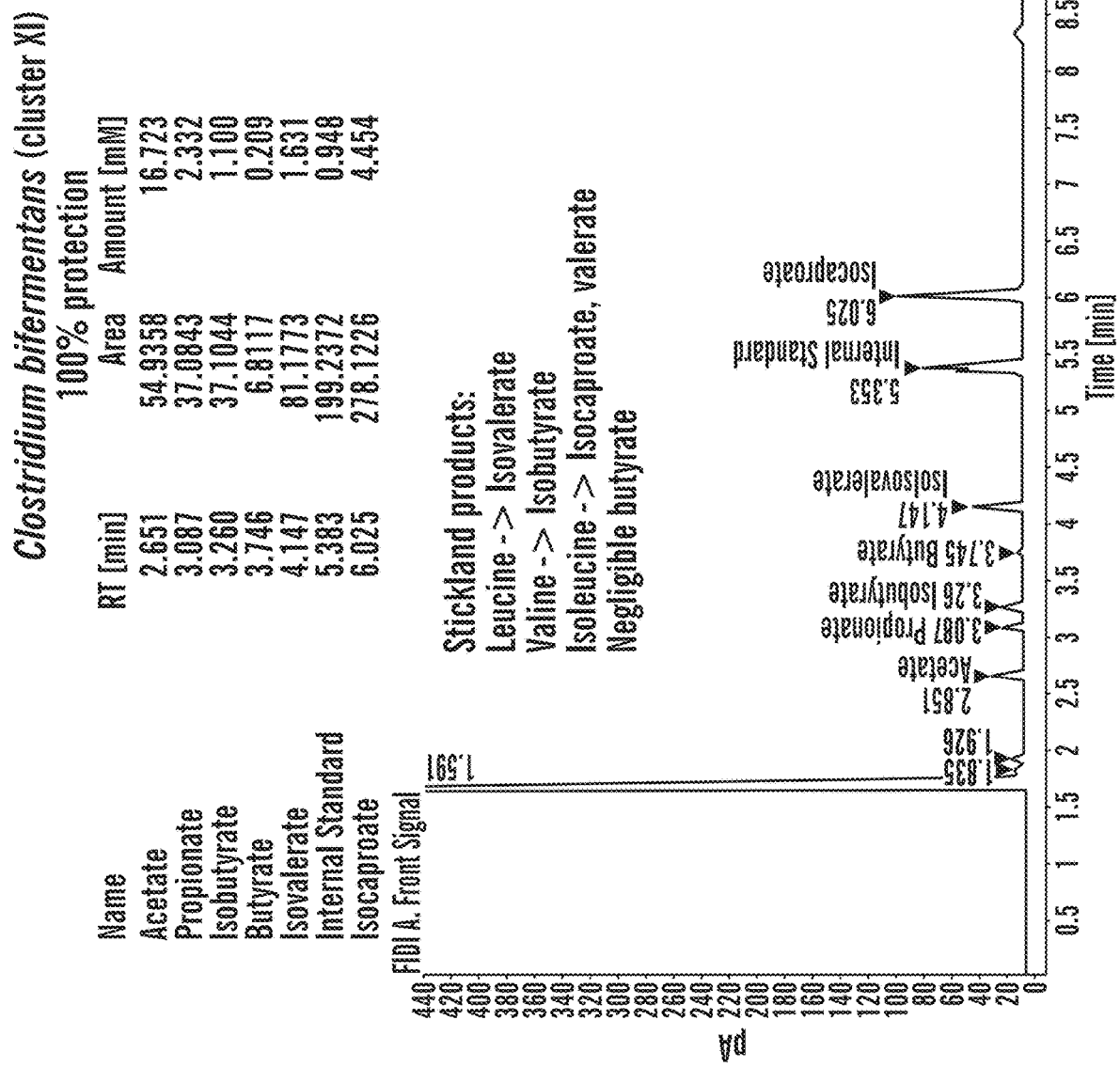
Figure 8A:
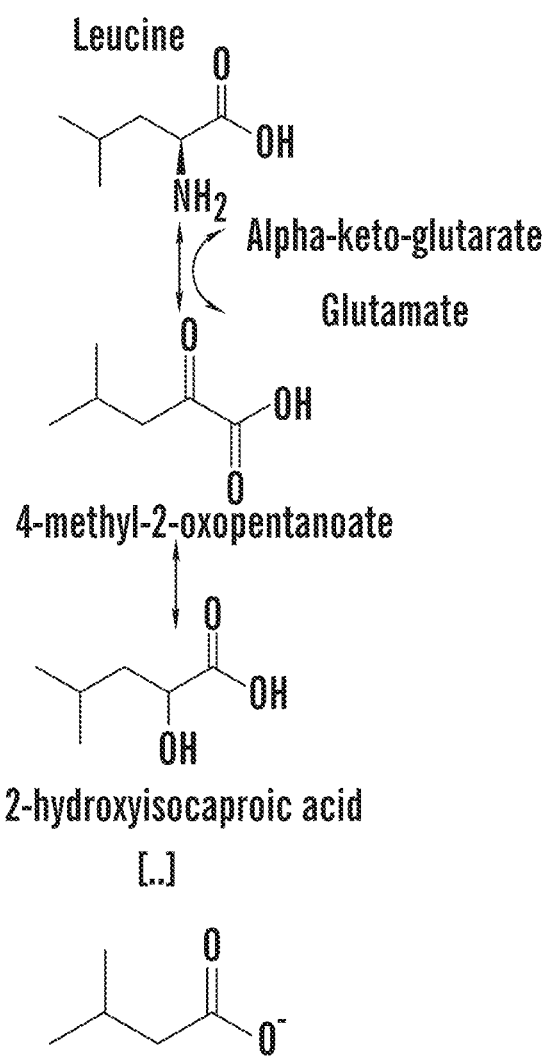
FIGS. 8A-8B show a schematic of Stickland Donor Branched Chain Amino Acids (FIG. 8A) and Stickland Donor Aromatic Amino Acids (FIG. 8B).
Figure 8A:
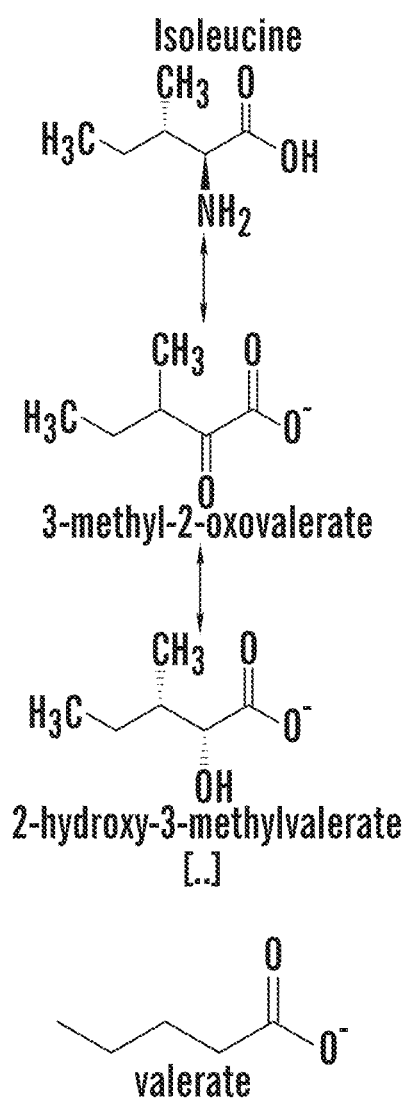
Figure 8A:
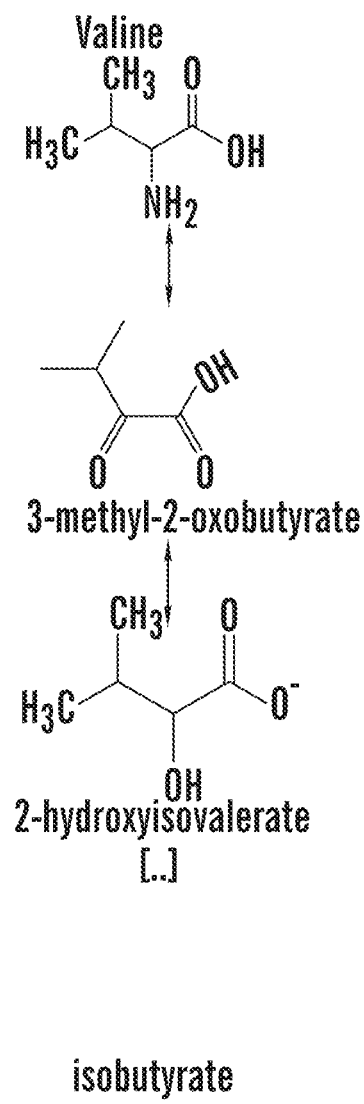
Figure 8B:
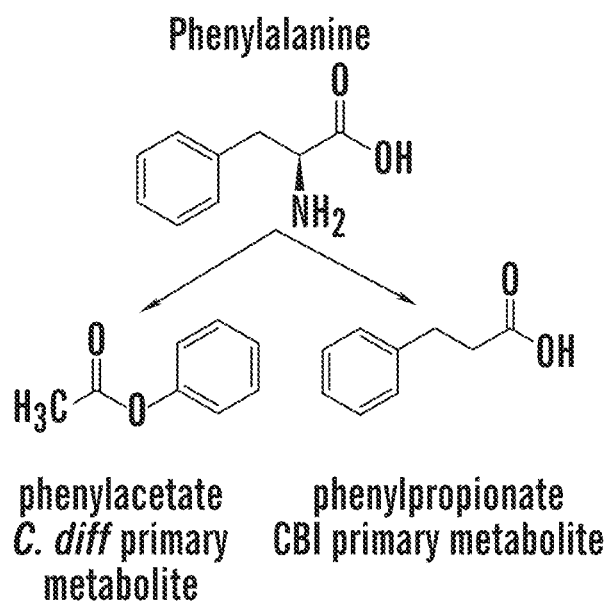
Figure 8B:
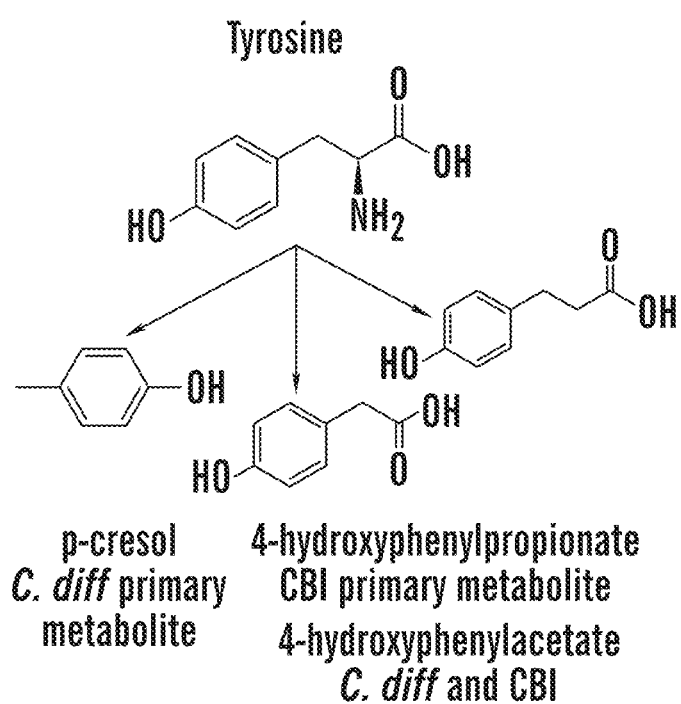
Figure 8B:
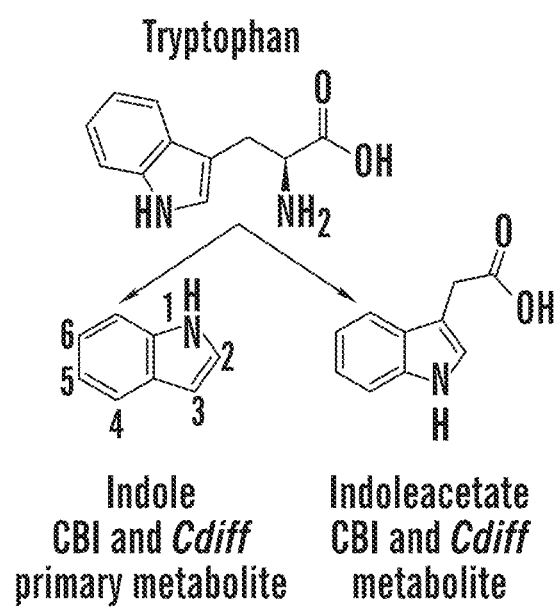

C. difficile metabolizes sugars such as glucose and fructose, and sugal alcohols such as sorbitol and mannitol for energy production. End metabolites and points of energy production are shown in FIG. 5G and in FIG. 9. Glycolytic pathways generate ATP and NADH and lead to production of pyruvate, lactate, propionate, acetate or ethanol as metabolites. The succinate pathway generates ATP and GTP and consumes NADH in the conversion of two pyruvates to succinate. Butyrate production can occur from condensation of two acetates into acetylCoA to butyrate, or from conversion of succinate to crotonylCoA to butyrylCoA and butyrate; while some ATP is produced in the process of butyrate production, substantive NADH is consumed in these pathways.

C. difficile Ethanolamine Utilization

Ethanolamine occurs abundantly in gut secretions, primarily from the breakdown of phosphatidyl ethanolamine from sloughed epithelial cells, as well as from dietary and other commensal sources. The C. difficile eut operons include a two-component ethanolamine sensing system and transporter, and downstream genes that encode the carboxysome, a polyhedral protein complex in which ethanolamine is metabolized to ammonia and acetaldehyde, resulting in the generation of NADH from NAD+. A schematic of the pathway is shown in FIG. 9.

C. difficile Reductive Leucine Pathway

C. difficile also uses the reductive leucine pathway for energy. Mediated by the had gene operon, the pathway generates 2 ATP from 3 leucine molecules. No net NADH/NAD+ is consumed, and the end product of this pathway is isocaproate.

Cysteine and Threonine Use

C. difficile can convert these amino acids to pyruvate with branch points for conversion of pyruvate to acetate, propionate or butyrate, that follow the glycolytic pathways.

SCFA, bSCFA and 5-Aminovalerate

Exogenous acetate and succinate are hypothesized to be taken up and converted to butyrate by C. difficile if it needs energy and does not have sugars or amino acids readily available. The capacity of C. difficile to use exogenous branched short-chain fatty acids and 5-aminovalerate is not known. Other organisms can use these compounds for further energy derivation. Without wishing to be bound by theory, another potential mechanism of protection provided by Stickland fermenting species could be cross-feeding these compounds to *C. difficile* for energy, or through other mechanisms of *C. difficile* sensing its extracellular environment.

PrdR

PrdR regulates that proline and glycine reductase enzymes, and also has indirect effects on toxin expression. With abundant proline, PrdR activates the proline reductase operon and inhibits the glycine reductase operon. PrdR activates the proline reductase operon and represses the glycine reductase operon. prdR suppresses the expression of *C. difficile* toxins by inhibiting butyrate, coDY, ccpA, tcdR, and/or tcdA production. The Stickland fermentation pathway using proline as the Stickland acceptor generates NADH and the metabolite 5-aminovalerate from proline. The acetate-generating pathway generates NADH and the metabolite acetate from glycine. *C. difficile* consumes large amounts of NADH in the carbohydrate metabolism pathway from acetate Therapeutic Microbiota Described herein are therapeutic microbiota that suppress toxin production by Gram positive, spore-forming bacteria such as *C. difficile*. As described herein above, commensal species that provide *C. difficile* with amino acids and other energy sources that promote Stickland fermentation can provide therapeutic benefits by suppressing *C. difficile* toxin production. Such species include, for example, species that express and secrete one or more protease enzymes that generate a supply of amino acids for *C. difficile* to derive energy from via Stickland fermentation, as well as species that themselves perform Stickland fermentation.

Proteases Expressed by Therapeutic Species

In one embodiment, a method of suppressing bacterial toxin production or treating or preventing a pathology caused by expression of a bacterial toxin compromises administering at least one bacterial organism that encodes and secretes a protease enzyme. Protease enzymes catalyze protein catabolism by hydrolysis of peptide bonds. Proteases are produced by all living organisms, in which they display many physiological functions ranging from generalized protein degradation to more specific and regulated processes such as blood coagulation, hormone activation, or transport of secretory proteins across membranes. Proteases can be either exopeptidases, whose actions are directed by the amino- or carboxyl terminus of proteins, or endopeptidases, which cleave internal peptide bonds. Extracellular proteases are made as precursors, containing an amino-terminal signal peptide, which is removed during the export to generate a mature, extracellular protease.

Proteolytic Clostridia elaborate a number of extracellular and membrane-bound metalloprotein, serine and other classes of proteases. The proteases generate free amino acids from available extracellular protein. An estimated 10-15 grams/day of undigested dietary protein enters the large intestine and remains available for microbial digestion and growth. The proteolytic species commonly use Stickland fermentations as core metabolic processes for energy generation under anaerobic conditions. Protease activity can be measured biochemically with lysis assays of casein, gelatin and other proteins, and with, e.g., FITC-conjugated substrates that release the fluorophore for detection. Microbiologically, protease activity can be measured on solid agar (casein hydrolysis agar), or with casein gelatin or meat granule hydrolysis in liquid media.

Among Stickland-fermenting Cluster XI Clostridia, *Clostridium bifermentans* is among the most highly proteolytic species, preferring Stickland fermentations over glycolytic pathways for energy extraction. In contrast, *C. sardiniense*, a non-proteolytic and strongly glycolytic Cluster I Clostridial species, produces abundant butyrate through anaerobic fermentation of available carbon sources.

In one embodiment, a bacterial organism administered as described herein, e.g., to suppress *C. difficile* toxin production, encodes and secretes at least one protease selected from the group shown in Table 2 or a homologue thereof. In another embodiment, the species administered encodes and secretes two or more, three or more, four or more, five or more, six or more, seven or more, eight or more, nine or more, ten or more, eleven or more, twelve or more, thirteen or more, fourteen or more, or all of the protease enzymes listed in Table 2. In another embodiment, the species administered expresses one or more (up to and including all) enzymes with the same Enzyme Commission (E.C.) number as an enzyme in Table 2. That is, the administered species can express and secrete one or more enzymes that catalyze the same reaction as an enzyme listed in Table 2. Additional bacteria that express and secrete such enzymes can be identified, for example, by analysis of bacterial genomic sequences for sequence encoding such secreted enzymes. For example, the sequence encoding a representative listed *C. bifermentans* protease can be used to query the genomic sequences of other non-pathogenic bacteria, including but not limited to other commensal bacteria, including but not limited to other Clostridial bacteria, for sequence encoding a homologous enzyme.

TABLE 2

Representative secreted proteases encoded by *Clostridium bifermentans* MHMC14 and the corresponding PATRIC (Pathosystems Resource Integration Center) ID Number (https://www.patricbrc.org/).

| Extracellular Proteases | PATRIC ID |
|---|---|
| Protease PrsW | fig\|186802.30.peg.279 |
| ATP-dependent protease La (EC 3.4.21.53) Type II | fig\|186802.30.peg.290 |
| Protease | fig\|186802.30.peg.313 |
| ATP-dependent Zn protease | fig\|186802.30.peg.414 |
| CAAX amino terminal protease family protein | fig\|186802.30.peg.543 |
| CAAX amino terminal protease family protein | fig\|186802.30.peg.2205 |
| CAAX amino terminal protease family protein | fig\|186802.30.peg.2313 |
| Putative membrane protease YugP | fig\|186802.30.peg.2680 |
| Uncharacterized zinc protease YmfH | fig\|186802.30.peg.2745 |
| FIG001621: Zinc protease | fig\|186802.30.peg.2746 |
| Major intracellular serine protease precursor (EC 3.4.21.—) | fig\|186802.30.peg.830 |
| CAAX amino terminal protease family protein | fig\|186802.30.peg.921 |
| Uncharacterized zinc protease YmxG | fig\|186802.30.peg.936 |
| Serine protease, DegP/HtrA, do-like (EC 3.4.21.) | fig\|186802.30.peg.3000 |
| ATP-dependent Clp protease ATP-binding subunit ClpX | fig\|186802.30.peg.3018 |
| ATP-dependent Clp protease proteolytic subunit (EC 3.4.21.92) | fig\|186802.30.peg.3019 |
| Tail-specific protease (EC 3.4.21.—) | fig\|186802.30.peg.3065 |

In one embodiment, a bacterial organism administered as described herein, e.g., to suppress *C. difficile* toxin production, encodes an enzyme that participates in Stickland fermentation. Such enzymes include, for example, D-proline reductase and glycine reductase. Species that encode one or both of such enzymes can be identified, for example, by analysis of genomic sequences for sequence that encodes the enzymes.

D-Proline Reductase (PR)

"prdA" or "D-Proline reductase (PR)" is encoded by the prdA gene. Sequences for prdA are known for a number of species, e.g., for *C. difficile* 630 (the prdA NCBI Gene ID is 4916399 and polypeptide sequence e.g., YP_001089760.1), as well as for *C. scindens* ATCC 35704 (the prdA NCBI polypeptide sequence e.g., EDS06621.1) and for *C. bifermentans* ATCC 638 (the prdA NCBI polypeptide sequence e.g., EQK41327.1). Proline reductase levels can be measured, for example, via immunoassay or by measurement of RNA encoding the enzyme, e.g., via RT-PCR. The sequence for the prdA gene product for *C. difficile* 630 is as follows (SEQ ID NO: 13):

```
                                                            (SEQ ID NO: 13)
    1   msitletaqa handpavccc rfeagtiiap enledpaifa dledsgllti pengltigqv
   61   lgaklketld alspmttdnv egykageake evveetveea apvseaavvp vstgvagetv
  121   kihigegkni sleiplsvag qagvaapvan vaapvasaaa evapkveekk llrsltkkhf
  181   kidkvefade tkiegttlyi rnaeeickea netqelvvdm kleiitpdky etyseavldi
  241   qpiatkeege lgsgitrvid gavmvltgtd edgvqigefg ssegelntti mwgrpgaadk
  301   geifikgqvt ikagtnmerp gplaahrafd yvtqeireal kkvdnslvvd eevieqyrre
  361   gkkkvvvike imgqgamhdn lilpvepvgt lgaqpnvdlg nmpvvlsple vldggihalt
  421   cigpaskems rhywreplvi ramedeeidl vgvvfvgspq vnaekfyvsk rlgmlveame
  481   vdgavvtteg fgnnhidfas hieqigmrgi pvvgvsfsav qgalvvgnky mthmvdnnks
  541   kqgieneils nntlapedav rimamlknai egvevkaper kwnpnvklnn ieaiekvtge
  601   kivleeneqs lpmskkrrei yekden
```

The prdA gene sequence for *C. difficile* 630 is as follows (SEQ ID NO:14):

```
                                                            (SEQ ID NO: 14)
    1   atgtcaataa ctttagaaac agctcaagcc catgcaaatg acccagcagt tgttgttgt
   61   agatttgaag cgggaacaat tatagcgcca gaaaacttag aagatccagc aatatttgca
  121   gacttagagg attctggatt attaacaata ccagaaaatg gattaactat aggtcaagta
  181   ctaggagcta agttaaaaga aactttagat gcactttctc caatgactac agataacgta
  241   gaaggataca aagcaggaga ggctaaagaa gaagtagtag aagaaacagt agaagaagca
  301   gctccagtat cagaagcagc agtagttcca gtaagcacag gagttgcagg tgaaacagtt
  361   aaaatacaca taggtgaagg taagaacata agcttagaga tacctttatc agtagctggt
  421   caagcaggag ttgctgctcc agtagcaaac gttgctgctc cagtggcaag tgcagcagca
  481   gaagtagctc caaaagttga agaaaagaaa cttttaagaa gcttaactaa aaaacacttt
  541   aaaatagata agttgaatt tgctgatgaa actaaaatag aaggaactac tttatacatc
  601   agaaacgcag aagaaatatg taagaagct aatgaaactc aagagttagt tgtagatatg
  661   aagttagaaa taataactcc tgataaatat gaaacttaca gtgaagctgt attagatata
  721   caaccaatcg ctactaaaga agaaggcgaa ttaggttcag gtataactag agttatagat
  781   ggagctgtaa tggtattaac tggtacagat gaagatggag ttcaaatagg tgaatttggt
  841   tcttcagaag gtgagttaaa tactactata atgtggggta gaccaggtgc tgctgacaaa
  901   ggtgaaatat tcatcaaagg tcaagtaaca ataaaagcag gaactaacat ggaaagacca
  961   ggacctttag ctgctcaccg tgcatttgac tatgtaactc aagaaataag agaagcatta
 1021   aagaaagttg acaactcttt agtagttgat gaagaagtaa tagagcaata cagaagagaa
 1081   ggtaaaaaga agttgttgt tataaaagaa ataatgggac aaggtgcaat gcatgataac
 1141   ctaatattac cagttgagcc agttggtaca ttaggagctc aaccaaacgt tgacttagga
 1201   aacatgccag ttgtattatc tccacttgaa gtattagatg gtggtatcca tgcattaact
```

-continued

```
1261   tgtataggac ctgcatcaaa agaaatgtca agacattact ggagagagcc attagtaata
1321   agagctatgg aagacgaaga aatagattta gtaggtgttg tatttgttgg ttctccacaa
1381   gtaaatgctg agaaattcta tgtatctaag agattaggta tgttagttga agctatggaa
1441   gttgatggag ctgtagtaac tactgaaggt ttcggaaaca accatataga tttcgcatct
1501   cacatagagc aaataggtat gagaggtata ccagtagttg gtgtaagttt ctcagctgtt
1561   caaggtgctc tagttgttgg taataaatac atgactcaca tggtagacaa caataagtct
1621   aagcaaggta tagagaatga aatattatct aacaacactt tagctccaga agatgctgtt
1681   agaataatgg ctatgcttaa aaatgctata gaaggtgtag aagttaaagc tcctgaaaga
1741   aaatggaatc caaatgttaa attaaataac atagaagcta tagaaaaagt tacaggagaa
1801   aaaatagtat tagaagagaa tgagcaatct ctaccaatga gtaagaagag aagagaaata
1861   tacgaaaaag acgaaaacta a
```

Each reductase is comprised of multiple polypeptides of which the sequences are listed below. In one embodiment, the prdA gene (D-proline reductase (EC 1.21.4.1)) sequence for *C. bifermentans* 638 is as follows (SEQ ID NO:15):

```
                                                   (SEQ ID NO: 15)
atgggtataggaccatcaactaaagaaacatcattacatcactttagaga
tccgcttcttgatatagttagtaatgacaaagacatagatcttctgggga
tagtagtagtaggaacacctcaggacaacaaagaaaaagaatttgttgga
caaagaacagctgcatggctagaagctatgagagcagatggtgttataat
ttcatgtgatgggtggggaaactcacacgtagattatgctaatactattg
aagaaataggaaaaagagagatcccggtagttggacttacatttaatgga
acacaagctaagtttgtagttacaaataaatatatggacacaatagtaga
ttttaataaatcagacaaggggatagaaacagaagttgtcggagagaaca
ctgtaagcgagttagacgcaaaaaaatcattagccttattaaaattaaaa
atgcaaagaaataataaaaaataa
```

In one embodiment, the prdA gene (D-proline reductase (EC 1.21.4.1)) sequence for *C. bifermentans* 638 is as follows (SEQ ID NO:16):

```
                                                   (SEQ ID NO: 16)
atgtcaataactgtagaaacagctaaagctcatgctaaagatccagcggt
atgctgctgtagatttgaagctgggactgtactagaaccatcaaatttag
aagatccagcaatattcgctgacttagaggattcaggattattaacaata
gcagatgattgtttaacaatagagcaagttttaggagctaaactattaaa
aactttagatgctttaactccaataactgctgactgtgtagaaggtgtag
tagcagtagctgaagaggctaaagaagaagttaaggaagaagttaaagaa
gtagcaccagttgcttcagtagctccagtatctcaaatagctccagtaaa
tggacaaactataaagatacatataggtgaaggtagagatataaacttag
aaatacctttaaatgtagctcaaggaatgggtgtagcaccagttgctcct
gtagctgtagcagaaaatgcagaagctgtagaagttaaagctgagccagt
tcaagaagctaaagcaatgagaagcttaactaaaaaacattttaaaatag
```

-continued

```
aaaaagtagttttcgctgaagaaactaaaatagatggaactactttatac
ttaagaactccagaagaattaactaaagaagctgtaaattcagaagaatt
agttgttgatatgaagttagaaataataactccagctgaatacaacaaat
acagtgaaactataatggatgttcaacctatagctgctaaagaagaagga
gaaataggagaaggtgtaacaagagttatagacggagttataatgatggt
aactggtactgatgaaaacggagttcaaataggtgaattcggttcttcag
aaggtgtattagaaactaacataatgtggggaagaccaggtgctcctgat
aaaggtgatatattcatcaaaactcaagtaacagttaaagctggtactaa
catggaaagaccaggaccattagctgctcactgtgcatctgattatataa
ctcaagaaataagagaagcattaaagaacgctgaagagtctttagtagtt
gatactgaagaattaactcaatatagaagacctggtaagaaaaaggttgt
tgtagttaaagagataatgggacaaggggcaatgcatgataacttaatat
tacctgttgagccagttggaacattaggagctaaaccaaacgttgactta
ggaaacgttccagtagtattatctccacttgaagtattagatggtggtat
acatgcattaacttgtataggacctgcatctaaagaaaactctagacatt
actggagagagccattagtaatagaagctatgcatgatgaagaaatagat
ttagtaggtgttatatttgtaggatctccacaagtaaatgctgagaaatt
ctatgtatctaagagattaggtatgatgatagaagctatgggtgttgatg
gtgctatagtaacaactgaaggattcggaaacaaccatatagatttcgct
tctcatatagagcaaataggtaagagagatgtagctgtagtaggtgtaag
tttctctgctgttcaaggtgctctagttgttggtaatgaatacatgaaat
acatgatagacaacaacaagtctaaacaaggtatagaaaatgaagtatta
tcaaacaatacattatgcccagaagatgctgtaagatctttagcaatgtt
aaagacagtaatgggtggagaagaagttaaagctgctgagagaaaatgga
atgctaacgttaaattaaataacgttgaattaatagaaaaagaaactggt
aagaagttagaacttgttgaaaacgagcaaactttaccaatgagtgaaaa
aagaaagaatatatacgaaaaagacgctaaatag
```

In one embodiment, the prdA gene (D-proline reductase (EC 1.21.4.1)) sequence for *C. bifermentans* 638 is as follows (SEQ ID NO:17):

```
                                          (SEQ ID NO: 17)
atggaagagaaaatacttagacgtttggtaattaaaccatttcatataa ataatgttgaattcaatgaaaagttctcaataaaaaaaggtacactatc cataaacaatgactacataaatgaaattaaaaattcacatgaattaata acggacataaaattagatataatcaaaccaggagattataacaaggaaa ttaatactatcatggatataatccctatatctactaaagttttaggtag attaggtgaaggaataacacacactttaacaggtgtttatgttatgctt actggtgttgatgaagatggaagacaaatgcatgaatttggatcttcag aaggtatactttctgagcaaatggtgtttggaagatatggtactccatc tactaatgattacataattcattttgatgttacagttaaaggtgggttg
```

-continued

```
ccatatgagagaaaacttccgatgatgacatttaaggcatgtgatactt ttatacaaggtataagaaatgttttaaaacagcaagacggaagagatgc tacagaaattcgtgaatattttgacaaaattagacctgacgctaaaaaa gttgtaatagtaaaacaaatagcaggtcagggtgcaatgtatgacaatc aattattttctcatgaaccaagtggtttagagggaggtacatccattat tgatatgggaaatgtaccgatgataatatcacctaatgaatacagagat ggcgccttgagagctatgacttaa
```

In one embodiment, the prdA gene (D-proline reductase (EC 1.21.4.1)) sequence for *C. bifermentans* 638 is as follows (SEQ ID NO:18):

```
                                          (SEQ ID NO: 18)
atgagccttacaacaataaaaggacttcaatctgaaatatttgtaccaat aacacctcctcctgtttggactcctgtaactaaagaactaaaggatatga ctatagctttagctacagcgtcaggtgtacatttaaaagctgataagaga ttcaacctagcaggtgactttacatttagagaaataccagacacagcaac tactgatgagatgatggtatctcacggaggatatgataacgctgatgtta
```

-continued

```
ataaagatataaactgtatgttccctatagacagactacatgaattagct aaagaaggatttataaaatctgtagctccagttcatataggattcatggg tggtggtggagaccaaactaaattcactgaagaaactggtcctgaaatcg ctaaaagattaaaagatgagggagtagacggtgtagttctaacagctggc tgaggtacttgccatagaactgccgtgatcgtgcagagagcaatagaaga agctggtataccaactataataatagcagctcttcctccagtagttagac aaaacggaactccaagagcagttgctccactagttccaatgggtgctaat gctggtgaaccaaacaataaagaaatgcaaatgcatatattaagagatac tttagagcaattaatagctataccatctgctggtaagataattcaattac catacgagtatgtagctcaagtataa
```

In one embodiment, the sequence for the prdA gene product for *C. scindens* 35704 is as follows (SEQ ID NO: 19):

```
                                                            (SEQ ID NO: 19)
  1  msitaetake handpavlcc raeagitiea anledpaifd dlvdsgllnl dgaltieevl 61  gakltktcds lcpltadvve gakaptapaa eeaeeeapaa papaaapvag paaggtlkih 121  igegkdidle ipvgalggga avaplpagae avvagaaape aageekvvrs ltrkhftite 181  vkrgpetkie gttlyiregi esevidnqel vkdfkleiit pdlyhtyset vmdvqpiatk 241  egddelgtgv trvldgvvmm ltgvdeggvq igefgssegy ldenimwnrp scpdkgeifi 301  kgniviqekt nmerrgpmaa htafdvitqe irevmkkldd slvadteelk qvrrpgkkkv 361  vivkeimgqg amhdnfilpv epvgvlgara nvdlgnvpvc vsplevldgc ihaltcigpa 421  skemsrhywr eplvlealhd pevdlcgvvf vgspqinaek fyvsrrvght vemmdadgaf 481  vttegfgnnh idfashieqi gmrgipvvgm sycavqgalv vgnkymtymv dnnkseagie 541  neilgnntlc pedavralam lktamagedv kaaekkwnpn vkstnvelie stygtkvdlv 601  eneqalpmse krrlkys
```

In one embodiment, the prdA gene (D-proline reductase (EC 1.21.4.1)) sequence for *C. scindens* 35704 is as follows (SEQ ID NO:20):

```
                                          (SEQ ID NO: 20)
ttggctgaagaggtaaaagacctgagacgtcttgtaattaaagcgttcca catgaatgatgtagagtggggtgaacataatgatattactgttgacggta atatgacagtcagtaaagaaatgattgatcagctggtggctcaggaggaa cacattgaaaaaattgatattcagattattaagccgggggatcatgaccg ttggacgaatacgattatggatatcataccgatctctacaaaggtacttg gaaaattaggggagggcattacccataccattaccggcgtatatgtaatg cttaccggcgttgacgtaaatggaaagcaatgccatgaattcggttcttc tgaggggaatctgaaagaccagctgtacttgaaccgtgcaggcacgccgg gggatgatgattacataatttcctttgatgtaacgcttgcagccggaatg gggcaggagaggcctggaccgactgccgcacatagggcgtgcgataagtt tatccagacataccgtgataagatgaagaagttcaaaggcgagaagtgta cggaacgccatgagtaccatgatgtggtaaggccgggaaagaaacgcgtc
```

-continued ctgatcgtaaagcaggtggcaggacagggagcaatgtatgatacgcatct gttttccaaagagccgtctggcgtagagggcggacgttcaattatcgata tgggcaatatgccgatccttgtaactccaaatgagtacagagacggtatt atccgctccatgcagtag In one embodiment, the prdA gene (D-proline reductase (EC 1.21.4.1)) sequence for *C. scindens* 35704 is as follows (SEQ ID NO:21):

(SEQ ID No: 21)
atgtcaatcacagctgaaacagcgaaagaacatgctcatgatcctgcggt attatgttgtagagccgaagcaggcattacaatcgaagctgctaatcttg aagatccggcgatctttgatgacttggtagattcaggattattgaacctg gatggtgcattgaccatcgaagaagtttttgggagcaaaacttacaaaaac atgtgattctctttgcccgttaactgcagatgtagttgaaggtgcaaaag cgccgactgctccagcagcagaagaggcagaagaggaagcgccggcagca ccggcaccggctgcagcacctgtagcaggacctgcggcaggcggaacact taagatccacattggagaaggcaaggacattgatcttgagatcccagttg gagcgcttggcggcggagcagcagttgcaccattgccggcaggagcagag gcagttgttgcaggagcagcagcaccagaagcagctggagaagaaaaggt tgtaagaagtttaacaagaaaacacttcacgatcacagaggttaagagag gaccagagaccaagatcgaaggaacaactctttacatccgtgaaggcatt gagtcagaagttattgacaaccaggagcttgtaaaagatttcaaactgga aatcatcactcctgatttatatcacacatattccgagactgttatggacg ttcagccaatcgctacaaaagaaggcgatgatgaactcggaacaggtgtt acaagagtacttgacgcgttgttatgatgctgacaggtgttgacgaagg cggagttcagattggcgagttcggttcttcagaaggataccttgatgaga acattatgtggaatcgtccgagctgcccagataaaggcgagatctttatc aagggtaacatcgtaatccaggaaaagacaaacatggaacgtcgtggacc tatggctgctcatacagcatttgatgtaatcacacaggaaatccgcgaag ttatgaagaaacttgatgacagccttgttgctgatacggaagaactgaag caggttcgccgtccgggcaagaagaaagtcgttatcgttaaggaaatcat gggacagggagctatgcatgacaactttatccttcctgtagagcctgttg gcgttctaggcgcaagagctaacgtagacttaggaaacgtaccggtttgc gtatctccattggaagttcttgatggatgtatccatgcattaacatgtat cggacctgcatctaaggaaatgtccagacattactggagagagccattgg ttctggaagcattgcatgacccggaagttgacctttgcggcgttgtatttt gtaggatctcctcagatcaatgctgagaaattctatgtatcccgtcgtgt aggccataccgtagaaatgatggatgctgatggagctttcgttacaacgg aaggttttggaaacaaccacatcgatttcgcaagccatatcgagcagatc ggtatgagaggaattccggttgttggcatgtcttactgtgcagttcaggg cgctctggttgttggtaacaagtatatgacatacatggttgacaataaca agtctgaagctggtatcgagaacgagattcttggtaacaatacgctttgc -continued ccggaagatgctgttcgtgcacttgctatgcttaagactgcaatggcagg cgaagacgttaaggctgctgagaagaagtggaatccaaacgttaagtcta caaacgtagagttaattgagagcacatacggtacaaaggttgatcttgtt gaaaatgagcaggctcttccgatgagtgaaaaacgtagattaaaatacag ctaa In one embodiment, the prdA gene (D-proline reductase (EC 1.21.4.1)) sequence for *C. scindens* 35704 is as follows (SEQ ID NO:22):

(SEQ ID NO: 22)
atgaatgtaggatcaaggctgacggttaaggcgtaccctgtcacagaagt gtgctatggggaggagaaccgagtgacggtggatggccggatgacggtct gtaagaacatagcagaaaagattctggcgcaggagccattgataaaggag attgatatccgtattatcatgccggatgagcaccgacagcataccaacac ggtgatggatgtgattcctctggcaaccaaagtgctgggacgggtgggg agggcattacccataccctgacaggcgtatacgtgatccttaccggtgtg gatgagagcgggcgtcagatatgtaattttggcgccagcgacggaatact cgaggagaagattgcctgggggcgggcgggaacgccgcttaggagcgacg tgctgatctcctttgacgtggttcttaaggaaggatcctgggcggatcgt ccgggtccggaagcagcccatcgcgcctgcgatacatactgccagatatt ccgggagcagataaagaagtttaatggatacaagtgcgcggaaaagcatg tctttcaggagacgtatgagccggggaaaaaagatgtctatattgtgaaa gaagtatccgggcaaggtgccgtatacgatacccggatgttcggacatga gccttgcggattcgaaggcgggaagtctgttattgatatgggctgcatgc ctgcgctggtgacgcccaatgaatttagggatggcattatgcgcgcgatg gattag In one embodiment, the prdA gene (D-proline reductase (EC 1.21.4.1)) sequence for *C. scindens* 35704 is as follows (SEQ ID NO:23):

(SEQ ID NO: 23)
atgtctattacagcagaaactgcaaaagaacatgcaaatgacccggctgt attatgctgccgggcagaagagggcattacaatacaggcttccaacttgg aagatcctgctattttgacgagttagtggattcagggctgctatctttg gatggctgtctgacaatcggacaagtcttaggggcaaccctgacaaagac aagcgattctttatgtccattgactgcagataacgtaggggcttcaaag aggtagttgaggaagaagagcctgcatcagagccagtcgaagaagcggta gccgcagatattaatattgggggcgcggtcaccacgatcaaaaatggaaa agttgttatttcaatcaaagaaggaaaagatatctatttagaacttcctg tttaa In one embodiment, the prdA gene (D-proline reductase (EC 1.21.4.1)) sequence for *C. scindens* 35704 is as follows (SEQ ID NO:24):

(SEQ ID NO: 24)
atgggaaatgtacagatttattacgtcagcatgttggtgcaccctgtga ggcaatcgtaaaggctggggataaggtggaaaaaggtaccttgattgcaa ctcctacaggacttggcgctaacatcttttccagcgtctatggcgtggtg gaagaagtcttggaagaccgaatcgttatcaagccggatgaagagcagaa agatgagtttgtacctattaaggaaggcagcaagcttgagatggttaagg aagccggaatcgtaggtatgggcggcgcaggattcccaactggcgtgaag attggaacggaccttcacggcggatatatcctggtaaatgctgcagaatg cgagcctggacttcgccacaatatccagcagattgaagaaaagacagata tcacaatccgcggattgaaatactgcatggagatatccaatgcggcaaaa ggaattattgctattaagaagaagaacgaaaaagcgatcgaatttctcag agaggcaatcaaggatgaagacaatatcacgatccatcttcttccggata tttacccaatgggagaggaaagagcggtagtaagagaatgcctcggaaaa ctgcttgatcctacacaacttccgtcagcagcagatgcagtcgtaatcaa ctgcgagaccctgcttcgtatcgcagaggcgatcgaacttaagaaaccct gctttagcaagaatatgacggttattggaaagattaacggtggaaacgag ccgcatgtattcatggatgttccggttggaacctgtgttgcagacatgat cgagaaggcaggcggaattgatggtacatatggcgagattatcatgggtg gagcatttactggaaagtccaccacattagacgcgcctactacgaagacg acaggcggaatcatcgttacggtagagttcccggatcttcacggagcgcc ggtaggattgcttgtctgtgcgtgcggcgaagcgaagaccgtatgcgcg aactttgcgaaaagatgaatggaaaggtcgtttctgtggcaagatgtaaa caggcggttgagccgaagccgggcgcagcgcttaagtgcgagaatcctgg aaactgtcctggacaggcacagaaatgtctgcagtttaagaaggacggcg cagagtacatcatcatcggtaactgctcagactgttccaacacagttatg ggatctgcaccaaagttaaaactgaagacattccatcagacagaccatgt gatgagaacaatcggtcatccattatacagaagactgaccgtgtccaaag aagttgaccagctgcccaacggcaaataa In one embodiment, the prdA gene (D-proline reductase (EC 1.21.4.1)) sequence for *C. scindens* 35704 is as follows (SEQ ID NO:25):

(SEQ ID NO: 25)
atgggtataggaccatcaacaaaagaaacatcattgcatcacttcaggga tccgctgctggatgtagtctcttcggatacagatctggatctgatgggaa ttatcatcgtaggaacaccggacgataatgaggataagatgcttgtagga accaggacggctgtttgggccgaggcaatgcgtgcggacggcgtaatcat ctcttcggacggatggggaaacagcgacgtggattacacgaatacatgcg agcaggtggggacgagaggcatcgcggtgacgggccttaatttcagcggt acggtagctcaatttgtagttgtaaataattacctggatggaattgtgga tatcaataagagcgcggacgggacagagaccaatgtggttggggaaaaca atatgtcgagctggattgcaaaaaggcgactgcgcttctgaaacttaag atgcgaaagaatgagaaaaagtag In one embodiment, the prdA gene (D-proline reductase (EC 1.21.4.1)) sequence for *C. scindens* 35704 is as follows (SEQ ID NO:26):

(SEQ ID NO: 26)
atgagtttaacggttgttaaaggtttacaatctgaaatattcgttcctat tactccaccatcagtatggactcctgtaacaaaagagttgaaagacatgt ctatcgctcttgcaacagctgccggtgttcataagaaggatcaggaaaga ttcaatcttgctggtgactttacatggagaaaaatagagaacacaacacc atctagcgaactgatggtatcccatggtggatatgataacagtgatgtta acaaagatatcaactgtatgttcccgattgacagaattcatgaattggct gctgaaggatttatcagggcttgtgctccggtacatgcaggattcatggg tggtggcggaaaccaggagaagttcaaaggcgaaactggtccggctatcg cgcagatgttcaaagaagaggacgttgacgcagtaattctcaccgctggc tgaggaacctgccaccgctctgcagtattggtgcagagagcgattgaaga agctggaattcctactattattattgcagctcttccaccagttgttcgcc agactggtactcctcgtgcagttgctccattggtacctatgggtgctaat gcaggtggaccgcacaatgttgaacagcagacacagatcgtaaaggcaac tctggagcagttagttgaaatccagacacctggaaagattgttccactgc cattcgagtatgtagctaagatttaa The sequence for the prdA gene product for *C. bifermentans* 638 is as follows (SEQ ID NO: 27):

(SEQ ID NO: 27)
  1 meekilrrlv ikpfhinnve fnekfsikkg tlsinndyin eiknshelit dikldiikpg 61 dynkeintim diipistkvl grlgegitht ltgvyvmltg vdedgrqmhe fgssegilse 121 qmvfgrygtp stndyiihfd vtvkgglpye rklpmmtfka cdtfiqgirn vlkqqdgrda 181 teireyfdki rpdakkvviv kqiagqgamy dnqlfsheps gleggtsiid mgnvpmiisp 241 neyrdgalra mt In some embodiments, it is useful to measure proline reductase levels or activity, e.g., as an indicator of the activity of the pathway in a sample, or, e.g., to identify a bacterial species as one that likely performs Stickland fermentation and/or can aid in suppressing *C. difficile* toxin expression. Measurement of proline reductase levels can be performed, for example, by immunoassay or by RT-PCR for the mRNA encoding the enzyme. Measurement of proline reductase activity can be performed, for example, with the fluorometric assay described by Jackson et al., J. Bacteriol. 188: 8487-8495 (2006), which is incorporated herein by reference. The assay follows the DTT- and d-proline-dependent production of δ-aminovaleric acid, which reacts with o-phthalaldehyde to generate a fluorescent product.

The nucleic acid and polypeptide sequences for the proline reductase expressed by *C. difficile* 630 are NCBI Gene ID 4916399, YP_001089760.1, respectively. The nucleic acid and polypeptide sequences for the proline reductase expressed by *C. scindens* 35704 NCBI Gene ID 167662491 and EDS06621.1, respectively. The nucleic acid and polypeptide sequences for the proline reductase expressed by *C. bifermentans* 638 are NCBI Gene ID 531765064 and EQK41327.1, respectively.

Glycine Reductase (GR)

The activity or expression of glycine reductase is important for Stickland fermentation via the glycine reductase pathway. In some embodiments, it is useful to measure glycine reductase levels or activity, e.g., as an indicator of the activity of the pathway in a sample, or, for example, to identify a bacterial species as one that likely performs Stickland fermentation. Measurement of glycine reductase levels in a sample can be performed, for example, by immunoassay and/or via RT-PCR for the mRNA encoding the enzyme. A biochemical assay for glycine reductase activity is described, for example, by Stadtman & Davis, J Biol Chem. 266(33):22147-53 (1991).

The nucleic acid and polypeptide sequences for the glycine reductase expressed by *C. difficile* 630 are NCBI Gene ID is 4915147 and YP_001088866.2, respectively.

The "grdA" or "glycine/sarcosine/betaine reductase complex protein A" glycine reductase is encoded by the grdA gene. Sequences for grdA are known for a number of species, e.g., for *C. difficile* 630 (the grdA NCBI Gene ID is 4915147) and polypeptide sequence (e.g., YP_001088866.2 (SEQ ID NO: 28). The sequence for the grdA gene product is as follows (SEQ ID NO: 28):

```
                                                        (SEQ ID NO: 28)
  1  msllsnkkvl iigdrdgipg paieecvktv egaevvfsst ecfvutaaga mdlenqnrvk 61  daadkfgaen vvillgaaea eaaglaaetv tagdptfagp lagvalglsv yhvveepiks 121  lfdesvyedq ismmemvlev eeieeemsgi reefckf
```

The grdA gene sequence for *C. difficile* 630 is as follows (SEQ ID NO:29):

```
                                                        (SEQ ID NO: 29)
  1  atgagtttac ttagtaataa aaaggttctt ataataggtg accgtgatgg tataccagga 61  cctgcgatag aagaatgtgt aaaaacagta gaaggagcag aggttgtttt ctcatctaca 121  gaatgctttg tctgaacagc tgctggggct atggacttag aaaatcaaaa cagagttaaa 181  gatgctgctg ataaattcgg agctgaaaat gttgtgattt tactaggtgc tgctgaagcc 241  gaagctgcag gtcttgcagc cgaaacagta actgctggag atccaacttt cgctggacca 301  cttgctggag ttgccttagg attaagtgtt taccacgttg ttgaggaacc aataaaatca 361  ttatttgatg aaagtgtata tgaagaccaa ataagtatga tggaaatggt tttagaagtt 421  gaagaaatag aagaagaaat gtctggtata agagaagaat tttgtaaatt ttaa
```

Defined Therapeutic Microbiota

Described herein are defined therapeutic microbiota that can be administered to suppress toxin expression by Gram positive, spore forming toxigenic bacteria such as *C. difficile*. In one embodiment, a defined therapeutic microbiota is or consists essentially of the single species, *C. bifermentans*. In another embodiment, the defined therapeutic microbiota comprises, consists essentially of or consists of *C. scindens*. In another embodiment, the defined therapeutic microbiota consists of, consists essentially of or comprises *C. bifermentans* and *C. scindens*. Strains of these species and others that express and secrete proteolytic enzymes into their surroundings and/or themselves perform Stickland fermentation are expected to promote suppression of *C. difficile* toxin expression. The following describes these species in further detail.

*Clostridium* Taxonomy: Clustering. As a starting point, species of the Genus *Clostridium* encompass a large number of anaerobic, spore-forming bacteria. In 1994, Collins et al. (Int. J. Systematic Biol. 44: 812-826 (1994), incorporated herein by reference) described a classification system that placed the species then known, and for which there was 16S rRNA sequence data available, into 19 "clusters," termed *Clostridium* Clusters I-XIX, based upon similarities and differences in 16S rRNA sequences. This taxonomy and nomenclature has been retained to date, with some refinement, e.g., classifications of some of the larger clusters into smaller sub-clusters given alphabetic identifiers, e.g., Cluster XIVa. *C. difficile* is in Cluster XI.

*Clostridium bifermentans*

*C. bifermentans* are anaerobic, motile, Gram positive bacteria that colonize the healthy human gut, and are not commonly found to be pathogenic. *C. bifermentans* is a member of *Clostridium* Cluster XI, the same cluster as *C. difficile. C. bifermentans* induces the *C. difficile* ethanolamine pathway genes and maintains proline reductase activity, glucose and sorbitol metabolism in vivo. Through the greater than 10× repression of tcdR expression and greater than 30× suppression of toxin production, strong codY activation and repression of the PaLoc genes is indicated. The *C. difficile* metabolic pathways influenced by *C. bifermentans* are also indicated to activate ccpA, rex and prdR to also inhibit toxin production.

Both *C. bifermentans* and *C. scindens* possess the enzymatic machinery for Stickland fermentations. Of the two, *C. bifermentans* preferentially uses Stickland fermentations over glycolytic pathways, including in the presence of glucose or other sugars (see FIG. 6A and FIG. 6B), while in vitro *C. scindens* is preferentially glycolytic and produces abundant acetate (FIG. 6B).

A genome of *C. bifermentans* was sequenced as part of the Human Microbiome Project, and can be found at, e.g., accession #PRJNA212658.

In one embodiment, the *C. bifermentans* strain is 76 (ATCC #638). The 16S rRNA gene sequence for *C. bifermentans* strain 76 (SEQ ID NO: 30) is as follows:

```
                                                       (SEQ ID NO: 30)
   1  catrgctcag gatgaacgct ggcggcgtgc ctaacacatg caagtcgagc gatctcttcg
  61  gagagagcgg cggacgggtg agtaacgcgt gggtaacctg ccctgtacac acggataaca
 121  taccgaaagg tatactaata cgggataaca tatgaaagtc gcatggcttt tgtatcaaag
 181  ctccggcggt acaggatgga cccgcgtctg attagctagt tggtaaggta atggcttacc
 241  aaggcaacga tcagtagccg acctgagagg gtgatcggcc acactggaac tgagacacgg
 301  tccagactcc tacgggaggc agcagtgggg aatattgcac aatgggcgaa agcctgatgc
 361  agcaacgccg cgtgagcgat gaaggccttc gggtcgtaaa gctctgtcct caaggaagat
 421  aatgacggta cttgaggagg aagccccggc taactacgtg ccagcagccg cggtaatatg
 481  taggggggcta gcgttatccg gaattactgg gcgtaaaggg tgcgtaggtg gtttttaag
 541  tcagaagtga aaggctacgg ctcaaccgta gtaagctttt gaaactagag aacttgagtg
 601  caggagagga gagtagaatt cctagtgtag cggtgaaatg cgtagatatt aggaggaata
 661  ccagtagcga aggcggctct ctggactgta actgacactg aggcacgaaa gcgtggggag
 721  caaacaggat tagataccct ggtagtccac gccgtaaacg atgagtacta ggtgtcgggg
 781  gttacccccc tcggtgccgc actaacgcat taagtactcc gcctgggaag tacgctcgca
 841  agagtgaaac tcaaaggaat ttdcggggac ccgcacaagt agcggagcat gtggtttaat
 901  tcgaagcaac gcgaagaacc ttacctaagc ttgacatccc actgacctct ccctaatcgg
 961  agatttccct tcggggacag tggtgacagg tggtgcatgg ttgtcgtcag ctcgtgtcgt
1021  gagatgttgg gttaagtccc gcaacgagcg caacccttgc ctttagttgc cagcattaag
1081  ttgggcactc tagagggact gccgaggata actcggagga aggtggggat gacgtcaaat
1141  catcatgccc cttatgctta gggctacaca cgtgctacaa tgggtggtac agagggttgc
1201  caagccgcga ggtggagcta atcccttaaa gccattctca gttcggattg taggctgaaa
1261  ctcgcctaca tgaagctgga gttactagta atcgcagatc agaatgctgc ggtgaatgcg
1321  ttcccgggtc ttgtacacac cgcccgtcac accatggaag ttgggggcgc ccgaagccgg
1381  ttagctaacc ttttaggaag cggccgtcga aggtgaacaa atgactgggg tgaagtcgta
1441  acaaggtanc cgtatcggaa ggtgcggcbg gatcaa
```

In another embodiment, the *C. bifermentans* strain is a bacterial strain comprising a 16S rRNA sequence that is at least 97%, at least 98%, at least 99%, or more identical to the sequence of SEQ ID NO: 30. A *C. bifermentans* strain useful in the methods and compositions described herein should express at least 75% of the extracellular proteolytic activity of *C. bifermentans* strain 76 (ATCC #638) when assayed with a meat granule digestion microbiological assay as described herein. In one embodiment, the *C. bifermentans* strain expresses at least 80%, at least 85%, at least 90%, at least 95%, at least 100% or more of the proteolytic activity of *C. bifermentans* strain 76 (ATCC #638).

*C. bifermentans* is an anaerobic bacterium that can be cultured under anaerobic and microaerophilic conditions, and thus should be cultured accordingly, e.g., in a manner that limits or inhibits the bacteria's exposure to oxygen. (*C. bifermentans* is described as being able to tolerate up to 8% $O_2$— see, e.g., Leja, K., Advances in Microbiology, 2014, however, growth under substantially anaerobic conditions is readily performed). Media and conditions for *C. bifermentans* growth in culture are known to those of ordinary skill in the art. As examples, *C. bifermentans* can be cultured under anaerobic conditions in, e.g., ATCC medium 2107 modified reinforced Clostridial agar/broth or ATCC medium 260 Trypticase soy agar/broth with defibrinated sheep blood (ATCC; Manassas, Va.), or grown on, e.g., *Brucella* Blood agar plates.

*Clostridium scindens*

*C. scindens* is an anaerobic, motile bacterium often found in the human gut, as well as in the soil. *C. scindens* is a member of *Clostridium* Cluster XIVa. *C. scindens* produces a 7-alpha bile acid dehydratase which converts primary bile acids to secondary bile acids that are strong inhibitors of *C. difficile* germination. It is noted that *C. bifermentans* has a choloylglycine deconjugating enzyme (which removes glycine from glycine-conjugated bile acids), but genomically does not possess comparable bile salt dehydroxylating enzymes.

While not wishing to be bound by theory, it is likely that at least part of the mechanism by which *C. scindens* promotes suppression of *C. difficile* infection is through bile acid metabolism to produce secondary bile acids (e.g., deoxycholic acid and lithocholic acid) that maintain an environment that is hostile to or not compatible with *C. difficile* and/or *C. difficile* infection. In this regard, *C. scindens* bacteria possess a complete secondary bile acid synthesis pathway, producing at least two enzymes active on the side-chain of the bile acid steroid nucleus and at least two enzymes active on the hydroxyl groups of the 7-position of bile acids. *C. scindens* expresses bile salt hydrolase/Choloylglycine hydrolase activity (E.C. #3.5.1.24), which catalyzes hydrolysis of the amide bond in conjugated bile salts, resulting in the release of free amino acids. This activity adds another source of free amino acid generation in the gut that can at least potentially contribute further substrate amino acids that promote Stickland fermentation.

A genome of *C. scindens* was sequenced as part of the Human Microbiome Project, and can be found at, e.g., accession #PRJNA18175.

*C. scindens* is an anaerobic bacterium, and thus should be cultured accordingly, e.g., in a manner the limits or inhibits the bacteria's exposure to oxygen. Media and conditions for *C. scindens* growth in culture are known to those of ordinary skill in the art. As examples, *C. scindens* can be cultured under anaerobic conditions in, e.g., ATCC medium 2107 modified reinforced Clostridial agar/broth or ATCC medium 260 Trypticase soy agar/broth with defibrinated sheep blood (ATCC; Manassas, Va.), or grown on, e.g., *Brucella* Blood agar plates.

In one embodiment, the *C. scindens* strain is VPI 13733 (ATCC #35704). The 16S rRNA gene sequence for *C. scindens* strain VPI 13733 (SEQ ID NO: 31) is as follows:

```
                                              (SEQ ID NO: 31)
gagagtttgatcctggctcaggatgaacgctggcggcgtgcctaacaca tgcaagtcgaacgaagcgcctggccccgacttcttcggaacgaggagcc ttgcgactgagtggcggacgggtgagtaacgcgtgggcaacctgccttg cactggggggataacagccagaaatggctgctaataccgcataagaccga agcgccgcatggcgcggcggccaaagccccggcggtgcaagatgggccc gcgtctgattaggtagttggcggggtaacggcccaccaagccgacgatc agtagccgacctgagagggtgaccggccacattgggactgagacacggc ccagactcctacgggaggcagcagtggggaatattgcacaatgggggaa accctgatgcagcgacgccgcgtgaaggatgaagtatttcggtatgtaa acttctatcagcagggaagaagatgacggtacctgactaagaagccccg gctaactacgtgccagcagccgcggtaatacgtagggggcaagcgttat ccggatttactgggtgtaaagggagcgtagacggcgatgcaagccagat gtgaaagcccggggctcaaccccgggactgcatttggaactgcgtggct ggagtgtcggagaggcaggcggaattcctagtgtagcggtgaaatgcgt agatattaggaggaacaccagtggcgaaggcggcctgctggacgatgac tgacgttgaggctcgaaagcgtggggagcaaacaggattagataccctg gtagtccacgccgtaaacgatgactactaggtgtcgggtggcaaggcca ttcggtgccgcagcaaacgcaataagtagtccacctggggagtacgttc gcaagaatgaaactcaaaggaattgacggggacccgcacaagcggtgga gcatgtggtttaattcgaagcaacgcgaagaaccttacctgatcttgac atcccgatgccaaagcgcgtaacgcgctctttcttcggaacatcggtga caggtggtgcatggttgtcgtcagctcgtgtcgtgagatgttgggttaa gtcccgcaacgagcgcaacccctatcttcagtagccagcattttggatg ggcactctggagagactgccagggagaacctggaggaaggtggggatga cgtcaaatcatcatgccccttatgaccagggctacacacgtgctacaat ggcgtaaacaaagggaggcgaacccgcgagggtgggcaaatcccaaaaa taacgtctcagttcggattgtagtctgcaactcgactacatgaagttgg aatcgctagtaatcgcgaatcagaatgtcgcggtgaatacgttcccggg tcttgtacacaccgcccgtcacaccatgggagtcagtaacgcccgaagc cggtgacccaacccgtaagggagggagccgtcgaaggtgggaccgataa ctggggtgaagtcgtaacaaggtagccgtatcggaaggtgcggctggat cacctccttc
```

In another embodiment, the *C. scindens* strain is a bacterial strain comprising a 16S rRNA sequence that is at least 97%, at least 98%, at least 99%, or more identical to the sequence of SEQ ID NO: 1. In one embodiment, the *C. scindens* strain expresses at least the level of bile salt hydrolase/Choloylglycine hydrolase expressed by *C. scindens* strain VPI 13733 (ATCC #35704). *C. scindens* is also proteolytic, albeit to a lesser degree than *C. bifermentans*. In one embodiment, the *C. scindens* strain used in a defined microbiota consortium as described herein has at least the proteolytic activity of *C. scindens* strain VPI 13733 (ATCC #35704).

Clostridium hylemonae

*C. hylemonae* is a naturally-occurring anaerobic commensal bacterium of the human gut. As described herein below, the relative abundance of *C. hylemonae* has been found, in combination with that of *C. scindens*, to be reliably predictive of the recurrence of *C. difficile* infection in human patients. *C. hylemonae* is a member of *Clostridium* Cluster XIVa. The 16S rRNA gene sequence for the *C. hylemonae* strain (SEQ ID NO: 32) is as follows:

```
                                              (SEQ ID NO: 32)
aggatgaacgctgccgccgtgcttaacacatgcaagtcgaacgaagcaa tactgtgtgaagagattagcttgctaagatcagaactttgtattgactg agtggcggacgggtgagtaacgcgtgggcaacctgccttacacaggggg ataacagctagaaatggctgctaataccgcataagacctcagtaccgca tggtagaggggtaaaaactccggtggtgtaagatgggcccgcgtctgat taggtagttggtagggtaacggcctaccaagccgacgatcagtagccga cctgagagggtgaccggccacattggactgagacacggcccaaactcct acgggaggcagcagtggggaatattgcacaatggggaaaccctgatgc agcgacgccgcgtgaaggatgaagtatttcggtatgtaaacttctatca gcagggaagaagatgacggtacctgactaagaagcccggctaactacg tgccagcagccgcggtaatacgtaggggcaagcgttatccggatttac tgggtgtaaaggagcgtagacggcatggcaagtctgaagtgaaagccc ggggctcaaccccgggactgctttggaaactgtcaggctagagtgtcgg agaggcaagtggaattcctagtgtagcggtgaaatgcgtagatattagg aggaacaccagtggcgaagcggcttgctggacgatgactgacgttgagg ctcgaaagcgtggggagcaaacaggattagataccctggtagtccacgc cgtaaacgatgattactaggtgtcgggaagcaaagcttttcggtgccgc agccaacgcaataagtaatccacctggggagtacgttcgcaagaatgaa actcaaaggaattgacggggacccgcacaagcggtggagcatgtggttt aattcgaagcaacgcgaagaaccttacctgatcttgacatcccggtgac aaagtatgtaacgtactctttcttcggaacaccggtgacaggtggtgca tggttgtcgtcagctcgtgtcgtgagatgttgggttaagtcccgcaacg gcgcaaccctta tctttagtagccagcatttgaggtgggcactctagag agactgccagggataacctggaggaaggtggggatgacgtcaaatcatc atgccccttatgaccagggctacacacgtgctacaatggcgtaaacaaa gggaagcgaccctgtgaaggcaagcaaatcccaaaaataacgtctcagt tcggattgtagtctgcaactcgactacatgaagctggaatcgctagtaa tcgcgaatcagaatgtcgcggtgaatacgttcccgggtcttgtacacac cgcccgtcacaccatgggggtcagtaacgcccgaagccggtgacctaacc gcaaaggaggagccgtcgaaggtg.
```

In one embodiment, the *C. hylemonae* bacterium useful in the reliable prediction of *C. difficile* infection recurrence or in the reliable prediction of initial *C. difficile* infection has a 16S rRNA gene sequence of SEQ ID NO: 32. In another embodiment, a *C. hylemonae* bacterium useful in the reliable prediction of *C. difficile* infection recurrence or in the reliable prediction of initial *C. difficile* infection has a 16S rRNA gene sequence at least 90%, at least 91%, at least 92%, at least 93%, at least 94%, at least 95%, at least 96%, at least 97%, at least 98%, at least 99%, or 100% identical to the sequence of SEQ ID NO: 32. It is also contemplated that *C. hylemonae* can provide therapeutic benefit, alone, or together with one or both of *C. bifermentans* and *C. scindens*.

Other potentially therapeutic Clostridial species that perform Stickland fermentation include, for example, *C. cadaveris* (Cluster I), and *C. hiranonis, C. sticklandii, Peptostreptococcus anaerobius* and *C. sporogenes* (Cluster XI).

The outcome of the studies described herein indicates that any or all of the following can have therapeutic benefit in combatting toxin production by Gram positive, spore-forming bacteria such as *C. difficile:*

A) Maintain metabolic and energy state in *C. difficile* through commensal proteolytic activity to release amino acids for Stickland fermentations (preferentially via the proline reductase pathway). Metabolites of Stickland fermentations can also be used or sensed by *C. difficile* through mechanisms that also reduce toxin production.

B) Induce or maintain expression of the *C. difficile* ethanolamine utilization pathway in *C. difficile* to help maintain energy state.

C) Prevent or limit production of butyrate by *C. difficile* and other commensals, to limit a stimulus of *C. difficile* toxin production.

D) Prevent *C. difficile* spore germination through production of secondary bile acids by *C. scindens* or other species that promote or produce such products.

E) Reduce biomass of *C. difficile* through, e.g., direct competition with *C. difficile* and by permitting recovery of other gut commensal species that directly compete and/or prevent spore germination through innate bile salt hydrolase activities.

F) Glycine Reductase activity or expression.

Defined Therapeutic Microbiota, and Compositions Comprising Them

It is demonstrated herein that *C. bifermentans* can completely protect GF and conventional mice from otherwise fatal infection with *C. difficile.*

In one aspect, then, described herein are compositions, including but not limited to pharmaceutical compositions, comprising an oral formulation comprising *C. bifermentans* bacteria. In one embodiment the *C. bifermentans* species is the only bacterial species in the formulation. In another embodiment, the *C. bifermentans* is the only Clostridial XI species in the formulation. In another embodiment, the *C. bifermentans* is the only Clostridial species in the formulation. In another embodiment, the *C. bifermentans* is the only bacterial species in the formulation. Such compositions can be used to treat or prevent *C. difficile* infection, including recurrent *C. difficile* infection, and/or toxin production.

Methods for the growth or preparation of *C. bifermentans* bacteria are known in the art. As noted herein above, this species is an obligate anaerobe, so culture under anaerobic conditions is required. Media for culture of *Clostridium* species are also known in the art, and are commercially available, as also noted elsewhere herein.

In another aspect, described herein is a composition, including a pharmaceutical composition, comprising *C. bifermentans* bacteria, wherein the *C. bifermentans* bacteria are in dried, viable form. Methods of drying *Clostridium* species in a manner that maintains viability upon re-hydration are known in the art.

In another aspect, described herein is a pharmaceutical composition comprising a formulation comprising *C. bifer-*

*mentans* bacteria, wherein the composition does not comprise *Bacteroides* species or *Escherichia* species.

It is contemplated that killed or proliferatively inactive, but metabolically active *C. bifermentans* bacteria could have beneficial effect, e.g., if administered repeatedly. However, in each of the aspects noted above, it is preferred that the bacteria are viable as the term is used herein. In this context, the bacterial species for any of the compositions described herein can be present in vegetative, metabolically and proliferatively active forms, dried viable form, spore form, or a combination of these forms. Thus, in one embodiment, the *C. bifermentans* bacteria are in spore form. In another embodiment, the *C. bifermentans* bacteria are in metabolically active form, including, but not limited to vegetative and/or actively proliferative forms. In another embodiment, the *C. bifermentans* bacteria are not in spore form. In another embodiment, the *C. bifermentans* bacteria are present as a mixture of vegetative, metabolically active and spore forms. Methods for inducing sporulation of *Clostridium* species are known to those of ordinary skill in the art.

Another aspect described herein provides a pharmaceutical composition comprising an oral formulation comprising a bacterial population that has 16S rDNA with a sequence at least 97% identical to a 16S rDNA sequence present in a reference *C. bifermentans* bacterium. In various embodiments, the bacterial population has 16S rDNA with a sequence at least 97%, 98%, 99% or more identical to the 16S rDNA of the reference bacterium.

Another aspect described herein provides a pharmaceutical composition comprising a bacterial population that has 16S rDNA with a sequence at least 97% identical to a 16S rDNA sequence present in a reference *C. bifermentans* bacterium, wherein the *C. bifermentans* bacteria is in dried, viable form. In various embodiments, either or both of the bacterial populations has 16S rDNA with a sequence at least 97%, 98%, 99% or more identical to the 16S rDNA of the reference bacterium.

Another aspect described herein provides a pharmaceutical composition comprising a formulation comprising a bacterial population that has 16S rDNA with a sequence at least 97% identical to a 16S rDNA sequence present in a reference *C. bifermentans* bacterium, wherein the composition does not comprise *Bacteroides* species or *Escherichia* species. In various embodiments, the bacterial population has 16S rDNA with a sequence at least 97%, 98%, 99% or more identical to the 16S rDNA of the reference bacterium.

In one embodiment of this or any other aspect described herein, the compositions described herein do not comprise viable *C. sardiniense* bacteria. As described herein, it was found that the presence of *C. sardiniense* in otherwise germ-free mice comprising pathogenic *C. difficile* bacteria increased the severity of the resulting *C. difficile* infection. Thus, in one embodiment, the technology described herein excludes *C. sardiniense* from a therapeutic composition as described herein.

In one embodiment of this or any aspect described herein, a therapeutic microbiota composition does not comprise a *Bacteroides* species or *Escherichia* species. *Bacteroides* is a genus of Gam-negative, obligate anaerobic bacteria. *Bacteroides* species can be identified by sphingolipids in their membranes, as well as by 16S rDNA sequence. They make up a substantial proportion of the gut microbiota, and are commonly mutualistic. *Escherichia* species are Gram-negative, non-spore forming, facultative anaerobic bacteria from the family Enterobacteriaceae. The majority of *Escherichia* species are commensal gut flora, although certain *Escherichia* strains are human pathogens. A skilled person can identify *Bacteroides* and *Escherichia* species, e.g., using PCR-based methods to quantify 16S rDNA genetic markers, among others.

In one embodiment of this or any aspect described herein, the compositions described herein do not comprise any additional viable *Clostridium* species. In another embodiment of any aspect described herein, the compositions described herein do not comprise any additional viable bacteria of any kind. A skilled person can identify the presence of other viable bacteria (e.g., additional *Clostridium* species, among others) in the composition, e.g., using anaerobic culture, and identify organisms in such culture using, for example, PCR-based methods to quantify 16S rDNA genetic markers.

It is also demonstrated herein that a defined consortium of *Clostridium* species comprising *C. scindens* and *C. bifermentans*, as those species are defined herein, is sufficient to treat or prevent *C. difficile* infection, including, but not limited to recurrent *C. difficile* infection, and to suppress toxin production by *C. difficile*.

In one aspect, then, described herein are compositions, including but not limited to pharmaceutical compositions, comprising an oral formulation comprising *C. scindens* and *C. bifermentans* bacteria. In another embodiment of this and all other aspects described herein that involve the *C. scindens* and *C. bifermentans* species, the only bacterial species in the formulation are *C. scindens* and *C. bifermentans*. Methods for the growth or preparation of *C. scindens* and *C. bifermentans* bacteria are known in the art. As noted herein above, these species are obligate anaerobes, so culture under anaerobic conditions is required. Media for culture of *Clostridium* species are also known in the art, and are commercially available, as also noted herein above.

In another aspect, described herein is a composition, including a pharmaceutical composition, comprising *C. scindens* and *C. bifermentans* bacteria, wherein one or both of the *C. scindens* and *C. bifermentans* bacteria is in dried, viable form. Methods of drying *Clostridium* species in a manner that maintains viability upon re-hydration are known in the art.

In another aspect, described herein is a pharmaceutical composition comprising a formulation comprising *C. scindens* and *C. bifermentans* bacteria, wherein the composition does not comprise *Bacteroides* species or *Escherichia* species.

It is contemplated that killed or proliferatively inactive, but metabolically active bacteria of these species could have beneficial effect if administered repeatedly. However, in each of the aspects noted above, it is preferred that the bacteria are viable as the term is used herein. In this context, the bacterial species for any of the compositions described herein can be present in vegetative, metabolically and proliferatively active forms, dried viable form, spore form, or a combination of these forms. Thus, in one embodiment, both of the *C. scindens* and *C. bifermentans* bacteria are in spore form. In another embodiment, both of the *C. scindens* and *C. bifermentans* bacteria are in metabolically active form, including, but not limited to vegetative and/or actively proliferative forms. In another embodiment, one or both of the *C. scindens* and *C. bifermentans* bacteria are not in spore form. In another embodiment, the *C. scindens* and *C. bifermentans* bacteria are present as a mixture of vegetative, metabolically active and spore forms. Methods for inducing sporulation of *Clostridium* species are known to those of ordinary skill in the art.

Another aspect described herein provides a pharmaceutical composition comprising an oral formulation comprising a first bacterial population that has 16S rDNA with a sequence at least 97% identical to a 16S rDNA sequence present in a reference *C. scindens* bacterium, and a second bacterial population that has 16S rDNA with a sequence at least 97% identical to a 16S rDNA sequence present in a reference *C. bifermentans* bacterium. In various embodiments, either or both of the bacterial populations has 16S rDNA with a sequence at least 97%, 98%, 99% or more identical to the 16S rDNA of the reference bacterium.

Another aspect described herein provides a pharmaceutical composition comprising a first bacterial population that has 16S rDNA with a sequence at least 97% identical to a 16S rDNA sequence present in a reference *C. scindens* bacterium, and a second bacterial population that has 16S rDNA with a sequence at least 97% identical to a 16S rDNA sequence present in a reference *C. bifermentans* bacterium, wherein one or both of the *C. scindens* and *C. bifermentans* bacteria is in dried, viable form. In various embodiments, either or both of the bacterial populations has 16S rDNA with a sequence at least 97%, 98%, 99% or more identical to the 16S rDNA of the reference bacterium.

Another aspect described herein provides a pharmaceutical composition comprising a formulation comprising a first bacterial population that has 16S rDNA with a sequence at least 97% identical to a 16S rDNA sequence present in a reference *C. scindens* bacterium, and a second bacterial population that has 16S rDNA with a sequence at least 97% identical to a 16S rDNA sequence present in a reference *C. bifermentans* bacterium wherein the composition does not comprise *Bacteroides* species or *Escherichia* species. In various embodiments, either or both of the bacterial populations has 16S rDNA with a sequence at least 97%, 98%, 99% or more identical to the 16S rDNA of the reference bacterium.

The above bacterial compositions can include, for example but are not limited to metabolically active bacteria, wet bacteria, dry viable bacteria (e.g., preparations including viable spray-dried cells, freeze-dried cells, vacuum-dried cells, drum-dried cells, vitrified etc.), and the like. Preparations of *Clostridium* species described herein can include, for example, suspensions of *Clostridium* bacteria, cultured cells of *Clostridium* bacteria (including bacterial cells, and optionally, supernatant and medium ingredients), and, for example, *Clostridium* culture biomass, removed from suspension culture, e.g., by centrifugation, filtration, or the like. While viable *Clostridium* bacteria are used in most applications considered herein, it is contemplated that in some embodiments, processed cells of *Clostridium* bacteria can include, for example, ground cells, crushed cells, liquefied cells (extracts etc.) and concentrates and preparations thereof, and the like.

Dried preservation removes water from the culture by evaporation (in the case of spray drying or 'cool drying') or by sublimation (e.g., for freeze drying, spray freeze drying). Removal of water improves long-term bacterial composition storage stability at temperatures elevated above cryogenic. If the bacterial composition comprises spore forming species and results in the production of spores, the final composition can be purified by additional means such as density gradient centrifugation.

Species effective for treatments as described herein are readily available. However, to maintain strain integrity over time, bacterial composition banking can be done by culturing and preserving the strains individually, or by mixing the strains together to create a combined bank. As an example of cryopreservation, a bacterial composition culture can be harvested by centrifugation to pellet the cells from the culture medium, the supernate decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

*C. bifermentans* and/or *C. scindens* can be in spore form or not in spore form in the compositions described herein. Bacterial spores are dormant, non-reproductive structures produced by certain bacteria from the Firmicute phylum, for example in an environment lacking nutrients. Spores can be preserved as described above, and can be reactivated, e.g., by heating the endospore. In addition, *C. bifermentans* and/or *C. scindens* can be present in a mixture of metabolically active bacteria and spores. Metabolically active bacteria can actively metabolize nutrients, and will have little lag time from administration to active participation in treating or preventing *C. difficile* infection. They will also likely have little lag time in beginning to proliferate in the gut if conditions are appropriate.

In one embodiment, any of the defined therapeutic microbiota compositions described herein further comprises a prebiotic. Prebiotics promote the growth, survival, and activity of beneficial microorganisms, or probiotics. Prebiotics have been shown to alter the compositions of microorganisms (microflora) in the gut microbiota, alone or in combination with probiotic organisms. In addition, prebiotics have been shown to increase calcium and magnesium absorption in the gut, increase bone density, enhance the immune system, reduce blood triglyceride levels, and control hormone levels. Prebiotics include any of a number of compositions that are generally not directly digestible by humans, but that are readily digestible by and promote the growth or establishment of probiotic microbes. In one embodiment, a preferred prebiotic comprises a sugar or carbohydrate, e.g., a starch or other carbohydrate-comprising polymer, that can be digested by *C. bifermentans* and/or *C. scindens*, but not readily so by other commensals, to thereby favor an increase in the relative proportion or abundance of the administered species. Non-limiting examples of prebiotics include but are not limited to inulin, fructooligosaccharides, galactooligosaccharides, hemicelluloses (e.g., arabinoxylan, xylan, xyloglucan, and glucomannan), chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides, and dietary proteins able to be digested by *C. bifermentans* and/or *C. scindens*.

In one embodiment, any of the defined therapeutic microbiota compositions described herein further comprise an effective amount of one or more free Stickland fermentable amino acids, e.g. a preparation of free proline alone or any combination of free amino acids selected from the group consisting of: alanine, leucine, valine, isoleucine, tryptophan, tyrosine, phenylalanine, proline or glycine.

In one embodiment, any of the defined therapeutic microbiota compositions described herein further comprise an effective amount of a polypeptide that can be proteolyzed by the administered species to generate free amino acids fermentable by Stickland fermentation. Inclusion of such a polypeptide provides a ready source of protein for an administered Stickland-fermenting bacterium to digest to amino acids useful for Stickland fermentation by *C. difficile*.

Non-limiting examples of such polypeptides include, but are not limited to casein, gelatin, collagen, and an artificial polymer comprising Stickland acceptor amino acids and/or Stickland donor amino acids. A proline-rich or proline+ leucine-rich protein can also be used. Where an artificial polymer is used, the polymer can comprise Stickland donor amino acids selected from the group consisting of: alanine, leucine, valine, isoleucine, tryptophan, tyrosine and phenylalanine, and/or Stickland acceptor amino acids including proline and/or glycine. The polymer can comprise e.g., a poly[N] amino acid polymer, e.g. a poly[alanine], poly[leucine], etc., or e.g. a copolymer of one or more of the Stickland fermentable amino acids. As a non-limiting example, copolymers can include, e.g. poly[alanine, leucine], poly[alanine, isoleucine],[poly[alanine, tryptophan], etc. Polymers rich in proline would be expected to preferentially promote fermentation via the Stickland proline reductase pathway and repression of *C. difficile* toxin production.

In one embodiment, any of the compositions described herein, except those which expressly exclude any species other than *C. scindens* and/or *C. bifermentans*, further comprise a microbe that supports (e.g., the growth, or viability) *C. bifermentans* and/or *C. scindens*. *Ruminococcus obeum* is an exemplary microbe that has been shown to support *C. scindens*. *Ruminococcus obeum* is a genus of bacteria in the class Clostridia found in an abundance in the human gut. A skilled person will be able to determine if a microbe supports *C. bifermentans* and/or *C. scindens*, e.g., using complementation assays known in the art.

Establishment of administered *C. scindens* and/or *C. bifermentans* as described herein can be evaluated by monitoring the proportion of these species in gut microbiota samples taken over time. An administered species can be considered to be established if that species remains at a level increased relative to its level pre-administration for at least two weeks, preferably at least three weeks, one month, five weeks, six weeks, seven weeks, two months, nine weeks, ten weeks, eleven weeks, three months or more following administration. The presence of the administered species at a relative level of abundance of at least 0.3%, at least 0.4%, 0.5%, 0.6%, 0.7%, 0.8%, 0.9%, 1% or more, maintained over time as noted is preferred. Tracking of the administered species can be facilitated by modification of the species to carry a genetic difference or barcode, but this is optional.

Diagnostic Methods

One aspect of the present technology is a method of predicting or determining the likelihood of *C. difficile* infection or recurrence of *C. difficile* infection in a subject. Such a prediction can guide prophylactic and subsequent therapeutic treatment decisions. Markers of likely infection or recurrence include, but are not limited to markers in the following classes:

Proteolytic activity of the subject's commensal microbiota, measured, for example, by biochemical assay for proteolysis of a substrate, e.g., one including but not limited to casein or gelatin. Relatively high proteolytic activity is a predictor of reduced likelihood of infection or recurrence.

DNA- or RNA-based studies for commensal proteases and Stickland reductase genes as described herein. The presence and/or expression of commensal protease genes is a predictor of reduced likelihood of infection or recurrence, with higher levels providing benefit.

Microbiologic, biochemical or molecular assays for proteolytic Clostridia, Stickland fermenters, or other highly proteolytic commensal species. The presence of such species is a predictor of reduced likelihood of infection or recurrence, with higher levels providing benefit.

Detection of energy-producing substrates for *C. difficile*, e.g., substrates selected from proline, Stickland donor amino acids, ethanolamine, glucose, fructose, mannitol, sorbitol, cysteine and threonine. Greater energy-producing substrate levels, and particularly greater levels of substrates preferred by *C. difficile* are predictors of reduced likelihood of infection or recurrence.

Detection of metabolites of Stickland fermentation including, for example, 5-amino valerate, branched SCFA amino acid metabolites and other Stickland amino acid metabolites. Greater levels of such metabolites are predictive of reduced risk of infection or recurrence. Greater levels of metabolites associated with the proline reductive pathway are particularly predictive.

Detection of metabolites of anaerobic carbohydrate metabolism including, for example the volatile SCFA acetate, propionate or butyrate, and non-volatile SCFA succinate, lactate or pyruvate, where increased levels of volatile SCFA, and of succinate, are predictive of increased likelihood of infection or recurrence.

Detection of microbial energy transporters including NADH/NAD+, NADPH/NADP+, ATP/ADP and GDP/GTP as indicative of the energy state in tested materials from microbial metabolism.

In one embodiment, any or all of the markers noted above can be used with detection of toxigenic *C. difficile* by microbiologic, toxin ELISA or molecular methods to predict likelihood of infection or recurrence. The presence and/or levels of the various markers can be compared, for example, to a reference to determine likelihood of infection or recurrence. The reference can be, for example, a sample from a healthy individual, or as the case may be a sample from an individual with active *C. difficile* infection.

In one embodiment, a method is provided for determining the efficacy of therapy for *C. difficile*. In one embodiment, the therapy is a bacteriotherapy, for example, as described herein. In another embodiment, the therapy is or comprises administration of a pre-biotic, and/or administration of an amino acid or amino acid derivative. In one embodiment, the method comprises measuring in a sample from an individual being treated for *C. difficile* infection, one or more markers from one or more, two or more, three or more, four or more, or from each of the classes of the markers listed above. In one embodiment, the reference is a sample from an individual with active *C. difficile* infection. The reference can, but does not necessarily have to be, a sample from the subject being treated, taken before treatment began. A level of activity or expression of one or more markers or classes of markers that is increased relative to the reference indicates effective therapy. In one embodiment, the sample is a stool sample.

In another embodiment, a method is provided for predicting the likelihood of recurrence in a subject being treated or who has been treated for *C. difficile* infection. In one embodiment, the method comprises measuring in a sample from an individual who has been treated for *C. difficile* infection, one or more markers from one or more, two or more, three or more, four or more, or from each of the classes of the markers listed above. In one embodiment, the reference is a sample from a healthy individual. A healthy individual is one without active *C. difficile* infection and who has not received antibiotic treatment within the past three months. A level of one or more biomarkers from one or more of the classes listed above that is below that of the reference indicates an increased risk of recurring *C. difficile* infection.

In one embodiment, the sample is a stool sample. The method can further comprise administering a bacteriotherapy as described herein to an individual for whom the level of such marker(s) is below the reference.

In another embodiment, a method is provided for predicting the risk of an individual for developing a first infection with *C. difficile*. This is applicable, for example, to those who are elderly, immunocompromised, hospitalized, in a nursing home, receiving antibiotics, or receiving proton pump inhibitors. In one embodiment, the method comprises measuring in a sample from a subject in one or more of these categories one or more markers in one or more of the classes listed above, and the subject is at increased risk of contracting active *C. difficile* infection if the level of such marker(s) is below a reference. In one embodiment, the reference can be a sample from a healthy individual as above. In another embodiment, the sample from the subject is assayed to determine the presence and/or amount of Stickland fermenting and/or proteolytic bacterial species, including, for example, non-pathogenic Clostridial species that are proteolytic and/or Stickland fermenting. A lack of such species indicates an increased risk for developing active *C. difficile* infection. A reduced number relative to a healthy reference also indicates increased risk. In one embodiment the method further comprises administering a bacteriotherapy as described herein to an individual for whom such species are lacking or for whom the level of such marker(s) is below the reference.

Further, the markers noted above can be used to define and monitor the efficacious activity of a therapeutic regimen, including, but not limited to a therapeutic regimen comprising administration of bacteriotherapeutic products, e.g., a defined therapeutic microbiota composition or product as described herein.

Also described herein are predictive methods that examine the presence of certain commensal species as a marker of likelihood of *C. difficile* infection and/or *C. difficile* toxin production. In one embodiment, such a method comprises: (a) determining the relative abundance of all operational taxonomic units (OTUs) in a sample of the subject's stool that are >90% identical to a reference sequence of *C. scindens*; (b) determining the relative abundance of all operational taxonomic units (OTUs) in a sample of the subject's stool that are >90% identical to a reference sequence of *C. hylemonae*; and (c) summing the relative abundances determined in steps (a) and (b), wherein a sum of relative abundances less than or equal to 1% indicates an increased risk of *C. difficile* recurrence relative to a subject in which the sum of relative abundances is greater than 1%. In one embodiment, relative abundance of the marker species indicative of increased risk is between 1% and 0.01%. As used herein, "relative abundance" refers to comparison with all species of microbes identified in the subject's sample, and is not limited to *Clostridium* species. The relative abundance of species in a sample can be measured, for example using Roche/454 pyrosequencing or Illumina sequencing for 16S rRNA gene sequencing. This approach, combined with multiplexing produces thousands of 16S rRNA sequences per sample. Microbiome sequencing techniques are further reviewed in, e.g., Grice, E A, and Segre J A. Annu Rev Genomics Hum Genet. 2012; 13:151-170. Relative abundance can additionally be measured using, e.g., using amplicons for microbiologic or microbial products and/or other gene-level targets (e.g., qPCR for genes (e.g., the bai gene, or the gene encoding a Stickland enzyme, a bile acid hydrolase, etc.)).

The predictive method can also be applied to prediction of susceptibility to a first *C. difficile* infection. Thus, in one embodiment, a sample can be taken from a patient who is at risk of having, has, or has previously had at least one *C. difficile* infection. A sample can be taken from a subject who has never had a *C. difficile* infection, but who is in a risk category as noted herein. A stool sample can be collected using standard techniques, e.g., passing stool directly into a clean, dry container.

At least one sample is taken from the subject for the predictive method. However, repeated sampling can also be performed. For example, a sample can be taken from a subject once a day, once a week, twice a month, once a month, or every 3 months following a *C. difficile* infection to assess the risk of a recurrent *C. difficile* infection, or a sample can be taken from a subject once a year following a *C. difficile* infection to assess the risk of a recurrent *C. difficile* infection. It has even been found that measurement of the relative abundance of the noted species (*C. scindens* and *C. hylemonae*) during treatment for an initial *C. difficile* infection can be predictive of likelihood of a recurrence. Thus, at least one sample can be taken from a subject during a *C. difficile* infection, e.g., a sample can be taken once a day for the entirety of the infection.

A sample can be taken from a subject who has not previously been treated with antibiotics to treat a *C. difficile* infection. Alternatively, a sample can be taken from a subject who has been treated with antibiotics to treat a *C. difficile* infection. The sample can be taken from the subject before, during, or after administration of antibiotics to treat a *C. difficile* infection. A sample can be taken from a subject before, during, and after administration of an antibiotic (e.g., a sample is taken from a subject during and after administration of an antibiotic).

The method can further comprise the step of administering a further therapeutic or prophylactic treatment, including, for example, an FMT or any of the bacterial compositions described herein to a subject when the sum of relative abundances relative level is at or below 0.01%, 0.1%, 0.2%, 0.3%, 0.4%, 0.5%, 0.6%, 0.7%, 0.8%, 0.9%, or 1.0%.

In this context, the reference sequence of *C. scindens* can be a sequence comprising at least 90%, at least 91%, at least 92%, at least 93%, at least 94%, at least 95%, at least 96%, at least 97%, at least 98%, at least 99%, or 100% sequence identity to the sequence of SEQ ID NO: 31. Similarly, in this context, the reference sequence of *C. hylemonae* can be a sequence comprising at least 90%, at least 91%, at least 92%, at least 93%, at least 94%, at least 95%, at least 96%, at least 97%, at least 98%, at least 99%, or 100% sequence identity to the sequence of SEQ ID NO: 32.

In another aspect of any of the embodiments, described herein is a method of treating a pathology involving expression of a bacterial toxin from a Gram positive, spore-forming species in a subject in need thereof, the method comprising: a) determining that the subject has a reduced amount and/or activity of secreted proteolytic enzymes in a gut or stool sample relative to healthy individual as described herein; and b) administering a therapeutic bacterial species as described herein to the subject. In some embodiments of any of the aspects, the step of determining that the subject has a reduced amount and/or activity of a secreted proteolytic enzyme can comprise i) obtaining or having obtained a biological sample from the subject and ii) performing or having performed an assay on the sample obtained from the subject to determine/measure the level of the proteolytic enzyme in the subject. Methods to measure amount of secreted proteolytic enzymes and/or activity are known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody. For example, the antibody can be labeled with a detectable marker whose presence and location in the subject is detected by standard imaging techniques. Methods to measure the activity of secreted proteolytic enzymes are known to a skilled artisan. For example, a protease activity assay that uses casein or gelatin as a substrate can be used to measure the activity of a protease in a biological sample (Cat. No. Ab111750; Abcam, Cambridge Mass.).

In another aspect, described herein is a method of treating a pathology involving expression of a bacterial toxin brom a Gram positive spore-forming bacterium in a subject in need thereof, the method comprising: a) determining that a sample from the subject has a decreased amount and/or activity of proline reductase relative to a sample from a healthy individual; and b) administering a therapeutic bacterial species as described herein to the subject. In one embodiment, the step of determining that a sample from the subject has reduced level or activity of proline reductase can comprise i) obtaining or having obtained a biological sample from the subject and ii) performing or having performed an assay on the sample obtained from the subject to determine/measure the level of the proline reductase in the subject. Methods to measure amount or activity of proline reductase are known to a skilled artisan and/or described herein. Such methods can include measurement of gene expression products, e.g., protein level, and include for example, ELISA (enzyme linked immunosorbent assay), western blot, immunoprecipitation, and immunofluorescence using detection reagents such as an antibody or protein binding agents.

In another aspect of any of the embodiments, described herein is a method of treating a pathology involving expression of a bacterial toxin brom a Gram positive spore-forming bacterium in a subject in need thereof, the method comprising: a) determining that a sample from the subject has a decreased amount and/or activity of glycine reductase relative to a sample from a healthy individual; and b) administering a therapeutic bacterial species as described herein to the subject. In one embodiment, the step of determining that a sample from the subject has reduced level or activity of glycine reductase can comprise i) obtaining or having obtained a biological sample from the subject and ii) performing or having performed an assay on the sample obtained from the subject to determine/measure the level of the glycine reductase in the subject. Methods to measure amount or activity of glycine reductase are known to a skilled artisan and/or described herein. Such methods can include measurement of gene expression products, e.g., protein level, and include for example, ELISA (enzyme linked immunosorbent assay), western blot, immunoprecipitation, and immunofluorescence using detection reagents such as an antibody or protein binding agents.

Dosage, Administration and Formulations

In one aspect, any of the compositions described herein is administered to a subject that has, or has been diagnosed with C. difficile infection. In one embodiment, the C. difficile infection is a recurrent C. difficile infection. Recurrent C. difficile infections can be caused by the same or a different C. difficile strain that caused a previous C. difficile infection. In one embodiment, the subject is at risk for a C. difficile infection or a recurrent C. difficile infection.

A clinician can diagnose a subject as having a C. difficile infection using standard methods to detect toxins that are produced by C. difficile bacteria. For example, a stool sample from subject suspected of having a C. difficile infection can be analyzed via an enzyme immunoassay or even dipstick/lateral flow immunoassay for the C. difficile toxin(s), PCR-based assays, GDH/EIA tests, or cell cytotoxicity assays are also commonly used to definitively determine C. difficile infection. Imaging, e.g., colonoscopy or abdominal x-ray or CT scan can also be used to assist the diagnosis of C. difficile infection.

A clinician can determine is a subject is at risk of having a C. difficile infection by assessing a subject's risk factors, including but not limited to the subject's proximity to an individual who has or has recently had a C. difficile infection, current medications that promote C. difficile growth in the intestine, age, antibiotic use (length of antibiotic regimen, use of broad-spectrum antibiotics, or use of multiple antibiotics, use of gastric acid inhibitors such as proton pump-inhibitors and or histamine-2 receptor antagonists. At present, a subject who has had previous C. difficile infection is at risk of a recurrent C. difficile infection; approximately 20% of subjects who have had a C. difficile infection will have a recurrent C. difficile infection. In a further embodiment, risk of recurrence can be evaluated with the method described herein above that measures the relative abundance of C. scindens and C. hylemonae. Risk of recurrence can also be predicted via one or more of the diagnostic methods described herein.

Dosage

The dosage ranges for the bacterial species described herein in a defined therapeutic microbiota composition depends upon the potency (including viability), and includes amounts large enough to produce the desired effect, e.g., reduction in at least one symptom of a C. difficile infection in a treated subject. The dosage should not be so large as to cause unacceptable adverse side effects. Generally, the dosage can vary with the type of illness, e.g., first infection vs. recurrent infection, and with the age, condition, and sex of the patient. The dosage can be determined by one of skill in the art and can also be adjusted by the individual physician in the event of any complication.

For use in the various aspects described herein, an effective amount of cells in a composition as described herein comprises at least $1 \times 10^5$ bacterial cells, at least $1 \times 10^6$ bacterial cells, at least $1 \times 10^7$ bacterial cells, at least $1 \times 10^8$ bacterial cells, at least $1 \times 10^9$ bacterial cells, at least $1 \times 10^{10}$ bacterial cells, at least $1 \times 10^{11}$ bacterial cells, at least $1 \times 10^{12}$ bacterial cells or more. In one embodiment, the microbial consortium or the individual bacterial components thereof can be obtained from a microbe bank. Members of a therapeutic or preventive/prophylactic consortium are generally administered together, e.g., in a single admixture. However, it is specifically contemplated herein that members of a given consortium can be administered as separate dosage forms or sub-mixtures or sub-combinations of the consortium members (e.g., C. scindens and C. bifermentans can be comprised in two separate compositions that are administered as separate doses). Thus, a consortium of e.g., C. scindens and C. bifermentans, can be administered, for example, as a single preparation including all members (in one or more dosage units, e.g., one or more capsules) or as two separate preparations that, in sum, include all members of the given consortium. While administration as a single admixture is preferred, a potential advantage of the use of e.g., individual units for each member of a consortium, is that the species administered to any given subject can be tailored, if necessary, by selecting the appropriate combination of, for example, single species dosage units that together comprise the desired consortium. With respect to the administration of two separate preparations, the route of administration can be the same for each preparation (e.g., the first and second preparation can be administered orally), or different for each preparation (e.g., the first preparation can be administered orally and the second preparation is administered directly to the colon via colonoscope, to the small intestine via endoscope, or to the colon via suppository or enema).

From the conventional mouse model (administer microbes after onset of symptomatic Cdiff infection) it was found that orally administered *C. bifermentans* rapidly changes the cecal environment 6-7 hr after administration (transit time through the gut). This does not occur with *C. sardiniense*. It is noted that *C. bifermentans* persistence in most conventional mice is only a few days but is sufficient to correct the gut environment and cause Cdiff to rapidly halt toxin production. The administered bacteriotherapy can, for example, provide long-term engraftment, e.g., weeks, months or longer, or, it can provide shorter term persistence or presence of the administered species. Where long-term engraftment does not occur, repeat dosing is warranted, for example to provide continuing protection for as long as needed, including days, weeks, months, years or longer, e.g., indefinitely if needed. The need for such continued dosing can be evaluated, e.g., using methods of evaluating risk of infection or recurrent infection as described herein.

One can also easily adjust the ratio of one species to another if separate dosage forms are administered. It is contemplated that the ratios of *C. scindens* to *C. bifermentans*, for example, can be varied, e.g. over a range of 1:10 to 10:1 with benefit to the patient under certain circumstances, especially where, for example, the persistence of one species is found to be less than that of the other. Such a finding would warrant, for example, increasing the ratio in favor of the species with the lower degree of persistence. In one embodiment, the ratio of *C. scindens* to *C. bifermentans* in a composition described herein is 1:1. The ratio of *C. scindens* to *C. bifermentans* in a composition described herein can be 1:1, 1:2, 1:3, 1:4, 1:5, 1:6, 1:7, 1:8, 1:9, or 1:10. The ratio of *C. bifermentans* to *C. scindens* in a composition described herein can be 1:1, 1:2, 1:3, 1:4, 1:5, 1:6, 1:7, 1:8, 1:9, or 1:10. The ratio should be such that the amount of each bacteria in the composition is sufficient to promote engraftment (i.e., in vivo replication) of each species in a subject's GI tract following administration of the composition.

A pharmaceutical composition comprising a microbial consortium can be administered by any method suitable for depositing in the gastrointestinal tract, preferably the colon, of a subject (e.g., human, mammal, animal, etc.). Examples of routes of administration include rectal administration by colonoscopy, suppository, enema, upper endoscopy, or upper push enteroscopy. Additionally, intubation through the nose or the mouth by nasogastric tube, nasoenteric tube, or nasal jejunal tube can be utilized. Oral administration by a solid such as a pill, tablet, a suspension, a gel, a geltab, a semisolid, a tablet, a sachet, a lozenge or a capsule or microcapsule, or as an enteral formulation, or re-formulated for final delivery as a liquid, a suspension, a gel, a geltab, a semisolid, a tablet, a sachet, a lozenge or a capsule, or as an enteral formulation can be utilized as well. Also contemplated herein are food items that are inoculated with a microbial consortium as described herein.

In some embodiments, the compositions described herein can be administered in a form containing one or more pharmaceutically acceptable carriers. Suitable carriers are well known in the art and vary with the desired form and mode of administration of the composition. For example, pharmaceutically acceptable carriers can include diluents or excipients such as fillers, binders, wetting agents, disintegrators, surface-active agents, glidants, lubricants, and the like. The carrier may be a solid (including powder), liquid, or combinations thereof. Each carrier is preferably "acceptable" in the sense of being compatible with the other ingredients in the composition and not injurious to the subject. The carrier may be biologically acceptable and inert (e.g., it permits the composition to maintain viability of the biological material until delivered to the appropriate site).

Oral compositions can include an inert diluent or an edible carrier. For the purpose of oral therapeutic administration, the active compound can be incorporated with excipients and used in the form of tablets, lozenges, pastilles, troches, or capsules, e.g., gelatin capsules. Oral compositions can also be prepared by combining a composition of the present disclosure with a food. In one embodiment a food used for administration is chilled, for instance, iced flavored water. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, orange flavoring, or other suitable flavorings. These are for purposes of example only and are not intended to be limiting.

The compositions comprising a microbial consortium can also be prepared in the form of suppositories (e.g., with conventional suppository bases such as cocoa butter and other glycerides) or retention enemas for rectal delivery. Suppositories can comprise one a number of species in a microbial consortium (e.g., a suppository can comprise a *C. scindens* and a *C. bifermentans*, or a suppository can comprise a *C. scindens* or a *C. bifermentans*). Suppositories comprising only one species of the microbial consortium can be co-administered with another composition comprising another species of the consortium, such that co-administration will equal the sum of the given consortium. The compositions can be prepared with carriers that will protect the consortium against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for instance, Alza Corporation and Nova Pharmaceuticals, Inc. Liposomal suspensions can also be used as pharmaceutically acceptable carriers. These can be prepared according to methods known to those skilled in the art.

In some embodiments, a composition can be encapsulated, e.g., enteric-coated formulations). For instance, when the composition is to be administered orally, the dosage form is formulated so the composition is not exposed to conditions prevalent in the gastrointestinal tract before the small intestine, e.g., high acidity and digestive enzymes present in the stomach. The encapsulation of compositions for therapeutic use is routine in the art. Encapsulation can include hard-shelled capsules, which can be used for dry, powdered ingredients soft-shelled capsules. Capsules can be made from aqueous solutions of gelling agents such as animal protein (e.g., gelatin), plant polysaccharides or derivatives like carrageenans and modified forms of starch and cellulose. Other ingredients can be added to a gelling agent solution such as plasticizers (e.g., glycerin and or sorbitol), coloring agents, preservatives, disintegrants, lubricants and surface treatment.

In one embodiment, a microbial consortium as described herein is formulated with an enteric coating. An enteric coating can control the location of where a microbial consortium is released in the digestive system. Thus, an enteric coating can be used such that a microbial consortium-containing composition does not dissolve and release the microbes in the stomach, which can be a toxic environment for many microbes, but rather travels to the small intestine, where it dissolves and releases the microbes in an environment where they can survive. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade names AQUACOAT™, AQUACOAT ECD™, SEPIFILM™, KLUCEL™, and METOLOSE™); polyvinylacetate phthalate (trade name SURETERIC™); and methacrylic acid (trade name EUDRAGIT™).

In one embodiment, an enteric coated prebiotic composition that additionally comprises members of a microbial consortium as described herein is administered to a subject. In another embodiment, an enteric coated probiotic and prebiotic composition is administered to a subject.

Formulations suitable for rectal administration include gels, aqueous or oily suspensions, dispersible powders or granules, emulsions, dissolvable solid materials, enemas, and the like. The formulations are preferably provided as unit-dose suppositories comprising the active ingredient in one or more solid carriers forming the suppository base, for example, cocoa butter. Suitable carriers for such formulations include petroleum jelly, lanolin, polyethyleneglycols, alcohols, and combinations thereof, provided they are compatible with the bacterial species preparation being administered.

In some embodiments, the microbial consortium can be formulated in a food item. Some non-limiting examples of food items to be used with the methods and compositions described herein include: popsicles, cheeses, creams, chocolates, milk, meat, drinks, yogurt, pickled vegetables, kefir, miso, sauerkraut, etc. In other embodiments, the food items can be juices, refreshing beverages, tea beverages, drink preparations, jelly beverages, and functional beverages; alcoholic beverages such as beers; carbohydrate-containing foods such as rice food products, noodles, breads, and pastas; paste products such as fish, hams, sausages, paste products of seafood; retort pouch products such as curries, food dressed with a thick starchy sauce, and Chinese soups; soups; dairy products such as milk, dairy beverages, ice creams, cheeses, and yogurts; fermented products such as fermented soybean pastes, fermented beverages, and pickles; bean products; various confectionery products including biscuits, cookies, and the like, candies, chewing gums, gummies, cold desserts including jellies, cream caramels, and frozen desserts; instant foods such as instant soups and instant soy-bean soups; and the like. It is preferred that food preparations not require cooking after admixture with the microbial consortium to avoid killing the microbes.

Formulations of a microbial consortium can be prepared by any suitable method, typically by uniformly and intimately admixing the consortium with liquids or finely divided solid carriers or both, in the required proportions and then, if necessary, shaping the resulting in mixture into the desired shape. In addition, the microbial consortium can be treated to prolong shelf-life, preferably the shelf-life of the pre-determined gut flora will be extended via freeze drying.

In some embodiments, the microbial consortium as described herein is combined with one or more additional probiotic organisms prior to treatment of a subject.

A nutrient supplement comprising the microbial consortium as described herein can include any of a variety of nutritional agents, including vitamins, minerals, essential and nonessential amino acids, carbohydrates, lipids, foodstuffs, dietary supplements, short chain fatty acids and the like. Preferred compositions comprise vitamins and/or minerals in any combination. Vitamins for use in a composition as described herein can include vitamins B, C, D, E, folic acid, K, niacin, and like vitamins. The composition can contain any or a variety of vitamins as may be deemed useful for a particularly application, and therefore, the vitamin content is not to be construed as limiting. Typical vitamins are those, for example, recommended for daily consumption and in the recommended daily amount (RDA), although precise amounts can vary. The composition can preferably include a complex of the RDA vitamins, minerals and trace minerals as well as those nutrients that have no established RDA, but have a beneficial role in healthy human or mammal physiology. The amount of material included in the composition can vary widely depending upon the material and the intended purpose for its absorption, such that the composition is not to be considered as limiting.

Also contemplated herein are kits comprising, at a minimum, a biotherapeutic microbial species or a consortium prep or formulations comprising the members of the consortium, e.g., *C. scindens* and *C. bifermentans* species, in an admixture or comprising the members of the consortium in sub-combinations or sub-mixtures. In some embodiments, the kit further comprises empty capsules to be filled by the practitioner and/or one or more reagents for enteric coating such capsules. It is also contemplated herein that the microbe preparation is provided in a dried, lyophilized or powdered form. In one embodiment, the kit comprises a strain of *C. bifermentans*. In another embodiment, the kit comprises a strain of *C. scindens* and a strain of *C. bifermentans*. The *C. scindens* strain comprised in the kit can be a *C. scindens* strain comprising a 16S rRNA sequence that is at least 97%, at least 98%, at least 99%, or 100% identical to the sequence of SEQ ID NO: 1. The *C. bifermentans* strain comprised in the kit can be a *C. bifermentans* strain comprising a 16S rRNA sequence that is at least 97%, at least 98%, at least 99%, or 100% identical to the sequence of SEQ ID NO: 2. In another embodiment, the kit comprises at least one reducing agent such as N-acetylcysteine, cysteine, or methylene blue for growing, maintaining and/or encapsulating the microbes under anaerobic conditions. The kits described herein are also contemplated to include cell growth media and supplements necessary for expanding the microbial preparation. The kits described herein are also contemplated to include one or more prebiotics as described herein.

Prior to administration of the bacterial composition, the patient may optionally have a pretreatment protocol to prepare the gastrointestinal tract to receive the bacterial composition. In these instances, the pretreatment protocol can enhance the ability of the bacterial composition to affect the patient's microbiota balance. In an alternative embodiment, the subject is not pre-treated with an antibiotic.

Generally, the defined therapeutic microbiota described herein can be administered after the completion of a course of antibiotics for the treatment of *C. difficile* infection. However, use of the defined therapeutic microbiota alone to prevent or, for that matter, directly combat the *C. difficile* infection is specifically contemplated. If a patient has received antibiotics for treatment of an infection other than *C. difficile* or for *C. difficile*, in one embodiment the antibiotic should be stopped in sufficient time to allow the antibiotic to be substantially reduced in concentration in the gut before the bacterial composition is administered. In one embodiment, the antibiotic may be discontinued 1, 2, or 3 days before the administration of the bacterial composition. In one embodiment, the antibiotic can be discontinued 3, 4, 5, 6, or 7 antibiotic half-lives before administration of the bacterial composition.

In another embodiment, the bacterial compositions described herein are administered before or concurrently with an antibiotic. In one embodiment, administration of therapeutic microbiota before or concurrently with antibiotic might be contemplated where the administered species are at least somewhat resistant to the effects of the antibiotic administered. In another embodiment, an antibiotic is administered before the administration to the bacterial composition (e.g., less than 1 day, 1, 2, 3, 4, 5, 6, or 7 days before administration of the bacterial composition). Longer times can help to prevent the antibiotic from killing the administered bacteriotherapeutic organism(s). In one embodiment, the antibiotic administered is an antibiotic used to treat *C. difficile* infection (e.g., metronidazole (Flagyl), vancomycin (Vancocin), or fidaxomicin (Dificid)). In another embodiment, the antibiotic is not specific to treatment of a *C. difficile* infection, but is an antibiotic known in the art to have therapeutic effects on the intestinal system (e.g., norfloxacin, cephalexin, trimethoprim-sulfamethoxazole, or levofloxacin). Antibiotics listed herein are for purposes of example only and are not intended to be limiting.

In one embodiment, the bacterial compositions described herein are administered with an antacid or proton pump inhibitor (PPI). An antacid works to neutralize the stomach acid, which can interfere to efficient delivery of the bacterial compositions described herein. An antacid can be administered prior to, in combination with, or after the administration of the bacterial compositions described herein. In one embodiment, the bacterial composition can be formulation in a composition that further comprises an antacid. Antacids are known in the art and can comprise the following active ingredients: calcium carbonate, aluminum, magnesium, sodium bicarbonate, and/or alginic acid. Proton pump inhibitors block activity of the H+/K+ ATPase proton pump in stomach epithelium.

Any of the preparations described herein can be administered once on a single occasion or on multiple occasions, such as once a day for several days or more than once a day on the day of administration (including twice daily, three times daily, or up to five times daily). Or the preparation can be administered intermittently according to a set schedule, e.g., once weekly, once monthly, or when the patient relapses from the primary illness. In another embodiment, the preparation can be administered on a long-term basis to assure the maintenance of a protective or therapeutic effect.

Efficacy

Typically, a *C. difficile* infection can manifest with one of more of the following clinical symptoms or indicators: (i) mild (at least 3 times a day) to severe (4 or more times a day) watery diarrhea, (ii) abdominal pain, (iii) blood and/or pus in the stool, (iv) fever, and (v) loss of appetite. Quantitatively, a *C. difficile* infection can be assessed by quantitative factors (i) detectable levels of *C. difficile* toxin, and (ii) detectable levels of *C. difficile* bacteria. Thus, efficacious treatment and/or prevention of a *C. difficile* infection using the methods and compositions described herein can reduce or eliminate at least one of the symptoms or indicators associated with a *C. difficile* infection, as described above. Methods for the measurement of each of these parameters (e.g., measuring the levels of *C. difficile* toxins) are known to those of ordinary skill in the art and/or described herein.

Effective treatment can be determined by an overall decrease in the Bristol Score from 7 or 6 to a lower value. Alternatively, or in addition, effective treatment can be determined by a decrease, as the term is used herein, in *C. difficile* biomass or relative abundance in the stool, or by a decrease in *C. difficile* toxin in the stool.

Efficacy can also be measured by failure of a subject to worsen as assessed by need for medical interventions (e.g., progression of infection is halted or at least slowed). Methods of measuring these indicators are known to those of skill in the art and/or described herein. Example methods include PCR-based or Enzyme-linked immunosorbent assay (ELISA) to detect *C. difficile* toxin. Treatment includes: (1) inhibiting the infection, e.g., arresting, or slowing symptoms of the infection, for example watery diarrhea; or (2) relieving the infection, e.g., causing regression of symptoms, reducing the symptoms by at least 10%, and/or reducing *C. difficile* toxin levels by at least 10% compared to a reference level (e.g., a *C. difficile* toxin level prior to administration; and (4) restoring healthy intestinal flora, thus preventing future *C. difficile* infection or production. It is expected that the levels of *C. difficile* toxin and/or *C. difficile* bacteria present in a subject's intestine should be reduced to levels seen in healthy individuals or below detectable levels at least 1 week, at least 2 weeks, at least 3, weeks, at least 4 weeks following administration of any of the therapeutic compositions described herein.

Therapeutic microbiota, including defined therapeutic microbiota as described herein, are administered in an amount sufficient, or an amount effective, to provide therapeutic benefit. An effective amount of a composition for the treatment of *C. difficile* infection means that amount which, when administered to a mammal in need thereof, is sufficient to result in effective treatment as that term is defined herein, for that infection. Efficacy of the composition can be determined by a physician by assessing physical indicators of *C. difficile* infection as described above.

The term "effective amount" as used herein refers to the amount of a therapeutic microbiota composition as described herein needed to alleviate at least one or more symptoms or reduces one or more indicator of a *C. difficile* infection, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the infection, alter the course of a symptom (for example but not limited to, slowing the progression of a symptom of the infection), or reverse a symptom of the infection. Thus, it is not generally practicable to specify an exact "effective amount." However, for any given case, an appropriate "effective amount" can be determined by one of ordinary skill in the art using only routine experimentation. The term "effective amount" is used interchangeably with the term "therapeutically effective amount" and refers to the amount of at least one agent, e.g., a bacterial composition that treats a *C. difficile* infection, at dosages and for periods of time necessary to achieve the desired therapeutic result, for example, to reduce or stop at least one symptom or indicator of such *C. difficile* infection, in the subject.

Repeated administration of the defined therapeutic microbiota composition may be beneficial to maintain a protective or curative effect.

Effective amounts, toxicity, and therapeutic efficacy of drug agents, e.g., for formulations or treatments using antibiotics in addition to microbes, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from in vivo assays. It is contemplated that the relevant level for an agent that treat a *C. difficile* infection may also be the level achieved in the lumen of the gut. The effects of any particular dosage can be monitored by a suitable bioassay or by measurement of administered and stable biomass (engraftment, persistence) and microbial metabolic activities (Stickland metabolite production, free amino acids, protease activities, associate gene content or expression levels)

The dosage can be determined by a physician and adjusted, as necessary, to suit observed effects of the treatment.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A pharmaceutical composition comprising an oral formulation comprising *C. scindens* and *C. bifermentans* bacteria.

2. A composition comprising *C. scindens* and *C. bifermentans* bacteria, wherein one or both of the *C. scindens* and *C. bifermentans* bacteria is in dried, viable form.

3. A pharmaceutical composition comprising a formulation comprising *C. scindens* and *C. bifermentans* bacteria, wherein the composition does not comprise *Bacteroides* species or *Escherichia* species.

4. The composition of any one of paragraphs 1-3, wherein one or both of the *C. scindens* and *C. bifermentans* bacteria are in spore form.

5. The composition of any one of paragraphs 1-3, wherein one or both of the *C. scindens* and *C. bifermentans* bacteria are not in spore form.

6. The composition of any one of paragraphs 1-3, wherein the *C. scindens* and *C. bifermentans* bacteria are present as a mixture of metabolically active and spore forms.

7. The composition of any one of paragraphs 1-3, wherein the composition comprises a capsule or microcapsule, or a composition formulated for enteric delivery.

8. The composition of paragraph 1 or paragraph 3, wherein one or both of the *C. scindens* and *C. bifermentans* bacteria are in dried viable form.

9. The composition of any one of paragraphs 1-3, which does not comprise *C. sardiniensis* bacteria.

10. The composition of any one of paragraphs 1-3, which does not comprise any other *Clostridium* species.

11. The composition of either of paragraphs 1 or 2, which does not contain *Bacteroides* species or *Escherichia coli*.

12. The composition of any one of paragraphs 1-3, in which the formulation comprises no other bacteria.

13. A pharmaceutical composition comprising an oral formulation comprising a first bacterial population that has 16S rDNA with a sequence at least 97% identical to a 16S rDNA sequence present in a reference *C. scindens* bacterium, and a second bacterial population that has 16S rDNA with a sequence at least 97% identical to a 16S rDNA sequence present in a reference *C. bifermentans* bacterium.

14. A composition comprising a first bacterial population that has 16S rDNA with a sequence at least 97% identical to a 16S rDNA sequence present in a reference *C. scindens* bacterium, and a second bacterial population that has 16S rDNA with a sequence at least 97% identical to a 16S rDNA sequence present in a reference *C. bifermentans* bacterium, wherein one or both of the *C. scindens* and *C. bifermentans* bacteria is in dried, viable form.

15. A pharmaceutical composition comprising a formulation comprising a first bacterial population that has 16S rDNA with a sequence at least 97% identical to a 16S rDNA sequence present in a reference *C. scindens* bacterium, and a second bacterial population that has 16S rDNA with a sequence at least 97% identical to a 16S rDNA sequence present in a reference *C. bifermentans* bacterium wherein the composition does not comprise *Bacteroides* species or *Escherichia* species.

16. The composition of any one of paragraphs 13-15, wherein one or both of the *C. scindens* and *C. bifermentans* bacteria are in spore form.

17. The composition of any one of paragraphs 13-15, wherein one or both of the *C. scindens* and *C. bifermentans* bacteria are not in spore form.

18. The composition of any one of paragraphs 13-15, wherein the *C. scindens* and *C. bifermentans* bacteria are present as a mixture of metabolically active and spore forms.

19. The composition of any one of paragraphs 13-15, wherein the composition comprises a capsule or microcapsule, or a composition formulated for enteric delivery.

20. The composition of paragraph 13 or paragraph 15, wherein one or both of the *C. scindens* and *C. bifermentans* bacteria are in dried viable form.

21. The composition of any one of paragraphs 13-15, which does not comprise *C. sardiniense* bacteria 22. The composition of either of paragraphs 13 or 14, which does not comprise *Bacteroides* species or *Escherichia coli.*

23. The composition of any one of paragraphs 13-15, which does not comprise any other *Clostridium* species.

24. The composition of any one of paragraphs 13-15, in which the formulation comprises no other bacteria.

25. The composition of any one of paragraphs 1-24, further comprising a prebiotic.

26. The composition of any one of paragraphs 1-11, 23, or 25, further comprising a microbe that supports *C. scindens* and/or *C. bifermentans.*

27. The composition of paragraph 26, wherein the microbe that supports *C. scindens* is *Ruminococcus obeum.*

28. The composition of any one of paragraphs 1-27, for use in the treatment of *C. difficile* infection.

29. The composition for use of paragraph 28, wherein the use comprises suppressing the expression of *C. difficile* toxin.

30. The composition for use of paragraph 28, wherein the use comprises promoting a shift towards use of the proline reductase pathway of Stickland fermentation in *C. difficile.*

31. The composition for use of paragraph 28, wherein the use comprises inducing CodY activity or expression in *C. difficile.*

32. The composition for use of paragraph 28, wherein the use comprises promoting ethanolamine utilization by *C. difficile.*

33. A method comprising administering a composition of any one of paragraphs 1-27 to a subject in need thereof.

34. The method of paragraph 33, wherein the subject has or has been diagnosed with *C. difficile* infection.

35. The method of paragraph 34, wherein the *C. difficile* infection is recurrent.

36. The method of paragraph 33, wherein the subject is at risk of *C. difficile* infection or recurrent *C. difficile* infection.

37. The method of paragraph 33, wherein the administration is oral.

38. A method comprising administering a composition of any one of paragraphs 2, 3, 14 or 15 directly to the colon of a subject in need thereof.

39. The method of paragraph 38, wherein administration is via colonoscope or enema.

40. The method of any of paragraphs 33-39, wherein the subject is receiving or has recently received antibiotic treatment.

41. A method of treating an infection, the method comprising administering an antibiotic and a composition of any one of paragraphs 1-27.

42. The method of paragraph 41, wherein the composition is administered before or concurrently with the antibiotic.

43. The method of paragraph 41, wherein the composition is administered after a course of an antibiotic.

44. A method of predicting recurrence of *C. difficile* infection in a subject, the method comprising:

(a) determining the relative abundance of all operational taxonomic units (OTUs) in a sample of the subject's stool that are >90% identical to a reference sequence of *C. scindens;*

(b) determining the relative abundance of all operational taxonomic units (OTUs) in a sample of the subject's stool that are >90% identical to a reference sequence of *C. hylemonae*; and (c) summing the relative abundances determined in steps (a) and (b), wherein a sum of relative abundances less than or equal to 1% indicates an increased risk of *C. difficile* recurrence relative to a subject in which the sum of relative abundances is greater than 1%.

45. The method of paragraph 44, wherein the reference sequences for *C. scindens* and *C. hylemonae* are 16S rDNA sequences.

46. The method of paragraph 44 or 45, wherein the determining steps are performed on samples taken before, during or after the subject has been treated with antibiotics for *C. difficile* infection.

47. The method of paragraph 44 or 45, wherein the determining steps are performed on samples taken after the subject has been treated with antibiotics for *C. difficile* infection 48. The method of paragraph 44, further comprising the step, when the sum of relative abundances is at or below 1%, of administering a composition of any one of paragraphs 1-27.

49. A method of suppressing expression of a bacterial toxin in a subject, the method comprising administering a defined bacterial microbiota comprising at least one bacterial organism that encodes and secretes a protease and/or performs Stickland fermentation.

50. A method of treating or preventing a pathology caused by expression of a bacterial toxin, the method comprising administering a defined bacterial microbiota comprising at least one bacterial organism that encodes and secretes a protease and/or performs Stickland fermentation.

51. A method of promoting CodY expression or activity in a *C. difficile* bacterium in a subject, the method comprising administering a defined bacterial microbiota comprising a bacterial organism that encodes and secretes a protease and/or performs Stickland fermentation.

52. A method of promoting ethanolamine utilization by a *C. difficile* bacterium in a subject, the method comprising administering a defined bacterial microbiota comprising a bacterial organism that encodes and secretes a protease and/or performs Stickland fermentation.

53. The method of any one of paragraphs 49-52, wherein at least one bacterial organism encodes and secretes at least one protease selected from the group consisting of: a protease of PATRIC ID fig|186802.30.peg.279; a protease of PATRIC ID fig|186802.30.peg.290; a protease of PATRIC ID fig|186802.30.peg.313; a protease of PATRIC ID fig|186802.30.peg.414; a protease of PATRIC ID fig|186802.30.peg.543; a protease of PATRIC ID fig|186802.30.peg.2205; a protease of PATRIC ID fig|186802.30.peg.2313; a protease of PATRIC ID fig|186802.30.peg.2680; a protease of PATRIC ID fig|186802.30.peg.2745; a protease of PATRIC ID fig|186802.30.peg.2746; a protease of PATRIC ID fig|186802.30.peg.830; a protease of PATRIC ID fig|186802.30.peg.921; a protease of PATRIC ID fig|186802.30.peg.936; a protease of PATRIC ID fig|186802.30.peg.3000; a protease of PATRIC ID fig|186802.30.peg.3018; a protease of PATRIC ID fig|186802.30.peg.3019; and a protease of PATRIC ID fig|186802.30.peg.3065.

54. The method of any of paragraphs 49-52, wherein at least one protease performs the proteolysis reaction of enzymes of Enzyme Commission number (E.C. number) EC 3.4.21.-; EC 3.4.21.53; or EC 3.4.21.92.

55. The method of any of paragraphs 49-52, wherein at least one bacterial organism encodes and expresses one or more of D-proline reductase, Glycine reductase, Thioredoxin, or Choloylglycine hydrolase.

56. The method of any of paragraphs 49-52, wherein the at least one bacterial organism falls within Clostridial cluster I, XI, or XIVa, and does not express a pathology-causing bacterial toxin.

57. The method of paragraph 56, wherein the bacterial organism in Clostridial cluster I is selected from *C. sporogenes*, and *C. histolyticum*.

58. The method of paragraph 56, wherein the bacterial organism in Clostridial cluster XI is selected from *C. bifermentans, C. hiranonis*, and *P. anaerobius*.

59. The method of paragraph 56, wherein the bacterial organism in Clostridial cluster XIVa is selected from *C. scindens, C. clostriiforme*, and *C. nexile*.

60. The method of any of paragraphs 49-52, wherein the at least one bacterial organism inhibits sorbitol/mannitol fermentation by *C. difficile*.

61. The method of any of paragraphs 49-52, wherein the at least one bacterial organism promotes Stickland fermentation through the acceptor amino acid proline, or activation of proline reductase.

62. The method of any of paragraphs 49-52, wherein the at least one bacterial organism promotes 5-aminovalerate production.

63. The method of any of paragraphs 49-52, wherein the bacterial toxin is a *C. difficile* toxin.

64. The method of any of paragraphs 49-52, wherein the bacterial organism is *C. bifermentans* and/or *C. scindens*.

65. The method of any of paragraphs 49-52, wherein suppressing expression of a bacterial toxin compromises by inhibition of butyrate, codY, ccpA, tcdR, and/or tcdA production.

66. A method of suppressing expression of a bacterial toxin in the gut of a subject, the method comprising administering at least one amino acid that is metabolized by Stickland fermentation.

67. A method of treating or preventing a pathology caused by expression of a bacterial toxin, comprising administering at least one amino acid that is metabolized by Stickland fermentation.

68. The method of paragraph 66 or 67, wherein at least one amino acid is a Stickland donor or Stickland acceptor.

69. The method of paragraph 68, wherein the Stickland donor is selected from the group consisting of: alanine, leucine, valine, isoleucine, tryptophan, tyrosine and phenylalanine.

70. The method of paragraph 68, wherein the Stickland acceptor is selected from the group consisting of: glycine and proline.

71. The method of paragraph 66 or 67, wherein the amino acid is a branched-chain amino acid, a branched-keto amino acid, or an aromatic amino acid.

72. The method of paragraph 66 or 67, wherein the at least one amino acid promotes 5-aminovalerate production.

73. The method of paragraph 66 or 67, wherein the bacterial toxin is a *C. difficile* toxin.

74. The method of paragraph 66 or 67, wherein suppression of the expression of a bacterial toxin comprises inhibition of butyrate, codY, ccpA, tcdR, and/or tcdA activity or production.

75. A method of determining the therapeutic efficacy of a bacterial organism for treatment of a pathology involving expression of a toxin, produced by a Gram-positive spore-forming bacterium, the method comprising measuring in a biological sample obtained from an individual administered the bacterial organism one or more of:
  a) the amount and/or activity of a secreted proteolytic enzyme;
  b) the amount and/or activity of bacterial proline reductase;
  c) the amount or concentration of one or more branched short-chain fatty acids;
  d) the amount or concentration of one or more branched keto acids; and
  e) the amount or concentration of Stickland donor and/or Stickland acceptor amino acids and/or 5-aminovalerate;
  wherein measurement of an increased amount, concentration or activity of one or more of (a)-(e) relative to the amount measured in a sample taken prior to administration the bacterial organism indicates that the bacterial organism is effective for the treatment.

76. The method of paragraph 75, wherein the bacterial toxin is produced by a Gram-positive, spore-forming bacterium.

77. The method of paragraph 75, wherein the bacterial toxin is a *C. difficile* toxin.

78. The method of paragraph 75, wherein the pathology comprises expression of a toxin by *C. difficile*.

79. The method of paragraph 75, wherein Stickland donor amino acids are selected from leucine, isoleucine, valine, alanine, phenylalanine, tryptophan, tyrosine and Stickland acceptor amino acids are selected from glycine, proline, and hydroxyproline.

80. The method of paragraph 75, wherein the sample is a stool sample or a sample from within the colon of the individual.

81. A method to predict the risk of developing a disease involving a toxin produced by a Gram positive, spore-forming bacterium, the method comprising measuring in a biological sample obtained from an individual one or more of the following:
- a) the amount and/or activity of a secreted proteolytic enzyme;
- b) the amount and/or activity of bacterial proline reductase;
- c) the amount or concentration of one or more branched short-chain fatty acids;
- d) the amount or concentration of one or more branched keto acids; and
- e) the amount or concentration of Stickland donor and/or Stickland acceptor amino acids; and comparing the amount, concentration or activity measured in one or more of (a)-(d) to a reference, wherein an amount, concentration or activity in one or more of (a)-(d) below the reference indicates increased risk of developing a disease involving a toxin produced by a Gram positive, spore-forming bacterium.

82. The method of paragraph 81, wherein the disease involves expression of a toxin by *C. difficile*.

83. The method of paragraph 81, wherein the reference comprises a biological sample from a healthy individual.

84. The method of paragraph 81, wherein the biological sample is a stool sample or a sample from within the colon of the individual.

85. The method of paragraph 81, wherein two or more, of (a)-(e) are measured.

86. The method of paragraph 81, wherein three or more, of (a)-(e) are measured.

87. The method of paragraph 81, wherein four or more, of (a)-(e) are measured.

88. A method of identifying a candidate bacterial organism that is likely to suppress the expression of a toxin by a Gram-positive, spore-forming bacterial pathogen, the method comprising:
- a) identifying from a database of bacterial genetic information a candidate bacterial organism having in its genome:
  - i) one or more genes encoding a secreted protease enzyme; and/or
  - ii) a gene encoding a proline reductase enzyme; and
- b) assaying a sample comprising the candidate bacterial organism for the expression of a secreted protease enzyme and/or the proline reductase enzyme;

wherein the detection of expression of the secreted protease enzyme and/or the expression of the proline reductase enzyme indicates that the candidate bacterial organism is likely to suppress expression of a toxin by a Gram-positive, spore-forming bacterial pathogen.

89. The method of paragraph 88, wherein the candidate bacterial organism is not an opportunistic gut pathogen in humans.

90. The method of paragraph 88, wherein the proline reductase enzyme is an enzyme of E.C. 1.21.4.1.

91. A method to predict the risk of developing a spore-forming, toxin-producing Gram-positive bacterial pathogen in the gut or other location, or its recurrence, comprising measuring in a biological sample
- (a) amounts or unit activity of proteolytic activity;
- (b) concentrations of branched short chain fatty acids;
- (c) concentrations of branched keto acids; and/or
- (d) concentrations of Stickland donor and Stickland acceptor amino acids, wherein an increase in the amount or activity of at least one of (a)-(d) relative to a biological sample obtained prior to administration identifies a risk of developing a spore-forming, toxin-producing Gram-positive bacterial pathogen in the gut or other location.

92. The method of paragraph 91, further comprising, prior to measuring, administering the bacterial organism or amino acid to the subject.

93. The method of paragraph 91, wherein the biological sample is obtained from a subject.

94. The method of paragraph 91, wherein the biological sample is a stool sample.

95. The method of paragraph 91, wherein the biological sample is obtained from the gut.

96. The method of paragraph 91, wherein the gram-positive bacterial pathogen is *C. difficile* infection.

97. The composition of any of paragraphs 1-24, further comprising an amount of one or more free Stickland donor and/or Stickland acceptor amino acids effective to promote Stickland fermentation by a species in the composition or by *C. difficile* after the composition is administered to a subject.

98. The composition of any of paragraphs 1-24, further comprising an amount of a polypeptide substrate effective for proteolysis by proteolytic activity of a bacterial species in the composition to generate amino acids fermentable by Stickland fermentation.

99. The composition of paragraph 25, further comprising an amount of one or more free Stickland donor and/or Stickland acceptor amino acids effective to promote Stickland fermentation by a species in the composition or by *C. difficile* after the composition is administered to a subject.

100. The composition of paragraph 25, further comprising an amount of a polypeptide substrate effective for proteolysis by proteolytic activity of a bacterial species in the composition to generate amino acids fermentable by Stickland fermentation.

101. The composition of any one of paragraphs 98 or 100, wherein the polypeptide substrate comprises casein, collagen and/or gelatin.

102. The composition of any one of claim 98 or 100, wherein the polypeptide substrate comprises a synthetic polymer or copolymer polypeptide hydrolysable by a proteolytic activity of a species in the composition to generate Stickland fermentable amino acids.

103. The composition of paragraph 102, wherein the synthetic polymer comprises a poly[N] polymer, where N is a Stickland donor amino acid selected from leucine, isoleucine, valine, alanine, phenylalanine, tryptophan, and tyrosine or a Stickland acceptor amino acids selected from glycine and proline.

104. The composition of paragraph 102, wherein the synthetic copolymer comprises a poly[N,X] copolymer, where N and X are Stickland donor amino acids selected from leucine, isoleucine, valine, alanine, phenylalanine, tryptophan, and tyrosine or Stickland acceptor amino acids selected from glycine and proline.

EXAMPLES

Example 1: *Clostridium bifermentans* can Provide Complete Protection Against Fatal *C. difficile* Infection The technology described herein is related to the surprising discovery that two human commensal species, *Clostridium scindens* and *Clostridium bifermentans*, offer protection from an otherwise lethal infection with the Gram-positive, toxigenic bacterium, *C. difficile*.

The effect of commensal species on the survival of mice infected with *C. difficile* spores was assessed using a gnotobiotic colonization model. FIG. 1A sets out the experimental approach schematically. Swiss-Webster germfree mice were pre-colonized with a commensal species (*C. bifermentans, C. sardiniense* or *C. scindens*) for 7 days, prior to challenge with 1000 spores of the *C. difficile* strain (ATCC43255). The survival of the mice was monitored for up to 28 days post-challenge with *C. difficile* (see, e.g., FIG. 1B). Body condition score (BCS) of the mice was monitored daily to assess activity, feeding, grooming and tissue turgor for additional clinical symptoms of infection (FIG. 1C).

Figure 1B:
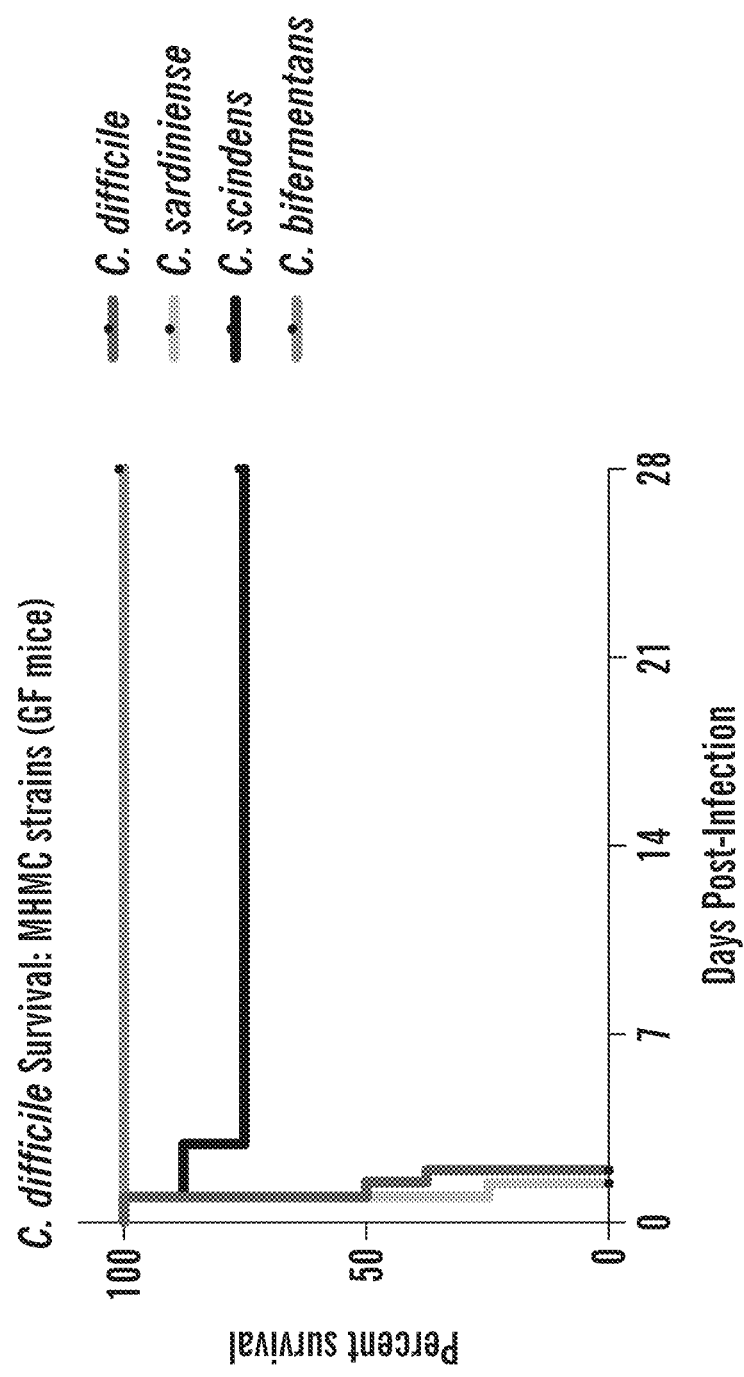
Figure 1C:
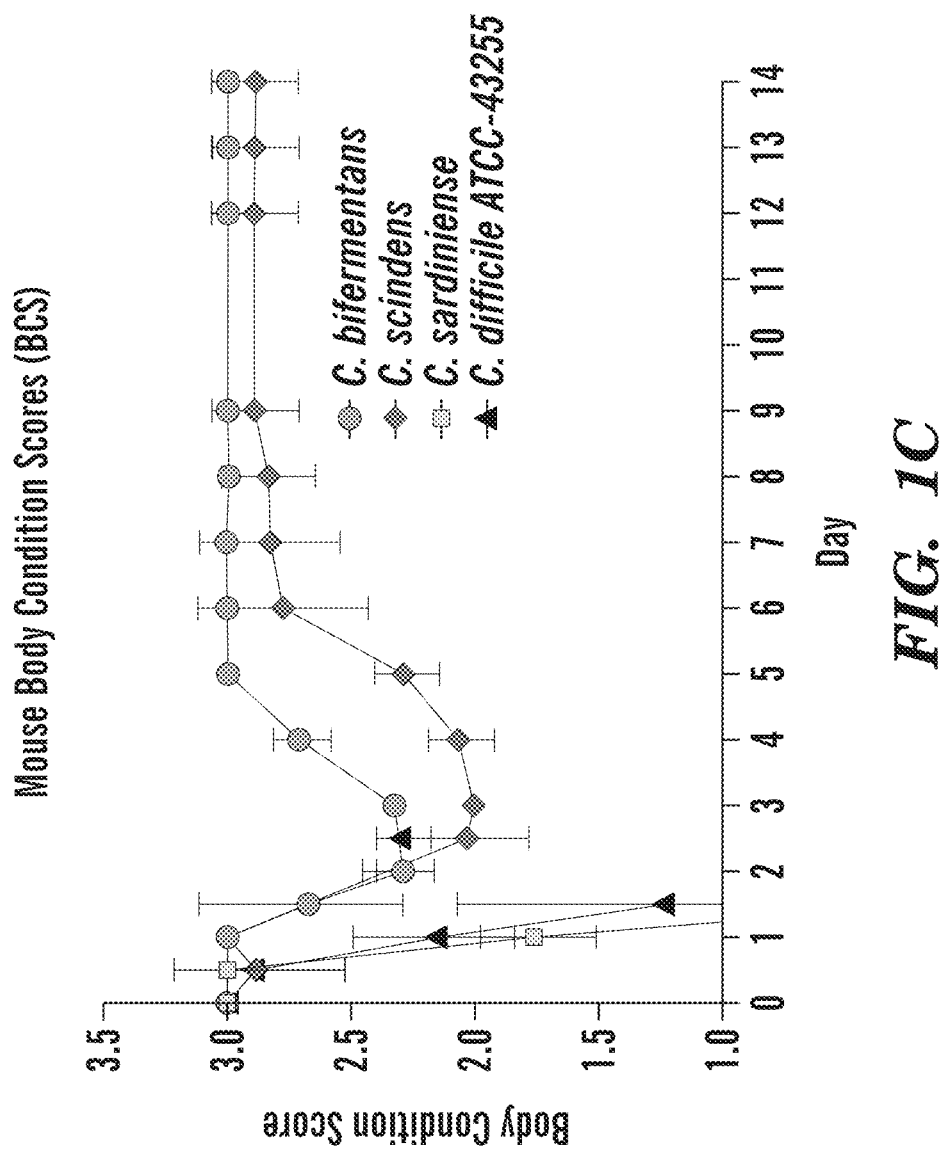

As expected, control mice that were challenged with *C. difficile* alone developed a severe toxin-mediated pathology and died within 5 days of the infection with the Gram-positive toxigenic bacterium *C. difficile* (FIG. 1B). Surprisingly, mice that were pre-colonized with the commensal species *C. bifermentans* were completely protected from the otherwise lethal infection with *C. difficile*. and showed a 100% survival rate compared to the control group infected with *C. difficile* without any pre-colonization treatment (FIG. 1B). Mice that were precolonized with the commensal species *C. scindens* showed a survival rate of 80% compared to the control group that was infected with *C. difficile* without any pre-colonization treatment (FIG. 1B). Precolonization with the commensal species *C. sardiniense* did not provide any protection against an acute infection with *C. difficile* (FIG. 1B).

Consistent with the survival data, the body condition scores (BCS) and histopathological assessment of the mice showed that *C. bifermentans* provided protection against an acute primary *C. difficile* infection, as shown by a milder acute tissue pathology and lower lymphocytic infiltration as compared to the control group (FIG. 1C and FIG. 1G). *C. bifermentans* also provided protection against epithelial disruptions and tissue edema (FIG. 1G and FIG. 1J). In contrast, even though 80% of the *C. scindens*-colonized mice survived the infection with *C. difficile*, the histopathological assessment showed an increased number of inflammatory infiltrates, including a neutrophilic infiltrate, in addition to rare focal areas of epithelial denudation. Consistent with the short survival data indicating no protection against an acute primary *C. difficile* infection, *C. sardiniense*-colonized mice (FIG. 1F) developed a dilation of the colon (megacolon) with rapidly advancing tissue edema, epithelial sloughing and neutrophil efflux into the gut lumen, comparable or worse to the pathology seen in the control mice (FIG. 1E).

Figure 2A:
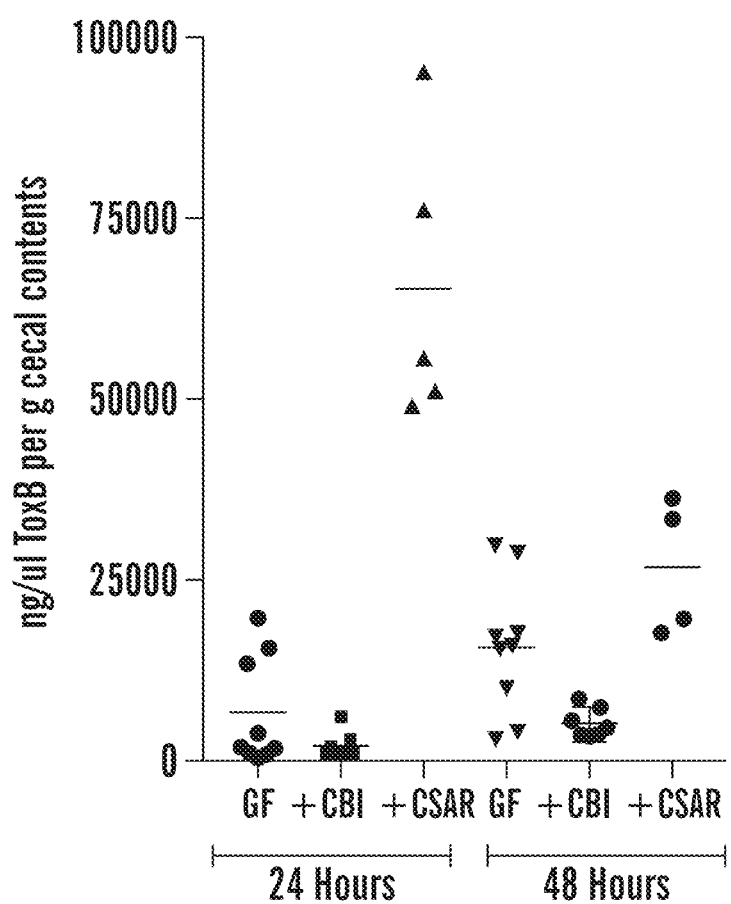
FIGS. 2A-2C present experimental data that shows that the commensal bacterium *C. bifermentans* suppresses toxin production by *C. difficile*.
Figure 2B:
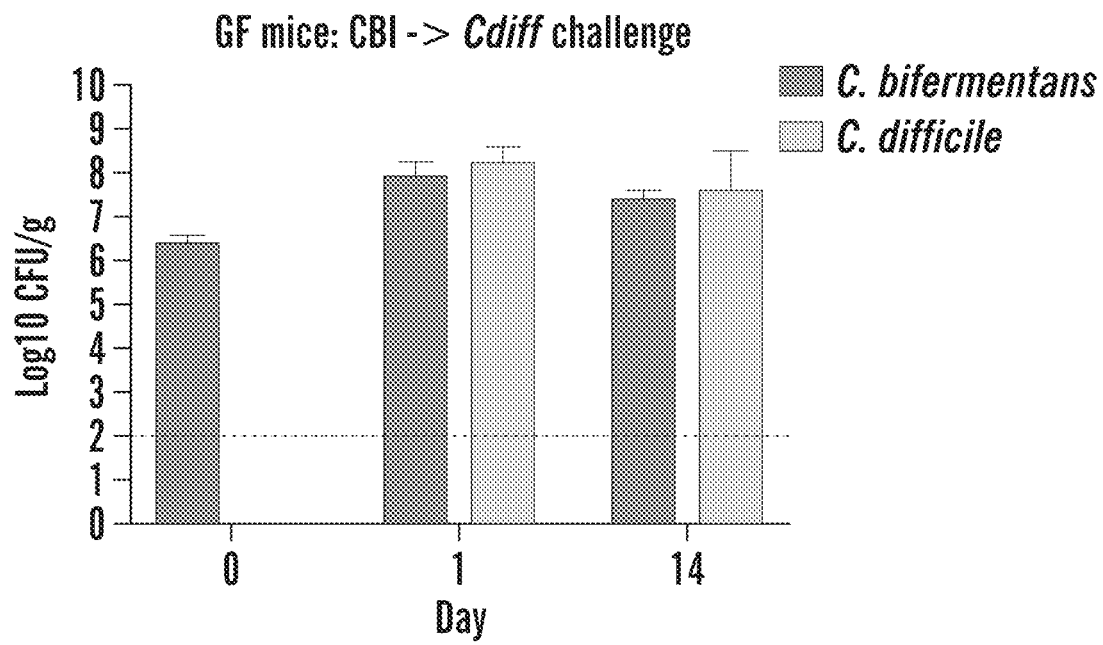
Figure 2C:
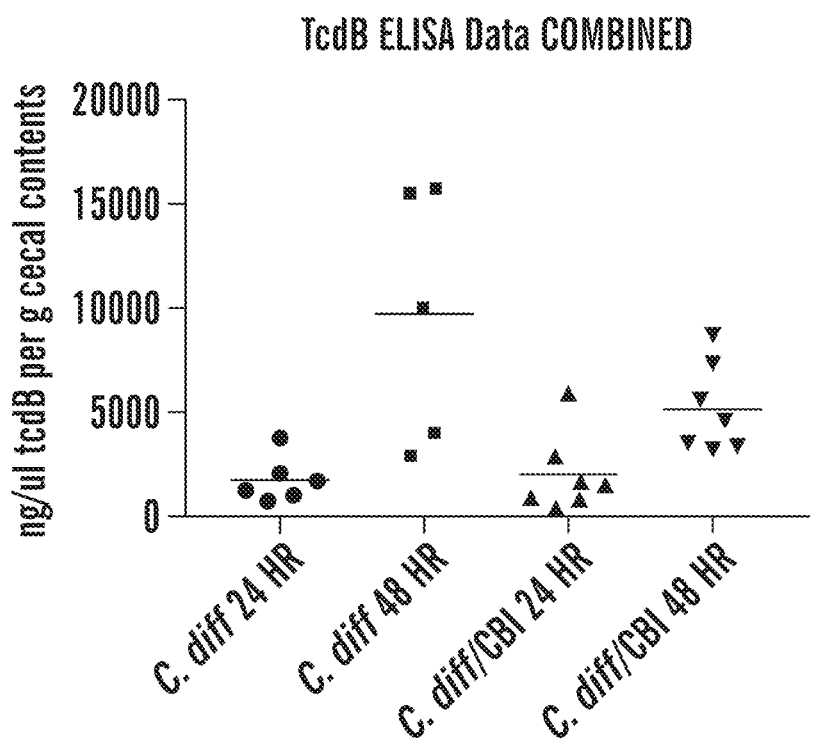

The *C. difficile* biomass and levels of *C. difficile* toxin were examined in the gnotobiotic mouse model. *C. difficile* toxin B levels were assessed in cecal samples collected from germfree Swiss-Webster mice infected with 1000 spores of the *C. difficile* ATCC-43255 strain (FIG. 2). ToxinB was detected using an enzyme-linked immunosorbent assay (ELISA). Germ-free animals infected with *C. difficile* alone, *C. difficile* plus *C. bifermentans*, and *C. difficile* plus *C. sardiniense* showed that *C. difficile* toxin B levels in cecal contents were dramatically lower in animals pre-colonized with *C. bifermentans* (FIGS. 2A, 2C), but that *C. sardiniense* actually promoted *C. difficile* toxin B levels (FIG. 2A). Interestingly, examination of biomass of the individual species showed that the biomass of *C. difficile* in *C. bifermentans* pre-colonized mice was considerable despite the complete protection from death (FIG. 2B). This indicates that the protective commensal *C. bifermentans* involves something other than killing the *C. difficile* or even suppressing growth of the *C. difficile* organism, and indicates that *C. bifermentans* can instead suppress *C. difficile* toxin production.

Figure 3A:
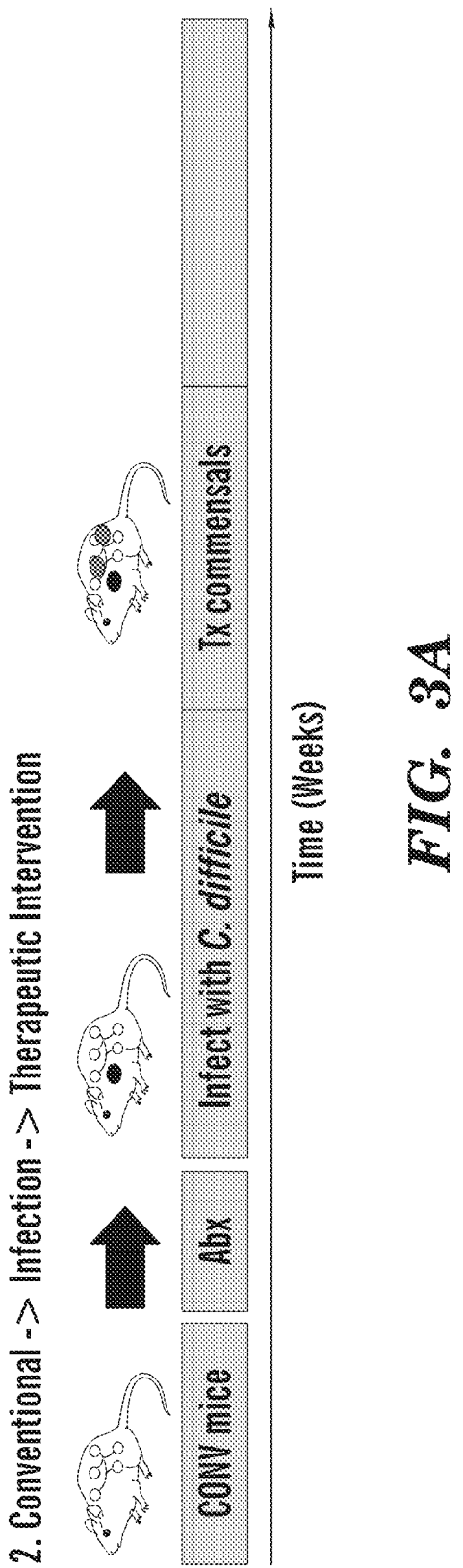
FIGS. 3A-3B show a schematic outlining of the infectious mouse model protocols using conventional mice and the therapeutic intervention.
Figure 3B:
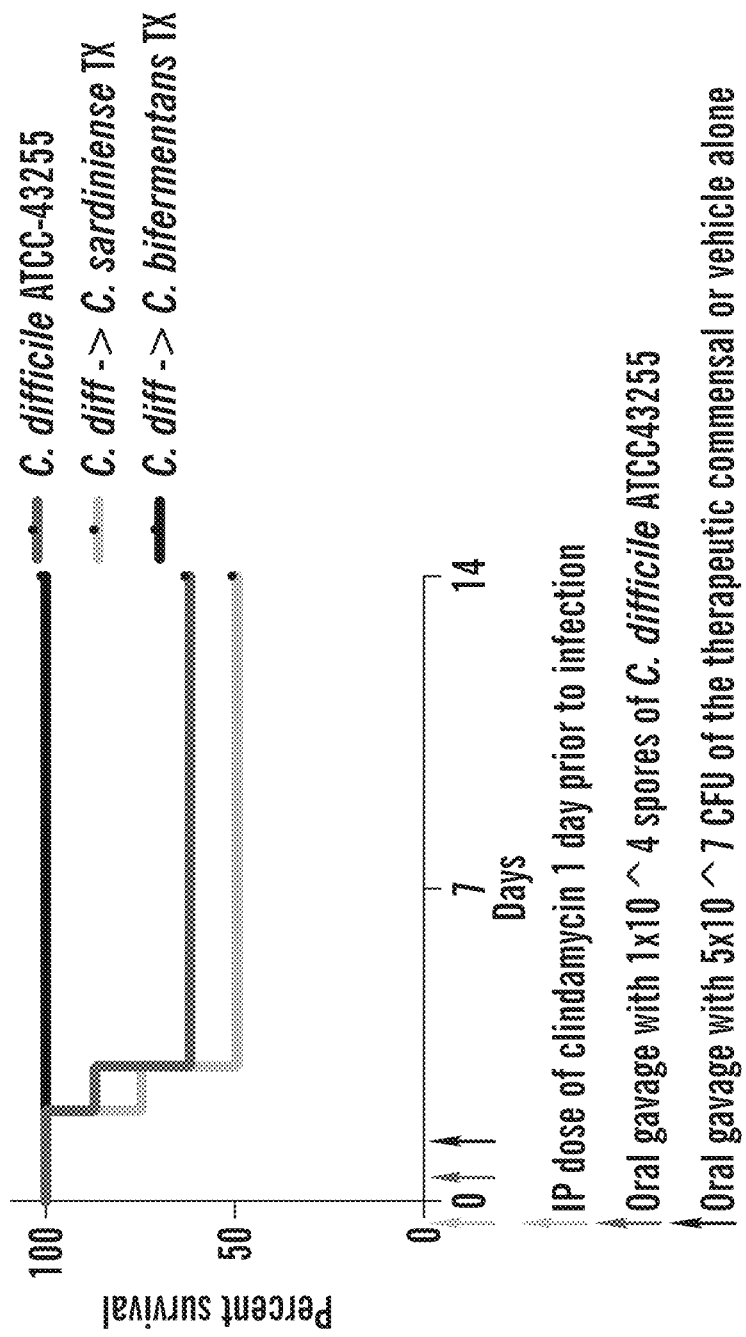

The effects of *C. bifermentans* and *C. sardiniense* were examined in conventional mice infected with *C. difficile*. FIG. 3A shows a schematic for the experiments in adult conventional mice. Briefly, adult conventional mice, with a complex gut microflora, were treated with intraperitoneal clindamycin for 24 hours before receiving $1 \times 10^4$ spores of the *C. difficile* strain ATCC 43255. Approximately 20 hours after dosing, as mice first developed signs of symptomatic infection, animals received $5 \times 10^7$ CFU of *C. bifermentans*, *C. sardiniense* or control vehicle alone by gavage, and survival was assessed for an additional 14 days. The results (shown in FIG. 3B) demonstrate that the protective effect of *C. bifermentans*, and the antagonistic effect of *C. sardiniense* is recapitulated in conventional mice, and that even in the more complex conventional mouse system, a single species of bacterium can provide complete therapeutic treatment and protection from an otherwise fatal *C. difficile* infection.

Example 2: *Clostridium bifermentans* is a Highly Proteolytic Species

Figure 4A:
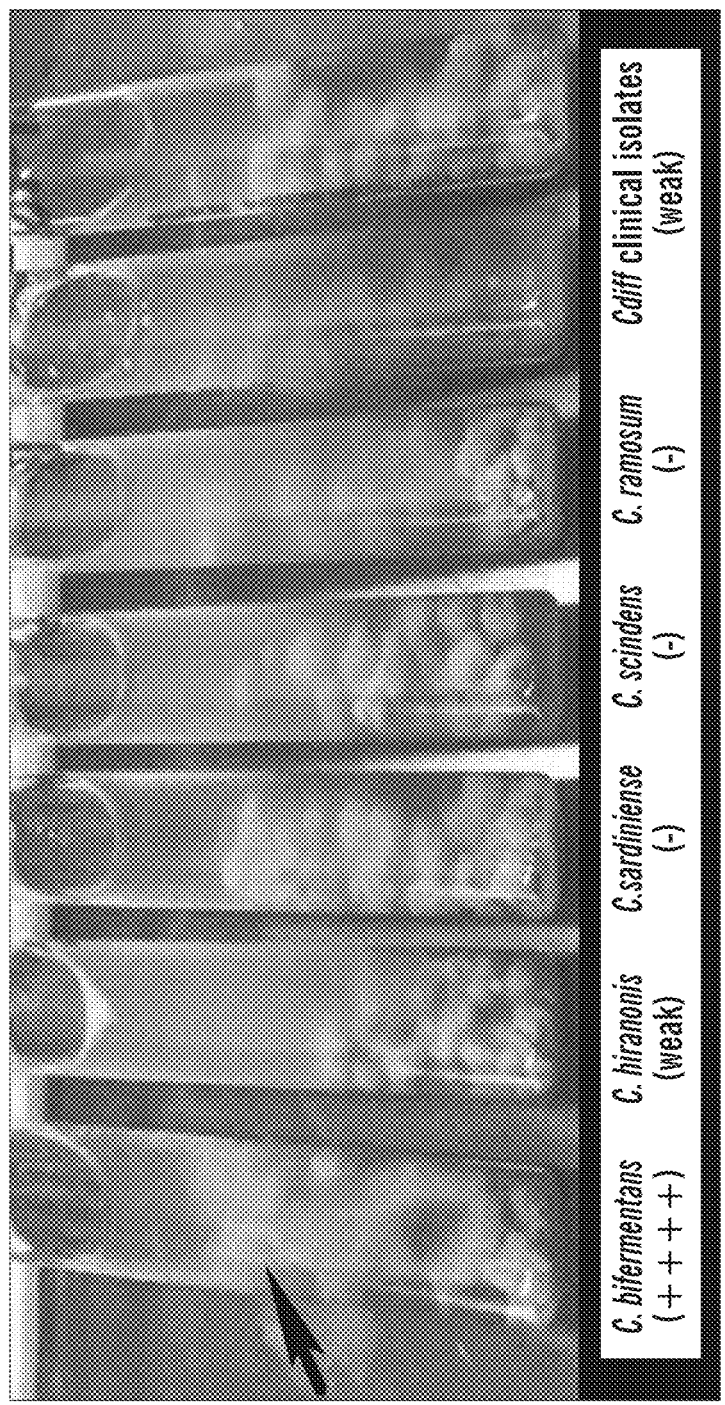

An examination of species that provided protective effects against *C. difficile* was undertaken in order to identify what characteristics of the protective species mediate the protection. Species including *C. bifermentans, C. hiranonis, C. sardinense, C. scindens, C. ramosum* and *C. difficile* clinical isolates were assessed for their proteolytic activity using both microbiological and biochemical assays. FIG. 4A shows results of a meat granule microbiological protease assay performed on *C. bifermentans, C. hiranonis, C. sardiniense, C. scindens, C. ramosum* and two clinical *C. difficile* isolates. FIG. 4B summarizes results for both microbiological and biochemical protease assays for *C. difficile, C. bifermentans, C. sardiniense*, and *C. scindens*. *Clostridium bifermentans* showed strikingly high proteolytic activity in the meat granule assay (FIG. 4A, 4B) and strong digestion in both gelatin and casein hydrolysis assays (FIG. 4B), while the other species were considerably less active in each of these assays (FIGS. 4A and 4B).

Example 3: *Clostridium bifermentans* Promotes Stickland Fermentation by the Gram-Positive Toxigenic Bacterium *C. difficile*

The cecal contents of germfree Swiss-Webster mice were collected 20 hours after infection with *C. difficile* and untargeted metabolomic analysis was performed. The metabolic profiles of Stickland donor and acceptor amino acids, branched-chain amino acids (FIGS. 5A-5G) and carbohydrates (FIG. 5H) were assessed. A liquid chromatography tandem mass spectrometry (LC-MS) method was used to measure polar metabolites and, amino acids and carbohydrates in each sample. In each of FIGS. 5A-5G, the Y axis shows the Log10 MassSpec units of detected compounds. The X axis shows the experimental condition: GF-germfree controls (no bacteria); Cdiff—challenge with 1000 *C. difficile* spores of strain ATCC43255; CSAR—7 days mono-association with *C. sardiniense*; CBI—7 days mono-association with *C. bifermentans*; Cdiff+CSAR—mice mono-associated with *C. sardiniense* for 7 days followed by *C. difficile* challenge; Cdiff+CBI—mice mono-associated with *C. bifermentans* for 7 days followed by *C. difficile* challenge. Each group had 8 mice across two experimental replicates. Levels of amino acids/metabolites including 4-hydroxyproline (FIG. 5A), proline (FIG. 5B), 5-aminovalerate (FIG. 5C), glycine (FIG. 5D), leucine (FIG. 5E), isoleucine (FIG.

5E), valine (FIG. 5E), isovalerate (FIG. 5E), phenylalanine (FIG. 5F), tryptophan (FIG. 5F), and tyrosine (FIG. 5F), among others, were examined. The levels of the Stickland donor amino acids proline and glycine were reduced in the cecal contents of animals monoassociated with *C. difficile* and *C. bifermentans* and in animals co-colonized with *C. bifermentans* and *C. difficile*, while 5-aminovalerate, the product of reduction of proline as a Stickland donor was significantly increased in animals monoassociated with *C. difficile, C. bifermentans* or co-colonized with these two species. This is in contrast, for example, with the results with animals monoassociated with *C. sardiniense*, which was not protective, and showed levels of proline similar to those seen in germ free mice. This indicates active Stickland fermentation through the proline reductase pathway in animals colonized with *C. difficile* and with *C. bifermentans* or both. Acetate, the product of Stickland fermentation reaction through glycine as donor amino acid is produced by a number of other pathways, making it more difficult to conclude that *C. bifermentans* promotes Stickland fermentation through glycine. However, levels of glycine were lower than in the gut of germ free mice when mice were monoassociated with the Stickland fermenting species *C. difficile* and *C. bifermentans*, consistent with ongoing reduction of glycine through the glycine reductase Stickland pathway. The mice mono-associated with *C. sardiniense* for 7 days followed by *C. difficile* challenge also showed a 50% reduction in the levels of 5-aminovalerate (FIG. 5C), while the mice mono-associated with *C. bifermentans* for 7 days followed by *C. difficile* challenge had increased 5-aminovalerate production (FIG. 5C). Taken together, these data indicate that *C. bifermentans* promotes Stickland fermentation by the Gram-positive toxigenic bacterium *C. difficile* when *C. bifermentans* suppresses *C. difficile* toxin production.

Analyses of Stickland donor amino acids including

The invention claimed is:

1. A method of suppressing toxin production by *C. difficile* bacteria in a subject in need thereof, the method comprising orally administering a formulation comprising viable *C. scindens* and *C. bifermentans* bacteria in an amount effective to reduce *C. difficile* toxin by at least 10% as compared to the level of *C. difficile* toxin prior to treatment onset, wherein one or both of the *C. scindens* and *C. bifermentans* bacteria are in spore form or in dried viable form; and wherein the formulation comprises no other bacteria.

2. The method of claim 1, wherein the formulation comprises a capsule or microcapsule, or a composition comprising an enteric coating.

3. The method of claim 1, wherein the formulation further comprises a prebiotic.

4. The method of claim 1, wherein the subject has or has been diagnosed with, or is at risk of *C. difficile* infection.

5. The method of claim 4, wherein the *C. difficile* infection is recurrent.

6. The method of claim 1, wherein the formulation is administered before or concurrently with an antibiotic.

7. The method of claim 1, wherein the formulation is administered after a course of an antibiotic.

8. A method of suppressing toxin production by *C. difficile* bacteria in a subject in need thereof, the method comprising orally administering a formulation comprising viable *C. scindens, C. bifermentans* and *Ruminococcus obeum* bacteria in an amount effective to reduce *C. difficile* toxin by at least 10% as compared to the level of *C. difficile* toxin prior to treatment onset, wherein the *C. scindens, C. bifermentans* and *R. obeum* bacteria are in spore form or in dried viable form.

* * * * *

SEQUENCE LISTING

<160> NUMBER OF SEQ ID NOS: 32

<210> SEQ ID NO 1
<211> LENGTH: 2710
<212> TYPE: PRT
<213> ORGANISM: Clostridium difficile

<400> SEQUENCE: 1

```
Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365
```

-continued

```
Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
```

```
              785                 790                 795                 800
Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
                820                 825                 830

Ser Ile Gly Asp Tyr Ile Tyr Tyr Glu Lys Leu Glu Pro Val Lys Asn
                835                 840                 845

Ile Ile His Asn Ser Ile Asp Asp Leu Ile Asp Glu Phe Asn Leu Leu
                850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
                900                 905                 910

Val Glu Thr Glu Lys Glu Ile Phe Ser Lys Tyr Ser Glu His Ile Thr
                915                 920                 925

Lys Glu Ile Ser Thr Ile Lys Asn Ser Ile Ile Thr Asp Val Asn Gly
                930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
                980                 985                 990

Ala Gln Leu Phe Ser Thr Gly Leu Asn Thr Ile Tyr Asp Ser Ile Gln
                995                1000                1005

Leu Val Asn Leu Ile Ser Asn Ala Val Asn Asp Thr Ile Asn Val
              1010                1015                1020

Leu Pro Thr Ile Thr Glu Gly Ile Pro Ile Val Ser Thr Ile Leu
              1025                1030                1035

Asp Gly Ile Asn Leu Gly Ala Ala Ile Lys Glu Leu Leu Asp Glu
              1040                1045                1050

His Asp Pro Leu Leu Lys Lys Glu Leu Glu Ala Lys Val Gly Val
              1055                1060                1065

Leu Ala Ile Asn Met Ser Leu Ser Ile Ala Ala Thr Val Ala Ser
              1070                1075                1080

Ile Val Gly Ile Gly Ala Glu Val Thr Ile Phe Leu Leu Pro Ile
              1085                1090                1095

Ala Gly Ile Ser Ala Gly Ile Pro Ser Leu Val Asn Asn Glu Leu
              1100                1105                1110

Ile Leu His Asp Lys Ala Thr Ser Val Val Asn Tyr Phe Asn His
              1115                1120                1125

Leu Ser Glu Ser Lys Lys Tyr Gly Pro Leu Lys Thr Glu Asp Asp
              1130                1135                1140

Lys Ile Leu Val Pro Ile Asp Asp Leu Val Ile Ser Glu Ile Asp
              1145                1150                1155

Phe Asn Asn Asn Ser Ile Lys Leu Gly Thr Cys Asn Ile Leu Ala
              1160                1165                1170

Met Glu Gly Gly Ser Gly His Thr Val Thr Gly Asn Ile Asp His
              1175                1180                1185

Phe Phe Ser Ser Pro Ser Ile Ser Ser His Ile Pro Ser Leu Ser
              1190                1195                1200
```

```
Ile Tyr Ser Ala Ile Gly Ile Glu Thr Glu Asn Leu Asp Phe Ser
1205             1210                1215

Lys Lys Ile Met Met Leu Pro Asn Ala Pro Ser Arg Val Phe Trp
1220             1225                1230

Trp Glu Thr Gly Ala Val Pro Gly Leu Arg Ser Leu Glu Asn Asp
1235             1240                1245

Gly Thr Arg Leu Leu Asp Ser Ile Arg Asp Leu Tyr Pro Gly Lys
1250             1255                1260

Phe Tyr Trp Arg Phe Tyr Ala Phe Phe Asp Tyr Ala Ile Thr Thr
1265             1270                1275

Leu Lys Pro Val Tyr Glu Asp Thr Asn Ile Lys Ile Lys Leu Asp
1280             1285                1290

Lys Asp Thr Arg Asn Phe Ile Met Pro Thr Ile Thr Thr Asn Glu
1295             1300                1305

Ile Arg Asn Lys Leu Ser Tyr Ser Phe Asp Gly Ala Gly Gly Thr
1310             1315                1320

Tyr Ser Leu Leu Leu Ser Ser Tyr Pro Ile Ser Thr Asn Ile Asn
1325             1330                1335

Leu Ser Lys Asp Asp Leu Trp Ile Phe Asn Ile Asp Asn Glu Val
1340             1345                1350

Arg Glu Ile Ser Ile Glu Asn Gly Thr Ile Lys Lys Gly Lys Leu
1355             1360                1365

Ile Lys Asp Val Leu Ser Lys Ile Asp Ile Asn Lys Asn Lys Leu
1370             1375                1380

Ile Ile Gly Asn Gln Thr Ile Asp Phe Ser Gly Asp Ile Asp Asn
1385             1390                1395

Lys Asp Arg Tyr Ile Phe Leu Thr Cys Glu Leu Asp Asp Lys Ile
1400             1405                1410

Ser Leu Ile Ile Glu Ile Asn Leu Val Ala Lys Ser Tyr Ser Leu
1415             1420                1425

Leu Leu Ser Gly Asp Lys Asn Tyr Leu Ile Ser Asn Leu Ser Asn
1430             1435                1440

Ile Ile Glu Lys Ile Asn Thr Leu Gly Leu Asp Ser Lys Asn Ile
1445             1450                1455

Ala Tyr Asn Tyr Thr Asp Glu Ser Asn Asn Lys Tyr Phe Gly Ala
1460             1465                1470

Ile Ser Lys Thr Ser Gln Lys Ser Ile Ile His Tyr Lys Lys Asp
1475             1480                1485

Ser Lys Asn Ile Leu Glu Phe Tyr Asn Asp Ser Thr Leu Glu Phe
1490             1495                1500

Asn Ser Lys Asp Phe Ile Ala Glu Asp Ile Asn Val Phe Met Lys
1505             1510                1515

Asp Asp Ile Asn Thr Ile Thr Gly Lys Tyr Tyr Val Asp Asn Asn
1520             1525                1530

Thr Asp Lys Ser Ile Asp Phe Ser Ile Ser Leu Val Ser Lys Asn
1535             1540                1545

Gln Val Lys Val Asn Gly Leu Tyr Leu Asn Glu Ser Val Tyr Ser
1550             1555                1560

Ser Tyr Leu Asp Phe Val Lys Asn Ser Asp Gly His His Asn Thr
1565             1570                1575

Ser Asn Phe Met Asn Leu Phe Leu Asp Asn Ile Ser Phe Trp Lys
1580             1585                1590
```

```
Leu Phe Gly Phe Glu Asn Ile Asn Phe Val Ile Asp Lys Tyr Phe
    1595                1600                1605

Thr Leu Val Gly Lys Thr Asn Leu Gly Tyr Val Glu Phe Ile Cys
    1610                1615                1620

Asp Asn Asn Lys Asn Ile Asp Ile Tyr Phe Gly Glu Trp Lys Thr
    1625                1630                1635

Ser Ser Ser Lys Ser Thr Ile Phe Ser Gly Asn Gly Arg Asn Val
    1640                1645                1650

Val Val Glu Pro Ile Tyr Asn Pro Asp Thr Gly Glu Asp Ile Ser
    1655                1660                1665

Thr Ser Leu Asp Phe Ser Tyr Glu Pro Leu Tyr Gly Ile Asp Arg
    1670                1675                1680

Tyr Ile Asn Lys Val Leu Ile Ala Pro Asp Leu Tyr Thr Ser Leu
    1685                1690                1695

Ile Asn Ile Asn Thr Asn Tyr Tyr Ser Asn Glu Tyr Tyr Pro Glu
    1700                1705                1710

Ile Ile Val Leu Asn Pro Asn Thr Phe His Lys Lys Val Asn Ile
    1715                1720                1725

Asn Leu Asp Ser Ser Phe Glu Tyr Lys Trp Ser Thr Glu Gly
    1730                1735                1740

Ser Asp Phe Ile Leu Val Arg Tyr Leu Glu Glu Ser Asn Lys Lys
    1745                1750                1755

Ile Leu Gln Lys Ile Arg Ile Lys Gly Ile Leu Ser Asn Thr Gln
    1760                1765                1770

Ser Phe Asn Lys Met Ser Ile Asp Phe Lys Asp Ile Lys Lys Leu
    1775                1780                1785

Ser Leu Gly Tyr Ile Met Ser Asn Phe Lys Ser Phe Asn Ser Glu
    1790                1795                1800

Asn Glu Leu Asp Arg Asp His Leu Gly Phe Lys Ile Ile Asp Asn
    1805                1810                1815

Lys Thr Tyr Tyr Tyr Asp Glu Asp Ser Lys Leu Val Lys Gly Leu
    1820                1825                1830

Ile Asn Ile Asn Asn Ser Leu Phe Tyr Phe Asp Pro Ile Glu Phe
    1835                1840                1845

Asn Leu Val Thr Gly Trp Gln Thr Ile Asn Gly Lys Lys Tyr Tyr
    1850                1855                1860

Phe Asp Ile Asn Thr Gly Ala Ala Leu Ile Ser Tyr Lys Ile Ile
    1865                1870                1875

Asn Gly Lys His Phe Tyr Phe Asn Asn Asp Gly Val Met Gln Leu
    1880                1885                1890

Gly Val Phe Lys Gly Pro Asp Gly Phe Glu Tyr Phe Ala Pro Ala
    1895                1900                1905

Asn Thr Gln Asn Asn Asn Ile Glu Gly Gln Ala Ile Val Tyr Gln
    1910                1915                1920

Ser Lys Phe Leu Thr Leu Asn Gly Lys Lys Tyr Tyr Phe Asp Asn
    1925                1930                1935

Asp Ser Lys Ala Val Thr Gly Trp Arg Ile Ile Asn Asn Glu Lys
    1940                1945                1950

Tyr Tyr Phe Asn Pro Asn Asn Ala Ile Ala Ala Val Gly Leu Gln
    1955                1960                1965

Val Ile Asp Asn Asn Lys Tyr Tyr Phe Asn Pro Asp Thr Ala Ile
    1970                1975                1980

Ile Ser Lys Gly Trp Gln Thr Val Asn Gly Ser Arg Tyr Tyr Phe
```

-continued

```
           1985                1990                1995
Asp Thr  Asp Thr Ala Ile Ala  Phe Asn Gly Tyr Lys  Thr Ile Asp
         2000                2005                2010

Gly Lys  His Phe Tyr Phe Asp  Ser Asp Cys Val Val  Lys Ile Gly
         2015                2020                2025

Val Phe  Ser Thr Ser Asn Gly  Phe Glu Tyr Phe Ala  Pro Ala Asn
         2030                2035                2040

Thr Tyr  Asn Asn Asn Ile Glu  Gly Gln Ala Ile Val  Tyr Gln Ser
         2045                2050                2055

Lys Phe  Leu Thr Leu Asn Gly  Lys Lys Tyr Tyr Phe  Asp Asn Asn
         2060                2065                2070

Ser Lys  Ala Val Thr Gly Trp  Gln Thr Ile Asp Ser  Lys Lys Tyr
         2075                2080                2085

Tyr Phe  Asn Thr Asn Thr Ala  Glu Ala Ala Thr Gly  Trp Gln Thr
         2090                2095                2100

Ile Asp  Gly Lys Lys Tyr Tyr  Phe Asn Thr Asn Thr  Ala Glu Ala
         2105                2110                2115

Ala Thr  Gly Trp Gln Thr Ile  Asp Gly Lys Lys Tyr  Tyr Phe Asn
         2120                2125                2130

Thr Asn  Thr Ala Ile Ala Ser  Thr Gly Tyr Thr Ile  Ile Asn Gly
         2135                2140                2145

Lys His  Phe Tyr Phe Asn Thr  Asp Gly Ile Met Gln  Ile Gly Val
         2150                2155                2160

Phe Lys  Gly Pro Asn Gly Phe  Glu Tyr Phe Ala Pro  Ala Asn Thr
         2165                2170                2175

Asp Ala  Asn Asn Ile Glu Gly  Gln Ala Ile Leu Tyr  Gln Asn Glu
         2180                2185                2190

Phe Leu  Thr Leu Asn Gly Lys  Lys Tyr Tyr Phe Gly  Ser Asp Ser
         2195                2200                2205

Lys Ala  Val Thr Gly Trp Arg  Ile Ile Asn Asn Lys  Lys Tyr Tyr
         2210                2215                2220

Phe Asn  Pro Asn Asn Ala Ile  Ala Ala Ile His Leu  Cys Thr Ile
         2225                2230                2235

Asn Asn  Asp Lys Tyr Tyr Phe  Ser Tyr Asp Gly Ile  Leu Gln Asn
         2240                2245                2250

Gly Tyr  Ile Thr Ile Glu Arg  Asn Asn Phe Tyr Phe  Asp Ala Asn
         2255                2260                2265

Asn Glu  Ser Lys Met Val Thr  Gly Val Phe Lys Gly  Pro Asn Gly
         2270                2275                2280

Phe Glu  Tyr Phe Ala Pro Ala  Asn Thr His Asn Asn  Asn Ile Glu
         2285                2290                2295

Gly Gln  Ala Ile Val Tyr Gln  Asn Lys Phe Leu Thr  Leu Asn Gly
         2300                2305                2310

Lys Lys  Tyr Tyr Phe Asp Asn  Asp Ser Lys Ala Val  Thr Gly Trp
         2315                2320                2325

Gln Thr  Ile Asp Gly Lys Lys  Tyr Tyr Phe Asn Leu  Asn Thr Ala
         2330                2335                2340

Glu Ala  Ala Thr Gly Trp Gln  Thr Ile Asp Gly Lys  Lys Tyr Tyr
         2345                2350                2355

Phe Asn  Leu Asn Thr Ala Glu  Ala Ala Thr Gly Trp  Gln Thr Ile
         2360                2365                2370

Asp Gly  Lys Lys Tyr Tyr Phe  Asn Thr Asn Thr Phe  Ile Ala Ser
         2375                2380                2385
```

```
Thr Gly  Tyr Thr Ser Ile Asn  Gly Lys His Phe Tyr  Phe Asn Thr
    2390                 2395                 2400

Asp Gly  Ile Met Gln Ile Gly  Val Phe Lys Gly Pro  Asn Gly Phe
    2405                 2410                 2415

Glu Tyr  Phe Ala Pro Ala Asn  Thr His Asn Asn Asn  Ile Glu Gly
    2420                 2425                 2430

Gln Ala  Ile Leu Tyr Gln Asn  Lys Phe Leu Thr Leu  Asn Gly Lys
    2435                 2440                 2445

Lys Tyr  Tyr Phe Gly Ser Asp  Ser Lys Ala Val Thr  Gly Leu Arg
    2450                 2455                 2460

Thr Ile  Asp Gly Lys Lys Tyr  Tyr Phe Asn Thr Asn  Thr Ala Val
    2465                 2470                 2475

Ala Val  Thr Gly Trp Gln Thr  Ile Asn Gly Lys Lys  Tyr Tyr Phe
    2480                 2485                 2490

Asn Thr  Asn Thr Ser Ile Ala  Ser Thr Gly Tyr Thr  Ile Ile Ser
    2495                 2500                 2505

Gly Lys  His Phe Tyr Phe Asn  Thr Asp Gly Ile Met  Gln Ile Gly
    2510                 2515                 2520

Val Phe  Lys Gly Pro Asp Gly  Phe Glu Tyr Phe Ala  Pro Ala Asn
    2525                 2530                 2535

Thr Asp  Ala Asn Asn Ile Glu  Gly Gln Ala Ile Arg  Tyr Gln Asn
    2540                 2545                 2550

Arg Phe  Leu Tyr Leu His Asp  Asn Ile Tyr Tyr Phe  Gly Asn Asn
    2555                 2560                 2565

Ser Lys  Ala Ala Thr Gly Trp  Val Thr Ile Asp Gly  Asn Arg Tyr
    2570                 2575                 2580

Tyr Phe  Glu Pro Asn Thr Ala  Met Gly Ala Asn Gly  Tyr Lys Thr
    2585                 2590                 2595

Ile Asp  Asn Lys Asn Phe Tyr  Phe Arg Asn Gly Leu  Pro Gln Ile
    2600                 2605                 2610

Gly Val  Phe Lys Gly Ser Asn  Gly Phe Glu Tyr Phe  Ala Pro Ala
    2615                 2620                 2625

Asn Thr  Asp Ala Asn Asn Ile  Glu Gly Gln Ala Ile  Arg Tyr Gln
    2630                 2635                 2640

Asn Arg  Phe Leu His Leu Leu  Gly Lys Ile Tyr Tyr  Phe Gly Asn
    2645                 2650                 2655

Asn Ser  Lys Ala Val Thr Gly  Trp Gln Thr Ile Asn  Gly Lys Val
    2660                 2665                 2670

Tyr Tyr  Phe Met Pro Asp Thr  Ala Met Ala Ala Ala  Gly Gly Leu
    2675                 2680                 2685

Phe Glu  Ile Asp Gly Val Ile  Tyr Phe Phe Gly Val  Asp Gly Val
    2690                 2695                 2700

Lys Ala  Pro Gly Ile Tyr Gly
    2705                 2710

<210> SEQ ID NO 2
<211> LENGTH: 8133
<212> TYPE: DNA
<213> ORGANISM: Clostridium difficile

<400> SEQUENCE: 2
atgtctttaa tatctaaaga agagttaata aaactcgcat atagcattag accaagagaa      60
aatgagtata aaactatact aactaattta gacgaatata ataagttaac tacaaacaat     120
```

```
aatgaaaata aatatttaca attaaaaaaa ctaaatgaat caattgatgt ttttatgaat      180
aaatataaaa cttcaagcag aaatagagca ctctctaatc taaaaaaaga tatattaaaa      240
gaagtaattc ttattaaaaa ttccaataca agccctgtag aaaaaaattt acattttgta      300
tggataggtg gagaagtcag tgatattgct cttgaataca taaaacaatg ggctgatatt      360
aatgcagaat ataatattaa actgtggtat gatagtgaag cattcttagt aaatacacta      420
aaaaaggcta tagttgaatc ttctaccact gaagcattac agctactaga ggaagagatt      480
caaaatcctc aatttgataa tatgaaattt tacaaaaaaa ggatggaatt tatatatgat      540
agacaaaaaa ggtttataaa ttattataaa tctcaaatca ataaacctac agtacctaca      600
atagatgata ttataaagtc tcatctagta tctgaatata atagagatga aactgtatta      660
gaatcatata gaacaaattc tttgagaaaa ataaatagta atcatgggat agatatcagg      720
gctaatagtt tgtttacaga acaagagtta ttaaatattt atagtcagga gttgttaaat      780
cgtggaaatt tagctgcagc atctgacata gtaagattat tagccctaaa aaattttggc      840
ggagtatatt tagatgttga tatgcttcca ggtattcact ctgatttatt taaaacaata      900
tctagaccta gctctattgg actagaccgt tgggaaatga taaaattaga ggctattatg      960
aagtataaaa aatatataaa taattataca tcagaaaact ttgataaact tgatcaacaa     1020
ttaaaagata attttaaact cattatagaa agtaaaagtg aaaaatctga gatattttct     1080
aaattagaaa atttaaatgt atctgatctt gaaattaaaa tagctttcgc tttaggcagt     1140
gttataaatc aagccttgat atcaaaacaa ggttcatatc ttactaacct agtaatagaa     1200
caagtaaaaa atagatatca attttttaaac caacaccttta acccagccat agagtctgat     1260
aataacttca cagatactac taaaattttt catgattcat tatttaattc agctaccgca     1320
gaaaactcta tgttttttaac aaaaaatagca ccatacttac aagtaggttt tatgccagaa     1380
gctcgctcca caataagttt aagtggtcca ggagcttatg cgtcagctta ctatgatttc     1440
ataaatttac aagaaaatac tatagaaaaa acttttaaaag catcagattt aatagaattt     1500
aaattcccag aaaataatct atctcaattg acagaacaag aaataaatag tctatggagc     1560
tttgatcaag caagtgcaaa atatcaattt gagaaatatg taagagatta tactggtgga     1620
tctctttctg aagacaatgg ggtagacttt aataaaaata ctgccctcga caaaaactat     1680
ttattaaata taaaaattcc atcaaacaat gtagaagaag ctggaagtaa aaattatgtt     1740
cattatatca tacagttaca aggagatgat ataagttatg aagcaacatg caatttattt     1800
tctaaaaatc ctaaaaatag tattattata caacgaaata tgaatgaaag tgcaaaaagc     1860
tactttttaa gtgatgatgg agaatctatt ttagaattaa ataaatatag gatacctgaa     1920
agattaaaaa ataaggaaaa agtaaaagta accttattg gacatggtaa agatgaattc     1980
aacacaagcg aatttgctag attaagtgta gattcacttt ccaatgagat aagttcattt     2040
ttagatacca taaaattaga tatcaccct aaaaatgtag aagtaaactt acttggatgt     2100
aatatgttta gttatgattt taatgttgaa gaaacttatc ctgggaagtt gctattaagt     2160
attatggaca aaattacttc cactttacct gatgtaaata aaattctat tactatagga     2220 gcaaatcaat atgaagtaag aattaatagt gagggaagaa aagaacttct ggctcactca     2280
ggtaaatgga taaataaaga agaagctatt atgagcgatt tatctagtaa agaatacatt     2340
ttttttgatt ctatagataa taagctaaaa gcaaagtcca agaatattcc aggattagca     2400
tcaatatcag aagatataaa aacattatta cttgatgcaa gtgttagtcc tgatacaaaa     2460
tttattttaa ataatcttaa gcttaatatt gaatcttcta ttggtgatta catttattat     2520
```

-continued

```
gaaaaattag agcctgttaa aaatataatt cacaattcta tagatgattt aatagatgag    2580
ttcaatctac ttgaaaatgt atctgatgaa ttatatgaat taaaaaaatt aaataatcta    2640
gatgagaagt atttaatatc ttttgaagat atctcaaaaa ataattcaac ttactctgta    2700
agatttatta acaaaagtaa tggtgagtca gtttatgtag aaacagaaaa agaaatttt     2760 tcaaaatata gcgaacatat tacaaaagaa ataagtacta taagaatag tataattaca    2820 gatgttaatg gtaatttatt ggataatata cagttagatc atacttctca agttaataca    2880
ttaaacgcag cattctttat tcaatcatta atagattata gtagcaataa agatgtactg    2940
aatgatttaa gtacctcagt taaggttcaa ctttatgctc aactatttag tacaggttta    3000
aatactatat atgactctat ccaattagta aatttaatat caaatgcagt aaatgatact    3060
ataaatgtac tacctacaat aacagagggg atacctattg tatctactat attagacgga    3120
ataaacttag gtgcagcaat taaggaatta ctagacgaac atgacccatt actaaaaaaa    3180
gaattagaag ctaaggtggg tgttttagca ataaatatgt cattatctat agctgcaact    3240
gtagcttcaa ttgttggaat aggtgctgaa gttactattt tcttattacc tatagctggt    3300
atatctgcag gaataccttc attagttaat aatgaattaa tattgcatga taaggcaact    3360
tcagtggtaa actattttaa tcatttgtct gaatctaaaa aatatggccc tcttaaaaca    3420
gaagatgata aaattttagt tcctattgat gatttagtaa tatcagaaat agattttaat    3480
aataattcga taaaactagg aacatgtaat atattagcaa tggaggggg atcaggacac     3540 acagtgactg gtaatataga tcactttttc tcatctccat ctataagttc tcatattcct    3600
tcattatcaa tttattctgc aataggtata gaaacagaaa atctagattt ttcaaaaaaa    3660
ataatgatgt tacctaatgc tccttcaaga gtgttttggt gggaaactgg agcagttcca    3720
ggtttaagat cattggaaaa tgacggaact agattacttg attcaataag agatttatac    3780
ccaggtaaat tttactggag attctatgct tttttcgatt atgcaataac tacattaaaa    3840
ccagtttatg aagacactaa tattaaaatt aaactagata aagatactag aaacttcata    3900
atgccaacta taactactaa cgaaattaga aacaaattat cttattcatt tgatggagca    3960
ggaggaactt actctttatt attatcttca tatccaatat caacgaatat aaatttatct    4020
aaagatgatt tatggatatt taatattgat aatgaagtaa gagaaatatc tatagaaaat    4080
ggtactatta aaaaggaaa gttaataaaa gatgttttaa gtaaaattga tataaataaa     4140
aataaactta ttataggcaa tcaaacaata gattttcag gcgatataga taataaagat     4200
agatatatat tcttgacttg tgagttagat gataaaatta gtttaataat agaaataaat    4260
cttgttgcaa aatcttatag tttgttattg tctggggata aaaattattt gatatccaat    4320
ttatctaata ttattgagaa aatcaatact ttaggcctag atagtaaaaa tatagcgtac    4380
aattacactg atgaatctaa taataaatat tttggagcta tatctaaaac aagtcaaaaa    4440
agcataatac attataaaaa agacagtaaa aatatattag aatttataa tgacagtaca     4500 ttagaattta acagtaaaga ttttattgct gaagatataa atgtatttat gaaagatgat    4560
attaatacta taacaggaaa atactatgtt gataataata ctgataaaag tatagatttc    4620
tctatttctt tagttagtaa aaatcaagta aaagtaaatg gattatattt aaatgaatcc    4680
gtatactcat cttaccttga ttttgtgaaa aattcagatg gacaccataa tacttctaat    4740
tttatgaatt tattttggga caatataagt ttctggaaat tgtttgggtt tgaaaatata    4800
aattttgtaa tcgataaata ctttacccct tgttggtaaaa ctaatcttgg atatgtagaa    4860
```

```
tttatttgtg acaataataa aaatatagat atatattttg gtgaatggaa aacatcgtca    4920
tctaaaagca ctatatttag cggaaatggt agaaatgttg tagtagagcc tatatataat    4980
cctgatacgg gtgaagatat atctacttca ctagattttt cctatgaacc tctctatgga    5040
atagatagat atatcaataa agtattgata gcacctgatt tatatacaag tttaataaat    5100
attaatacca attattattc aaatgagtac taccctgaga ttatagttct taacccaaat    5160
acattccaca aaaagtaaa tataaattta gatagttctt cttttgagta taaatggtct    5220
acagaaggaa gtgactttat tttagttaga tacttagaag aaagtaataa aaaaatatta    5280
caaaaaataa gaatcaaagg tatcttatct aatactcaat catttaataa aatgagtata    5340
gattttaaag atattaaaaa actatcatta ggatatataa tgagtaatttt taaatcattt    5400
aattctgaaa atgaattaga tagagatcat ttaggattta aaataataga taataaaact    5460
tattactatg atgaagatag taaattagtt aaaggattaa tcaatataaa taattcatta    5520
ttctattttg atcctataga atttaactta gtaactggat ggcaaactat caatggtaaa    5580
aaatattatt ttgatataaa tactggagca gcttttaatta gttataaaat tattaatggt    5640
aaacactttt atttttaataa tgatggtgtg atgcagttgg gagtatttaa aggacctgat    5700
ggatttgaat attttgcacc tgccaatact caaaataata acatagaagg tcaggctata    5760
gtttatcaaa gtaaattctt aactttgaat ggcaaaaaat attattttga taatgactca    5820
aaagcagtca ctggatggag aattattaac aatgagaaat attactttaa tcctaataat    5880
gctattgctg cagtcggatt gcaagtaatt gacaataata agtattattt caatcctgac    5940
actgctatca tctcaaaagg ttggcagact gttaatggta gtagatacta ctttgatact    6000
gataccgcta ttgcctttaa tggttataaa actattgatg gtaaacactt ttatttttgat    6060
agtgattgtg tagtgaaaat aggtgtgttt agtacctcta atggatttga atattttgca    6120
cctgctaata cttataataa taacatagaa ggtcaggcta gtttatca aagtaaattc    6180
ttaactttga atggtaaaaa atattacttt gataataact caaaagcagt taccggatgg    6240
caaactattg atagtaaaaa atattacttt aatactaaca ctgctgaagc agctactgga    6300
tggcaaacta ttgatggtaa aaatatattac tttaatacta cactgctga agcagctact    6360
ggatggcaaa ctattgatgg taaaaaatat tactttaata ctaacactgc tatagcttca    6420
actggttata caattattaa tggtaaacat tttattttta atactgatgg tattatgcag    6480
ataggagtgt ttaaaggacc taatggattt gaatattttg cacctgctaa tacggatgct    6540
aacaacatag aaggtcaagc tatactttac caaaatgaat tcttaacttt gaatggtaaa    6600
aaatattact ttggtagtga ctcaaaagca gttactggat ggagaattat taacaataag    6660
aaatattact ttaatcctaa taatgctatt gctgcaattc atctatgcac tataaataat    6720
gacaagtatt actttagtta tgatggaatt cttcaaaatg gatatattac tattgaaaga    6780
aataatttct attttgatgc taataatgaa tctaaaatgg taacaggagt atttaaagga    6840
cctaatggat ttgagtattt tgcacctgct aatactcaca ataataacat agaaggtcag    6900
gctatagttt accagaacaa attcttaact ttgaatggca aaaaatatta ttttgataat    6960
gactcaaaag cagttactgg atggcaaacc attgatggta aaaaatatta ctttaatctt    7020
aacactgctg aagcagctac tggatggcaa actattgatg gtaaaaaata ttactttaat    7080
cttaacactg ctgaagcagc tactggatgg caaactattg atggtaaaaa atattacttt    7140
aatactaaca ctttcatagc ctcaactggt tatacaagta ttaatggtaa acattttat    7200
tttaatactg atggtattat gcagatagga gtgtttaaag gacctaatgg atttgaatac    7260
```

-continued

```
tttgcacctg ctaatactca taataataac atagaaggtc aagctatact ttaccaaaat    7320
aaattcttaa ctttgaatgg taaaaaatat tactttggta gtgactcaaa agcagttacc    7380
ggattgcgaa ctattgatgg taaaaaatat tactttaata ctaacactgc tgttgcagtt    7440
actggatggc aaactattaa tggtaaaaaa tactactttaa atactaacac ttctatagct    7500
tcaactggtt atacaattat tagtggtaaa catttttatt ttaatactga tggtattatg    7560
cagataggag tgtttaaagg acctgatgga tttgaatact ttgcacctgc taatacagat    7620
gctaacaata tagaaggtca agctatacgt tatcaaaata gattcctata tttacatgac    7680
aatatatatt attttggtaa taattcaaaa gcagctactg gttgggtaac tattgatggt    7740
aatagatatt acttcgagcc taatacagct atgggtgcga atggttataa aactattgat    7800
aataaaaatt tttactttag aaatggttta cctcagatag gagtgtttaa agggtctaat    7860
ggatttgaat actttgcacc tgctaatacg gatgctaaca atatagaagg tcaagctata    7920
cgttatcaaa atagattcct acatttactt ggaaaaatat attactttgg taataattca    7980
aaagcagtta ctggatggca aactattaat ggtaaagtat attactttat gcctgatact    8040
gctatggctg cagctggtgg acttttcgag attgatggtg ttatatattt ctttggtgtt    8100
gatggagtaa aagcccctgg gatatatggc taa                                 8133
```

<210> SEQ ID NO 3
<211> LENGTH: 2366
<212> TYPE: PRT
<213> ORGANISM: Clostridium difficile

<400> SEQUENCE: 3

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
```

-continued

```
                210                 215                 220
Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
                260                 265                 270

Arg Ile Ser Ala Leu Lys Glu Ile Gly Gly Met Tyr Leu Asp Val Asp
                275                 280                 285

Met Leu Pro Gly Ile Gln Pro Asp Leu Phe Glu Ser Ile Glu Lys Pro
290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
                340                 345                 350

Lys Ser Asp Lys Ser Glu Ile Phe Ser Ser Leu Gly Asp Met Glu Ala
                355                 360                 365

Ser Pro Leu Glu Val Lys Ile Ala Phe Asn Ser Lys Gly Ile Ile Asn
                370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
                420                 425                 430

Asp Ser Ile Met Ala Glu Ala Asn Ala Asp Asn Gly Arg Phe Met Met
                435                 440                 445

Glu Leu Gly Lys Tyr Leu Arg Val Gly Phe Phe Pro Asp Val Lys Thr
450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Asp Ala Arg Ala Lys
                515                 520                 525

Ala Gln Phe Glu Glu Tyr Lys Arg Asn Tyr Phe Glu Gly Ser Leu Gly
                530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
                580                 585                 590

Ala Ala Cys Asn Leu Phe Ala Lys Thr Pro Tyr Asp Ser Val Leu Phe
                595                 600                 605

Gln Lys Asn Ile Glu Asp Ser Glu Ile Ala Tyr Tyr Tyr Asn Pro Gly
                610                 615                 620

Asp Gly Glu Ile Gln Glu Ile Asp Lys Tyr Lys Ile Pro Ser Ile Ile
625                 630                 635                 640
```

```
Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
                660                 665                 670

Thr Glu Ile Glu Ala Ala Ile Asp Leu Ala Lys Glu Asp Ile Ser Pro
                675                 680                 685

Lys Ser Ile Glu Ile Asn Leu Leu Gly Cys Asn Met Phe Ser Tyr Ser
            690                 695                 700

Ile Asn Val Glu Glu Thr Tyr Pro Gly Lys Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Ser Ile
            755                 760                 765

Ile Lys Asp Ile Ser Ser Lys Glu Tyr Ile Ser Phe Asn Pro Lys Glu
            770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
                820                 825                 830

Asp Thr Gln Ile Val Glu Glu Arg Ile Glu Glu Ala Lys Asn Leu Thr
                835                 840                 845

Ser Asp Ser Ile Asn Tyr Ile Lys Asp Glu Phe Lys Leu Ile Glu Ser
        850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
                900                 905                 910

Thr Glu Lys Thr Ile Phe Ser Glu Tyr Ala Asn His Ile Thr Glu Glu
                915                 920                 925

Ile Ser Lys Ile Lys Gly Thr Ile Phe Asp Thr Val Asn Gly Lys Leu
        930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
                980                 985                 990

Leu Phe Ser Thr Gly Leu Asn Thr Ile Thr Asp Ala Ala Lys Val Val
                995                1000                1005

Glu Leu Val Ser Thr Ala Leu Asp Glu Thr Ile Asp Leu Leu Pro
    1010                1015                1020

Thr Leu Ser Glu Gly Leu Pro Ile Ile Ala Thr Ile Ile Asp Gly
    1025                1030                1035

Val Ser Leu Gly Ala Ala Ile Lys Glu Leu Ser Glu Thr Ser Asp
    1040                1045                1050
```

```
Pro Leu Leu Arg Gln Glu Ile Glu Ala Lys Ile Gly Ile Met Ala
    1055                1060                1065

Val Asn Leu Thr Thr Ala Thr Thr Ala Ile Ile Thr Ser Ser Leu
    1070                1075                1080

Gly Ile Ala Ser Gly Phe Ser Ile Leu Leu Val Pro Leu Ala Gly
    1085                1090                1095

Ile Ser Ala Gly Ile Pro Ser Leu Val Asn Asn Glu Leu Val Leu
    1100                1105                1110

Arg Asp Lys Ala Thr Lys Val Val Asp Tyr Phe Lys His Val Ser
    1115                1120                1125

Leu Val Glu Thr Glu Gly Val Phe Thr Leu Leu Asp Asp Lys Ile
    1130                1135                1140

Met Met Pro Gln Asp Asp Leu Val Ile Ser Glu Ile Asp Phe Asn
    1145                1150                1155

Asn Asn Ser Ile Val Leu Gly Lys Cys Glu Ile Trp Arg Met Glu
    1160                1165                1170

Gly Gly Ser Gly His Thr Val Thr Asp Asp Ile Asp His Phe Phe
    1175                1180                1185

Ser Ala Pro Ser Ile Thr Tyr Arg Glu Pro His Leu Ser Ile Tyr
    1190                1195                1200

Asp Val Leu Glu Val Gln Lys Glu Glu Leu Asp Leu Ser Lys Asp
    1205                1210                1215

Leu Met Val Leu Pro Asn Ala Pro Asn Arg Val Phe Ala Trp Glu
    1220                1225                1230

Thr Gly Trp Thr Pro Gly Leu Arg Ser Leu Glu Asn Asp Gly Thr
    1235                1240                1245

Lys Leu Leu Asp Arg Ile Arg Asp Asn Tyr Glu Gly Glu Phe Tyr
    1250                1255                1260

Trp Arg Tyr Phe Ala Phe Ile Ala Asp Ala Leu Ile Thr Thr Leu
    1265                1270                1275

Lys Pro Arg Tyr Glu Asp Thr Asn Ile Arg Ile Asn Leu Asp Ser
    1280                1285                1290

Asn Thr Arg Ser Phe Ile Val Pro Ile Ile Thr Thr Glu Tyr Ile
    1295                1300                1305

Arg Glu Lys Leu Ser Tyr Ser Phe Tyr Gly Ser Gly Gly Thr Tyr
    1310                1315                1320

Ala Leu Ser Leu Ser Gln Tyr Asn Met Gly Ile Asn Ile Glu Leu
    1325                1330                1335

Ser Glu Ser Asp Val Trp Ile Ile Asp Val Asp Asn Val Val Arg
    1340                1345                1350

Asp Val Thr Ile Glu Ser Asp Lys Ile Lys Lys Gly Asp Leu Ile
    1355                1360                1365

Glu Gly Ile Leu Ser Thr Leu Ser Ile Glu Glu Asn Lys Ile Ile
    1370                1375                1380

Leu Asn Ser His Glu Ile Asn Phe Ser Gly Glu Val Asn Gly Ser
    1385                1390                1395

Asn Gly Phe Val Ser Leu Thr Phe Ser Ile Leu Glu Gly Ile Asn
    1400                1405                1410

Ala Ile Ile Glu Val Asp Leu Leu Ser Lys Ser Tyr Lys Leu Leu
    1415                1420                1425

Ile Ser Gly Glu Leu Lys Ile Leu Met Leu Asn Ser Asn His Ile
    1430                1435                1440

Gln Gln Lys Ile Asp Tyr Ile Gly Phe Asn Ser Glu Leu Gln Lys
```

-continued

```
               1445                1450                1455

Asn Ile Pro Tyr Ser Phe Val Asp Ser Glu Gly Lys Glu Asn Gly
        1460                1465                1470

Phe Ile Asn Gly Ser Thr Lys Glu Gly Leu Phe Val Ser Glu Leu
        1475                1480                1485

Pro Asp Val Val Leu Ile Ser Lys Val Tyr Met Asp Asp Ser Lys
        1490                1495                1500

Pro Ser Phe Gly Tyr Tyr Ser Asn Asn Leu Lys Asp Val Lys Val
        1505                1510                1515

Ile Thr Lys Asp Asn Val Asn Ile Leu Thr Gly Tyr Tyr Leu Lys
        1520                1525                1530

Asp Asp Ile Lys Ile Ser Leu Ser Leu Thr Leu Gln Asp Glu Lys
        1535                1540                1545

Thr Ile Lys Leu Asn Ser Val His Leu Asp Glu Ser Gly Val Ala
        1550                1555                1560

Glu Ile Leu Lys Phe Met Asn Arg Lys Gly Asn Thr Asn Thr Ser
        1565                1570                1575

Asp Ser Leu Met Ser Phe Leu Glu Ser Met Asn Ile Lys Ser Ile
        1580                1585                1590

Phe Val Asn Phe Leu Gln Ser Asn Ile Lys Phe Ile Leu Asp Ala
        1595                1600                1605

Asn Phe Ile Ile Ser Gly Thr Thr Ser Ile Gly Gln Phe Glu Phe
        1610                1615                1620

Ile Cys Asp Glu Asn Asp Asn Ile Gln Pro Tyr Phe Ile Lys Phe
        1625                1630                1635

Asn Thr Leu Glu Thr Asn Tyr Thr Leu Tyr Val Gly Asn Arg Gln
        1640                1645                1650

Asn Met Ile Val Glu Pro Asn Tyr Asp Leu Asp Asp Ser Gly Asp
        1655                1660                1665

Ile Ser Ser Thr Val Ile Asn Phe Ser Gln Lys Tyr Leu Tyr Gly
        1670                1675                1680

Ile Asp Ser Cys Val Asn Lys Val Val Ile Ser Pro Asn Ile Tyr
        1685                1690                1695

Thr Asp Glu Ile Asn Ile Thr Pro Val Tyr Glu Thr Asn Asn Thr
        1700                1705                1710

Tyr Pro Glu Val Ile Val Leu Asp Ala Asn Tyr Ile Asn Glu Lys
        1715                1720                1725

Ile Asn Val Asn Ile Asn Asp Leu Ser Ile Arg Tyr Val Trp Ser
        1730                1735                1740

Asn Asp Gly Asn Asp Phe Ile Leu Met Ser Thr Ser Glu Glu Asn
        1745                1750                1755

Lys Val Ser Gln Val Lys Ile Arg Phe Val Asn Val Phe Lys Asp
        1760                1765                1770

Lys Thr Leu Ala Asn Lys Leu Ser Phe Asn Phe Ser Asp Lys Gln
        1775                1780                1785

Asp Val Pro Val Ser Glu Ile Ile Leu Ser Phe Thr Pro Ser Tyr
        1790                1795                1800

Tyr Glu Asp Gly Leu Ile Gly Tyr Asp Leu Gly Leu Val Ser Leu
        1805                1810                1815

Tyr Asn Glu Lys Phe Tyr Ile Asn Asn Phe Gly Met Met Val Ser
        1820                1825                1830

Gly Leu Ile Tyr Ile Asn Asp Ser Leu Tyr Tyr Phe Lys Pro Pro
        1835                1840                1845
```

Val Asn Asn Leu Ile Thr Gly Phe Val Thr Val Gly Asp Asp Lys
1850                1855                1860

Tyr Tyr Phe Asn Pro Ile Asn Gly Gly Ala Ala Ser Ile Gly Glu
1865                1870                1875

Thr Ile Ile Asp Asp Lys Asn Tyr Tyr Phe Asn Gln Ser Gly Val
1880                1885                1890

Leu Gln Thr Gly Val Phe Ser Thr Glu Asp Gly Phe Lys Tyr Phe
1895                1900                1905

Ala Pro Ala Asn Thr Leu Asp Glu Asn Leu Glu Gly Glu Ala Ile
1910                1915                1920

Asp Phe Thr Gly Lys Leu Ile Ile Asp Glu Asn Ile Tyr Tyr Phe
1925                1930                1935

Asp Asp Asn Tyr Arg Gly Ala Val Glu Trp Lys Glu Leu Asp Gly
1940                1945                1950

Glu Met His Tyr Phe Ser Pro Glu Thr Gly Lys Ala Phe Lys Gly
1955                1960                1965

Leu Asn Gln Ile Gly Asp Tyr Lys Tyr Tyr Phe Asn Ser Asp Gly
1970                1975                1980

Val Met Gln Lys Gly Phe Val Ser Ile Asn Asp Asn Lys His Tyr
1985                1990                1995

Phe Asp Asp Ser Gly Val Met Lys Val Gly Tyr Thr Glu Ile Asp
2000                2005                2010

Gly Lys His Phe Tyr Phe Ala Glu Asn Gly Glu Met Gln Ile Gly
2015                2020                2025

Val Phe Asn Thr Glu Asp Gly Phe Lys Tyr Phe Ala His His Asn
2030                2035                2040

Glu Asp Leu Gly Asn Glu Glu Gly Glu Glu Ile Ser Tyr Ser Gly
2045                2050                2055

Ile Leu Asn Phe Asn Asn Lys Ile Tyr Tyr Phe Asp Asp Ser Phe
2060                2065                2070

Thr Ala Val Val Gly Trp Lys Asp Leu Glu Asp Gly Ser Lys Tyr
2075                2080                2085

Tyr Phe Asp Glu Asp Thr Ala Glu Ala Tyr Ile Gly Leu Ser Leu
2090                2095                2100

Ile Asn Asp Gly Gln Tyr Tyr Phe Asn Asp Asp Gly Ile Met Gln
2105                2110                2115

Val Gly Phe Val Thr Ile Asn Asp Lys Val Phe Tyr Phe Ser Asp
2120                2125                2130

Ser Gly Ile Ile Glu Ser Gly Val Gln Asn Ile Asp Asp Asn Tyr
2135                2140                2145

Phe Tyr Ile Asp Asp Asn Gly Ile Val Gln Ile Gly Val Phe Asp
2150                2155                2160

Thr Ser Asp Gly Tyr Lys Tyr Phe Ala Pro Ala Asn Thr Val Asn
2165                2170                2175

Asp Asn Ile Tyr Gly Gln Ala Val Glu Tyr Ser Gly Leu Val Arg
2180                2185                2190

Val Gly Glu Asp Val Tyr Tyr Phe Gly Glu Thr Tyr Thr Ile Glu
2195                2200                2205

Thr Gly Trp Ile Tyr Asp Met Glu Asn Glu Ser Asp Lys Tyr Tyr
2210                2215                2220

Phe Asn Pro Glu Thr Lys Lys Ala Cys Lys Gly Ile Asn Leu Ile
2225                2230                2235

-continued

| | | | | | | | | | | | | |
|---|---|---|---|---|---|---|---|---|---|---|---|---|
| Asp | Asp | Ile | Lys | Tyr | Tyr | Phe | Asp | Glu | Lys | Gly | Ile | Met | Arg | Thr |
| | 2240 | | | | 2245 | | | | | 2250 | | | |

| Gly | Leu | Ile | Ser | Phe | Glu | Asn | Asn | Asn | Tyr | Tyr | Phe | Asn | Glu | Asn |
|---|---|---|---|---|---|---|---|---|---|---|---|---|---|---|
| | 2255 | | | | 2260 | | | | | 2265 | | | |

| Gly | Glu | Met | Gln | Phe | Gly | Tyr | Ile | Asn | Ile | Glu | Asp | Lys | Met | Phe |
|---|---|---|---|---|---|---|---|---|---|---|---|---|---|---|
| | 2270 | | | | 2275 | | | | | 2280 | | | |

| Tyr | Phe | Gly | Glu | Asp | Gly | Val | Met | Gln | Ile | Gly | Val | Phe | Asn | Thr |
|---|---|---|---|---|---|---|---|---|---|---|---|---|---|---|
| | 2285 | | | | 2290 | | | | | 2295 | | | |

| Pro | Asp | Gly | Phe | Lys | Tyr | Phe | Ala | His | Gln | Asn | Thr | Leu | Asp | Glu |
|---|---|---|---|---|---|---|---|---|---|---|---|---|---|---|
| | 2300 | | | | 2305 | | | | | 2310 | | | |

| Asn | Phe | Glu | Gly | Glu | Ser | Ile | Asn | Tyr | Thr | Gly | Trp | Leu | Asp | Leu |
|---|---|---|---|---|---|---|---|---|---|---|---|---|---|---|
| | 2315 | | | | 2320 | | | | | 2325 | | | |

| Asp | Glu | Lys | Arg | Tyr | Tyr | Phe | Thr | Asp | Glu | Tyr | Ile | Ala | Ala | Thr |
|---|---|---|---|---|---|---|---|---|---|---|---|---|---|---|
| | 2330 | | | | 2335 | | | | | 2340 | | | |

| Gly | Ser | Val | Ile | Ile | Asp | Gly | Glu | Glu | Tyr | Tyr | Phe | Asp | Pro | Asp |
|---|---|---|---|---|---|---|---|---|---|---|---|---|---|---|
| | 2345 | | | | 2350 | | | | | 2355 | | | |

| Thr | Ala | Gln | Leu | Val | Ile | Ser | Glu |
|---|---|---|---|---|---|---|---|
| | 2360 | | | | 2365 | | |

<210> SEQ ID NO 4
<211> LENGTH: 7101
<212> TYPE: DNA
<213> ORGANISM: Clostridium difficile

<400> SEQUENCE: 4

| | |
|---|---|
| atgagtttag ttaatagaaa acagttagaa aaaatggcaa atgtaagatt tcgtactcaa | 60 |
| gaagatgaat atgttgcaat attggatgct ttagaagaat atcataatat gtcagagaat | 120 |
| actgtagtcg aaaatatttt aaaattaaaa gatataaata gtttaacaga tatttatata | 180 |
| gatacatata aaaaatctgg tagaaataaa gccttaaaaa aatttaagga atatctagtt | 240 |
| acagaagtat tagagctaaa gaataataat ttaactccag ttgagaaaaa tttacatttt | 300 |
| gtttggattg gaggtcaaat aaatgacact gctattaatt atataaatca atggaaagat | 360 |
| gtaaatagtg attataatgt taatgttttt tatgatagta atgcattttt gataaacaca | 420 |
| ttgaaaaaaa ctgtagtaga atcagcaata aatgatacac ttgaatcatt tagagaaaac | 480 |
| ttaaatgacc ctagatttga ctataataaa ttcttcagaa aacgtatgga ataatttat | 540 |
| gataaacaga aaaatttcat aaactactat aaagctcaaa gagaagaaaa tcctgaactt | 600 |
| ataattgatg atattgtaaa gacatatctt tcaaatgagt attcaaagga gatagatgaa | 660 |
| cttaataccct atattgaaga atccttaaat aaaattacac agaatagtgg aaatgatgtt | 720 |
| agaaactttg aagaatttaa aaatggagag tcattcaact tatatgaaca agagttggta | 780 |
| gaaaggtgga atttagctgc tgcttctgac atattaagaa tatctgcatt aaaagaaatt | 840 |
| ggtggtatgt atttagatgt tgatatgtta ccaggaatac aaccagactt atttgagtct | 900 |
| atagagaaac ctagttcagt aacagtggat ttttgggaaa tgacaaagtt agaagctata | 960 |
| atgaaataca agaatatat accagaatat acctcagaac attttgacat gttagacgaa | 1020 |
| gaagttcaaa gtagttttga atctgttcta gcttctaagt cagataaatc agaaatattc | 1080 |
| tcatcacttg gtgatatgga ggcatcacca ctagaagtta aaattgcatt taatagtaag | 1140 |
| ggtattataa atcaagggct aatttctgtg aaagactcat attgtagcaa tttaatagta | 1200 |
| aaacaaatcg agaatagata taaaatattg aataatagtt taaatccagc tattagcgag | 1260 |
| gataatgatt ttaatactac aacgaatacc tttattgata gtataatggc tgaagctaat | 1320 |

```
gcagataatg gtagatttat gatggaacta ggaaagtatt taagagttgg tttcttccca    1380
gatgttaaaa ctactattaa cttaagtggc cctgaagcat atgcggcagc ttatcaagat    1440
ttattaatgt ttaaagaagg cagtatgaat atccatttga tagaagctga tttaagaaac    1500
tttgaaatct ctaaaactaa tatttctcaa tcaactgaac aagaaatggc tagcttatgg    1560
tcatttgacg atgcaagagc taaagctcaa tttgaagaat ataaaaggaa ttattttgaa    1620
ggttctcttg gtgaagatga taatcttgat ttttctcaaa atatagtagt tgacaaggag    1680
tatcttttag aaaaaatatc ttcattagca agaagttcag agagaggata tatacactat    1740
attgttcagt tacaaggaga taaaattagt tatgaagcag catgtaactt atttgcaaag    1800
actccttatg atagtgtact gtttcagaaa aatatagaag attcagaaat tgcatattat    1860
tataatcctg gagatggtga aatacaagaa atagacaagt ataaaattcc aagtataatt    1920
tctgatagac ctaagattaa attaacattt attggtcatg gtaaagatga atttaatact    1980
gatatatttg caggttttga tgtagattca ttatccacag aaatagaagc agcaatagat    2040
ttagctaaag aggatatttc tcctaagtca atagaaataa atttattagg atgtaatatg    2100
tttagctact ctatcaacgt agaggagact tatcctggaa aattattact taaagttaaa    2160
gataaaatat cagaattaat gccatctata agtcaagact ctattatagt aagtgcaaat    2220
caatatgaag ttagaataaa tagtgaagga agaagagaat tattggatca ttctggtgaa    2280
tggataaata aagaagaaag tattataaag gatatttcat caaagaata tatatcattt    2340 aatcctaaag aaaataaaat tacagtaaaa tctaaaaatt tacctgagct atctacatta    2400
ttacaagaaa ttagaaataa ttctaattca agtgatattg aactagaaga aaaagtaatg    2460
ttaacagaat gtgagataaa tgttatttca aatatagata cgcaaattgt tgaggaaagg    2520
attgaagaag ctaagaattt aacttctgac tctattaatt atataaaaga tgaatttaaa    2580
ctaatagaat ctatttctga tgcactatgt gacttaaaac aacagaatga attagaagat    2640 tctcattttta tatcttttga ggacatatca gagactgatg agggatttag tataagatttt   2700 attaataaag aaactggaga atctatattt gtagaaactg aaaaaacaat attctctgaa    2760
tatgctaatc atataactga agagatttct aagataaaag gtactatatt tgatactgta    2820
aatggtaagt tagtaaaaaa agtaaattta gatactacac acgaagtaaa tactttaaat    2880
gctgcatttt ttatacaatc attaatagaa tataatagtt ctaaagaatc tcttagtaat    2940
ttaagtgtag caatgaaagt ccaagtttac gctcaattat ttagtactgg tttaaatact    3000
attacagatg cagccaaagt tgttgaatta gtatcaactg cattagatga aactatagac    3060
ttacttccta cattatctga aggattacct ataattgcaa ctattataga tggtgtaagt    3120
ttaggtgcag caatcaaaga gctaagtgaa acgagtgacc cattattaag acaagaaata    3180
gaagctaaga taggtataat ggcagtaaat ttaacaacag ctacaactgc aatcattact    3240
tcatctttgg ggatagctag tggatttagt atacttttag ttcctttagc aggaatttca    3300
gcaggtatac caagcttagt aaacaatgaa cttgtacttc gagataaggc aacaaaggtt    3360
gtagattatt ttaaacatgt ttcattagtt gaaactgaag gagtatttac tttattagat    3420
gataaaataa tgatgccaca agatgattta gtgatatcag aaatagattt taataataat    3480
tcaatagttt taggtaaatg tgaaatctgg agaatggaag gtggttcagg tcatactgta    3540
actgatgata tagatcactt cttttcagca ccatcaataa catatagaga gccacactta    3600
tctatatatg acgtattgga agtacaaaaa gaagaacttg atttgtcaaa agatttaatg    3660
gtattaccta atgctccaaa tagagtatttt gcttgggaaa caggatggac accaggttta    3720
```

```
agaagcttag aaaatgatgg cacaaaactg ttagaccgta taagagataa ctatgaaggt  3780
gagttttatt ggagatattt tgcttttata gctgatgctt taataacaac attaaaacca  3840
agatatgaag atactaatat aagaataaat ttagatagta atactagaag ttttatagtt  3900
ccaataataa ctacagaata tataagagaa aaattatcat attctttcta tggttcagga  3960
ggaacttatg cattgtctct ttctcaatat aatatgggta taaatataga attaagtgaa  4020
agtgatgttt ggattataga tgttgataat gttgtgagag atgtaactat agaatctgat  4080
aaaattaaaa aaggtgattt aatagaaggt attttatcta cactaagtat tgaagagaat  4140
aaaattatct taaatagcca tgagattaat ttttctggtg aggtaaatgg aagtaatgga  4200
tttgtttctt taacattttc aattttagaa ggaataaatg caattataga agttgattta  4260
ttatctaaat catataaatt acttatttct ggcgaattaa aaatattgat gttaaattca  4320
aatcatattc aacagaaaat agattatata ggattcaata gcgaattaca gaaaaatata  4380
ccatatagct ttgtagatag tgaaggaaaa gagaatggtt ttattaatgg ttcaacaaaa  4440
gaaggtttat ttgtatctga attacctgat gtagttctta taagtaaggt ttatatggat  4500
gatagtaagc cttcatttgg atattatagt aataatttga aagatgtcaa agttataact  4560
aaagataatg ttaatatatt aacaggttat tatcttaagg atgatataaa aatctctctt  4620
tctttgactc tacaagatga aaaaactata aagttaaata gtgtgcattt agatgaaagt  4680
ggagtagctg agattttgaa gttcatgaat agaaaaggta atacaaatac ttcagattct  4740
ttaatgagct ttttagaaag tatgaatata aaaagtattt tcgttaattt cttacaatct  4800
aatattaagt ttatattaga tgctaatttt ataataagtg gtactacttc tattggccaa  4860
tttgagtttta tttgtgatga aaatgataat atacaaccat atttcattaa gtttaataca  4920
ctagaaacta attatacttt atatgtagga aatagacaaa atatgatagt ggaaccaaat  4980
tatgatttag atgattctgg agatatatct tcaactgtta tcaatttctc tcaaaagtat  5040
ctttatggaa tagacagttg tgttaataaa gttgtaattt caccaaatat ttatacagat  5100
gaaataaata taacgcctgt atatgaaaca aataatactt atccagaagt tattgtatta  5160
gatgcaaatt atataaatga aaaaataaat gttaatatca atgatctatc tatacgatat  5220
gtatggagta atgatggtaa tgattttatt cttatgtcaa ctagtgaaga aaataaggtg  5280
tcacaagtta aaataagatt cgttaatgtt tttaaagata gactttggc aaataagcta  5340
tcttttaact ttagtgataa acaagatgta cctgtaagtg aaataatctt atcatttaca  5400
ccttcatatt atgaggatgg attgattggc tatgatttgg gtctagtttc tttatataat  5460
gagaaattt atattaataa ctttggaatg atggtatctg gattaatata tattaatgat  5520
tcattatatt attttaaacc accagtaaat aaatttgataa ctggatttgt gactgtaggc  5580
gatgataaat actactttaa tccaattaat ggtggagctg cttcaattgg agagacaata  5640
attgatgaca aaaattatta tttcaaccaa agtggagtgt tacaaacagg tgtatttagt  5700
acagaagatg gatttaaata ttttgcccca gctaatacac ttgatgaaaa cctagaagga  5760
gaagcaattg attttactgg aaaattaatt attgacgaaa atatttatta ttttgatgat  5820
aattatagag gagctgtaga atggaaagaa ttagatggtg aaatgcacta ttttagccca  5880
gaaacaggta agcttttaa aggtctaaat caaataggtg attataaata ctatttcaat  5940
tctgatggag ttatgcaaaa aggatttgtt agtataaatg ataataaaca ctattttgat  6000
gattctggtg ttatgaaagt aggttacact gaaatagatg gcaagcattt ctactttgct  6060
```

-continued

```
gaaaacggag aaatgcaaat aggagtattt aatacagaag atggatttaa atattttgct   6120
catcataatg aagatttagg aaatgaagaa ggtgaagaaa tctcatattc tggtatatta   6180
aatttcaata ataaaattta ctattttgat gattcattta cagctgtagt tggatggaaa   6240
gatttagagg atggttcaaa gtattatttt gatgaagata cagcagaagc atatataggt   6300
ttgtcattaa taaatgatgg tcaatattat tttaatgatg atggaattat gcaagttgga   6360
tttgtcacta taaatgataa agtcttctac ttctctgact ctggaattat agaatctgga   6420
gtacaaaaca tagatgacaa ttatttctat atagatgata atggtatagt tcaaattggt   6480
gtatttgata cttcagatgg atataaatat tttgcacctg ctaatactgt aaatgataat   6540
atttacggac aagcagttga atatagtggt ttagttagag ttggtgaaga tgtatattat   6600
tttggagaaa catatacaat tgagactgga tggatatatg atatggaaaa tgaaagtgat   6660
aaatattatt tcaatccaga aactaaaaaa gcatgcaaag gtattaattt aattgatgat   6720 ataaatatt attttgatga aagggcata atgagaacgg gtcttatatc atttgaaaat   6780
aataattatt actttaatga gaatggtgaa atgcaatttg gttatataaa tatagaagat   6840
aagatgttct attttggtga agatggtgtc atgcagattg gagtatttaa tacaccagat   6900
ggatttaaat actttgcaca tcaaaatact ttggatgaga attttgaggg agaatcaata   6960
aactatactg gttggttaga tttagatgaa aagagatatt attttacaga tgaatatatt   7020
gcagcaactg gttcagttat tattgatggt gaggagtatt attttgatcc tgatacagct   7080
caattagtga ttagtgaata g                                             7101
```

```
<210> SEQ ID NO 5
<211> LENGTH: 184
<212> TYPE: PRT
<213> ORGANISM: Clostridium difficile

<400> SEQUENCE: 5

Met Gln Lys Ser Phe Tyr Glu Leu Ile Val Leu Ala Arg Asn Asn Ser
1               5                   10                  15

Val Asp Asp Leu Gln Glu Ile Leu Phe Met Phe Lys Pro Leu Val Lys
            20                  25                  30

Lys Leu Ser Arg Val Leu His Tyr Glu Glu Gly Glu Thr Asp Leu Ile
        35                  40                  45

Ile Phe Phe Ile Glu Leu Ile Lys Asn Ile Lys Leu Ser Ser Phe Ser
    50                  55                  60

Glu Lys Ser Asp Ala Ile Ile Val Lys Tyr Ile His Lys Ser Leu Leu
65                  70                  75                  80

Asn Lys Thr Phe Glu Leu Ser Arg Arg Tyr Ser Lys Met Lys Phe Asn
                85                  90                  95

Phe Val Glu Phe Asp Glu Asn Ile Leu Asn Met Lys Asn Asn Tyr Gln
            100                 105                 110

Ser Lys Ser Val Phe Glu Glu Asp Ile Cys Phe Phe Glu Tyr Ile Leu
        115                 120                 125

Lys Glu Leu Ser Gly Ile Gln Arg Lys Val Ile Phe Tyr Lys Tyr Leu
    130                 135                 140

Lys Gly Tyr Ser Asp Arg Glu Ile Ser Val Lys Leu Lys Ile Ser Arg
145                 150                 155                 160

Gln Ala Val Asn Lys Ala Lys Asn Arg Ala Phe Lys Lys Ile Lys Lys
                165                 170                 175

Asp Tyr Glu Asn Tyr Phe Asn Leu
            180
```

<210> SEQ ID NO 6
<211> LENGTH: 555
<212> TYPE: DNA
<213> ORGANISM: Clostridium difficile

<400> SEQUENCE: 6

```
atgcaaaagt cttttatga attaattgtt ttagcaagaa ataactcagt agatgatttg      60
caagaaattt tatttatgtt taagccatta gtaaaaaaac ttagtagagt tttacattat     120
gaagagggag aaacagattt aataatattt tttattgaat taataaaaaa tattaaatta     180
agtagctttt cagaaaaaag cgatgctatt atagtcaaat atattcataa atcattactg     240
aataagactt ttgagttgtc tagaagatat tctaaaatga gtttaatttt tgtagaattt     300
gatgaaaata tcttaaatat gaaaataat tatcaaagta agtctgtttt tgaggaagat     360
atttgttttt tcgaatatat tttgaaagaa ttatctggta ttcaaagaaa agttattttt     420
tataaatatt taaaggata ttctgataga gaaatatcag tgaaattaaa aatatctaga     480
caagctgtta ataaggctaa aaatagagca tttaaaaaaa taaaaaaaga ctatgaaaat     540
tattttaact tgtaa                                                      555
```

<210> SEQ ID NO 7
<211> LENGTH: 261
<212> TYPE: PRT
<213> ORGANISM: Clostridium difficile

<400> SEQUENCE: 7

```
Met Ala Ser Glu Val Leu Gln Lys Thr Arg Lys Ile Asn Lys Thr Leu
1               5                   10                  15

Gln Thr Ser Gly Gly Ser Ser Val Ser Phe Asp Leu Leu Ala Gly Ala
            20                  25                  30

Leu Gly Asp Val Leu Ser Ser Asn Val Tyr Val Val Ser Ala Lys Gly
        35                  40                  45

Lys Val Leu Gly Leu His Leu Asn Asp Val Gln Asp Ser Ser Val Ile
    50                  55                  60

Glu Asp Glu Tyr Thr Lys Gln Lys Lys Phe Ser Asp Glu Tyr Thr Gln
65                  70                  75                  80

Asn Val Leu Lys Ile Asp Glu Thr Leu Glu Asn Leu Asn Gly Glu Lys
                85                  90                  95

Ile Leu Glu Ile Phe Pro Glu Glu His Gly Arg Leu Gln Lys Tyr Thr
            100                 105                 110

Thr Val Val Pro Ile Leu Gly Ser Gly Gln Arg Leu Gly Thr Leu Val
        115                 120                 125

Leu Ser Arg Tyr Ser Asn Ser Phe Asn Asp Asp Leu Val Ile Ala
    130                 135                 140

Glu Tyr Ser Ala Thr Val Val Gly Leu Glu Ile Leu Arg Ala Ile Gly
145                 150                 155                 160

Glu Glu Leu Glu Glu Glu Met Arg Lys Lys Ala Val Val Gln Met Ala
                165                 170                 175

Ile Gly Thr Leu Ser Tyr Ser Glu Leu Glu Ala Val Glu His Ile Phe
            180                 185                 190

Ala Glu Leu Asp Gly Lys Glu Gly Leu Leu Val Ala Ser Lys Ile Ala
        195                 200                 205

Asp Arg Val Gly Ile Thr Arg Ser Val Ile Val Asn Ala Leu Arg Lys
    210                 215                 220
```

```
Phe Glu Ser Ala Gly Val Ile Glu Ser Arg Ser Leu Gly Met Lys Gly
225                 230                 235                 240

Thr His Ile Arg Ile Leu Asn Asp Lys Leu Thr Asp Glu Leu Lys Lys
                245                 250                 255

Leu Lys Asn Asn Gln
            260

<210> SEQ ID NO 8
<211> LENGTH: 786
<212> TYPE: DNA
<213> ORGANISM: Clostridium difficile

<400> SEQUENCE: 8
atggcaagtg aagtgttaca aaaaacaagg aaaataaata aaacattaca acaagtggt       60 ggaagcagtg tctcttttga tttactggcc ggagcattgg gcgacgtttt aagttctaat    120
gtttatgtag taagtgcaaa aggtaaagta ctaggtcttc atttaaatga tgttcaagac    180
agttcagtta tagaagatga gtatactaag caaagagaat tttcagatga atatactcaa    240
aatgtgttaa aaattgatga acattagaa aatttaaatg gtgagaagat attagaaatc     300
tttcctgaag aacatggaag attacaaaaa tatactacag tagttccaat attaggaagc    360
ggtcaaagat taggaacatt ggtactttca agatattcaa attcattcaa tgatgatgat    420
ttagtaatag ctgaatacag tgcaactgtt gttggtcttg aaatattaag agcaataggt    480
gaagaattag aagaagaaat gagaaagaaa gctgtagttc aaatggcaat aggcactctg    540
tcctactccg agcttgaagc agttgaacat attttttgctg aattggatgg aaaagaaggt    600
ctacttgtag caagtaagat agctgataga gttggtataa ctaggtctgt aatagtaaat    660
gcacttagaa aatttgagag tgcaggtgtg atagaatcaa gatcattagg tatgaaaggt    720
actcatataa gaatacttaa tgacaaactt acagatgaat taaaaaaatt aaaaaacaat    780
caataa                                                                786

<210> SEQ ID NO 9
<211> LENGTH: 338
<212> TYPE: PRT
<213> ORGANISM: Clostridium difficile

<400> SEQUENCE: 9

Met Lys Gly Asn Ile Thr Ile Lys Asp Val Ala Lys Gln Ala Gly Val
1               5                   10                  15

Ser Ile Ser Thr Val Ser Arg Val Ile Asn Asp Ser Lys Pro Val Thr
            20                  25                  30

Asp Glu Val Lys Gln Lys Val Leu Glu Val Ile Lys Glu Thr Gly Tyr
        35                  40                  45

Ile Pro Asn Pro Leu Ala Arg Ser Leu Val Thr Lys Lys Ser Gln Leu
    50                  55                  60

Ile Gly Val Ile Val Pro Glu Val Ser Asp Ser Phe Val Asn Glu Val
65                  70                  75                  80

Leu Asn Gly Ile Glu Glu Val Ala Lys Met Tyr Asp Tyr Asp Ile Leu
                85                  90                  95

Leu Ala Asn Thr Tyr Ser Asp Lys Glu Gln Glu Leu Lys Ser Ile Asn
            100                 105                 110

Leu Leu Arg Ala Lys Gln Val Glu Gly Ile Val Met Ile Ser Trp Ile
        115                 120                 125

Val Glu Gln Glu His Ile Asn Tyr Ile Gln Asn Cys Gly Ile Pro Ala
    130                 135                 140
```

```
Thr Tyr Ile Ser Lys Thr Ala Arg Asn Tyr Asp Ile Tyr Thr Val Ser
145                 150                 155                 160

Thr Ser Asn Glu Glu Ala Thr Phe Asp Met Thr Glu His Leu Ile Lys
            165                 170                 175

Lys Gly His Glu Lys Ile Ala Phe Ile Met Thr Ser Lys Asp Asp Thr
        180                 185                 190

Val Leu Glu Met Glu Arg Leu Ala Gly Tyr Glu Lys Ala Leu Ser Asn
    195                 200                 205

Asn Asn Ile Glu Leu Asp Lys Ser Leu Ile Lys Tyr Gly Gly Thr Asp
210                 215                 220

Tyr Glu Ser Gly Tyr Asn Ser Met Lys Glu Leu Leu Asp Asp Gly Ile
225                 230                 235                 240

Ile Pro His Ala Ala Phe Val Thr Gly Asp Glu Ala Ala Ile Gly Ala
            245                 250                 255

Ile Asn Ala Ile Cys Asp Ala Gly Tyr Lys Val Pro Glu Asp Ile Ser
        260                 265                 270

Val Ala Gly Phe Asn Asp Val Lys Ile Ala Arg Met Tyr Arg Pro Lys
    275                 280                 285

Leu Thr Thr Val Tyr Gln Pro Leu Tyr Asp Met Gly Ala Val Ala Ile
        290                 295                 300

Arg Met Val Ile Lys Leu Ile Asn Lys Glu Leu Ile Glu Asn Lys Lys
305                 310                 315                 320

Ile Glu Leu Pro Tyr Arg Ile Val Asp Arg Glu Ser Val Thr Glu Arg
                325                 330                 335

Lys Lys

<210> SEQ ID NO 10
<211> LENGTH: 1017
<212> TYPE: DNA
<213> ORGANISM: Clostridium difficile

<400> SEQUENCE: 10
atgaaaggca atataacgat aaaagatgtt gctaaacaag caggagtgtc aatatctact      60
gtatctagag ttataaatga ttcaaaacct gtaactgatg aagtcaaaca aaagttttta     120
gaggttataa aagagactgg atatatacca atccacttg ctagaagctt agtaacaaag      180
aagagtcaat aatagggggt aatagttcca gaagtttcag attcttttgt taatgaggtg     240
ttaaatggga tagaagaggt tgctaaaatg tatgactatg atattctttt agcgaataca     300
tactctgata aggaacaaga acttaagagt ataaatctat tgagagcaaa acaagtggaa     360
ggtatagtta tgatttcatg gatagttgaa caagaacata tcaactatat acaaaattgt     420
ggaataccag cgacatatat aagtaaaact gctagaaatt atgatatata cagtaagt       480 actagcaacg aagaagctac ttttgatatg acagagcatc ttataaagaa aggtcatgaa     540
aagatagctt ttataatgac gagtaaagat gatactgttt tagaaatgga agacttgct     600 ggttatgaga agcactttc aaataacaat atagaattag acaagagttt gattaagtat      660
ggtggaactg attatgagag tggatacaat agtatgaaag aactattaga tgatggaata     720
atacctcatg cggcttttgt aacaggtgat gaggctgcca taggtgctat aaatgctata     780
tgtgatgctg gatataaggt tccagaagac atatctgttg caggatttaa tgatgttaag     840
atagctagaa tgtatagacc taaacttact acagtatatc aacctctata cgatatggga     900
gcagtagcaa taagaatggt tataaaatta ataataagg aattaattga aaataagaaa      960
```
atagaattac cttatagaat tgttgataga gaaagtgtta cagaaagaaa aaaataa    1017

<210> SEQ ID NO 11
<211> LENGTH: 210
<212> TYPE: PRT
<213> ORGANISM: Clostridium difficile

<400> SEQUENCE: 11

```
Met Leu Gly Asn Lys Asn Ile Ser Met Ala Val Ile Arg Arg Leu Pro
1               5                   10                  15
Lys Tyr His Arg Tyr Leu Gly Asp Leu Leu Asp Arg Asp Ile Gln Arg
            20                  25                  30
Ile Ser Ser Lys Glu Leu Ser Asp Ile Ile Gly Phe Thr Ala Ser Gln
        35                  40                  45
Ile Arg Gln Asp Leu Asn Asn Phe Gly Gly Phe Gly Gln Gln Gly Tyr
    50                  55                  60
Gly Tyr Asn Val Glu Ala Leu His Thr Glu Ile Gly Lys Ile Leu Gly
65                  70                  75                  80
Leu Asp Arg Pro Tyr Asn Ala Val Leu Val Gly Ala Gly Asn Leu Gly
                85                  90                  95
Gln Ala Ile Ala Asn Tyr Ala Gly Phe Arg Lys Ala Gly Phe Glu Ile
            100                 105                 110
Lys Ala Leu Phe Asp Ala Asn Pro Arg Met Ile Gly Leu Lys Ile Arg
        115                 120                 125
Glu Phe Glu Val Leu Asp Ser Asp Thr Leu Glu Asp Phe Ile Lys Asn
    130                 135                 140
Asn Asn Ile Asp Ile Ala Val Leu Cys Ile Pro Lys Asn Gly Ala Gln
145                 150                 155                 160
Glu Val Ile Asn Arg Val Val Lys Ala Gly Ile Lys Gly Val Trp Asn
                165                 170                 175
Phe Ala Pro Leu Asp Leu Glu Val Pro Lys Gly Val Ile Val Glu Asn
            180                 185                 190
Val Asn Leu Thr Glu Ser Leu Phe Thr Leu Ser Tyr Leu Met Lys Glu
        195                 200                 205
Gly Lys
    210
```

<210> SEQ ID NO 12
<211> LENGTH: 633
<212> TYPE: DNA
<213> ORGANISM: Clostridium difficile

<400> SEQUENCE: 12
atgttgggaa ataaaaatat atcaatggca gttataagaa ggctcccaaa atatcataga     60
tatcttggag acttattaga tagggatata caaagaatat cttctaaaga attgagtgat    120
ataatagggt ttaccgcttc tcaaataaga caagatttaa acaactttgg tggatttgga    180
caacaaggat atggttataa tgtagaagct cttcatactg ataggtaa aattcttggg     240 ttggatcgac catacaacgc agttcttgta ggagcaggta acttaggaca agctatagcc    300
aattatgcag gatttagaaa agctggattc gagataaaag ctttatttga tgcaaatcct    360
agaatgatag gtttaaagat aagagagttt gaagtattag attcagatac tttagaagac    420
tttataaaaa acaataatat agatattgct gtattatgta tacctaaaaa tggagcacaa    480
gaagttatta tagagttgt aaaagctgga atcaaaggtg tatggaattt tgcacccttta    540 gatttagaag ttccgaaagg tgttatagtt gaaaatgtaa acttaacaga aagtttatttt  600 accttatcgt atttaatgaa agaaggaaag tag                             633

<210> SEQ ID NO 13
<211> LENGTH: 626
<212> TYPE: PRT
<213> ORGANISM: Clostridium difficile

<400> SEQUENCE: 13

Met Ser Ile Thr Leu Glu Thr Ala Gln Ala His Ala Asn Asp Pro Ala
1               5                   10                  15

Val Cys Cys Cys Arg Phe Glu Ala Gly Thr Ile Ile Ala Pro Glu Asn
            20                  25                  30

Leu Glu Asp Pro Ala Ile Phe Ala Asp Leu Glu Asp Ser Gly Leu Leu
        35                  40                  45

Thr Ile Pro Glu Asn Gly Leu Thr Ile Gly Gln Val Leu Gly Ala Lys
    50                  55                  60

Leu Lys Glu Thr Leu Asp Ala Leu Ser Pro Met Thr Thr Asp Asn Val
65                  70                  75                  80

Glu Gly Tyr Lys Ala Gly Glu Ala Lys Glu Val Val Glu Thr
                85                  90                  95

Val Glu Ala Ala Pro Val Ser Glu Ala Ala Val Val Pro Val Ser
            100                 105                 110

Thr Gly Val Ala Gly Glu Thr Val Lys Ile His Ile Gly Glu Gly Lys
            115                 120                 125

Asn Ile Ser Leu Glu Ile Pro Leu Ser Val Ala Gly Gln Ala Gly Val
130                 135                 140

Ala Ala Pro Val Ala Asn Val Ala Ala Pro Val Ala Ser Ala Ala Ala
145                 150                 155                 160

Glu Val Ala Pro Lys Val Glu Glu Lys Lys Leu Leu Arg Ser Leu Thr
                165                 170                 175

Lys Lys His Phe Lys Ile Asp Lys Val Glu Phe Ala Asp Glu Thr Lys
            180                 185                 190

Ile Glu Gly Thr Thr Leu Tyr Ile Arg Asn Ala Glu Glu Ile Cys Lys
            195                 200                 205

Glu Ala Asn Glu Thr Gln Glu Leu Val Val Asp Met Lys Leu Glu Ile
210                 215                 220

Ile Thr Pro Asp Lys Tyr Glu Thr Tyr Ser Glu Ala Val Leu Asp Ile
225                 230                 235                 240

Gln Pro Ile Ala Thr Lys Glu Glu Gly Glu Leu Gly Ser Gly Ile Thr
                245                 250                 255

Arg Val Ile Asp Gly Ala Val Met Val Leu Thr Gly Thr Asp Glu Asp
            260                 265                 270

Gly Val Gln Ile Gly Glu Phe Gly Ser Ser Glu Gly Leu Asn Thr
            275                 280                 285

Thr Ile Met Trp Gly Arg Pro Gly Ala Ala Asp Lys Gly Glu Ile Phe
    290                 295                 300

Ile Lys Gly Gln Val Thr Ile Lys Ala Gly Thr Asn Met Glu Arg Pro
305                 310                 315                 320

Gly Pro Leu Ala Ala His Arg Ala Phe Asp Tyr Val Thr Gln Glu Ile
                325                 330                 335

Arg Glu Ala Leu Lys Lys Val Asp Asn Ser Leu Val Val Asp Glu Glu
            340                 345                 350

Val Ile Glu Gln Tyr Arg Arg Glu Gly Lys Lys Val Val Ile
            355                 360                 365

```
Lys Glu Ile Met Gly Gln Gly Ala Met His Asp Asn Leu Ile Leu Pro
    370                 375                 380

Val Glu Pro Val Gly Thr Leu Gly Ala Gln Pro Asn Val Asp Leu Gly
385                 390                 395                 400

Asn Met Pro Val Val Leu Ser Pro Leu Glu Val Leu Asp Gly Gly Ile
                405                 410                 415

His Ala Leu Thr Cys Ile Gly Pro Ala Ser Lys Glu Met Ser Arg His
            420                 425                 430

Tyr Trp Arg Glu Pro Leu Val Ile Arg Ala Met Glu Asp Glu Glu Ile
        435                 440                 445

Asp Leu Val Gly Val Val Phe Val Gly Ser Pro Gln Val Asn Ala Glu
    450                 455                 460

Lys Phe Tyr Val Ser Lys Arg Leu Gly Met Leu Val Glu Ala Met Glu
465                 470                 475                 480

Val Asp Gly Ala Val Val Thr Thr Glu Gly Phe Gly Asn Asn His Ile
                485                 490                 495

Asp Phe Ala Ser His Ile Glu Gln Ile Gly Met Arg Gly Ile Pro Val
            500                 505                 510

Val Gly Val Ser Phe Ser Ala Val Gln Gly Ala Leu Val Val Gly Asn
        515                 520                 525

Lys Tyr Met Thr His Met Val Asp Asn Asn Lys Ser Lys Gln Gly Ile
    530                 535                 540

Glu Asn Glu Ile Leu Ser Asn Asn Thr Leu Ala Pro Glu Asp Ala Val
545                 550                 555                 560

Arg Ile Met Ala Met Leu Lys Asn Ala Ile Glu Gly Val Glu Val Lys
                565                 570                 575

Ala Pro Glu Arg Lys Trp Asn Pro Asn Val Lys Leu Asn Asn Ile Glu
            580                 585                 590

Ala Ile Glu Lys Val Thr Gly Glu Lys Ile Val Leu Glu Glu Asn Glu
        595                 600                 605

Gln Ser Leu Pro Met Ser Lys Lys Arg Arg Glu Ile Tyr Glu Lys Asp
    610                 615                 620

Glu Asn
625
```

<210> SEQ ID NO 14
<211> LENGTH: 1881
<212> TYPE: DNA
<213> ORGANISM: Clostridium difficile

<400> SEQUENCE: 14

```
atgtcaataa ctttagaaac agctcaagcc catgcaaatg acccagcagt ttgttgttgt     60
agatttgaag cgggaacaat tatagcgcca gaaaacttag aagatccagc aatatttgca    120
gacttagagg attctggatt attaacaata ccagaaaatg gattaactat aggtcaagta    180
ctaggagcta agttaaaaga aactttagat gcactttctc caatgactac agataacgta    240
gaaggataca aagcaggaga ggctaaagaa gaagtagtag aagaaacagt agaagaagca    300
gctccagtat cagaagcagc agtagttcca gtaagcacag gagttgcagg tgaaacagtt    360
aaaatacaca taggtgaagg taagaacata agcttagaga tacctttatc agtagctggt    420
caagcaggag ttgctgctcc agtagcaaac gttgctgctc cagtggcaag tgcagcagca    480
gaagtagctc caaaagttga agaaaagaaa cttttaagaa gcttaactaa aaaacacttt    540
aaaatagata aagttgaatt tgctgatgaa actaaaatag aaggaactac tttatacatc    600
```

```
agaaacgcag aagaaatatg taaagaagct aatgaaactc aagagttagt tgtagatatg      660
aagttagaaa taataactcc tgataaatat gaaacttaca gtgaagctgt attagatata      720
caaccaatcg ctactaaaga agaaggcgaa ttaggttcag gtataactag agttatagat      780
ggagctgtaa tggtattaac tggtacagat gaagatggag ttcaaatagg tgaatttggt      840
tcttcagaag gtgagttaaa tactactata atgtggggta gaccaggtgc tgctgacaaa      900
ggtgaaatat tcatcaaagg tcaagtaaca ataaaagcag gaactaacat ggaaagacca      960
ggacctttag ctgctcaccg tgcatttgac tatgtaactc aagaaataag agaagcatta     1020
aagaaagttg acaactcttt agtagttgat gaagaagtaa tagagcaata cagaagagaa     1080
ggtaaaaaga agttgttgt tataaaagaa ataatgggac aaggtgcaat gcatgataac     1140
ctaatattac cagttgagcc agttggtaca ttaggagctc aaccaaacgt tgacttagga     1200
aacatgccag ttgtattatc tccacttgaa gtattagatg gtggtatcca tgcattaact     1260
tgtataggac ctgcatcaaa agaaatgtca agacattact ggagagagcc attagtaata     1320
agagctatgg aagacgaaga atagattta gtaggtgttg tatttgttgg ttctccacaa     1380
gtaaatgctg agaaattcta tgtatctaag agattaggta tgttagttga agctatggaa     1440
gttgatggag ctgtagtaac tactgaaggt ttcggaaaca accatataga tttcgcatct     1500
cacatagagc aaataggtat gagaggtata ccagtagttg gtgtaagttt ctcagctgtt     1560
caaggtgctc tagttgttgg taataaatac atgactcaca tggtagacaa caataagtct     1620
aagcaaggta tagagaatga atatattatct aacaacactt tagctccaga agatgctgtt     1680
agaataatgg ctatgcttaa aaatgctata gaaggtgtag aagttaaagc tcctgaaaga     1740
aaatggaatc caaatgttaa attaaataac atagaagcta tagaaaaagt tacaggagaa     1800
aaaatagtat tagaagagaa tgagcaatct ctaccaatga gtaagaagag aagagaaata     1860
tacgaaaaag acgaaaacta a                                              1881

<210> SEQ ID NO 15
<211> LENGTH: 474
<212> TYPE: DNA
<213> ORGANISM: Clostridium bifermentans

<400> SEQUENCE: 15
atgggtatag gaccatcaac taaagaaaca tcattacatc actttagaga tccgcttctt       60
gatatagtta gtaatgacaa agacatagat cttctgggga tagtagtagt aggaacacct      120
caggacaaca aagaaaaaga atttgttgga caaagaacag ctgcatggct agaagctatg      180
agagcagatg gtgttataat ttcatgtgat gggtggggaa actcacacgt agattatgct      240
aatactattg aagaaatagg aaaaagagag atcccggtag ttggacttac atttaatgga      300
acacaagcta agtttgtagt tacaaataaa tatatggaca caatagtaga ttttaataaa      360
tcagacaagg ggatagaaac agaagttgtc ggagagaaca ctgtaagcga gttagacgca      420
aaaaaatcat tagccttatt aaaattaaaa atgcaaagaa ataataaaaa ataa            474

<210> SEQ ID NO 16
<211> LENGTH: 1884
<212> TYPE: DNA
<213> ORGANISM: Clostridium bifermentans

<400> SEQUENCE: 16
atgtcaataa ctgtagaaac agctaaagct catgctaaag atccagcggt atgctgctgt       60
```
agatttgaag ctgggactgt actagaacca tcaaatttag aagatccagc aatattcgct 120
gacttagagg attcaggatt attaacaata gcagatgatt gtttaacaat agagcaagtt 180
ttaggagcta aactattaaa aactttagat gctttaactc caataactgc tgactgtgta 240
gaaggtgtag tagcagtagc tgaagaggct aaagaagaag ttaaggaaga agttaaagaa 300
gtagcaccag ttgcttcagt agctccagta tctcaaatag ctccagtaaa tggacaaact 360
ataaagatac atataggtga aggtagagat ataaacttag aaataccttt aaatgtagct 420
caaggaatgg gtgtagcacc agttgctcct gtagctgtag cagaaaatgc agaagctgta 480
gaagttaaag ctgagccagt tcaagaagct aaagcaatga gaagcttaac taaaaaacat 540
tttaaaatag aaaaagtagt tttcgctgaa gaaactaaaa tagatggaac tactttatac 600
ttaagaactc cagaagaatt aactaaagaa gctgtaaatt cagaagaatt agttgttgat 660
atgaagttag aaataataac tccagctgaa tacaacaaat acagtgaaac tataatggat 720
gttcaaccta tagctgctaa agaagaagga gaaataggag aaggtgtaac aagagttata 780
gacggagtta taatgatggt aactggtact gatgaaaacg gagttcaaat aggtgaattc 840
ggttcttcag aaggtgtatt agaaactaac ataatgtggg gaagaccagg tgctcctgat 900
aaaggtgata tattcatcaa aactcaagta acagttaaag ctggtactaa catggaaaga 960
ccaggaccat tagctgctca ctgtgcatct gattatataa ctcaagaaat aagagaagca 1020
ttaaagaacg ctgaagagtc tttagtagtt gatactgaag aattaactca atatagaaga 1080
cctggtaaga aaaaggttgt tgtagttaaa gagataatgg gacaaggggc aatgcatgat 1140
aacttaatat tacctgttga gccagttgga acattaggag ctaaaccaaa cgttgactta 1200
ggaaacgttc cagtagtatt atctccactt gaagtattag atggtggtat acatgcatta 1260
acttgtatag gacctgcatc taaagaaaac tctagacatt actggagaga gccattagta 1320
atagaagcta tgcatgatga agaaatagat ttagtaggtg ttatatttgt aggatctcca 1380
caagtaaatg ctgagaaatt ctatgtatct aagagattag gtatgatgat agaagctatg 1440
ggtgttgatg gtgctatagt aacaactgaa ggattcggaa acaaccatat agatttcgct 1500
tctcatatag agcaaatagg taagagagat gtagctgtag taggtgtaag tttctctgct 1560
gttcaaggtg ctctagttgt tggtaatgaa tacatgaaat acatgataga caacaacaag 1620
tctaaacaag gtatagaaaa tgaagtatta tcaaacaata cattatgccc agaagatgct 1680
gtaagatctt tagcaatgtt aaagacagta atgggtggag aagaagttaa agctgctgag 1740
agaaaatgga atgctaacgt taaattaaat aacgttgaat taatagaaaa agaaactggt 1800
aagaagttag aacttgttga aaacgagcaa actttaccaa tgagtgaaaa aagaaagaat 1860
atatacgaaa aagacgctaa atag 1884

<210> SEQ ID NO 17
<211> LENGTH: 759
<212> TYPE: DNA
<213> ORGANISM: Clostridium bifermentans

<400> SEQUENCE: 17
atggaagaga aaatacttag acgtttggta attaaaccat ttcatataaa taatgttgaa 60
ttcaatgaaa agttctcaat aaaaaaaggt acactatcca taaacaatga ctacataaat 120
gaaattaaaa attcacatga attaataacg gacataaaat tagatataat caaaccagga 180
gattataaca aggaaattaa tactatcatg gatataatcc ctatatctac taaagtttta 240
ggtagattag gtgaaggaat aacacacact ttaacaggtg tttatgttat gcttactggt 300

```
gttgatgaag atggaagaca aatgcatgaa tttggatctt cagaaggtat actttctgag    360
caaatggtgt ttggaagata tggtactcca tctactaatg attacataat tcattttgat    420
gttacagtta aaggtgggtt gccatatgag agaaaacttc cgatgatgac atttaaggca    480
tgtgatactt ttatacaagg tataagaaat gttttaaaac agcaagacgg aagagatgct    540
acagaaattc gtgaatattt tgacaaaatt agacctgacg ctaaaaaagt tgtaatagta    600
aaacaaatag caggtcaggg tgcaatgtat gacaatcaat tattttctca tgaaccaagt    660
ggtttagagg gaggtacatc cattattgat atgggaaatg taccgatgat aatatcacct    720
aatgaataca gagatggcgc cttgagagct atgacttaa                           759
```

```
<210> SEQ ID NO 18
<211> LENGTH: 726
<212> TYPE: DNA
<213> ORGANISM: Clostridium bifermentans

<400> SEQUENCE: 18
atgagcctta caacaataaa aggacttcaa tctgaaatat ttgtaccaat aacacctcct     60
cctgtttgga ctcctgtaac taaagaacta aaggatatga ctatagcttt agctacagcg    120
tcaggtgtac atttaaaagc tgataagaga ttcaacctag caggtgactt tacatttaga    180
gaaataccag acacagcaac tactgatgag atgatggtat ctcacggagg atatgataac    240
gctgatgtta ataaagatat aaactgtatg ttccctatag acagactaca tgaattagct    300
aaagaaggat ttataaaatc tgtagctcca gttcatatag gattcatggg tggtggtgga    360
gaccaaacta aattcactga agaaactggt cctgaaatcg ctaaaagatt aaaagatgag    420
ggagtagacg gtgtagttct aacagctggc tgaggtactt gccatagaac tgccgtgatc    480
gtgcagagag caatagaaga agctggtata ccaactataa taatagcagc tcttcctcca    540
gtagttagac aaaacggaac tccaagagca gttgctccac tagttccaat gggtgctaat    600
gctggtgaac caaacaataa agaaatgcaa atgcatatat taagagatac tttagagcaa    660
ttaatagcta taccatctgc tggtaagata attcaattac catacgagta tgtagctcaa    720
gtataa                                                               726
```

```
<210> SEQ ID NO 19
<211> LENGTH: 617
<212> TYPE: PRT
<213> ORGANISM: Clostridium scindens

<400> SEQUENCE: 19

Met Ser Ile Thr Ala Glu Thr Ala Lys Glu His Ala His Asp Pro Ala
1               5                   10                  15

Val Leu Cys Cys Arg Ala Glu Ala Gly Ile Thr Ile Glu Ala Ala Asn
            20                  25                  30

Leu Glu Asp Pro Ala Ile Phe Asp Asp Leu Val Asp Ser Gly Leu Leu
        35                  40                  45

Asn Leu Asp Gly Ala Leu Thr Ile Glu Glu Val Leu Gly Ala Lys Leu
    50                  55                  60

Thr Lys Thr Cys Asp Ser Leu Cys Pro Leu Thr Ala Asp Val Val Glu
65                  70                  75                  80

Gly Ala Lys Ala Pro Thr Ala Pro Ala Ala Glu Glu Ala Glu Glu Glu
                85                  90                  95

Ala Pro Ala Ala Pro Ala Pro Ala Ala Ala Pro Val Ala Gly Pro Ala
            100                 105                 110
```

```
Ala Gly Gly Thr Leu Lys Ile His Ile Gly Glu Gly Lys Asp Ile Asp
            115                 120                 125

Leu Glu Ile Pro Val Gly Ala Leu Gly Gly Gly Ala Val Ala Pro
130                 135                 140

Leu Pro Ala Gly Ala Glu Ala Val Val Ala Gly Ala Ala Pro Glu
145                 150                 155                 160

Ala Ala Gly Glu Glu Lys Val Val Arg Ser Leu Thr Arg Lys His Phe
            165                 170                 175

Thr Ile Thr Glu Val Lys Arg Gly Pro Glu Thr Lys Ile Glu Gly Thr
            180                 185                 190

Thr Leu Tyr Ile Arg Glu Gly Ile Glu Ser Glu Val Ile Asp Asn Gln
            195                 200                 205

Glu Leu Val Lys Asp Phe Lys Leu Glu Ile Ile Thr Pro Asp Leu Tyr
            210                 215                 220

His Thr Tyr Ser Glu Thr Val Met Asp Val Gln Pro Ile Ala Thr Lys
225                 230                 235                 240

Glu Gly Asp Asp Glu Leu Gly Thr Gly Val Thr Arg Val Leu Asp Gly
            245                 250                 255

Val Val Met Met Leu Thr Gly Val Asp Glu Gly Gly Val Gln Ile Gly
            260                 265                 270

Glu Phe Gly Ser Ser Glu Gly Tyr Leu Asp Glu Asn Ile Met Trp Asn
            275                 280                 285

Arg Pro Ser Cys Pro Asp Lys Gly Glu Ile Phe Ile Lys Gly Asn Ile
            290                 295                 300

Val Ile Gln Glu Lys Thr Asn Met Glu Arg Arg Gly Pro Met Ala Ala
305                 310                 315                 320

His Thr Ala Phe Asp Val Ile Thr Gln Glu Ile Arg Glu Val Met Lys
            325                 330                 335

Lys Leu Asp Asp Ser Leu Val Ala Asp Thr Glu Glu Leu Lys Gln Val
            340                 345                 350

Arg Arg Pro Gly Lys Lys Val Val Ile Val Lys Glu Ile Met Gly
            355                 360                 365

Gln Gly Ala Met His Asp Asn Phe Ile Leu Pro Val Glu Pro Val Gly
            370                 375                 380

Val Leu Gly Ala Arg Ala Asn Val Asp Leu Gly Asn Val Pro Val Cys
385                 390                 395                 400

Val Ser Pro Leu Glu Val Leu Asp Gly Cys Ile His Ala Leu Thr Cys
            405                 410                 415

Ile Gly Pro Ala Ser Lys Glu Met Ser Arg His Tyr Trp Arg Glu Pro
            420                 425                 430

Leu Val Leu Glu Ala Leu His Asp Pro Glu Val Asp Leu Cys Gly Val
            435                 440                 445

Val Phe Val Gly Ser Pro Gln Ile Asn Ala Glu Lys Phe Tyr Val Ser
            450                 455                 460

Arg Arg Val Gly His Thr Val Glu Met Met Asp Ala Asp Gly Ala Phe
465                 470                 475                 480

Val Thr Thr Glu Gly Phe Gly Asn Asn His Ile Asp Phe Ala Ser His
            485                 490                 495

Ile Glu Gln Ile Gly Met Arg Gly Ile Pro Val Val Gly Met Ser Tyr
            500                 505                 510

Cys Ala Val Gln Gly Ala Leu Val Val Gly Asn Lys Tyr Met Thr Tyr
            515                 520                 525
```

Met Val Asp Asn Asn Lys Ser Glu Ala Gly Ile Glu Asn Glu Ile Leu
530                 535                 540

Gly Asn Asn Thr Leu Cys Pro Glu Asp Ala Val Arg Ala Leu Ala Met
545                 550                 555                 560

Leu Lys Thr Ala Met Ala Gly Glu Asp Val Lys Ala Ala Glu Lys Lys
                565                 570                 575

Trp Asn Pro Asn Val Lys Ser Thr Asn Val Glu Leu Ile Glu Ser Thr
                580                 585                 590

Tyr Gly Thr Lys Val Asp Leu Val Glu Asn Glu Gln Ala Leu Pro Met
                595                 600                 605

Ser Glu Lys Arg Arg Leu Lys Tyr Ser
610                 615

<210> SEQ ID NO 20
<211> LENGTH: 768
<212> TYPE: DNA
<213> ORGANISM: Clostridium scindens

<400> SEQUENCE: 20
ttggctgaag aggtaaaaga cctgagacgt cttgtaatta aagcgttcca catgaatgat      60
gtagagtggg gtgaacataa tgatattact gttgacggta atatgacagt cagtaaagaa     120
atgattgatc agctggtggc tcaggaggaa cacattgaaa aaattgatat tcagattatt     180
aagccggggg atcatgaccg ttggacgaat acgattatgg atatcatacc gatctctaca     240
aaggtacttg aaaattaggg gagggcatt acccatacca ttaccggcgt atatgtaatg     300
cttaccggcg ttgacgtaaa tggaaagcaa tgccatgaat tcggttcttc tgaggggaat     360
ctgaaagacc agctgtactt gaaccgtgca ggcacgccgg ggatgatga ttacataatt     420 tcctttgatg taacgcttgc agccggaatg gggcaggaga ggcctggacc gactgccgca     480
catagggcgt gcgataagtt tatccagaca taccgtgata agatgaagaa gttcaaaggc     540
gagaagtgta cggaacgcca tgagtaccat gatgtggtaa ggccgggaaa gaaacgcgtc     600
ctgatcgtaa agcaggtggc aggacaggga gcaatgtatg atacgcatct gttttccaaa     660
gagccgtctg gcgtagaggg cggacgttca attatcgata tgggcaatat gccgatcctt     720
gtaactccaa atgagtacag agacggtatt atccgctcca tgcagtag                  768

<210> SEQ ID NO 21
<211> LENGTH: 1854
<212> TYPE: DNA
<213> ORGANISM: Clostridium scindens

<400> SEQUENCE: 21
atgtcaatca cagctgaaac agcgaaagaa catgctcatg atcctgcggt attatgttgt      60
agagccgaag caggcattac aatcgaagct gctaatcttg aagatccggc gatctttgat     120
gacttggtag attcaggatt attgaacctg gatggtgcat tgaccatcga agaagttttg     180
ggagcaaaac ttacaaaaac atgtgattct ctttgcccgt taactgcaga gtagttgaa     240 ggtgcaaaag cgccgactgc tccagcagca gaagaggcag agaggaagc gccggcagca     300 ccggcaccgg ctgcagcacc tgtagcagga cctgcggcag gcggaacact taagatccac     360
attggagaag gcaaggacat tgatcttgag atcccagttg gagcgcttgg cggcggagca     420
gcagttgcac cattgccggc aggagcagag gcagttgttg caggagcagc agcaccagaa     480
gcagctggaa agaaaaaggt tgtaagaagt ttaacaagaa aacacttcac gatcacagag     540
gttaagagag gaccagagac caagatcgaa ggaacaactc tttacatccg tgaaggcatt     600

```
gagtcagaag ttattgacaa ccaggagctt gtaaaagatt tcaaactgga aatcatcact    660
cctgatttat atcacacata ttccgagact gttatggacg ttcagccaat cgctacaaaa    720
gaaggcgatg atgaactcgg aacaggtgtt acaagagtac ttgacggcgt tgttatgatg    780
ctgacaggtg ttgacgaagg cggagttcag attggcgagt tcggttcttc agaaggatac    840
cttgatgaga acattatgtg gaatcgtccg agctgcccag ataaaggcga gatctttatc    900
aagggtaaca tcgtaatcca ggaaaagaca aacatggaac gtcgtggacc tatggctgct    960
catacagcat ttgatgtaat cacacaggaa atccgcgaag ttatgaagaa acttgatgac   1020
agccttgttg ctgatacgga agaactgaag caggttcgcc gtccgggcaa gaagaaagtc   1080
gttatcgtta aggaaatcat gggacaggga gctatgcatg acaactttat ccttcctgta   1140
gagcctgttg gcgttctagg cgcaagagct aacgtagact taggaaacgt accggtttgc   1200
gtatctccat tggaagttct tgatggatgt atccatgcat taacatgtat cggacctgca   1260
tctaaggaaa tgtccagaca ttactggaga gagccattgg ttctggaagc attgcatgac   1320
ccggaagttg accttttgcgg cgttgtattt gtaggatctc ctcagatcaa tgctgagaaa   1380
ttctatgtat cccgtcgtgt aggccatacc gtagaaatga tggatgctga tggagctttc   1440
gttacaacgg aaggttttgg aaacaaccac atcgatttcg caagccatat cgagcagatc   1500
ggtatgagag gaattccggt tgttggcatg tcttactgtg cagttcaggg cgctctggtt   1560
gttggtaaca agtatatgac atacatggtt gacaataaca agtctgaagc tggtatcgag   1620
aacgagattc ttggtaacaa tacgctttgc ccggaagatg ctgttcgtgc acttgctatg   1680
cttaagactg caatggcagg cgaagacgtt aaggctgctg agaagaagtg gaatccaaac   1740
gttaagtcta caaacgtaga gttaattgag agcacatacg gtacaaaggt tgatcttgtt   1800
gaaaatgagc aggctcttcc gatgagtgaa aaacgtagat aaaatacag ctaa          1854

<210> SEQ ID NO 22
<211> LENGTH: 756
<212> TYPE: DNA
<213> ORGANISM: Clostridium scindens

<400> SEQUENCE: 22
atgaatgtag gatcaaggct gacggttaag gcgtaccctg tcacagaagt gtgctatggg     60
gaggagaacc gagtgacggt ggatggccgg atgacggtct gtaagaacat agcagaaaag    120
attctggcgc aggagccatt gataaaggag attgatatcc gtattatcat gccggatgag    180
caccgacagc ataccaacac ggtgatggat gtgattcctc tggcaaccaa agtgctggga    240
cgggtggggg agggcattac ccatacccctg acaggcgtat acgtgatcct taccggtgtg    300
gatgagagcg ggcgtcagat atgtaatttt ggcgccagcg acggaatact cgaggagaag    360
attgcctggg ggcgggcggg aacgccgctt aggagcgacg tgctgatctc ctttgacgtg    420
gttcttaagg aaggatcctg gcggatcgt ccgggtccgg aagcagccca tcgcgcctgc    480
gatacatact gccagatatt ccgggagcag ataaagaagt ttaatggata caagtgcgcg    540
gaaaagcatg tctttcagga gacgtatgag ccggggaaaa aagatgtcta tattgtgaaa    600
gaagtatccg gcaaggtgc cgtatacgat acccggatgt cggacatga gccttgcgga    660 ttcgaaggcg ggaagtctgt tattgatatg ggctgcatgc ctgcgctggt gacgcccaat    720
gaatttaggg atggcattat gcgcgcgatg gattag                              756

<210> SEQ ID NO 23
```

```
<211> LENGTH: 405
<212> TYPE: DNA
<213> ORGANISM: Clostridium scindens

<400> SEQUENCE: 23
atgtctatta cagcagaaac tgcaaaagaa catgcaaatg acccggctgt attatgctgc      60
cgggcagaag agggcattac aatacaggct tccaacttgg aagatcctgc tattttgac     120 gagttagtgg attcagggct gctatctttg gatggctgtc tgacaatcgg acaagtctta    180
ggggcaaccc tgacaaagac aagcgattct ttatgtccat tgactgcaga taacgtaggg    240
ggcttcaaag aggtagttga ggaagaagag cctgcatcag agccagtcga agaagcggta    300
gccgcagata ttaatattgg gggcgcggtc accacgatca aaaatggaaa agttgttatt    360
tcaatcaaag aaggaaaaga tatctattta gaacttcctg tttaa                    405

<210> SEQ ID NO 24
<211> LENGTH: 1329
<212> TYPE: DNA
<213> ORGANISM: Clostridium scindens

<400> SEQUENCE: 24
atgggaaatg tacagatttt attacgtcag catgttggtg caccctgtga ggcaatcgta     60
aaggctgggg ataaggtgga aaaaggtacc ttgattgcaa ctcctacagg acttggcgct    120
aacatctttt ccagcgtcta tggcgtggtg gaagaagtct tggaagaccg aatcgttatc    180
aagccggatg aagagcagaa agatgagttt gtacctatta aggaaggcag caagcttgag    240
atggttaagg aagccggaat cgtaggtatg gcggcgcag gattcccaac tggcgtgaag    300
attggaacgg accttcacgg cggatatatc ctggtaaatg ctgcagaatg cgagcctgga    360
cttcgccaca atatccagca gattgaagaa agacagata tcacaatccg cggattgaaa    420
tactgcatgg agatatccaa tgcggcaaaa ggaattattg ctattaagaa gaagaacgaa    480
aaagcgatcg aatttctcag agaggcaatc aaggatgaag acaatatcac gatccatctt    540
cttccggata tttacccaat gggagaggaa agagcggtag taagagaatg cctcggaaaa    600
ctgcttgatc ctacacaact tccgtcagca gcagatgcag tcgtaatcaa ctgcgagacc    660
ctgcttcgta tcgcagaggc gatcgaactt aagaaaccct gctttagcaa gaatatgacg    720
gttattggaa agattaacgg tggaaacgag ccgcatgtat tcatggatgt tccggttgga    780
acctgtgttg cagacatgat cgagaaggca ggcggaattg atggtacata tggcgagatt    840
atcatgggtg gagcatttac tggaaagtcc accacattag acgcgcctac tacgaagacg    900
acaggcggaa tcatcgttac ggtagagttc ccggatcttc acggagcgcc ggtaggattg    960
cttgtctgtg cgtgcggcgg aagcgaagac cgtatgcgcg aactttgcga aaagatgaat   1020
ggaaaggtcg tttctgtggc aagatgtaaa caggcggttg agccgaagcc gggcgcagcg   1080
cttaagtgcg agaatcctgg aaactgtcct ggacaggcac agaaatgtct gcagtttaag   1140
aaggacggcg cagagtacat catcatcggt aactgctcag actgttccaa cacagttatg   1200
ggatctgcac caaagttaaa actgaagaca ttccatcaga cagaccatgt gatgagaaca   1260
atcggtcatc cattatacag aagactgacc gtgtccaaag aagttgacca gctgcccaac   1320
ggcaaataa                                                            1329

<210> SEQ ID NO 25
<211> LENGTH: 474
<212> TYPE: DNA
<213> ORGANISM: Clostridium scindens
```

<400> SEQUENCE: 25
atgggtatag gaccatcaac aaaagaaaca tcattgcatc acttcaggga tccgctgctg 60
gatgtagtct cttcggatac agatctggat ctgatgggaa ttatcatcgt aggaacaccg 120
gacgataatg aggataagat gcttgtagga accaggacgg ctgtttgggc cgaggcaatg 180
cgtgcggacg gcgtaatcat ctcttcggac ggatggggaa acagcgacgt ggattacacg 240
aatacatgcg agcaggtggg gacgagaggc atcgcggtga cgggccttaa tttcagcggt 300
acggtagctc aatttgtagt tgtaaataat tacctggatg gaattgtgga tatcaataag 360
agcgcggacg ggacagagac caatgtggtt ggggaaaaca atatggtcga gctggattgc 420
aaaaaggcga ctgcgcttct gaaacttaag atgcgaaaga atgagaaaaa gtag 474

<210> SEQ ID NO 26
<211> LENGTH: 726
<212> TYPE: DNA
<213> ORGANISM: Clostridium scindens

<400> SEQUENCE: 26
atgagtttaa cggttgttaa aggtttacaa tctgaaatat tcgttcctat tactccacca 60
tcagtatgga ctcctgtaac aaaagagttg aaagacatgt ctatcgctct tgcaacagct 120
gccggtgttc ataagaagga tcaggaaaga ttcaatcttg ctggtgactt tacatggaga 180
aaaatagaga acacaacacc atctagcgaa ctgatggtat cccatggtgg atatgataac 240
agtgatgtta acaaagatat caactgtatg ttcccgattg acagaattca tgaattggct 300
gctgaaggat ttatcagggc ttgtgctccg gtacatgcag gattcatggg tggtggcgga 360
aaccaggaga agttcaaagg cgaaactggt ccggctatcg cgcagatgtt caaagaagag 420
gacgttgacg cagtaattct caccgctggc tgaggaacct gccaccgctc tgcagtattg 480
gtgcagagag cgattgaaga agctggaatt cctactatta ttattgcagc tcttccacca 540
gttgttcgcc agactggtac tcctcgtgca gttgctccat tggtacctat gggtgctaat 600
gcaggtggac cgcacaatgt tgaacagcag acacagatcg taaaggcaac tctggagcag 660
ttagttgaaa tccagacacc tggaaagatt gttccactgc cattcgagta tgtagctaag 720
atttaa 726

<210> SEQ ID NO 27
<211> LENGTH: 252
<212> TYPE: PRT
<213> ORGANISM: Clostridium bifermentans

<400> SEQUENCE: 27

Met Glu Glu Lys Ile Leu Arg Arg Leu Val Ile Lys Pro Phe His Ile
1 5 10 15

Asn Asn Val Glu Phe Asn Glu Lys Phe Ser Ile Lys Lys Gly Thr Leu
20 25 30

Ser Ile Asn Asn Asp Tyr Ile Asn Glu Ile Lys Asn Ser His Glu Leu
35 40 45

Ile Thr Asp Ile Lys Leu Asp Ile Ile Lys Pro Gly Asp Tyr Asn Lys
50 55 60

Glu Ile Asn Thr Ile Met Asp Ile Ile Pro Ile Ser Thr Lys Val Leu
65 70 75 80

Gly Arg Leu Gly Glu Gly Ile Thr His Thr Leu Thr Gly Val Tyr Val
85 90 95

```
Met Leu Thr Gly Val Asp Glu Asp Gly Arg Gln Met His Glu Phe Gly
            100                 105                 110

Ser Ser Glu Gly Ile Leu Ser Glu Gln Met Val Phe Gly Arg Tyr Gly
        115                 120                 125

Thr Pro Ser Thr Asn Asp Tyr Ile Ile His Phe Asp Val Thr Val Lys
    130                 135                 140

Gly Gly Leu Pro Tyr Glu Arg Lys Leu Pro Met Met Thr Phe Lys Ala
145                 150                 155                 160

Cys Asp Thr Phe Ile Gln Gly Ile Arg Asn Val Leu Lys Gln Gln Asp
                165                 170                 175

Gly Arg Asp Ala Thr Glu Ile Arg Glu Tyr Phe Asp Lys Ile Arg Pro
            180                 185                 190

Asp Ala Lys Lys Val Val Ile Val Lys Gln Ile Ala Gly Gln Gly Ala
        195                 200                 205

Met Tyr Asp Asn Gln Leu Phe Ser His Glu Pro Ser Gly Leu Glu Gly
    210                 215                 220

Gly Thr Ser Ile Ile Asp Met Gly Asn Val Pro Met Ile Ile Ser Pro
225                 230                 235                 240

Asn Glu Tyr Arg Asp Gly Ala Leu Arg Ala Met Thr
                245                 250
```

```
<210> SEQ ID NO 28
<211> LENGTH: 157
<212> TYPE: PRT
<213> ORGANISM: Clostridium difficile
<220> FEATURE:
<221> NAME/KEY: MOD_RES
<222> LOCATION: (45)..(45)
<223> OTHER INFORMATION: Selenocysteine

<400> SEQUENCE: 28
```

```
Met Ser Leu Leu Ser Asn Lys Val Leu Ile Ile Gly Asp Arg Asp
1               5                   10                  15

Gly Ile Pro Gly Pro Ala Ile Glu Glu Cys Val Lys Thr Val Glu Gly
            20                  25                  30

Ala Glu Val Val Phe Ser Ser Thr Glu Cys Phe Val Xaa Thr Ala Ala
        35                  40                  45

Gly Ala Met Asp Leu Glu Asn Gln Asn Arg Val Lys Asp Ala Ala Asp
    50                  55                  60

Lys Phe Gly Ala Glu Asn Val Val Ile Leu Leu Gly Ala Ala Glu Ala
65                  70                  75                  80

Glu Ala Ala Gly Leu Ala Ala Glu Thr Val Thr Ala Gly Asp Pro Thr
                85                  90                  95

Phe Ala Gly Pro Leu Ala Gly Val Ala Leu Gly Leu Ser Val Tyr His
            100                 105                 110

Val Val Glu Glu Pro Ile Lys Ser Leu Phe Asp Glu Ser Val Tyr Glu
        115                 120                 125

Asp Gln Ile Ser Met Met Glu Met Val Leu Glu Val Glu Glu Ile Glu
    130                 135                 140

Glu Glu Met Ser Gly Ile Arg Glu Glu Phe Cys Lys Phe
145                 150                 155
```

```
<210> SEQ ID NO 29
<211> LENGTH: 474
<212> TYPE: DNA
<213> ORGANISM: Clostridium difficile

<400> SEQUENCE: 29
```

```
atgagtttac ttagtaataa aaaggttctt ataataggtg accgtgatgg tataccagga     60
cctgcgatag aagaatgtgt aaaaacagta gaaggagcag aggttgtttt ctcatctaca    120
gaatgctttg tctgaacagc tgctggggct atggacttag aaaatcaaaa cagagttaaa    180
gatgctgctg ataaattcgg agctgaaaat gttgtgattt tactaggtgc tgctgaagcc    240
gaagctgcag gtcttgcagc cgaaacagta actgctggag atccaacttt cgctggacca    300
cttgctggag ttgccttagg attaagtgtt taccacgttg ttgaggaacc aataaaatca    360
ttatttgatg aaagtgtata tgaagaccaa ataagtatga tggaaatggt tttagaagtt    420
gaagaaatag aagaagaaat gtctggtata agagaagaat tttgtaaatt ttaa          474
```

```

<210> SEQ ID NO 30
<211> LENGTH: 1476
<212> TYPE: DNA
<213> ORGANISM: Clostridium bifermentans
<220> FEATURE:
<221> NAME/KEY: modified_base
<222> LOCATION: (1449)..(1449)
<223> OTHER INFORMATION: a, c, t, g, unknown or other

<400> SEQUENCE: 30
```

```
catrgctcag gatgaacgct ggcggcgtgc ctaacacatg caagtcgagc gatctcttcg     60
gagagagcgg cggacgggtg agtaacgcgt gggtaacctg ccctgtacac acggataaca    120
taccgaaagg tatactaata cgggataaca tatgaaagtc gcatggcttt tgtatcaaag    180
ctccggcggt acaggatgga cccgcgtctg attagctagt tggtaaggta atggcttacc    240
aaggcaacga tcagtagccg acctgagagg gtgatcggcc acactggaac tgagacacgg    300
tccagactcc tacgggaggc agcagtgggg aatattgcac aatgggcgaa agcctgatgc    360
agcaacgccg cgtgagcgat gaaggccttc gggtcgtaaa gctctgtcct caaggaagat    420
aatgacggta cttgaggagg aagccccggc taactacgtg ccagcagccg cggtaatatg    480
tagggggcta gcgttatccg gaattactgg gcgtaaaggg tgcgtaggtg gtttttttaag    540 tcagaagtga aaggctacgg ctcaaccgta gtaagctttt gaaactagag aacttgagtg    600
caggagagga gagtagaatt cctagtgtag cggtgaaatg cgtagatatt aggaggaata    660
ccagtagcga aggcggctct ctggactgta actgacactg aggcacgaaa gcgtggggag    720
caaacaggat tagataccct ggtagtccac gccgtaaacg atgagtacta ggtgtcgggg    780
gttacccccc tcggtgccgc actaacgcat taagtactcc gcctgggaag tacgctcgca    840
agagtgaaac tcaaaggaat ttdcggggac ccgcacaagt agcggagcat gtggtttaat    900
tcgaagcaac gcgaagaacc ttacctaagc ttgacatccc actgacctct ccctaatcgg    960
agatttccct tcggggacag tggtgacagg tggtgcatgg ttgtcgtcag ctcgtgtcgt   1020
gagatgttgg gttaagtccc gcaacgagcg caacccttgc ctttagttgc cagcattaag   1080
ttgggcactc tagagggact gccgaggata actcggagga aggtggggat gacgtcaaat   1140
catcatgccc cttatgctta gggctacaca cgtgctacaa tgggtggtac agagggttgc   1200
caagccgcga ggtggagcta atcccttaaa gccattctca gttcggattg taggctgaaa   1260
ctcgcctaca tgaagctgga gttactagta atcgcagatc agaatgctgc ggtgaatgcg   1320
ttcccgggtc ttgtacacac cgcccgtcac accatggaag ttgggggcgc ccgaagccgg   1380
ttagctaacc ttttaggaag cggccgtcga aggtgaacaa atgactgggg tgaagtcgta   1440
acaaggtanc cgtatcggaa ggtgcggcbg gatcaa                             1476
```

<210> SEQ ID NO 31
<211> LENGTH: 1529
<212> TYPE: DNA
<213> ORGANISM: Clostridium scindens

<400> SEQUENCE: 31

```
gagagtttga tcctggctca ggatgaacgc tggcggcgtg cctaacacat gcaagtcgaa      60
cgaagcgcct ggccccgact tcttcggaac gaggagcctt gcgactgagt ggcggacggg     120
tgagtaacgc gtgggcaacc tgccttgcac tggggdataa cagccagaaa tggctgctaa     180
taccgcataa gaccgaagcg ccgcatggcg cggcggccaa agccccggcg gtgcaagatg     240
ggcccgcgtc tgattaggta gttggcgggg taacggccca ccaagccgac gatcagtagc     300
cgacctgaga gggtgaccgg ccacattggg actgagacac ggcccagact cctacgggag     360
gcagcagtgg ggaatattgc acaatggggg aaaccctgat gcagcgacgc cgcgtgaagg     420
atgaagtatt tcggtatgta aacttctatc agcagggaag aagatgacgg tacctgacta     480
agaagccccg gctaactacg tgccagcagc cgcggtaata cgtaggggc aagcgttatc      540 cggatttact gggtgtaaag ggagcgtaga cggcgatgca agccagatgt gaaagcccgg     600
ggctcaaccc cgggactgca tttgaactg cgtggctgga tgtcggaga ggcaggcgga       660 attcctagtg tagcggtgaa atgcgtagat attaggagga acaccagtgg cgaaggcggc     720
ctgctggacg atgactgacg ttgaggctcg aaagcgtggg gagcaaacag gattagatac     780
cctggtagtc cacgccgtaa acgatgacta ctaggtgtcg ggtggcaagg ccattcggtg     840
ccgcagcaaa cgcaataagt agtccacctg gggagtacgt tcgcaagaat gaaactcaaa     900
ggaattgacg gggacccgca caagcggtgg agcatgtggt ttaattcgaa gcaacgcgaa     960
gaaccttacc tgatcttgac atcccgatgc caaagcgcgt aacgcgctct ttcttcggaa    1020
catcggtgac aggtggtgca tggttgtcgt cagctcgtgt cgtgagatgt tgggttaagt    1080
cccgcaacga gcgcaacccc tatcttcagt agccagcatt ttggatgggc actctggaga    1140
gactgccagg agaacctgg aggaaggtgg ggatgacgtc aaatcatcat gccccttatg      1200
accagggcta cacacgtgct acaatggcgt aaacaaaggg aggcgaaccc gcgagggtgg    1260
gcaaatccca aaaataacgt ctcagttcgg attgtagtct gcaactcgac tacatgaagt    1320
tggaatcgct agtaatcgcg aatcagaatg tcgcggtgaa tacgttcccg ggtcttgtac    1380
acaccgcccg tcacaccatg ggagtcagta acgcccgaag ccggtgaccc aacccgtaag    1440
ggagggagcc gtcgaaggtg ggaccgataa ctggggtgaa gtcgtaacaa ggtagccgta    1500
tcggaaggtg cggctggatc acctccttc                                      1529
```

<210> SEQ ID NO 32
<211> LENGTH: 1445
<212> TYPE: DNA
<213> ORGANISM: Clostridium hylemonae

<400> SEQUENCE: 32

```
aggatgaacg ctgccgccgt gcttaacaca tgcaagtcga acgaagcaat actgtgtgaa      60
gagattagct tgctaagatc agaactttgt attgactgag tggcggacgg gtgagtaacg     120
cgtgggcaac ctgccttaca caggggggata acagctagaa atggctgcta ataccgcata    180
agacctcagt accgcatggt agaggggtaa aaactccggt ggtgtaagat gggcccgcgt     240
ctgattaggt agttggtagg gtaacggcct accaagccga cgatcagtag ccgacctgag    300
agggtgaccg gccacattgg gactgagacac ggcccaaact cctacgggag gcagcagtgg    360
```

```
ggaatattgc acaatggggg aaaccctgat gcagcgacgc cgcgtgaagg atgaagtatt       420
tcggtatgta aacttctatc agcagggaag aagatgacgg tacctgacta agaagccccg       480
gctaactacg tgccagcagc cgcggtaata cgtaggcggc aagcgttatc cggatttact       540
gggtgtaaag ggagcgtaga cggcatggca agtctgaagt gaaagccgg ggctcaaccc        600 cgggactgct ttggaaactg tcaggctaga gtgtcggaga ggcaagtgga attcctagtg       660
tagcggtgaa atgcgtagat attaggagga acaccagtgg cgaagcggct tgctggacga       720
tgactgacgt tgaggctcga aagcgtgggg agcaaacagg attagatacc ctggtagtcc       780
acgccgtaaa cgatgattac taggtgtcgg gaagcaaagc ttttcggtgc cgcagccaac       840
gcaataagta atccacctgg ggagtacgtt cgcaagaatg aaactcaaag gaattgacgg       900
ggacccgcac aagcggtgga gcatgtggtt taattcgaag caacgcgaag aaccttacct       960
gatcttgaca tcccggtgac aaagtatgta acgtactctt cttcggaac accggtgaca      1020 ggtggtgcat ggttgtcgtc agctcgtgtc gtgagatgtt gggttaagtc ccgcaacggc      1080
gcaaccctta tctttagtag ccagcatttg aggtgggcac tctagagaga ctgccaggga      1140
taacctggag gaaggtgggg atgacgtcaa atcatcatgc cccttatgac cagggctaca      1200
cacgtgctac aatggcgtaa acaaagggaa gcgaccctgt gaaggcaagc aaatcccaaa      1260
aataacgtct cagttcggat tgtagtctgc aactcgacta catgaagctg gaatcgctag      1320
taatcgcgaa tcagaatgtc gcggtgaata cgttcccggg tcttgtacac accgcccgtc      1380
acaccatggg gtcagtaacg cccgaagccg gtgacctaac cgcaaaggag gagccgtcga      1440
aggtg                                                                  1445
```